(12) United States Patent
Tang et al.

(10) Patent No.: US 6,531,502 B1
(45) Date of Patent: Mar. 11, 2003

(54) 3-METHYLIDENYL-2-INDOLINONE MODULATORS OF PROTEIN KINASE

(75) Inventors: Pen Cho Tang, Moraga, CA (US); Li Sun, Foster City, CA (US); Todd Anthony Miller, Bend, OR (US); Congxin Liang, Sunnyvale, CA (US); Ngoc My Tran, Redwood City, CA (US); Anh Thi Nguyen, Fremont, CA (US); Asaad Nematalla, Walnut Creek, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/762,198

(22) PCT Filed: Aug. 4, 1999

(86) PCT No.: PCT/US99/17845

§ 371 (c)(1),
(2), (4) Date: May 22, 2001

(87) PCT Pub. No.: WO00/08202

PCT Pub. Date: Feb. 17, 2000

Related U.S. Application Data

(60) Provisional application No. 60/095,470, filed on Aug. 5, 1998, provisional application No. 60/102,178, filed on Sep. 28, 1998, and provisional application No. 60/072,023, filed on Jan. 21, 1998.

(51) Int. Cl.$^7$ ............... A61K 31/4015; C07D 209/12; C07D 209/14
(52) U.S. Cl. ............... 514/414; 514/418; 548/455; 548/468; 548/486
(58) Field of Search ............... 514/414, 418; 548/455, 468, 486

(56) References Cited

U.S. PATENT DOCUMENTS

| | | |
|---|---|---|
| 2,872,372 A | 2/1959 | Hull |
| 2,968,557 A | 1/1961 | Burgardt et al. |
| 4,376,110 A | 3/1983 | David et al. |
| 4,642,309 A | 2/1987 | Michel et al. |
| 4,826,847 A | 5/1989 | Michel et al. |
| 4,853,403 A | 8/1989 | Shiraishi et al. |
| 4,868,304 A | 9/1989 | Larock et al. |
| 4,966,849 A | 10/1990 | Vallee et al. |
| 4,971,996 A | 11/1990 | Shiraishi et al. |
| 5,051,417 A | 9/1991 | Nadler et al. |
| 5,057,538 A | 10/1991 | Shiraishi et al. |
| 5,089,516 A | 2/1992 | Shiraishi et al. |
| 5,124,347 A | 6/1992 | Connor et al. |
| 5,202,341 A | 4/1993 | Shiraishi et al. |
| 5,206,261 A | 4/1993 | Kawaguchi et al. |
| 5,217,999 A | 6/1993 | Levitzki |
| 5,302,606 A | 4/1994 | Spada et al. |
| 5,322,950 A | 6/1994 | Sircar et al. |
| 5,330,992 A | 7/1994 | Eissenstat et al. |
| 5,339,992 A | 8/1994 | Barthomeuf et al. |
| 5,374,652 A | 12/1994 | Buzzetti et al. |
| 5,382,593 A | 1/1995 | Le Baut et al. |
| 5,409,949 A | 4/1995 | Buzzetti et al. |
| 5,650,415 A | 7/1997 | Tang et al. |
| 5,792,783 A * | 8/1998 | Tang et al. |
| 5,834,504 A | 11/1998 | Tang et al. |
| 5,849,710 A | 12/1998 | Battistini et al. |
| 5,880,141 A | 3/1999 | Tang et al. |
| 5,883,113 A | 3/1999 | Tang et al. |
| 5,883,116 A | 3/1999 | Tang et al. |
| 5,886,020 A | 3/1999 | Tang et al. |
| RE36,256 E | 7/1999 | Spada et al. |
| 6,313,158 B1 * | 11/2001 | Tang et al. |

FOREIGN PATENT DOCUMENTS

| | | |
|---|---|---|
| AU | 286870 | 12/1964 |
| CA | 2012634 | 9/1991 |
| DE | 878539 | 5/1953 |
| DE | 2159360 | 6/1973 |
| DE | 2159361 | 6/1973 |
| DE | 2159362 | 6/1973 |
| DE | 2159363 | 6/1973 |
| DE | 2321656 | 11/1973 |
| DE | 3310891 | 9/1984 |
| DE | 3426419 | 1/1986 |
| EP | 0 351 213 | 1/1990 |
| EP | 0 566 226 | 1/1993 |
| EP | 0 525 472 | 2/1993 |
| EP | 0 580 502 | 1/1994 |
| EP | 0 632 102 | 6/1994 |
| EP | 0 626 377 | 11/1994 |
| EP | 0 662 473 | 7/1995 |
| EP | 0 788 890 | 8/1997 |
| FR | 1398224 | 3/1965 |
| FR | 2689397 | 10/1993 |
| GB | 809691 | 4/1959 |
| GB | 835473 | 5/1960 |
| GB | 1384599 | 2/1975 |
| JP | 62-29570 | 2/1987 |
| JP | 62-39564 | 2/1987 |
| JP | 63-141955 | 6/1988 |
| JP | 5-58894 | 3/1993 |

(List continued on next page.)

OTHER PUBLICATIONS

Mohammadi et al. CAS Online search Accession No.: 1997:322412 Science (Washington, D.C.) (1997), 276(5314), 955–960.*

(List continued on next page.)

*Primary Examiner*—Deborah C. Lambkin
*Assistant Examiner*—Sonya N. Wright
(74) *Attorney, Agent, or Firm*—Beth A. Burrous; Foley & Lardner

(57) ABSTRACT

The present invention relates to novel 3-methylidenyl-2-indolinone compounds and physiologically acceptable salts and prodrugs thereof which modulate the activity of protein kinases and therefore are expected to be useful in the prevention and treatment of protein kinase related cellular disorders such as cancer.

17 Claims, No Drawings

FOREIGN PATENT DOCUMENTS

| | | |
|---|---|---|
| JP | 9-286777 | 11/1997 |
| WO | 88/07035 | 9/1988 |
| WO | 91/15495 | 10/1991 |
| WO | 92/21660 | 4/1992 |
| WO | 92/07830 | 5/1992 |
| WO | 91/13055 | 9/1992 |
| WO | 92/20642 | 11/1992 |
| WO | 93/01182 | 1/1993 |
| WO | 94/03427 | 2/1994 |
| WO | 94/10202 | 5/1994 |
| WO | 94/14808 | 7/1994 |
| WO | 95/01349 | 1/1995 |
| WO | 95/14667 | 6/1995 |
| WO | 95/17181 | 6/1995 |
| WO | 96/00226 | 1/1996 |
| WO | 96/16964 | 6/1996 |
| WO | 96/22976 | 8/1996 |
| WO | 96/32380 | 10/1996 |
| WO | 96/40116 | * 12/1996 |
| WO | 97/25986 | 7/1997 |
| WO | 97/36867 | 10/1997 |
| WO | 98/07695 | 2/1998 |
| WO | 99/10325 | 4/1999 |

OTHER PUBLICATIONS

U.S. patent application Ser. No. 09/322,297, Tang et al., filed May 28, 1999.*

Abramovitch and Hey, "Internuclear cyclisation. Part VII. Naphth[3:2:1–cd]oxindoles," *J. Chem. Soc.* pp. 1697–1703 (1954).

Abramovitch et al., "A Novel Synthesis of a Cyclic Hydroxamic Acid Involving a Molecular Rearrangement," *Chemistry and Industry* 44:1871 (1967).

Abramovitch, Beilstein Reg. No. 236050, *J. Chem. Soc.,* pp. 1697, 1700 (1954).

Akbasak and Suner–Akbasak et al., "Oncogenes: cause or consequence in the development of glial tumors," *J. Neurol. Sci.* 111:119–133 (1992).

Andreani et al., "In Vivo Cardiotonic Activity of Pyridylmethylene–2–indolinones," *Arzneimittel–Forschung Drug Research* 48 (II): 727–729(1998).

Andreani et al., "Potential antitumor agents. 25[1]. Synthesis and cyclotoxic activity of 3–(2–chloro–3–indolylmethlene) 1,3–Dyhydroindol–2–ones," *AntiCancer Research* 16:3585–3588 (1996).

Andreani et al., "Synthesis and cardiotonic activity of 2–indolinones," *Eur. J. Med. Chem.* 25:187–190 (1990).

Andreani et al., "Synthesis and cardiotonic activity of 2–indolinones," *Chemical Abstracts*, vol. 113, abstract No. 78106 (1990).

Andreani et al., "Synthesis and cardiotonic activity of 2–indolinones bearing pyridyl groups," *Eur. J. Med. Chem.* 28:653–657 (1993).

Andreani et al., "Synthesis and cardiotonic activity of pyridylmethylene–2–indolinones," *Eur. J. Med. Chem.* 27:167–170 (1992).

Andreani et al., "Synthesis and potential coanthracyclinic activity of substituted 3–(5–imidazo [2, 1–b] thiazolymethylene)–2–indolinones," Eur. J. Med. Chem. 32:919–924 (1997).

Andreani et al., "Synthesis of lacatams with potential cardiotonic activity," *Eur. J. Med. Chem.* 28:825–829 (1993).

Arteaga et al., "Blockade of the type I somatomedin receptor inhibits growth of human breast cancer cells in athymic mice," *J. Clin. Invest.* 84:1418–1423 (1989).

Autrey and Tahk, "The Synthesis and Sterochemistry of Some Isatylideneacetic Acid Derivatives," *Tetrahedron* 23:901–917 (1967).

Bahner et al., "Benzylideneindenes with Oxygen Attached to the Indene Ring," *J. Med. Chem.* 12:721–722 (1969).

Bamfield et al., "Diels–Alder Reactions of Oxindolylidene-acetone," *J. Chem. Soc (C)* pp. 1028–1030 (1966).

Baserga, "Oncogenes and the strategy of growth factors," *Cell* 79:927–930 (1994).

Baserga, "The insulin–like growth factor I receptor: a key to tumor growth?" *Cancer Res.* 55:249–252 (1995).

Beilstein Reg. No.: 252929 (1998).

Bolen et al., "The Src family of tyrosine protein kinases in hemopoietic signal transduction," *FASEB J.* 6:3403–3409 (1992).

Buzzetti et al., "Cinnamamide Analogs as Inhibitors of Protein Tyrosine Kinases," II *Farmaco* 48 (5):615–636 (1993).

Carpenedo et al., "Identification and Measurement of Oxindole (2–Indolinone) in the Mammalian Brain and Other Rat Organs," *Analytical Biochemistry* 244:74–79 (1997).

Chao, "Growth Factor Signaling: Where is the Specificity?" *Cell* 68:995–997 (1992).

Chen et al., "Effects of 3,3–Dipyridylmethyl–1–Phenyl–2–Indolinone on γ–Aminobutyric Acid Elicited Chloride Current of Snail Central Neuron," *Chinese Journal of Physiology* 40(3):149–156 (1997).

Coda et al., "3–(4–methylbenzilidene)–1–, 3–dihydroindol–2–one," Journal of the Chemical Society, Perkin Transactions 2 4: 615–620 (1984).

Coppola et al., A Functional Insulin–Like Growth Factor I Receptor is Required for the Mitogenic and Transforming Activities of the Epidermal Growth Factor *Molecular and Cellular Biology* 14:4588–4595 (1994).

Damiani et al., "Inhibition of Cooper–Mediated Low Density Lipoprotein Peroxidation by Quinoline and Indolinone Nitroxide Radicals," *Biochemical Pharmacology* 48(6):1155–1161 (1994).

Davis et al., "Synthesis and Microbiological Properties of 3–Amino–1–Hydroxy–2–Indolinone and Related Compounds," *Journal of Medicinal Chemistry* 16(9):1043–1045 (1973).

De Vries et al., "The fms–Like Tyrosine Kinase, a Receptor for Vascular Endothelial Growth Factor," *Science* 255:989–991 (1992).

Dickson et al., "Tyrosine kinase receptor—nuclear protooncogene interactions in breast cancer," *Cancer Treatment Res.* 61:249–273 (1992).

Elliot, "1–methyl–2–(3–oxindolidenmethyl)–pyridinium," Databse Crossfire, Beilstein Ref. No. 5–24, Mar. 19, 1991, XP 002049951.

Elliott and Rivers, "Reduction of some oxindolylidene derivatives to 3–substituted oxindoles by sodium borohydride," *J. Med. Chem.* 29:2438–2440 (1964).

Fantl et al., "Distinct Phosphotyrosines on a Growth Factor Receptor Bind to Specific Molecules That Mediate Different Signaling Pathways," *Cell* 69:413–423 (1992).

Fendly et al., "Characterization of Murine Monoclonal Antibodies Reactive to Either the Human or Epidermal Growth Factor Receptor or HER2lneu Gene Product" *Cancer Research* 50:1550–1558 (1990).

Ferrara and Henzel, "Pituitary Follicular Cells Secrete a Novel Heparin–Binding Growth Factor Specific for Vascular Endothelial Cells," *Biochemical and Biophysical Research Communications* 161:851–858 (1989).

Fingl and Woodbury, Chapter 1, pp. 1–46 in *The Pharmacological Basis of Therapeutic* (5th edition), eds. Goodman et al., MacMillan Publishing Co., Inc., New York (1975).

Floege et al., "Factors involved in the regulation of mesangial cell proliferation in vitro in vivo," *Kidney International* 43S:47–54 (1993).

Folkman and Shing, "Angiogenesis," *J. Biol. Chem.* 267:10931–10934 (1992).

Folkman, "What is the Evidence that Tumors are Angiogenesis Dependent?" *Journal the National Cancer Institute* 82:4–7 (1990).

Gennaro (editor), *Remington's Pharmaceutical Sciences* (1990)(Table of contents only).

Goldring, "Cytokines and cell growth control," *Critical Reviews in Eukaryotic Gene Expression* 1:301–326 (1991).

Gottardis et al., "Estradiol–Stimulated Growth of MCF–7 Tumors Implanted in Athymmic Mice: A Model to Study the Tumoristatic Action of Tamoxifen," *J. Steroid Biochem.* 30(1–6):311–314 (1988).

Graziani et al., "Hepatocyte Growth Factor/Scatter Factor Stimulates the Ras–Guanine Nucleotide Exchanger," *The Journal of Biological Chemistry* 268(13):9165–9168 (1993).

Hewgill and Stewart, "Phenanthrene–4,5–quinones: a Synthesis of Morphenol," *J. Chem. Soc. Perkin Trans. 1* pp. 1305–1311 (1988).

Hodges et al., "Chemical and biological properties of some oxindolidyl–3–methines," *Canadian J. Chemistry* 46:2189–2194 (1968).

Honegger et al., "Point Mutation at the ATP Binding Site of EGF Receptor Abolishes Protein–Tyrosine Kinase Activity and Alters Cellular Routing," *Cell* 5:199–209 (1987).

Houck et al., "Dual Regulation of Vascular Endothelial Growth Factor Bioavailability Genetic and Proteolytic Mechanisms," *J. Biol. Chem.* 267:26031–26037 (1992).

Howard et al., "Synthesis and aldose reductase inhibitory activity of substituted 2(1H)–benzimidazolone– and oxindole–1–acetic acids," *Eur. J. Med. Chem.* 27:779–789 (1992).

Howard et al., "Synthesis and aldose reductase inhibitory activity of substituted 2(1H)–benzimidazolone– and oxindole–1 acetic acids" *Chemical Abstracts*, vol. 118, abstract No. 254813 (1993).

Ijaz et al., "The Conversion of o,β–Dinitrostyrenes into indoles and the Preparation of Oxindole Quinones," *J. Chem. Res. (S)* pp. 116 (1990).

Ijaz et al., "The Conversion of o,β–Dinitrostyrenes into Indoles and the Preparation of Oxindole Quinones," *Chemical Abstracts*, vol. 113, abstract No. 93739 (1990).

Jellinek et al., "Inhibition of Receptor Binding by High–Affinity RNA Ligands to Vascular Endothelial Growth Factor," *Biochemistry* 33:10450–10456 (1994).

Kato et al., "Simultaneous Determination of Amfenac Sodium and its Metabolite (7–Benzoyl–2–Oxindole) in Human Plasma by High–Performance Liquid Chromatography," *Journal of Chromatography* 616:67–71 (1993).

Katritzky et al., "Color and Constitution. Part 8[1]. Some Novel Dyestuffs Containing Indoxyl Residues," *J. Heterocyclic Chem.* 25:1287–1292 (1988).

Kendall and Thomas, "Inhibition of vascular edothelial cell growth factor activity by an endogenously encoded soluble receptor," *Proc. Natl. Acad. Sci. USA* 90:10705–10709 (1993).

Khalil and Abdel–Rahman, "Synthesis of New Mero– and Asymmetrical Pyrazolo–Monomethine Cyanine Dyes," *J. Indian Chem. Soc.* 54:904–907 (1977).

Kim et al., "Inhibition of Vascular endothelial growth factor–induced angiogenesis suppresses tumor growth in vivo," *Nature* 362:841–844 (1993).

Kinsella et al., "Protein Kinase C Regulates Endothelial Cell Tube Formation on Basement Membrane Matrix, Matrigel," *Exp. Cell Research* 199:52–62 (1992).

Klagsburn and Soker, "VEGF/VPF: the angiogenesis factor found?" *Current Biology* 3:699–702 (1993).

Kobayashi et al., "Anti–tumor Activity of Indole Derivatives," *Yakugaku Zasshi* 97(9):1033–1039 (1977).

Koch et al., "SH2 and SH3 Domains: Elements that Control Interactions of Cytoplasmic Signalling Proteins," *Science* 252:668–674 (1991).

Köhler and Milstein, "Continuous cultures of fused cells secreting antibody of predefined specificity," *Nature* 256:495–497 (1975).

Korc et al., "Overexpression of the epidermal growth factor receptor in human pancreatic cancer is associated with concomitant increases in the levels of epidermal growth factor and transforming growth factor alpha," *J. Clin. Invest.* 90:1352–1360 (1992).

Korzeniewski and Cellewaert, "An Enzyme–Release Assay for Natural Cytotoxicity[1]," *J. Immunol. Methods* 64:313–320 (1983).

Kovac and Stetinova, "Furan derivatives LXXX. Synthesis and properties of substituted furfurylidenoxindoles," *Chem. rvesu* 30:484–492 (1976).

Krueger and Saito, "A human transmembrane protein–tyrosine–phosphatase, PTP, is expressed in brain and has an N–terminal receptor domain homologous to carbonic anhydrases," *Proc. Natl. Acad. Sci. USA* 89:7417–7421 (1992).

Kumbae et al., "Amplificiation of α–platelet–derived growth factor receptor gene lacking an exon coding for a portion of the extracellular region in a primary brain tumor of glial origin," *Oncogene* 7:627–633 91992).

Larock and Babu, "Synthesis of Nitrogen Heterocycles via Palladium–catalyzed Intramolecular Cyclization," *Tetrahedron Letters* 28:52991–52994 (1987).

Lee and Donoghue, "Intracellular retention of membrane–anchored v–sis protein abrogates autocrine signal transduction," *Journal of Cell Biology* 118:1057–1070 (1992).

Maass et al., "Viral Resistance to the Thiazolo–Iso–Indolinones, a New Class of Nonnucleoside Inhibitors of Human Immunodeficiency Virus Type 1 Reverse Transcriptase," *Antimicrobial Agents and Chemotherapy* 37(12):2612–2617 (1993).

Macauley et al., "Autocrine function for insulin–like growth factor I in human small cell lung cancer cell lines and fresh tumor cells," *Cancer Res.* 50:2511–2517 (1990).

Mariani et al., "Inhibition of angiogenesis by PCE 26806, a potent tyrosine kinase inhibitor," *Experimental Therapeutics—Proceedings of the American Association for Cancer Research* 35:381 at abstract No. 2268 (Mar. 1994).

Martin–Leòn et al., "On the Cyclization to the Elusive Amino–4H–pyran Ring," *Liebigs Ann. Chem.* pp. 101–104 (1990).

Mirand et al., Synthesis Entry in the Aristotelia Alkaloids, *J. Org. Chem.* 47:4169–4170 (1982).

Moreto et al., "3,3–Bis–(4–Hydroxyphenyl)–7–Methyl–2–Indolinone (BHMI), the Active Metabolite of the Laxative Sulisatin," *Arzneimittel–Forschung Drug Research* 29(II):1561–1564 (1979).

Moreto et al., "Study of the Laxative Properties of the Disodium Salt of the Sulfuric Diester of 3,3 Bis–(4–Hydroxyphenyl)–7–Methyl–2–Indolinone (Dan–603) in the Rat," *European Journal of Pharmacology* 36:221–226 (1976).

Morrison et al., "Signal transduction from membrane to cytoplasm: Growth factors and membrane–bound oncogene products increase Raf-1 phosphorylation and associated protein kinase activity," *Proc. Natl. Acad. Sci. USA* 85:8855–8859 (1988).

Mosmann, "Rapid Colorimetric Assay for Cellular Growth and Survival: Application to Proliferation and Ccytotoxicity Assays," *J. Immunol. Methods* 65:55–63 (1983).

Neber and Rocker, "Ueber die einwirkung vbon benzaldehyden auf die freie o–aminophenyl–essigsaure," *Chem. Ber.* 56:1710–1717 (1923) (with translation).

Nodiff et al., "Antimalarial Phenanthrene Amino Alcohols. 1. Fluorine–Containing 3– and 6–Substituted 9–Phenanthrenemethanols," *Chemical Abstracts*, vol. 76, abstract No. 21121 (1972).

Nodiff et al., "Antimalarial Phenanthrene Amino Alcohols. 3. Halogen–contaiing 9–phenanthrenemethanols," *Chemical Abstracts*, vol. 83, abstract No. 188214 (1975).

Nodiff et al., "Antimalarial Phenanthrene Amino Alcohols. 1. Fluorine–Containing 3– and 6–Substituted 9–Phenanthrenemethanols," *J. Med. Chem.* 14:921–925 (1971).

O'Sullivan and Rothery, "The Preparation and Possible Clinical Significance of 4'–Dialkylaminoisoindogenides," *Clinica Chimica Acta* 62:181–182 (1975).

Osborne et al., "Effect of Estrogens and Antiestrogens on Growth of Human Breast Cancer Cells in Athymic Nude Mice," *Cancer Research* 45:584–590 (1985).

Ozzello and Sordat, "Behavior of Tumors Produced by Transplantation of Human Mammary Cell Lines in Athymic Nude Mice," *Eur. J. Cancer* 16:553–559 (1980).

Pavlenko et al., "Introduction of aminomethyl groups into heterocyclic CH–acid molecules," *Dopov. Akad. Nauk Ukr, RSR* 7:64–66 (1980).

Plate, "Vascular endothelial growth factor is potential tumor angiogenesis factor in human gilomas in vivo," *Nature* 359:845–848 (1992).

Plowman et al., "Receptor Tyrosine Kinases as Targets for Drug Intervention," *DN&P* 7(6):334–339 (1994).

Ruveda and Gonzalez, "Geometric isomerism in benzylideneoxindoles," *Spectrochimica Acta* 26A:1275–1277 (1970).

Rygaard and Povlsen, "Heterotransplantation of a Human Malignant Tumour to 'Nude' Mice," *Acta path. microbiol. scand.* 77:758–760 (1969).

Saito and Streuli, "Molecular Characterization of Protein Tyrosine Phosphatases," *Cell Growth & Differentation* 2:59–65 (1991).

Sandberg–Nordqvist et al., "Characterization of insulin–like growth factor 1 in human primary brain tumors," *Cancer Res.* 53:2475–2478 (1993).

Schindler et al., "Über Dibenz(b,f)–azocin–Derivate," *Helvetica Chimica Acta* 49:985–989 (1966).

Schlessinger and Ullrich, "Growth Factor Signalling by Receptor Tyrosine Kinases," *Neuron* 9:383–391 (1992).

Schnierle et al., "Vilsmeier–Reaktion mit Pyrrol– und Pyrrolon–Derivaten," *Liebigs Ann. Chem.* 715:90–97 (1968).

Schuchter et al., "Successful Treatment of Murine Melanoma With Bryostatin 1," *Cancer Research* 51:682–687 (1991).

Seibert et al., "Clonal Variation of MCF–7 Breast Cancer Cells in Vitro and in Athymic Nude Mice," *Cancer Research* 43:2223–2239 (1983).

Shafie and Grantham, "Role of Hormones in Growth and Regression of Human Breast Cancer Cells (MCF–7) Transplanted into Athymic Nude Mice," *J. Natl Cancer Institute* 67(1):51–56 (1981).

Shibuya et al., "Nucleotide sequence and expression of a novel human receptor–type tyrosine kinase gene (flt) closely related to the fms family," *Oncogene* 5:519–524 (1990).

Shiraishi et al., "Specific Inhibitors of Tyrosine–specific Protein Kinases: Properties of 4–Hydroxycinnamamide Derivatives in Vitro," *Cancer Research* 49:2374–2378 (1989).

Shiraishi, "Specific inhibitors of Tyrosine–Specific Protein Kinase, Synthetic 4–Hydroxycinnamamide Derivatives," *Biochemical and Biophysical Research Communications* 147:322–328 (1987).

Shweiki et al., "Vascular endothelial growth factor induced by hypoxia may mediate hypoxia–initiated angiogenesis," *Nature* 359:843–845 (1992).

Singh et al., "Indolinone Derivatives as Potential Antimicrobial Agents," *Zentralbl. Mikrobiol.* 144:105–109 (1989).

Singh et al., "Synthesis and Anticonvulsant Activity of New 1–Substituted 1'–Methyl–3–Chloro–2–Oxosprio (Azetidin–3',4–Indol–2' Ones)," *Bollettino Chimico Farmaceutico* 133:76–79 (1994).

Skehan et al., New Colorimetric Cytotoxicity Assay for Anticancer–Drug Screening *J. Natl. Cancer Inst.* 82:1107–1112 (1990).

Slamon et al., "Studies of the HER–2lneu Proto–oncogene in Human Breast and Ovarian Cancer," *Science* 244:707–712 (1989).

Soldi et al, "Platelet–Activating Factor (PAF) Induces the Early Tyrosine Phosphorylation of Focal Adhesion Kinase ($p125^{FAK}$) in Human Endothelial Cells," *Oncogene* 13(3):515–525 (1996).

Songyang et al., "SH2 Domain Recognize Specific Phosphopeptide Sequences," *Cell* 72:767–778 (1993).

Songyang et al., Specific motifs recognized by the SH2 domains of Csk, 3BP2, fps/fes, GRB–2, HCP, SHC, Syk and Vav, *Molecular and Cellular Biology* 14:2777–2785 (1994).

Stetinova et al., "Stereochemistry and Photoisomerisation of Furfurylideneoxindoles," *Collection Czecholslov. Chem. Commun.* 42:2201–2206 (1976).

Stolle, Beilstein Reg. No. 273650, *J. Prakt. Chem.*, vol. 2, p. 128 (1930).

Sumpter and Miller "Chapter IV—Oxindole," in *Heterocyclic Compounds With Indole and Carbazole Systems*, Interscience Publishers, Inc., New York, pp. 134–153 (1954).

Tacconi and Marinone, "Preparazione e caratteristiche di alcuni 3–ossindolidenderivati," *Ricerca Scientifica* 38:1239–1244 (1968).

Tacconi et al., "(Z)– and (E)–3–Alkylidene–1, 3–dihydroindol–2–ones: Influence of Configuration of the Transmission of the Inductive Effect to the Carbonyl Group," *J.C.S. Perkin II* pp. 150–154 (1976).

Takano et al., "Inhibition of angiogenesis by a novel diaminoanthraquinone that inhibits protein kinase C," *Mol. Bio. Cell* 4:358A (1993), Abstract #2076.

Terrett et al., "Combinatorial synthesis—the design of comound libraries and their application to drug discovery," *Tetrahedron* 51(30):8135–8173 (1995).

Thompson et al., "Facile Dimerisation of 3–Benzylideneindoline–2–thiones," *J. Chem. Soc. Perkin Trans.* (I) pp. 1835–1837 (1993).

Torp et al., "Expression of the epidermal growth factor receptor gene in human brain metastases," *AMPIS* 100:713–719 (1992).

Treibs et al, "Uber isoindigoide Farbstroffe der Pyrrol–Reihe," *Liebigs Ann. Chem.* 702:112–130 (1967).

Tsai et al., "The Effect of 3,3–Di–Pyridyl–Methyl–1–Phenyl–2–Indolinone on the Nerve Terminal Currents of Mouse Skeletal Muscles," *Neuropharmacology* 31(9):943–947 (1992).

Tuzi et al., "Expression of growth factor receptors in human brain tumours," *Br. J. Cancer* 63:227–233 (1991).

Ullrich and Schlessinger, "Signal Transduction by Receptors with Tyrosine Kinase Activity," *Cell* 61:203–212 (1990).

Vaisman et al., "Characterization of the Receptors for Vascular Endothelial Growth Factor," *J. Biol Chem.* 265:19461–19466 (1990).

Varma and Gupta, "Nucleophilic Reactions of 2–Methyl–3–(4'–carbomethoxyphenyl)–4–quinazolinones with 2–Indolinones," *J. Indian Chem. Soc.* 66:804–805 (1989).

Voller et al., "Enzyme–Linked Immunosorbent Assay," in *Manual of Clinical Immunology*, $2^{nd}$ edition, Rose and Friedman editors, American Society of Microbiology, Washington, D.C., pp. 359–371 (1980).

von Dobeneck et al., "α,β'–Diinodolylmethane und–methene. Der Urorosein–Chromophor," *Zur Chemie des Indols* VI:1347–1357 (1969).

Wahl et al., "Chimie Organique—Sur les iso–indogenides," *C.R. Hebd. Seancest Acad. Sci.* 149:132–134 (Jul. 1909).

Wahl, "3–benzilidene–5–methyl–1,3–dihydroindol–2–one," Ann. Chim. p. 350 (1926).

Wahl, Beilstein Reg. No. 191439, *Bull. Soc. Chim. Fr.*, p. 1038 (1909).

Wahl, Beilstein Reg. No. 231732, *Bull. Soc. Chim. Fr.*, pp. 1035–1038 (1909).

Walker, "Synthesis of a α–(p–Aminophenyl)– and α–(p–Chlorophenyl)–β–aryl–propionitriles by Catalytic Reduction of Stilbenenitriles," *J. Med. Chem.* 8(5):583–588 (1965).

Walker, "Synthesis of New 3–(Pyridylmethylene)–, 3–(Pyridylmethyl)–, 3–(Piperidylmethyl)– and 3–(β–Alkylaminoethyl)–2–indolinones. The Reduction of Isoindogenides, Nitro Compounds, and Pyridines in a Series of 2–Indolinones," *J. Med. Chem.* 8(5):626–637 (1965).

Warri et al., "Estrogen Suppression of erbB2 Expression is Associated with Increased Growth Rate of ZR–75–I Human Breast Cancer Cells In Vitro and in Nude Mice," *Int. J. Cancer* 49:616–623 (1991).

Weidner et al., "Tumor Angiogenesis and Metastasis—Correlation in Invasive Breast Carcinoma," *New England J. Medicine* 324:1–7 (1991).

Winkelmann et al., "Chemotherapeutically Active Nitro Compounds: 4. 5–Nitroimidazoles (Part I)," *Arzneim.–Forsch./Drug Res.* 27(II):2251–2263 (1977).

Wright et al., "Cyclic Hydroxamic Acids Derived from Indole," *J. Amer. Chem. Soc.* 78:221–224 (1956).

Wright et al., "Inhibition of Angiogenesis in Vitro and In Oyo With an Inhibitor of Cellular Protein Kinases, MDL 27032," *J. Cellular Physiology* 152:448–457 (1992).

Wright, Beilstein Reg. No. 224658, *J. Amer. Chem. Soc.* 78:221–224 (1956).

Wright, Beilstein Reg. No. 235900, *J. Amer. Chem. Soc.* 78:221–224 (1956).

Young and Babbitt, "2–(2–Methyl–3–indolyl)–1,4–benzoquinone, A Reversible Redox Substrate at the Carbon Paste Electrode in Acidic Aqueous–Ethanolic Media," *J. Org. Chem.* 47:1571–1572 (1982).

Zaman et al., "Tyrosine Kinase Activity of Purified Recombinant Cytoplasmic Domain of Platelet–Derived Growth Factor β–Receptor (β–PDGFR) and Discovery of a Novel Inhibitor of Receptor Tyrosine Kinases," *Biochemical Pharmacology* 57(1):57–64 (1999).

Zhang et al., "Microtubule Effects of Welwistatin, a Cyanobacterial Indolinone that Circumvents Multiple Drug Resistance," *Molecular Pharmacology* 49:288–294 (1996).

Zhungietu et al., "Reaction of Indoles and 2–Ketoindolines With Some Aldehydes," *Chemical Abstracts*, vol. 78, abstract No. 111201 (1973).

* cited by examiner

3-METHYLIDENYL-2-INDOLINONE MODULATORS OF PROTEIN KINASE

This application is a 371 of PCT/US99/17845 filed Aug. 4, 1999 which claims the benefit of provisional application No. 60/095,470 filed Aug. 5, 1998 which claims the benefit of provisional application No. 60/102,178 filed Sep. 28, 1998 which claims the benefit of provisional application No. 60/072,023 filed Jan. 21, 1998.

INTRODUCTION

The present invention relates generally to organic chemistry, biochemistry, pharmacology and medicine. More particularly, it relates to 3-methylidenyl-2-indolinone derivatives, and their physiologically acceptable salts and prodrugs, which modulate the activity of protein kinases ("PKs") and are expected to exhibit a salutary effect against disorders related to abnormal PK activity.

BACKGROUND OF THE INVENTION

The following is offered as background information only and is not admitted to be prior art to the present invention.

PKs are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently be broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of cellular metabolic processes to the extracellular microenvironment, etc. For a more complete discussion, see Schlessinger and Ullrich, *Neuron*, 9:303–391 (1992) which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated a subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1).

A further member of the tyrosine kinase growth factor receptor family is the fibroblast growth factor ("FGF") receptor subgroup. This group consists of four receptors, FGFR1-4, and seven ligands, FGF1-7. While not yet well defined, it appears that, like the PDGF receptors, the FGF receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor (VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

A more complete listing of the known RTK subfamilies is described in Plowman et al., *DN&P,* 7(6):334–339 (1994) which is incorporated by reference, including any drawings, as if fully set forth herein.

In addition to the RTKS, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene,* 8:2025–2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. Pat. No. 4,966,849); soluble receptors and antibodies (App. No. WO 94/10202, Kendall and Thomas, *Proc. Nat'l Acad. Sci.,* 90:10705–09 (1994), Kim, et al., *Nature,* 362:841–844 (1993)); RNA ligands (Jelinek, et al., *Biochemistry,* 33:10450–56); Takano, et al., *Mol. Bio. Cell* 4:358A (1993); Kinsella, et al., *Exp. Cell Res.* 199:56–62 (1992); Wright, et al., *J. Cellular Phys.,* 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.,* 35:2268 (1994)).

In addition to the above, attempts have been made to identify small molecules which act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP App. No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY OF THE INVENTION

Our own efforts to identify small organic molecules which modulate PK activity and which, therefore, are expected to be useful in the treatment and prevention of disorders involving abnormal PK activity, has led us to the discovery of a family of 3-methylidenyl-2-indolinone derivatives and their prodrugs and physiologically acceptable salts, which exhibit PK modulating ability and are thereby expected to have a salutary effect against disorders related to abnormal PK activity; it is these compounds which is the subject of this invention.

Thus, the present invention relates generally to 3-methylidenyl-2-indolinones and their prodrugs and physiologically acceptable salts, which modulate the activity of receptor tyrosine kinases (RTKs), non-receptor protein tyrosine kinases (CTKs) and serine/threonine protein kinases (STKs). In addition, the present invention relates to the preparation and use of pharmaceutical compositions of the disclosed compounds and their physiologically acceptable salts and prodrugs in the treatment or prevention of PK driven disorders such as, by way of example and not limitation, cancer, diabetes, hepatic cirrhosis, cardiovasacular disease such as atherosclerosis, angiogenesis, immunological disease such as autoimmune disease and renal disease.

The terms "2-indolinone," indolin-2-one and "2-oxindole" are used interchangeably herein to refer to a molecule having the chemical structure:

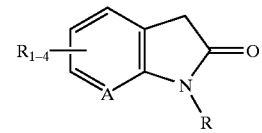

where A is carbon or nitrogen.

A "3-methylidenyl-2-indolinone" refers to a molecule having the chemical structure:

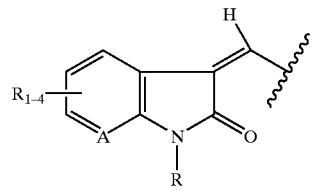

where, again, A can be carbon or nitrogen.

A "pharmaceutical composition" refers to a mixture of one or more of the compounds described herein, or physiologically acceptable salts or prodrugs thereof, with other chemical components, such as physiologically acceptable carriers and excipients. The purpose of a pharmaceutical composition is to facilitate administration of a compound to an organism.

A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

A further example of a prodrug might be a short polypeptide, for example, without limitation, a 2–10 amino acid polypeptide, bonded through a terminal amino group to a carboxy group of a compound of this invention wherein the polypeptide is hydrolyzed or metabolized in vivo to release the active molecule.

As used herein, a "physiologically acceptable carrier" or a "pharmaceutically acceptable carrier" refers to a carrier or diluent that does not cause significant irritation to an organism and does not abrogate the biological activity and properties of the administered compound.

A "carrier" refers to a chemical compound which faciliates the incorporation of a compound of interest into cells and tissues. An example, without limitation, of a carrier is dimethyl sulfoxide (DMSO).

A "diluent" refers to a chemical compound, usually a liquid, which dissolves or disperses a compound of interest thereby reducing the concentration of the compound to less than that of the compound alone.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

1. Chemistry

A. General Structural Features

In one aspect, the the present invention relate to 2-indolinones having chemical structure 1:

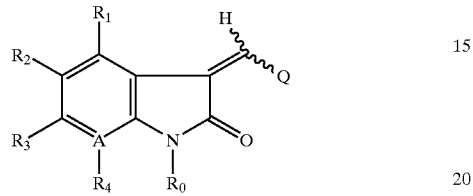

wherein:
A is selected from the group consisting of carbon and nitrogen;
Q is selected from the group consisting of

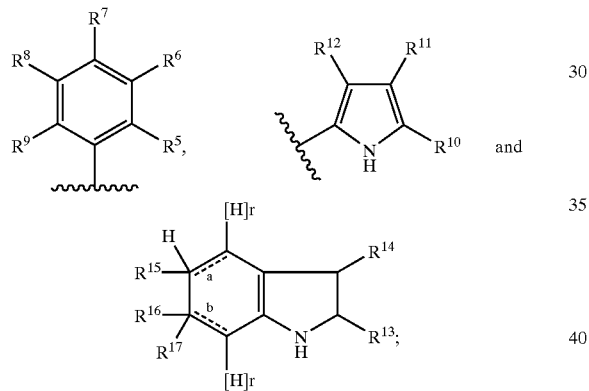

bonds a and b may be either single or double bonds as indicated by the dotted lines with the proviso that a and b are both single bonds or both double bonds in any one compound of this invention;
r is 1 when a and b are double bonds;
r is 2 when a and b are single bonds;
$R^0$ is selected from the group consisting of hydrogen, alkyl, —C(O)OR$^{19}$ and —C(O)R$^{19}$;
$R^1$ is selected from the group consisting of hydrogen, alkyl, aryl, alkoxy, halo, —C(O)OR$^{19}$, —(CH$_2$)$_n$OC(O)R$^{19}$, —C(O)NR$^{19}$ and (CH$_2$)$_n$R$^{20}$, wherein:
$R^{19}$ is selected from the group consisting of hydrogen, alkyl, alkenyl, alkynyl, cycloalkyl and aryl;
n is 1, 2, 3 or 4;
$R^{20}$ is selected from the group consisting of hydroxy, halo, —OC(O)NR$^{21}$R$^{22}$; —OC(S)NR$^{21}$R$^{22}$; —OC(O)NHSO$_2$R$^{21}$, —C(O)OR$^{19}$, —NR$^{21}$R$^{22}$ and a heteroalicylic group containing at least one nitrogen atom in the ring, the ring being bonded to the adjacent CH$_2$ group through the nitrogen atom;
$R^2$ is selected from the group consisting of hydrogen, alkyl, trihalomethyl, aryl, heteroaryl, heteroalicyclic, alkoxy, halo, —(CH$_2$)$_n$R$^{20}$, —SO$_2$NR$^{21}$R$^{22}$, —C(O)OR$^{19}$, —C(O)R$^{19}$, —NHC(O)OR$^{19}$, NHC(O)R$^{19}$, —C(O)(CH$_2$)$_n$R$^{20}$, —NR$^{21}$R$^{22}$ and —N=CR$^{23}$ wherein
$R^{21}$ and $R^{22}$ are independently selected from the group consisting of hydrogen, alkyl, alkenyl, alkynyl, cycloalkyl, aryl, heteroaryl and heteroalicyclic;
$R^{23}$ is selected from the group consisting of alkyl, alkenyl, alkynyl, cycloalkyl, aryl and heteroaryl;
$R^3$ is selected from the group consisting of hydrogen, alkyl, trihalomethyl, alkoxy, aryl, aryloxy, heteroaryl, heteroalicyclic, hydroxy, halo, —SO$_2$NR$^{21}$R$^{22}$, —NHSO$_2$R$^{19}$, —C(O)OR$^{19}$, —NR$^{21}$R$^{22}$ and —NHC(O)R$^{24}$, wherein
$R^{24}$ is selected from the group consisting of alkyl, alkenyl, alkynyl, aryl, heteroaryl and heteroalicyclic;
$R^4$ is selected from the group consisting of hydrogen, alkyl, alkoxy and halo;
$R^5$ is selected from the group consisting of hydrogen, alkyl, cycloalkyl, halo, aryl and heteroaryl;
$R^6$ is selected from the group consisting of hydrogen, alkyl, alkoxy, halo, cycloalkyl, aryl and, combined with $R^{18}$, a heteroalicyclic group having the structure

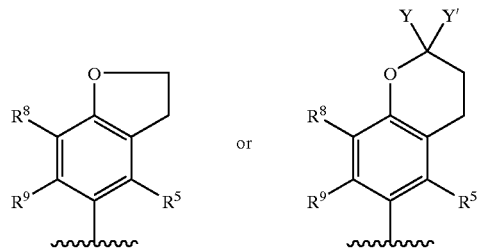

wherein
y and y' are independently selected from the group consisting of hydrogen, alkyl and aryl;
$R^7$ is OR$^{18}$, wherein $R^{18}$ is selected from the group consisting of alkyl, —(CH)$_n$R$^{20}$ and, combined with $R^6$ or $R^8$, a heteroalicyclic group having the structure

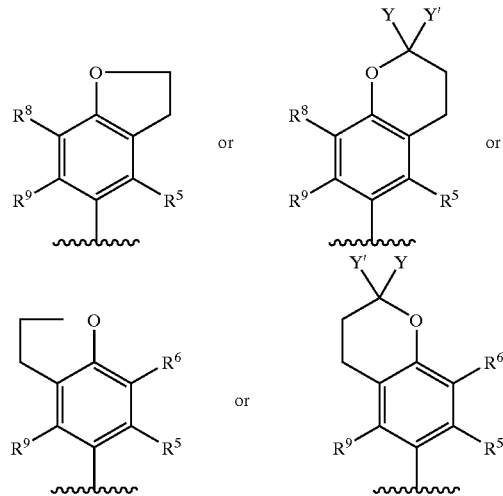

$R^8$ is selected from the group consisting of hydrogen, alkyl, cycloalkyl, alkoxy, halo, aryl, heteroaryl and, combined with $R^{18}$, a heteroalicyclic ring having the structure

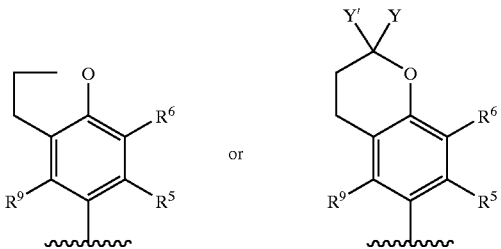

R[9] is selected from the group consisting of hydrogen, alkyl, alkoxy, halo and —NR[21]R[22];

R[10] is selected from the group consisting of alkyl and —C(O)OR[19];

R[11] is selected from the group consisting of hydrogen, alkyl and —C(O)OR[19];

R[12] is —(CH$_2$)$_n$R[20];

R[13] is either a bond through which Q is bonded to the rest of the molecule or, when it is not, a group selected from the group consisting of hydrogen and alkyl;

R[14] is either a bond through which Q is bonded to the rest of the molecule or, when it is not, a group selected from the group consisting of hydrogen, alkyl and —(CH$_2$)$_n$R[20];

R[15] is either a bond through which Q is bonded to the rest of the molecule or, when it is not, hydrogen; with the proviso that only one of R[13], R[14] or R[15] is the bond linking Q to the rest of the molecule in any one compound herein;

R[16] and R[17], when a and b are single bonds, are independently selected from the group consisting of hydrogen, alkyl and aryl and, when a and b are double bonds, R[16] is hydrogen and R[17] does not exist; and, physiologically acceptable salts and prodrugs thereof.

As used herein, the term "alkyl" refers to a saturated aliphatic hydrocarbon including straight chain and branched chain groups. Preferably, the alkyl group has 1 to 20 carbon atoms (whenever a numerical range; e.g. "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more independently selected from the group consisting of halo hydroxy, unsubstituted lower alkoxy, aryl optionally substituted with one or more halo, hydroxy, unsubstituted lower alkyl or unsubstituted lower alkoxy groups, aryloxy optionally substituted with one or more halo, hydroxy, unsubstituted lower alkyl or unsubstituted lower alkoxy groups, 6-member heteroaryl having from 1 to 3 nitrogen atoms in the ring, the carbons in the ring being optionally substituted with one or more halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon atoms of the group being optionally substituted with one or more halo, hydroxy, unsubstituted lower alkyl or unsubstituted lower alkoxy groups, 5- or 6-member heteroalicyclic group having from 1 to 3 heteroatoms selected from the group consisting of nitrogen, oxygen and sulfur, the carbon and nitrogen (if present) atoms in the group being optionally substituted with one or more halo, hydroxy, unsubstituted lower alkyl or unsubstituted lower alkoxy groups, mercapto, (unsubstituted lower alkyl)thio, arylthio optionally substituted with one or more halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, R[25]S(O)—, R[25]S(O)$_2$—, —C(O)OR[25], R[25]C(O)O—, and —NR[25]R[26], wherein R[25] and R[26] are independently selected from the group consisting of hydrogen, unsubstituted lower alkyl, trihalomethyl, unsubstituted (C$_3$–C$_6$)cycloalkyl, unsubstituted lower alkenyl, unsubstituted lower alkynyl and aryl optionally optionally substituted with one or more halo, hydroxy, unsubstituted lower alkyl or unsubstituted lower alkoxy groups.

A "cycloalkyl" group refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system)group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane and, cycloheptatriene. A cycloalkyl group may be substituted or unsubstituted. When substituted, the substituent group(s) is preferably one or more independently selected from the group consisting of unsubstituted lower alkyl, trihaloalkyl, halo, hydroxy, unsubstituted lower alkoxy, aryl optionally substituted with one or more halo, hydroxy, unsubstituted lower alkyl or unsubstituted lower alkoxy groups, aryloxy optionally substituted with one or more halo, hydroxy, unsubstituted lower alkyl or unsubstituted lower alkoxy groups, 6-member heteroaryl having from 1 to 3 nitrogen atoms in the ring, the carbons in the ring being optionally substituted with one or more halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon atoms of the group being optionally substituted with one or more halo, hydroxy, unsubstituted lower alkyl or unsubstituted lower alkoxy groups, 5- or 6-member heteroalicyclic group having from 1 to 3 heteroatoms selected from the group consisting of nitrogen, oxygen and sulfur, the carbon and nitogen (if present)atoms in the group being optionally substituted with one or more halo, hydroxy, unsubstituted lower alkyl or unsubstituted lower alkoxy groups, mercapto, (unsubstituted lower alkyl)thio, arylthio optionally substituted with one or more halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, R[25]S(O)—, R[25]S(O)$_2$—, —C(O)OR[25], R[25]C(O)O—, and —NR[25]R[26] are as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituted group(s) is preferably one or more independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{25}S(O)$—, $R^{25}S(O)_2$—, —$C(O)OR^{25}$, $R^{25}C(O)O$—, and —$NR^{25}R^{26}$, with $R^{25}$ and $R^{26}$ as defined above.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, Isoquinoline, purine and carbazole. The heteroaryl group may be substituted or unsubstituted. When substituted, the substituted group(s) is preferably one or more independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{25}S(O)$—, $R^{25}S(O)_2$—, —$C(O)OR^{25}$, $R^{25}C(O)O$—, and —$NR^{25}R^{26}$, with $R^{25}$ and $R^{26}$ as defined above.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted. When substituted, the substituted group(s) is preferably one or more independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{25}S(O)$—, $R^{25}S(O)_2$—, —$C(O)OR^{25}$, $R^{25}C(O)O$—, and —$NR^{25}R^{26}$, with $R^{25}$ and $R^{26}$ as defined above.

A "hydroxy" group refers to an —OH group.

An "alkoxy" group refers to both an —O-(unsubstituted alkyl) and an —O-(unsubstituted cycloalkyl) group.

An "aryloxyl" group refers to both an —O-aryl and an —O-heteroaryl group, as defined herein.

A "mercapto" group refers to an —SH group.

A "alkylthio" group refers to both an S-(unsubstituted alkyl) and an —S-(unsubstituted cycloalkyl) group.

A "arylthio" group refers to both an —S-aryl and an —S-heteroaryl group, as defined herein.

An "acyl" group refers to a —C(O)—R" group, where R" is selected from the group consisting of hydrogen, unsubstituted lower alkyl, trihalomethyl, unsubstituted cycloalkyl, aryl optionally substituted with one or more unsubstituted lower alkyl, trihalomethyl, unsubstituted lower alkoxy, halo and —$NR^{25}R^{26}$ groups, heteroaryl (bonded through a ring carbon) optionally substituted with one or more unsubstituted lower alkyl, trihaloalkyl, unsubstituted lower alkoxy, halo and —$NR^{25}R^{26}$ groups and heteroalicyclic (bonded through a ring carbon) optionally substituted with one or more unsubstituted lower alkyl, trihaloalkyl, unsubstituted lower alkoxy, halo and —$NR^{25}R^{26}$ groups.

An "aldehyde" group refers to an acyl group in which R" is hydrogen.

A "thioacyl" group refers to a —C(S)—R" group, with R" as defined herein.

An "ester" group refers to a —C(O)O—R" group with R" as defined herein except that R" cannot be hydrogen.

An "acetyl" group refers to a —$C(O)CH_3$ group.

A "halo" group refers to fluorine, chlorine, bromine or iodine.

A "trihalomethyl" group refers to a —$CX_3$ group wherein X is a halo group as defined herein.

A "trihalomethanesulfonyl" group refers to a $X_3CS(=O)_2$— groups with X as defined above.

A "cyano" group refers to a —C≡N group.

A "methylenedioxy" group refers to a —$OCH_2O$— group where the two oxygen atoms are bonded to adjacent carbon atoms.

An "ethylenedioxy" group refers to a —$OCH_2CH_2O$— where the two oxygen atoms are bonded to adjacent carbon atoms.

An "O-carbamyl" group refers to a —$OC(O)NR^{25}R^{26}$ group with $R^{25}$ and $R^{26}$ as defined herein.

An "N-carbamyl" group refers to an $R^{25}OC(O)NR^{26}$— group, with $R^{25}$ and $R^{26}$ as defined herein.

An "O-thiocarbamyl" group refers to a —$OC(S)NR^{25}R^{26}$ group with $R^{25}$ and $R^{26}$ as defined herein.

An "N-thiocarbamyl" group refers to a $R^{25}OC(S)NR^{26}$— group, with $R^{25}$ and $R^{26}$ as defined herein.

An "amino" group refers to an —$NR^{25}R^{26}$ group, wherein $R^{25}$ and $R^{26}$ are both hydrogen.

A "C-amido" group refers to a —$C(O)NR^{25}R^{26}$ group with $R^{25}$ and $R^{26}$ as defined herein.

An "N-amido" group refers to a $R^{25}C(O)NR^{26}$— group, with $R^{25}$ and $R^{26}$ as defined herein.

A "nitro" group refers to a —$NO_2$ group.

B. Preferred Structural Features

A presently preferred aspect of this invention is a compound in which Q is

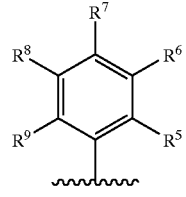

Another presently preferred aspect of this invention is a compound in which Q is

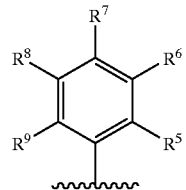

and $R^1$ is selected from the group consisting of hydrogen, lower alkyl and —C(O)OH;

$R^2$ is selected from the group consisting of hydrogen, lower alkyl, halo, —$C(O)R^{19}$, —$C(O)OR^{19}$, lower alkoxy, —$NR^{21}R^{22}$, —$(CH_2)_nR^{20}$ and —NHC(O)$OR^{19}$;

$R^3$ is selected from the group consisting of hydrogen, hydroxy, halo, —NHC(O)O(lower alkyl), —NHSO$_2$R$^{19}$, —NHC(O)R$^{24}$, trihalomethyl, and aryl optionally substituted with one or more lower alkoxy groups;

$R^4$ is hydrogen;

$R^{19}$ is selected from the group consisting of hydrogen and lower alkyl;

n is 2 or 3;

$R^{20}$ is selected from the group consisting of hydroxy, —C(O)OH, morpholin-4-yl, piperidin-1-yl, piperazin-1-yl, pyrrolidin-1-yl and —NR$^{21}$R$^{22}$;

$R^{21}$ and $R^{22}$ are independently selected from the group consisting of hydrogen and lower alkyl; and, $R^{24}$ is selected from the group consisting of hydrogen and lower alkyl.

It is likewise a presently preferred embodiment of this invention that Q is

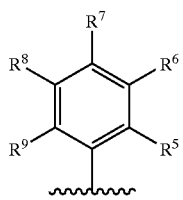

$R^1$ is selected from the group consisting of hydrogen, lower alkyl and —C(O)OH;

$R^2$ is selected from the group consisting of hydrogen, lower alkyl, halo, —C(O)R$^{19}$, —C(O)OR$^{19}$, lower alkoxy, —NR$^{21}$R$^{22}$, —(CH$_2$)$_n$R$^{20}$ and —NHC(O)OR$^{19}$;

$R^3$ is selected from the group consisting of hydrogen, hydroxy, halo, —NHC(O)O(lower alkyl), —NHSO$_2$R$^{19}$, —NHC(O)R$^{24}$, trihalomethyl, and aryl optionally substituted with one or more lower alkoxy groups;

$R^4$ is hydrogen;

$R^{19}$ is selected from the group consisting of hydrogen and lower alkyl;

n is 2 or 3;

$R^{20}$ is selected from the group consisting of hydroxy, —C(O)OH, morpholin-4-yl, piperidin-1-yl, piperazin-1-yl, pyrrolidin-1-yl and —NR$^{21}$R$^{22}$;

$R^{21}$ and $R^{22}$ are independently selected from the group consisting of hydrogen and lower alkyl;

$R^{24}$ is selected from the group consisting of hydrogen and lower alkyl;

$R^5$ is selected from the group consisting of hydrogen, lower alkyl, halo, five-member ring heteroaryl and aryl optionally substituted with one or more groups selected from the group consisting of lower alkyl, halo, hydroxy, —NR$^{21}$R$^{22}$ and lower alkoxy;

$R^6$ is selected from the group consisting of hydrogen, lower alkyl, 3 to 7-member cycloalkyl, lower alkoxy, halo, aryl optionally substituted with one or more groups independently selected from the group consisting of lower alkyl, halo, hydroxy, —NR$^{21}$R$^{22}$ and lower alkoxy and, combined with R$^{18}$, a group having the structure

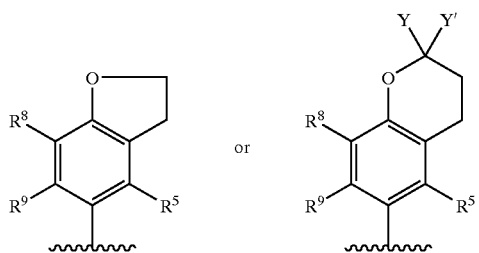

wherein y and y' are either both hydrogen or both lower alkyl;

$R^7$ is —OR$^{18}$ wherein R$^{18}$ is selected from the group consisting of lower alkyl, —(CH$_2$)$_n$R$^{20}$ and, combined with R$^6$ or R$^8$, a group having the structure

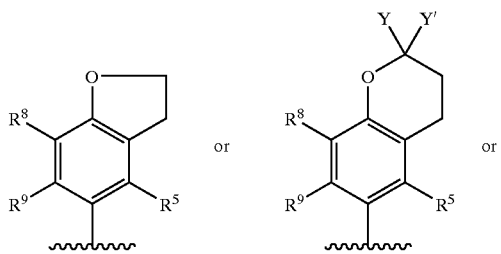

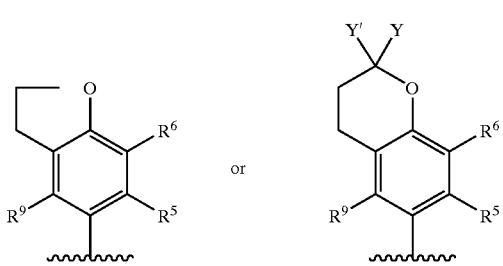

$R^8$ is selected from the group consisting of hydrogen, lower alkyl, 3 to 6-member ring cycloalkyl, lower alkoxy, halo, aryl optionally substituted with one or more groups selected from the group consisting of lower alkyl, lower alkoxy, halo, —NR$^{21}$R$^{22}$ and —NHC(O)(lower alkyl), five-member heteroaryl having from 1 to 3 heteroatoms in the ring and 6-member heteroaryl having from 1 to 3 heteroatoms in the ring and, combined with R$^{18}$ a group having the structure

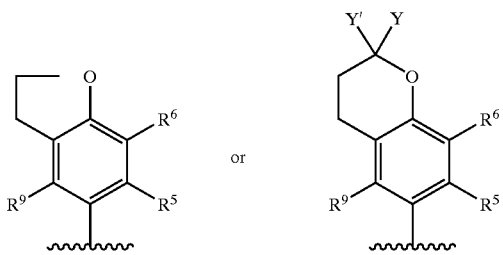

$R^9$ is selected from the group consisting of hydrogen, lower alkyl; hydroxy, lower alkoxy, halo and —NR$^{21}$R$^{22}$.

A further presently preferred aspect of this invention is a compound in which Q is

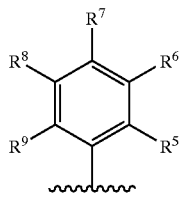

- $R^1$ is selected from the group consisting of hydrogen, lower alkyl and —C(O)OH;
- $R^2$ is selected from the group consisting of hydrogen, lower alkyl, halo, —C(O)$R^{19}$, —C(O)O$R^{19}$, lower alkoxy, —N$R^{21}R^{22}$, —(CH$_2$)$_n R^{20}$ and —NHC(O)O$R^{19}$;
- $R^3$ is selected from the group consisting of hydrogen, hydroxy, halo, —NHC(O)O(lower alkyl), —NHSO$_2 R^{19}$, —NHC(O)$R^{24}$, trihalomethyl, and aryl optionally substituted with one or more lower alkoxy groups;
- $R^4$ is hydrogen;
- $R^{19}$ is selected from the group consisting of hydrogen and lower alkyl;
- n is 2 or 3;
- $R^{20}$ is selected from the group consisting of hydroxy, —C(O)OH, morpholin-4-yl, piperidin-1-yl, piperazin-1-yl, pyrrolidin-1-yl and —N$R^{21}R^{22}$;
- $R^{21}$ and $R^{22}$ are independently selected from the group consisting of hydrogen and lower alkyl;
- $R^{24}$ is selected from the group consisting of hydrogen and lower alkyl;
- $R^5$ is selected from the group consisting of hydrogen, lower alkyl, thien-2-yl, thien-3-yl and aryl optionally substituted with one or more lower alkoxy groups;
- $R^6$ is selected from the group consisting of hydrogen, lower alkyl, 5 or 6-member cycloalkyl, aryl optionally substituted with one or more lower alkoxy groups and, combined with $R^{18}$, a group having the structure

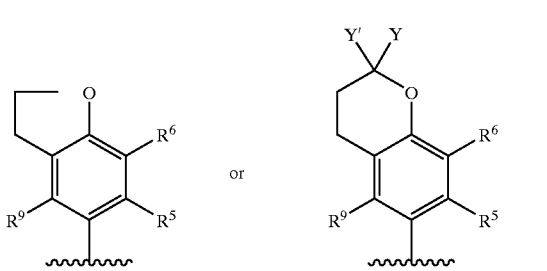

wherein y and y' are either both hydrogen or both lower alkyl;
- $R^7$ is —O$R^{18}$, wherein $R^{18}$ is selected from the group consisting of lower alkyl, —(CH$_2$)$_n R^{20}$ and, combined with $R^6$ or $R^8$, a group having the structure

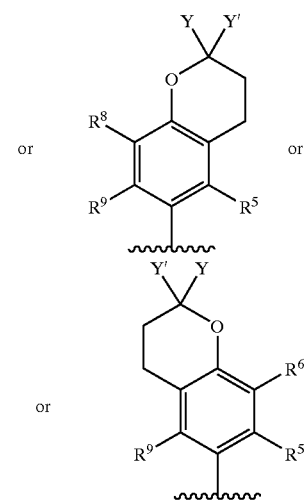

n is 2 or 3;
- $R^{20}$ is selected from the group consisting of hydroxy, —C(O)OH, morpholin-4-yl, piperidin-1-yl, piperazin-1-yl pyrrolidin-1-yl and —N$R^{21}R^{22}$;
- $R^8$ is selected from the group consisting of hydrogen, lower alkyl, 5 or 6-member ring cycloalkyl, lower alkoxy, aryl optionally substituted with a —NHC(O)(lower alkyl) group, thien-2-yl, thien-3-yl, pyridin-2-yl, pyridin-3-yl and, combined with $R^{18}$, a group having the structure

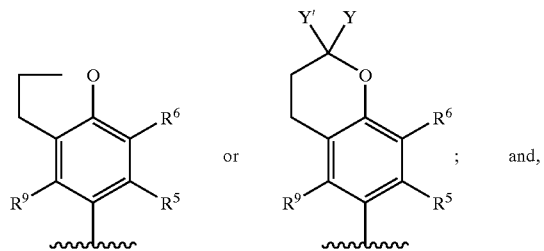

- $R^9$ is selected from the group consisting of hydrogen and lower alkyl.

Still another presently preferred aspect of this invention is a compound in which Q is:

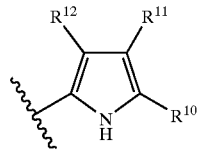

It is a presently preferred aspect of this compound that, in a compound in which Q is

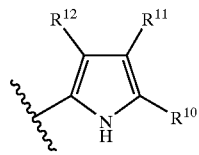

R[1] is selected from the group consisting of hydrogen, lower alkyl and —(CH$_2$)$_n$R[20];
n is 2 or 3;
R[20] is selected from the group consisting of hydroxy and —C(O)OH;
R[2] is selected from the group consisting of hydrogen, halo, lower alkyl, lower alkoxy, —SO$_2$NR[21]R[22] and —C(O)OH;
R[3] is selected from the group consisting of hydrogen, halo, lower alkyl, lower alkoxy and aryl optionally substituted with one or more lower alkoxy groups; and,
R[4] is hydrogen.
Likewise, in a compound in which Q is

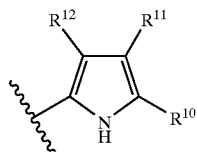

it is a presently preferred aspect of this invention that
R[1] is selected from the group consisting of hydrogen, lower alkyl and —(CH$_2$)$_n$R[20];
n is 2 or 3;
R[20] is selected from the group consisting of hydroxy and —C(O)OH;
R[2] is selected from the group consisting of hydrogen, halo, lower alkyl, lower alkoxy, —SO$_2$NR[21]R[22] and —C(O)OH;
R[3] is selected from the group consisting of hydrogen, halo, lower alkyl, lower alkoxy and aryl optionally substituted with one or more lower alkoxy groups;
R[4] is hydrogen;
R[10] is selected from the group consisting of lower alkyl and —C(O)OR[19];
R[11] is selected from the group consisting of hydrogen, lower alkyl and —C(O)OR[19];
R[12] is —(CH$_2$)$_n$R[20];
R[19] is selected from the group consisting of hydrogen and lower alkyl;
n is 2 or 3; and,
R[20] is selected from the group consisting of hydroxy, —C(O)OH, morpholin-4-yl, piperidin-1-yl, piperazin-1-yl, pyrrolidin-1-yl and —NR[21]R[22].
It is yet another presently preferred aspect of this invention that, in a compound in which Q is

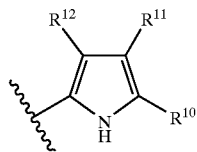

R[1] is selected from the group consisting of hydrogen, lower alkyl and —(CH$_2$)$_n$R[20];
n is 2 or 3;
R[20] is selected from the group consisting of hydroxy and —C(O)OH;
R[2] is selected from the group consisting of hydrogen, halo, lower alkyl, lower alkoxy, —SO$_2$NR[21]R[22] and —C(O)OH;
R[3] is selected from the group consisting of hydrogen, halo, lower alkyl, lower alkoxy and aryl optionally substituted with one or more lower alkoxy groups;

R[4] is hydrogen;
R[10] is selected from the group consisting of lower alkyl and —C(O)O(lower alkyl);
R[11] is selected from the group consisting of hydrogen, lower alkyl and —C(O)OR[19];
R[12] is —(CH$_2$)$_n$R[20];
R[19] is selected from the group consisting of hydrogen and lower alkyl;
n is 2; and,
R[20] is selected from the group consisting of —C(O)OH, morpholin-1-yl, piperidin-1-yl, piperazin-1-yl, pyrrolidin-1-yl and —N(lower alkyl)$_2$.
It is also a presently preferred aspect of this invention that Q is

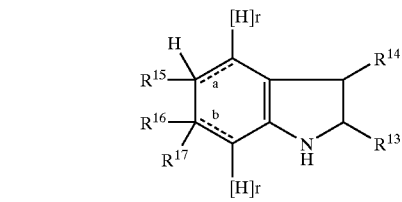

R[1] is selected from the group consisting of hydrogen and lower alkyl;
R[2] is selected from the group consisting of hydrogen, lower alkyl, halo, —C(O)OR[19], —C(O)R[19], —NR[21]R[22], —SO$_2$NR[21]R[22] and —N=C—R[23];
R[3] is selected from the group consisting of hydrogen, halo, lower alkyl, lower alkoxy, morpholin-4-yl, piperidin-1-yl, piperazin-1-yl, pyrrolidin-1-yl and aryl optionally substituted with one or more lower alkoxy groups,; and,
R[4] is hydrogen.
It is a presently preferred aspect of this invention that, in a compound in which Q is

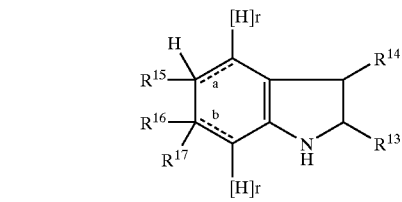

a and b are both single bonds;
r is 2;
R[1] is selected from the group consisting of hydrogen and lower alkyl;
R[2] is selected from the group consisting of hydrogen, lower alkyl, halo, —C(O)OR[19], —C(O)R[19], —NR[21]R[22], —SO$_2$NR[21]R[22] and —N=C—R[23];
R[3] is selected from the group consisting of hydrogen, halo, lower alkyl, lower alkoxy, morpholin-4-yl, piperidin-1-yl, piperazin-1-yl, pyrrolidin-1-yl and aryl optionally substituted with one or more lower alkoxy groups;
R[4] is hydrogen;
R[13] is a covalent bond through which Q is bonded to the rest of the molecule;
R[14] is selected from the group consisting of hydrogen, lower alkyl and —(CH$_2$)$_n$R[20];
R[15] is hydrogen; and, $R^{16}$ and $R^{17}$ are independently selected from the group consisting of hydrogen and lower alkyl.

It is also a presently preferred aspect of this invention that, in a compound having the substituents indicated in the paragraph immediately above, $R^{20}$ is —$NR^{21}R^{22}$ wherein $R^{21}$ and $R^{22}$ are independently selected from the group consisting of hydrogen and lower alkyl.

It is yet another presently preferred aspect of this invention that, in a compound in which Q is

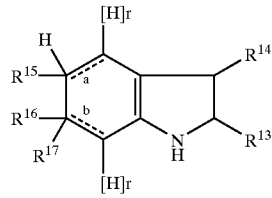

a and b are both double bonds;
r is 1;
$R^1$ is selected from the group consisting of hydrogen and lower alkyl;
$R^2$ is selected from the group consisting of hydrogen, lower alkyl, halo, —C(O)OR$^{19}$, —C(O)R$^{19}$, —NR$^{21}$R$^{22}$, —SO$_2$NR$^{21}$R$^{22}$ and —N=C—R$^{23}$;
$R^3$ is selected from the group consisting of hydrogen, halo, lower alkyl, lower alkoxy, morpholin-4-yl, piperidin-1-yl, piperazin-1-yl, pyrrolidin-1-yl and aryl optionally substituted with one or more lower alkoxy groups;
$R^4$ is hydrogen;
$R^{13}$ is a covalent bond through which Q is bonded to the rest of the molecule;
$R^{14}$ is selected from the group consisting of hydrogen, lower alkyl and —(CH$_2$)$_n$R$^{20}$;
$R^{15}$ and $R^{16}$ are hydrogen; and,
$R^{17}$ does not exist.

A compound in which Q is

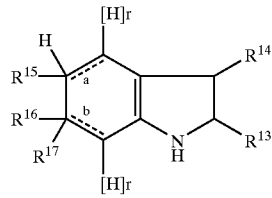

a and b are both double bonds;
r is 1;
$R^1$ is selected from the group consisting of hydrogen and lower alkyl;
$R^2$ is selected from the group consisting of hydrogen, lower alkyl, halo, —C(O)OR$^{19}$, —C(O)R$^{19}$, —NR$^{21}$R$^{22}$, —SO$_2$NR$^{21}$R$^{22}$ and —N=C—R$^{23}$;
$R^3$ is selected from the group consisting of hydrogen, halo, lower alkyl, lower alkoxy, morpholin-4-yl, piperidin-1-yl, piperazin1-yl, pyrrolidin-1-yl and aryl optionally substituted with one or more lower alkoxy groups;
$R^4$ is hydrogen;
$R^{13}$ is selected from the group consisting of hydrogen and lower alkyl;

$R^{14}$ is a covalent bond through which Q is bonded to the rest of the molecule;
$R^{15}$ and $R^{16}$ are hydrogen; and,
$R^{17}$ does not exist is another presently preferred aspect of this invention.

It is a presently preferred aspect of this invention that, in a compound where Q is

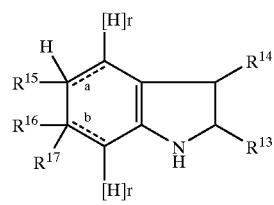

a and b are double bonds;
r is 1;
$R^1$ is selected from the group consisting of hydrogen and lower alkyl;
$R^2$ is selected from the group consisting of hydrogen, lower alkyl, halo, —C(O)OR$^{19}$, —C(O)R$^{19}$, —NR$^{21}$R$^{22}$, —SO$_2$NR$^{21}$R$^{22}$ and —N=C—R$^{23}$;
$R^3$ is selected from the group consisting of hydrogen, halo, lower alkyl, lower alkoxy, morpholin-4-yl, piperidin-1-yl, piperazin-1-yl, pyrrolidin-1-yl and aryl optionally substituted with one or more lower alkoxy groups;
$R^4$ is hydrogen;
$R^{13}$ is selected from the group consisting of hydrogen and lower alkyl;
$R^{14}$ is selected from the group consisting of hydrogen, lower alkyl and —(CH$_2$)$_n$R$^{20}$;
$R^{15}$ is a covalent bond through which Q is bonded to the rest of the molecule;
$R^{16}$ are hydrogen; and,
$R^{17}$ does not exist.

A compound selected from the group consisting of:

3-(3,5-Diisopropyl-4-methoxybenzylidene)-1,3-dihydroindol-2-one

5-Chloro-3-(3,5-diisopropyl-4-methoxybenzylidene)-1,3-dihydroindol-2-one

N-[3-(3,5-Diisopropyl-4-methoxybenzylidene)-2-oxo-2,3-dihydro-1H-indol-6-yl]-acetamide 3-(3,5-Diisopropyl-4-methoxybenzylidene)-6-hydroxy-1,3-dihydroindol-2-one 5-Acetyl-3-(3,5-diisopropyl-4-methoxybenzylidene)-1,3-dihydroindol-2-one 3-(3,5-Diisopropyl-4-methoxybenzylidene)-2-oxo-2,3-dihydro-1H-indole-5-carboxylic acid methyl ester 3-(3-Isopropyl-4-methoxybenzylidene)-1,3-dihydroindol-2-one 3-(5-Isopropyl-4-methoxy-2-methylbenzylidene)-1,3-dihydroindol-2-one 5-Chloro-3-(5-isopropyl-4-methoxy-2-methylbenzylidene)-1,3-dihydroindol-2-one 3-(3-Cyclopentyl-4-methoxybenzylidene)-1,3-dihydroindol-2-one 3-(3-Cyclopentyl-4-methoxybenzylidene)-5-fluoro-1,3-dihydroindol-2-one 3-(3-Cyclohexyl-4-methoxybenzylidene)-1,3-dihydroindol-2-one 5-Bromo-3-(6-methoxybiphenyl-3-ylmethylene)-1,3-dihydroindol-2-one 5-Chloro-3-(2,3-dihydrobenzofuran-5-ylmethylene)-1,3-dihydroindol-2-one
5-Chloro-3-(2,2-dimethylchroman-6-ylmethylene)-1,3-dihydroindol-2-one
N-{3-[3-Cyclohexyl-4-(2-morpholin-4-ylethoxy)-benzylidene]-2-oxo-2,3-dihydro-1H-indol-6-yl}-acetamide
3-(3,5-Diisopropyl-4-methoxybenzylidene)-5-methoxy-1,3-dihydroindol-2-one
N-[3-(4-Methoxy-3-thiophen-3-ylbenzylidene)-2-oxo-2,3-dihydro-1H-indol-6-yl]-acetamide
3-(3,5-Diisopropyl-4-methoxybenzylidene)-5-methyl-1,3-dihydroindol-2-one
5-Amino-3-(3,5-diisopropyl-4-methoxybenzylidene)-1,3-dihydroindol-2-one
5-Chloro-3-(4-methoxy-3,5-dimethylbenzylidene)-1,3-dihydroindol-2-one
3-(3,5-Diisopropyl-4-methoxybenzylidene)-6-fluoro-1,3-dihydroindol-2-one
3-(2,2-Dimethylchroman-6-ylmethylene)-5-fluoro-1,3-dihydroindol-2-one
5-Chloro-3-[3,5-diisopropyl-4-(2-morpholin-4-ylethoxy)-benzylidene]-1,3-dihydroindol-2-one
3-(3,5-Diisopropyl-4-methoxybenzylidene)-7-fluoro-1,3-dihydroindol-2-one
3-(4-Methoxy-3-thiophen-3-ylbenzylidene)-5-(2-morpholin-4-ylethyl)-1,3-dihydroindol-2-one
N-[3-(5-Isopropyl-4-methoxy-2-methylbenzylidene)-2-oxo-2,3-dihydro-1H-indol-6-yl]-acetamide
3-(3,5-Diisopropyl-4-methoxybenzylidene)-5-ethyl-1,3-dihydroindol-2-one
N-[2'-Methoxy-5'-(2-oxo-1,2-dihydroindol-3-ylidenemethyl)-biphenyl-3-yl]-acetamide
5-Fluoro-3-(5-isopropyl-4-methoxy-2-methylbenzylidene)-1,3-dihydroindol-2-one
N-[3-(4-Methoxy-3-thiophen-2-ylbenzylidene)-2-oxo-2,3-dihydro-1H-indol-6-yl]-acetamide
6-Amino-3-(3,5-diisopropyl-4-methoxybenzylidene)-1,3-dihydroindol-2-one
N-[3-(2,2-Dimethylchroman-6-ylmethylene)-2-oxo-2,3-dihydro-1H-indol-6-yl]-acetamide
5-Bromo-3-(2,2-dimethylchroman-6-ylmethylene)-1,3-dihydroindol-2-one
3-(4-Methoxy-3-thiophen-3-ylbenzylidene)-1,3-dihydroindol-2-one
5-Bromo-3-(5-isopropyl-4-methoxy-2-methylbenzylidene)-1,3-dihydroindol-2-one
5-Fluoro-3-(6-methoxybiphenyl-3-ylmethylene)-1,3-dihydroindol-2-one
3-(3-Isopropyl-4-methoxybenzylidene)-4-methyl-1,3-dihydroindol-2-one
3-(4,5-Dimethoxy-2-thiophen-2-ylbenzylidene)-1,3-dihydroindol-2-one
N-{3-[4-(2-Morpholin-4-ylethoxy)-3-thiophen-2-ylbenzylidene]-2-oxo-2,3-dihydro-1H-indol-6-yl}-acetamide
3-(2,2-Dimethylchroman-6-ylmethylene)-4-methyl-1,3-dihydroindol-2-one
3-(2,3-Dihydrobenzofuran-5-ylmethylene)-5-fluoro-1,3-dihydroindol-2-one
3-(3-Cyclohexyl-4-methoxybenzylidene)-5-fluoro-1,3-dihydroindol-2-one
5-Fluoro-3-(3-isopropyl-4-methoxybenzylidene)-1,3-dihydroindol-2-one
3-(5-Isopropyl-4-methoxy-2-methylbenzylidene)-1,3-dihydropyrrolo[2,3-b]pyridin-2-one
3-(3'-Ethoxy-6-methoxybiphenyl-3-ylmethylene)-1,3-dihydroindol-2-one
3-(3-Cyclopentyl-4-methoxybenzylidene)-1,3-dihydropyrrolo[2,3-b]pyridin-2-one
3-(3-Cyclopentyl-4-methoxybenzylidene)-4-methyl-1,3-dihydroindol-2-one
3-(4,5,2'-Trimethoxybiphenyl-2-ylmethylene)-1,3-dihydroindol-2-one
N-{3-[4-(2-Morpholin-4-ylethoxy)-3-thiophen-3-ylbenzylidene]-2-oxo-2,3-dihydro-1H-indol-6-yl}-acetamide
5-Chloro-3-(3-cyclohexyl-4-methoxybenzylidene)-1,3-dihydroindol-2-one
[3-(3,5-Diisopropyl-4-methoxybenzylidene)-2-oxo-2,3-dihydro-1H-indol-6-yl]-carbamic acid tert-butyl ester
3-(3,5-Diisopropyl-4-methoxybenzylidene)-4-methyl-1,3-dihydroindol-2-one
5-Bromo-3-(3,5-diisopropyl-4-methoxybenzylidene)-1,3-dihydroindol-2-one
N-{3-[3-tert-Butyl-4-(2-morpholin-4-ylethoxy)-benzylidene]-2-oxo-2,3-dihydro-1H-indol-6-yl}-acetamide
3-(4-Methoxy-3,5-dimethylbenzylidene)-1,3-dihydropyrrolo[2,3-b]pyridin-2-one
5-Bromo-3-[3,5-diisopropyl-4-(2-morpholin-4-ylethoxy)-benzylidene]-1,3-dihydroindol-2-one
3-(3'-Ethoxy-4,5-dimethoxybiphenyl-2-ylmethylene)-1,3-dihydroindol-2-one
5-Chloro-3-(4-methoxy-3-thiophen-2-ylbenzylidene)-1,3-dihydroindol-2-one
5-Chloro-3-(4-methoxy-3-pyridin-3-ylbenzylidene)-1,3-dihydroindol-2-one
5-Chloro-3-(4,5,3'-trimethoxybiphenyl-2-ylmethylene)-1,3-dihydroindol-2-one
3-(4,5-Dimethoxy-2-naphthalen-2-ylbenzylidene)-1,3-dihydroindol-2-one
N-[3-(3'-Acetylamino-6-methoxybiphenyl-3-ylmethylene)-2-oxo-2,3-dihydro-1H-indol-6-yl]-acetamide
6-Methoxy-3-(4-methoxy-3-thiophen-3-ylbenzylidene)-1,3-dihydroindol-2-one
3-(6-Methoxybiphenyl-3-ylmethylene)-1,3-dihydroindol-2-one
3-(2,3-Dihydrobenzofuran-5-ylmethylene)-1,3-dihydroindol-2-one
5-Chloro-3-(6-methoxybiphenyl-3-ylmethylene)-1,3-dihydroindol-2-one
3-(3-Cyclohexyl-4-methoxybenzylidene)-4-methyl-1,3-dihydroindol-2-one
3-(2,3-dihydrobenzofuran-5-ylmethylene)-4-methyl-1,3-dihydroindol-2-one
3-(3-Isopropyl-4-methoxybenzylidene)-1,3-dihydropyrrolo[2,3-b]pyridin-2-one
3-(6-Methoxybiphenyl-3-ylmethylene)-1,3-dihydropyrrolo[2,3-b]pyridin-2-one
3-(3-Cyclohexyl-4-methoxybenzylidene)-1,3-dihydropyrrolo[2,3-b]pyridin-2-one
3-(2,3-Dihydrobenzofuran-5-ylmethylene)-1,3-dihydropyrrolo[2,3-b]pyridin-2-one
3-(3,5-Diisopropyl-4-methoxybenzylidene)-1,3-dihydropyrrolo[2,3-b]pyridin-2-one
5-Bromo-3-(3-isopropyl-4-methoxybenzylidene)-1,3-dihydroindol-2-one
5-Bromo-3-(3-cyclopentyl-4-methoxybenzylidene)-1,3-dihydroindol-2-one
5-Chloro-3-(3-cyclopentyl-4-methoxybenzylidene)-4-methyl-1,3-dihydroindol-2-one
5-Chloro-3-(6-methoxybiphenyl-3-ylmethylene)-4-methyl-1,3-dihydroindol-2-one
5-Chloro-3-(5-isopropyl-4-methoxy-2-methylbenzylidene)-4-methyl-1,3-dihydroindol-2-one 5-Chloro-3-(4-methoxy-3,5-dimethylbenzylidene)-4-methyl-1,3-dihydroindol-2-one
3-(3,5-Diisopropyl-4-methoxybenzylidene)-6-trifluoromethyl-1,3-dihydroindol-2-one
6-Chloro-3-(3,5-diisopropyl-4-methoxybenzylidene)-1,3-dihydroindol-2-one
3-[3-(3,5-Diisopropyl-4-methoxybenzylidene)-2-oxo-2,3-dihydro-1H-indol-5-yl]-propionic acid
3-(3,5-Diisopropyl-4-methoxybenzylidene)-6-methoxy-1,3-dihydroindol-2-one
5-Butyl-3-(3,5-diisopropyl-4-methoxybenzylidene)-1,3-dihydroindol-2-one
3-(3,5-Diisopropyl-4- methoxybenzylidene)-2-oxo-2,3-dihydro-1H-indole-4-carboxylic acid
3-(3,5-Diisopropyl-4-methoxybenzylidene)-6-(3-methoxyphenyl)-1,3-dihydroindol-2-one
7-Chloro-3-(3,5-diisopropyl-4-methoxybenzylidene)-5-methyl-1,3-dihydroindol-2-one
[3-(3,5-Diisopropyl-4-methoxybenzylidene)-2-oxo-2,3-dihydro-1H-indol-5-yl]-carbamic acid tert-butyl ester
5-Chloro-3-(3-isopropyl-4-methoxybenzylidene)-1,3-dihydroindol-2-one
5-Chloro-3-(3-cyclopentyl-4-methoxybenzylidene)-1,3-dihydroindol-2-one
3-(6-Methoxybiphenyl-3-ylmethylene)-4-methyl-1,3-dihydroindol-2-one
3-(5-Isopropyl-4-methoxy-2-methylbenzylidene)-4-methyl-1,3-dihydroindol-2-one
5-Bromo-3-(2,3-dihydrobenzofuran-5-ylmethylene)-1,3-dihydroindol-2-one
5-Chloro-3-(3-isopropyl-4-methoxybenzylidene)-4-methyl-1,3-dihydroindol-2-one
5-Chloro-3-(3,5-diisopropyl-4-methoxybenzylidene)-4-methyl-1,3-dihydroindol-2-one
5-Chloro-3-(2,2-dimethylchroman-6-ylmethylene)-4-methyl-1,3-dihydroindol-2-one
3-(3,5-Diisopropyl-4-methoxybenzylidene)-2-oxo-2,3-dihydro-1H-indole-5-carboxylic acid
3-(3,5-Diisopropyl-4-methoxybenzylidene)-5,6-dimethoxy-1,3-dihydroindol-2-one
N-[3-(3,5-Diisopropyl-4-methoxybenzylidene)-2-oxo-2,3-dihydro-1H-indol-6-yl]-methanesulfonamide
N-[3-(3,5-Diisopropyl-4-methoxybenzylidene)-2-oxo-2,3-dihydro-1H-indol-6-yl]-benzamide
3-(3,5-Diisopropyl-4-methoxybenzylidene)-6-(3-ethoxyphenyl)-1,3-dihydroindol-2-one
3-(3,5-Diisopropyl-4-methoxybenzylidene)-6-phenyl-1,3-dihydroindol-2-one
3-(3,5-Diisopropyl-4-methoxybenzylidene)-5-fluoro-1,3-dihydroindol-2-one
5-Fluoro-3-(4-methoxy-3, 5-dimethylbenzylidene)-1,3-dihydroindol-2-one
3-(2,2-dimethylchroman-6-ylmethylene)-1,3-dihydroindol-2-one is also a preferred embodiment of this invention.

Likewise, a compound selected from the group consisting of:

5-methyl-3-(3-methyl-1H-indol-2-ylmethylene)-1,3-dihydroindol-2-one,
3-(3-methyl-1H-indol-2-ylmethylene)-2-oxo-2,3-dihydro-1H-indol-5-sulfonic acid amide,
3(3-methyl-1H-indol-2-ylmethylene)-2-oxo-2,3-dihydro-1H-indole-5-sulfonic acid methylamide,
3-(3-methyl-1H-indole-2-ylmethylene)-2-oxo-2,3-dihydro-1H-indole-5-sulfonic acid dimethylamide,
3-(3-methyl-1H-indol-2-ylmethylene)-2-oxo-2,3-dihydro-1H-indole-5-carboxylic acid,
5-acetyl-3-(3-methyl-1H-indol-2-ylmethylene)-1,3-dihydroindol-2-one,
5-acetyl-3-(1H-indol-2-ylmethylene)-1,3-dihydroindol-2-one,
3-(1H-indol-2-ylmethylene)-2-oxo-2,3-dihydro-1H-indol-5-sulfonic acid amide,
5-amino-3-(1H-indol-2-ylmethylene)-1,3-dihydroindol-2-one,
3-(1H-indol-2-ylmethylene)-2-oxo-2,3-dihydro-1H-indole-5-carboxylic acid,
6-chloro-3-(1H-indol-2-ylmethylene)-1,3-dihydroindol-2-one,
3-(1H-indol-2-ylmethylene)-1,3-dihydroindol-2-one,
5-chloro-3-(1H-indol-2-ylmethylene)-1,3-dihydroindol-2-one,
5-bromo-3-(1H-indol-2-ylmethylene)-1,3-dihydroindol-2-one,
3-(1H-indol-2-ylmethylene)-4-methyl-1,3-dihydroindol-2-one,
3-(3-methyl-1H-indol-2-ylmethylene)-1,3-dihydroindol-2-one,
5-chloro-3-(3-methyl-1H-indol-2-ylmethylene)-1,3-dihydroindol-2-one,
5-bromo-3-(3-methyl-1H-indol-2-ylmethylene)-1,3-dihydroindol-2-one,
4-methyl-3-(3-methyl-1H-indol-2-ylmethylene)-1,3-dihydroindol-2-one, and
3-(1H-indol-2-ylmethylene)-5[(1H-indol-2-ylmethylene)amino]-1,3-dihydroindol-2-one is also a presently preferred embodiment of this invention.

Finally, with regard to chemical compounds of this invention, a presently preferred embodiment comprises compounds selected from the group consisting of:

3-[2-(2-oxo-1,2-dihydro-indol-3-ylidenemethyl)-4,5,6,7-tetrahydro-1H-indol-3-yl]-propionic acid,
3-[2-(5-chloro-2-oxo-1,2-dihydro-indol-3-ylidenemethyl)-4,5,6,7-tetrahydro-1H-indol-3-yl]-propionic acid,
3-2-(5-bromo-2-oxo-1,2-dihydro-indol-3-ylidenemethyl)-4,5,6,7-tetrahydro-1H-indol-3-yl]-propionic acid,
3-[2-(4-methyl-2-oxo-1,2-dihydro-indol-3-ylidenemethyl)-4,5,6,7-tetrahydro-1H-indol-3-yl]-propionic acid,
3-[2-(5-methyl-2-oxo-1,2-dihydro-indol-3-ylidenemethyl)-4,5,6,7-tetrahydro-1H-indol-3-yl]-propionic acid,
3-[2-(6-chloro-2-oxo-1,2-dihydro-indol-3-ylidenemethyl)-4,5,6,7-tetrahydro-1H-indol-3-yl]-propionic acid,
3-[2-(6-methoxy-2-oxo-1,2-dihydro-indol-3-ylidenemethyl)-4,5,6,7-tetrahydro-1H-indol-3-yl]-propionic acid,
N,N-dimethyl-3-[2-(2-oxo-1,2-dihydro-indol-3-ylidenemethyl)-4,5,6,7-tetrahydro-1H-indol-3-yl]-propionamide,
3-[3-(3-dimethylamino-propyl)-4,5,6,7-tetrahydro-1H-indol-2-ylmethylene]-1,3-dihydro-indol-2-one,
3-[2-(2-oxo-1,2-dihydro-indol-3-ylidenemethyl)-4,5,6,7-tetrahydro-1H-indol-3-yl]-propionamide,
3-[3-(3-morpholin-4-yl-3-oxo-propyl)-4,5,6,7-tetrahydro-1H-indol-2-ylmethylene]-1,3-dihydro-indol-2-one,
N-methyl-3-[2-(2-oxo-1,2-dihydro-indol-3-ylidenemethyl)-4,5,6,7-tetrahydro-1H-indol-3-yl]-propionamide, N-(2-morpholin-4-yl-ethyl)-3-[2-(2-oxo-1,2-dihydro-indol-3-ylidenemethyl)-4,5,6,7-tetrahydro-1H-indol-3-yl]-propionamide, 3-[2-(2-oxo-1,2-dihydro-pyrrolo[2,3-b]pyridin-3-ylidenemethyl)-4,5,6,7-tetrahydro-1H-indol-3-yl]-propionic acid, 3-{2-[6-(3-methoxy-phenyl)-2-oxo-1,2-dihydro-indol-3-ylidenemethyl]-4,5,6,7-tetrahydro-1H-indol-3-yl}-propionic acid, 3-{2-[6-(4-methoxy-phenyl)-2-oxo-1,2-dihydro-indol-3-ylidenemethyl]-4,5,6,7-tetrahydro-1H-indol-3-yl}-propionic acid, 3-[2-(2-oxo-6-phenyl-1,2-dihydro-indol-3-ylidenemethyl)-4,5,6,7-tetrahydro-1H-indol-3-yl]-propionic acid, 3-{2-[6-(2-methoxy-phenyl)-2-oxo-1,2-dihydro-indol-3-ylidenemethyl]-4,5,6,7-tetrahydro-1H-indol-3-yl}-propionic acid, 3-[2-(5-isopropylsulfamoyl-2-oxo-1,2-dihydro-indol-3-ylidenemethyl)-4,5,6,7-tetrahydro-1H-indol-3-yl]-propionic acid, 3-[2-(6-morpholin-4-yl-2-oxo-1,2-dihydro-indol-3-ylidenemethyl)-4,5,6,7-tetrahydro-1H-indol-3-yl]-propionic acid, 3-[2-(5-chloro-4-methyl-2-oxo-1,2-dihydro-indol-3-ylidenemethyl)-4,5,6,7-tetrahydro-1H-indol-3-yl]-propionic acid, 3-[2-(5-bromo-4-methyl-2-oxo-1,2-dihydro-indol-3-ylidenemethyl)-4,5,6,7-tetrahydro-1H-indol-3-yl]-propionic acid, 3-[2-(5-bromo-2-oxo-1,2-dihydro-indol-3-ylidenemethyl)-4,5,6,7-tetrahydro-1H-indol-3-yl]-N-(2-morpholin-4-yl-ethyl)-propionamide, 3-[2-(5-chloro-2-oxo-1,2-dihydro-indol-3-ylidenemethyl)-4,5,6,7-tetrahydro-1H-indol-3-yl]-N-(2-morpholin-4-yl-ethyl)-propionamide, and 3-[2-(2-oxo-1,2-dihydro-indol-3-ylidenemethyl)-phenyl]-propionic acid.

2. Synthesis/Combinatorial Libraries

An additional aspect of this invention is a combinatorial library of at least ten 3-methylidenyl-2-indolinone compounds that can be formed by reacting oxindoles of structure 5 with aldehydes of structure 6, 7 or 8:

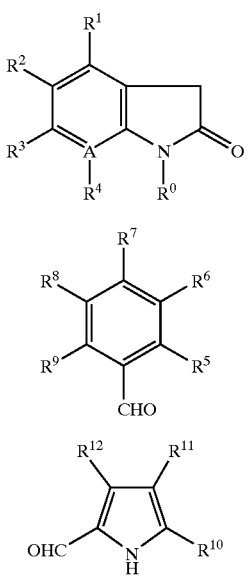

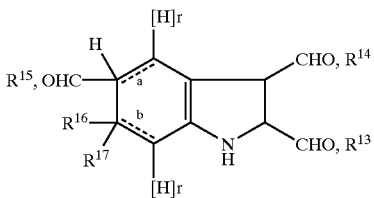

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ have the meanings set forth above.

As used herein, a "combinatorial library" refers to all the compounds formed by the reaction of each compound of one dimension with a compound in each of the other dimensions in a multi-dimensional array of compounds. In the context of the present invention, the array is two dimensional and one dimension represents all the oxindoles of the invention and the second dimension represents all the aldehydes of the invention. Each oxindole may be reacted with each and every aldehyde in order to form a substituted 3-methylidenyl-2-indolinone compound. All substituted 3-methylidenyl-2-indolinone compounds formed in this way are within the scope of the present invention. Also within the scope of the present invention are smaller combinatorial libraries formed by the reaction of some of the oxindoles with all of the aldehydes, all of the oxindoles with some of the aldehydes, or some of the oxindoles with some of the aldehydes.

The oxindole in the above combinatorial library is preferably selected from the group consisting of oxindole itself and substituted oxindoles such as, without limitation, 6-bromooxindole, 5-hydroxyoxindole, 5-methoxyoxindole, 6-methoxyoxindole, 5-phenylaminosulfonyloxindole, 4-[2-(2-isopropylphenoxy)ethyl]oxindole, 4-[2-(3-isopropylphenoxy)-ethyl]oxindole, 4-[2-(4-isopropylphenoxy)-ethyl]oxindole, 5-fluorooxindole, 6-fluorooxindole, 7-fluorooxindole, 6-trifluoromethyloxindole, 5-chlorooxindole, 6-chlorooxindole, 4-carboxyindole, 5-bromooxindole, 5-bromo-4-methyloxindole, 6-(N-acetamido)oxindole, 4-methyloxindole, 5-methyloxindole, 4-methyl-5-chlorooxindole, 5-ethyloxindole, 6-hydroxyoxindole, 5-acetyloxindole, 5-carboxyindole, 5-aminooxindole, 6-aminooxindole, 4-(2-N-morpholinoethyl)oxindole, 7-azaoxindole, oxindole-4-carabamic acid t-butyl ester, oxindole-6-carbamic acid t-butyl ester, 4-(2-carboxyethyl)oxindole, 5-n-butyloxindole, 5,6-dimethoxyoxindole, 6-(methanesulfonamido)oxindole, 6-(benzamido)oxindole, 5-ethoxyoxindole, 6-phenyloxindole, 6-(2-methoxyphenyl)oxindole, 6-(3-methoxyphenyl)oxindole, 6-(4-methoxyphenyl)oxindole, 5-aminosulfonyloxindole, 5-isopropyl-aminosulfonyloxindole, 5-dimethylaminosulfonyloxindole, 5-(N-morpholinosulfonyl)oxindole, 4-(2-hydroxyethyl)oxindole, 6-(3-ethoxyphenyl)oxindole, 6-(morpholin-4-yl)oxindole, 5-(2-(N-morpholino)ethyl)oxindole, 5-(methanesulfonamido)oxindole, 5-methoxycarbonyloxindole and 5-carboxyethyloxindole.

The aldehyde in the above combinatorial library is preferably selected from the group consisting of 3-(1-Benzyl-5-formyl-2,4-dimethyl-1H-pyrrol-3-yl)propionic acid, 3-(5-Formyl-1-methoxycarbonylmethyl-2,4-dimethyl-1H-pyrrol-3-yl)propionic acid, 3-(5-Formyl-1,2,4-trimethyl-1H-pyrrol-3-yl)propionic acid, 3-[5-Formyl-1-(3-methoxybenzyl)-2,4-dimethyl-1H-pyrrol-3-yl]propionic acid methyl ester, 3-(1-Cyclohexylmethyl-5-formyl-2,4-dimethyl-1H-pyrrol-3-yl)-propionic acid methyl ester, 3-[1-(2,2-Dimethyl-propyl)-5-formyl-2,4-dimethyl-1H-pyrrol-3-yl]propionic acid methyl ester, 1,3,5-Trimethyl-4-(3-morpholin-4-yl-3-oxo-propyl)1H-pyrrole-2-carbaldehyde, 3-(5-Formyl-1,2,4-trimethyl-1H-pyrrol-3-yl)-N-(2-morpholin-4-ylethyl)propionamide, 3-(5-Formyl-1,2,4-trimethyl-1H-pyrrol-3-yl)-N-phenylpropionamide, 1,3,5-trimethyl-4-(3-oxo-3-piperidin-1-ylpropyl)-1H-pyrrole-2-carbaldehyde, 1,3,5-Trimethyl-4-(3-oxo-3-pyrrolidin-1-ylpropyl)-1H-pyrrole-2-carbaldehyde, 3-(5-formyl-1,2,4-trimethyl-1H-pyrrol-3-yl)-N-(4-methoxyphenyl) propionamide, 3-(5-Formyl-1,2,4-trimethyl-1H-pyrrol-3-yl)-N-(4-methoxyphenyl)propionamide, N-(4-fluorophenyl)-3-(5-formyl-1,2,4-trimethyl-1H-pyrrol-3-yl)-propionamide, 3-(5-Formyl-1,2,4-trimethyl-1H-pyrrol-3-yl)-N-(4-trifluoromethylphenyl)-propionamide, 3-[5-Formyl-1-(3-methoxy-benzyl)-2,4-dimethyl-1H-pyrrol-3-yl]propionic acid, 3-(1-cyclohexylmethyl-5-formyl-2,4-dimethyl-1H-pyrrol-3-yl)propionic acid, 3-[1-(3-fluorobenzyl)-5-formyl-2,4-dimethyl-1H-pyrrol-3-yl] propionic acid methyl ester, 3-(1-Benzyl-5-formyl-2,4-dimethyl-1H-pyrrol-3-yl)propionic acid, 3-[1-(4-fluorobenzyl)-5-formyl-2,4-dimethyl-1H-pyrrol-3-yl] propionic acid methyl ester, 3-[1-(4-fluorobenzyl)-5-formyl-2,4-dimethyl-1H-pyrrol-3-yl]-propionic acid, 3-[1-(3-fluorobenzyl)-5-formyl-2,4-dimethyl-1H-pyrrol-3-yl] propionic acid, 3,5-dimethyl-4-(3-morpholin-4-yl-propyl)-1H-pyrrole-2-carbaldehyde, 4-(3-dimethylaminopropyl)-3,5-dimethyl-1H-pyrrole-2-carbaldehyde, 5-formyl-2,4-dimethyl-1H-pyrrole-3-carboxylic acid, 3,5-dimethyl-4-(4-methylpiperazine-1-carbonyl)-1H-pyrrole-2-carbaldehyde, 5-formyl-2,4-dimethyl-1H-pyrrole-3-carboxylic acid (2-dimethylaminoethyl)amide, 3-(2-formyl-4,5,6,7-tetrahydro-1H-indol-3-yl)propionic acid, 3-(3-dimethylaminopropyl)-2-formyl-4,5,6,7-tetrahydro-1H-indole, indole-2-carbaldehyde and 3-methylindole-2-carbaldehyde.

Another aspect of this invention provides a method for the synthesis of a 3-methylidenyl-2-indolinone of formula 1 comprising reacting an oxindole of formula 5 with an aldehyde of formula 6, 7 or 8 in a solvent, preferably in the presence of a base.

Examples of the oxindoles of formula 5 which may be reacted with an aldehyde of formula 6, 7 or 8 to give the substituted 3-methylidenyl-2-indolinones of formula 1 are oxindole itself and substituted oxindoles such as, without limitation, 6-bromooxindole, 5-hydroxyoxindole, 5-methoxyoxindole, 6-methoxyoxindole, 5-phenylaminosulfonyloxindole, 4-[2-(2-isopropylphenoxy) ethyl]oxindole, 4-[2-(3-isopropylphenoxy)-ethyl]oxindole, 4-[2-(4-isopropylphenoxy)-ethyl]oxindole, 5-fluorooxindole, 6-fluorooxindole, 7-fluorooxindole, 6-trifluoromethyloxindole, 5-chlorooxindole, 6-chlorooxindole, 4-carboxyindole, 5-bromooxindole, 5-bromo-4-methyloxindole, 6-(N-acetamido)oxindole, 4-methyloxindole, 5-methyloxindole, 4-methyl-5-chlorooxindole, 5-ethyloxindole, 6-hydroxyoxindole, 5-acetyloxindole, 5-carboxyindole, 5-aminooxindole, 6-aminooxindole, 4-(2-N-morpholinoethyl)oxindole, 7-azaoxindole, oxindole-4-carabamic acid t-butyl ester, oxindole-6-carbamic acid t-butyl ester, 4-(2-carboxyethyl) oxindole, 5-n-butyloxindole, 5,6-dimethoxyoxindole, 6-(methanesulfonamido)oxindole, 6-(benzamido)oxindole, 5-ethoxyoxindole, 6-phenyloxindole, 6-(2-methoxyphenyl) oxindole, 6-(3-methoxyphenyl)oxindole, 6-(4-methoxyphenyl)oxindole, 5-aminosulfonyloxindole, 5-isopropyl-aminosulfonyloxindole, 5-dimethylaminosulfonyloxindole, 5-(N-morpholinosulfonyl)oxindole, 4-(2-hydroxyethyl) oxindole, 6-(3-ethoxyphenyl) oxindole, 6-(morpholin-4-yl)oxindole, 5-(2-(N-morpholino)ethyl)oxindole, 5-(methanesulfonamido)oxindole, 5-methoxycarbonyloxindole and 5-carboxyethyloxindole.

Examples of aldehydes of structure 6, 7 or 8 which may be reacted with oxindoles of structure 2 are, without limitation, 3-(1-benzyl-5-formyl-2,4-dimethyl-1H-pyrrol-3-yl)propionic acid, 3-(5-formyl-1-methoxycarbonylmethyl-2,4-dimethyl-1H-pyrrol-3-yl)-propionic acid, 3-(5-formyl-1,2,4-trimethyl-1H-pyrrol-3-yl)-propionic acid, 3-[5-formyl-1-(3-methoxybenzyl)-2,4-dimethyl-1H-pyrrol-3-yl] propionic acid methyl ester, 3-(1-cyclohexylmethyl-5-formyl-2,4-dimethyl-1H-pyrrol-3-yl)propionic acid methyl ester, 3-[1-(2,2-dimethylpropyl)-5-formyl-2,4-dimethyl-1H-pyrrol-3-yl]-propionic acid methyl ester, 1,3,5-trimethyl-4-(3-morpholin-4-yl-3-oxopropyl)-1H-pyrrole-2-carbaldehyde, 3-(5-formyl-1,2,4-trimethyl-1H-pyrrol-3-yl)-N-(2-morpholin-4-ylethyl)propionamide, 3-(5-formyl-1,2,4-trimethyl-1H-pyrrol-3-yl)-N-phenylpropionamide, 1,3,5-trimethyl-4-(3-oxo-3-piperidin-1-ylpropyl)-1H-pyrrole-2-carbaldehyde, 1,3,5-trimethyl-4-(3-oxo-3-pyrrolidin-1-ylpropyl)-1H-pyrrole-2-carbaldehyde, 3-(5-formyl-1,2,4-trimethyl-1H-pyrrol-3-yl)-N-(4-methoxyphenyl) propionamide, 3-(5-formyl-1,2,4-trimethyl-1H-pyrrol-3-yl)-N-(4-methoxyphenyl)propionamide, N-(4-fluorophenyl)-3-(5-formyl-1,2,4-trimethyl-1H-pyrrol-3-yl)-propionamide, 3-(5-formyl-1,2,4-trimethyl-1H-pyrrol-3-yl)-N-(4-trifluoromethylphenyl)propionamide, 3-[5-formyl-1-(3-methoxy-benzyl)-2,4-dimethyl-1H-pyrrol-3-yl]propionic acid, 3-(1-cyclohexylmethyl-5-formyl-2,4-dimethyl-1H-pyrrol-3-yl)propionic acid, 3-[1-(3-fluorobenzyl)-5-formyl-2,4-dimethyl-1H-pyrrol-3-yl]propionic acid methyl ester, 3-(1-benzyl-5-formyl-2,4-dimethyl-1H-pyrrol-3-yl) propionic acid, 3-[1-(4-fluorobenzyl)-5-formyl-2,4-dimethyl-1H-pyrrol-3-yl]propionic acid methyl ester, 3-[1-(4-fluorobenzyl)-5-formyl-2,4-dimethyl-1H-pyrrol-3-yl]-propionic acid, 3-[1-(3-fluorobenzyl)-5-formyl-2,4-dimethyl-1H-pyrrol-3-yl]propionic acid, 3,5-dimethyl-4-(3-morpholin-4-yl-propyl)-1H-pyrrole-2-carbaldehyde, 4-(3-dimethylaminopropyl)-3,5-dimethyl-1H-pyrrole-2-carbaldehyde, 5-formyl-2,4-dimethyl-1H-pyrrole-3-carboxylic acid, 3,5-dimethyl-4-(4-methylpiperazine-1-carbonyl)-1H-pyrrole-2-carbaldehyde, 5-formyl-2,4-dimethyl-1H-pyrrole-3-carboxylic acid (2-dimethylaminoethyl)amide, 3-(2-formyl-4,5,6,7-tetrahydro-1H-indol-3-yl)propionic acid, 3-(3-dimethylaminopropyl)-2-formyl-4,5,6,7-tetrahydro-1H-indole, indole-2-carbaldehyde and 3-methylindole-2-carbaldehyde.

The synthesis of an aminopropyl-4,5,6,7-tetrahydro-1H-indole, structure 9, below, which is an intermediate to some of the compounds of this invention, is another aspect of this invention:

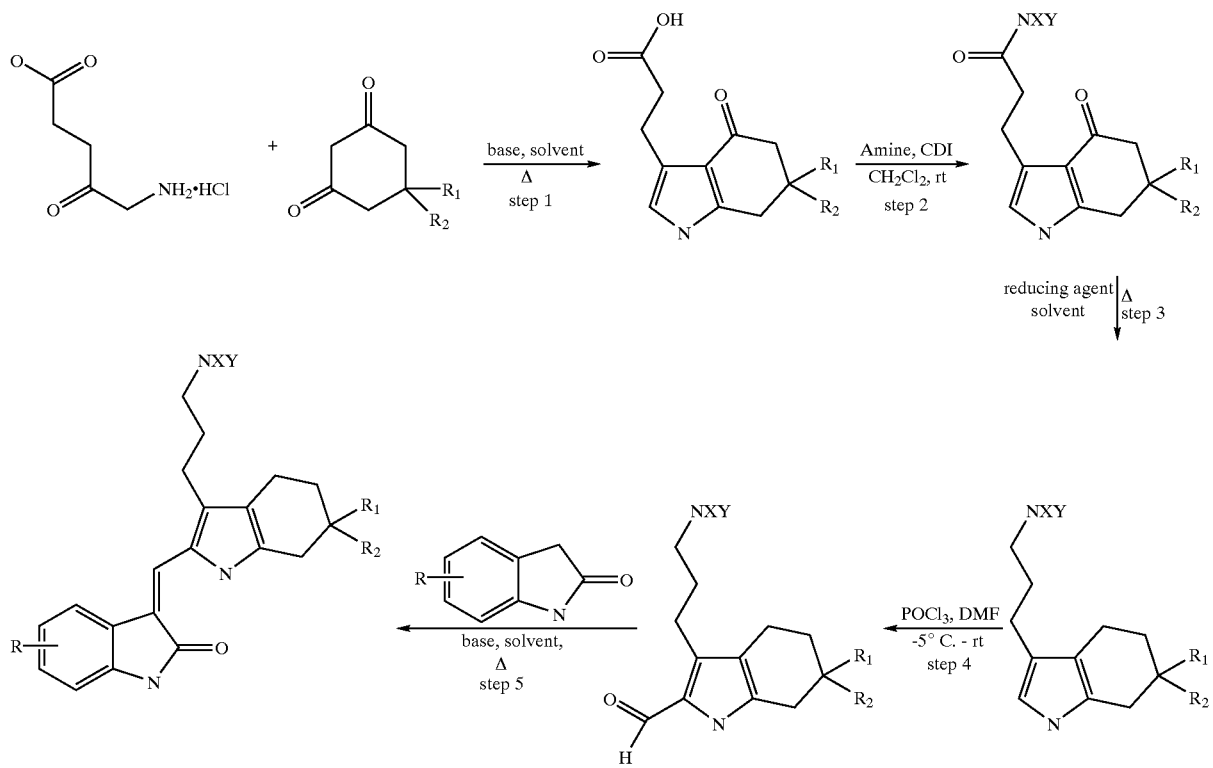

In Step 1, the base can be an inorganic or an organic base. Examples of inorganic and organic bases are presented elsewhere herein. Preferrably the base is sodium acetate. The "solvent" may be any solvent in which base and the other reactants are sufficiently soluble for reaction to take place. Preferred solvents are polar protic solvents (defined elsewhere herein) such as water, methanol and ethanol. The presently preferred solvent is water. The reaction is carried out at temperatures of from about 60° C. to about 180° C. Preferably the temperature is between about 60° C. and 180° C., more preferably between 80° C. and 150° C., most preferably between 100 and 120° C. The reaction is allowed to run for from 1 to 30 hours, preferably from 2 to 20 hours, most preferably from 4 to 15 hours.

In step 2, a carboxylic acid group is converted to an amide group. Procedures for accomplishing this conversion are well-known in the art. The reaction of an amine with the carboxylic acid in the presence of 1,1'-carbonyl diimidazole is the presently preferred method. Any aprotic solvent may be used; in a presently preferred embodiment the solvent is a non-polar aprotic solvent, in particular dichoromethane. The reaction may be carried out at room temperature or at an elevated temperature up to about 100° C.; a presently preferred embodiment is to run the reaction at about room temperature.

Step 3 is the simultaneous reduction of the keto and the amido group using a reducing agent such as, for example and without limitation, lithium aluminum hydride. The reaction is carried out in an aprotic solvent (defined elsewhere herein). A presently preferred solvent is tetrahydrofuran. The reaction is carried out at temperatures from about room temperature to about 80° C., preferrably from about 50° C. to about 70° C., most preferably, the reaction is carried out in tetrahydrofuran at reflux.

Step 4 is the well-known formylation of the aromatic pyrrole ring using phosphorus oxychloride and N,N-dimethyl formamide.

Step 5, the condensation of an aldehyde with an oxindole to form a 3-methylidenyl-2-indolinone of this invention is carried out in a solvent which may contain a base. The base may be an organic or an inorganic base. If an organic base is used, preferably it is a nitrogen base. Examples of organic nitrogen bases include, but are not limited to, diisopropylamine, trimethylamine, triethylamine, aniline, pyridine, 1,8-diazabicyclo-[5.4.1]undec-7-ene, pyrrolidine and piperidine.

Examples of inorganic bases are, without limitation, ammonia, alkali metal or alkaline earth hydroxides, phosphates, carbonates, bicarbonates, acetates, bisulfates and amides. The alkali metals include, lithium, sodium and potassium while the alkaline earths include calcium, magnesium and barium.

In a presently preferred embodiment of this invention, when the solvent is a protic solvent, such as water or alcohol, the base is an alkali metal or an alkaline earth inorganic base, preferably, a alkali metal or an alkaline earth hydroxide.

It will be clear to those skilled in the art, based both on known general principles of organic synthesis and on the disclosures herein which base would be most appropriate for the reaction contemplated.

The solvent in which the reaction is carried out may be a protic or an aprotic solvent, preferably it is a protic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. Examples of protic solvents include, without limitation, water and alcohols.

An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride and carbon tetrachloride. Examples of polar aprotic solvents are chloroform, tetrahydro-furan, dimethylsulfoxide and dimethylformamide.

In a presently preferred embodiment of this invention, the solvent is a protic solvent, preferably water or an alcohol such as ethanol.

The reaction is carried out at temperatures greater than room temperature. The temperature is generally from about 30° C. to about 150° C., preferably about 80° C. to about 100° C., most preferable about 75° C. to about 85° C., which is about the boiling point of ethanol.

By "about" is meant that a temperature range described herein is preferably within 10 degrees Celcius of the indicated temperature, more preferably within 5 degrees Celcius of the indicated temperature and, most preferably, within 2 degrees Celcius of the indicated temperature. Thus, for example, by "about 75° C." is meant 75° C.±10° C., preferably 75° C.±5° C. and most preferably, 75° C.±2° C.

Some representative compounds of this invention are shown in Table 1. The compounds shown are examples only and are not to be construed as limiting the scope of this invention in any manner whatsoever.

TABLE 1

| Compound | Structures | Names |
|---|---|---|
| 1 | 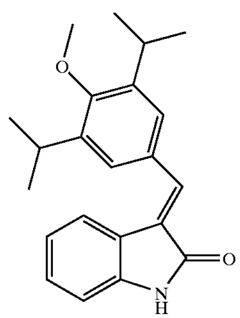 | 3-(3,5-Diisopropyl-4-methoxybenzylidene)-1,3-dihydroindol-2-one |
| 2 | 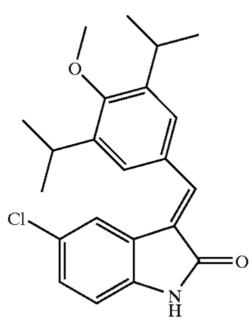 | 5-Chloro-3-(3,5-diisopropyl-4-methoxybenzylidene)-1,3-dihydroindol-2-one |
| 3 | 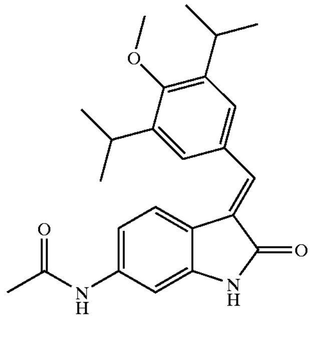 | N-[3-(3,5-Diisopropyl-4-methoxybenzylidene)-2-oxo-2,3-dihydro-1H-indol-6-yl]-acetamide |

TABLE 1-continued

| Compound | Structures | Names |
|---|---|---|
| 4 | 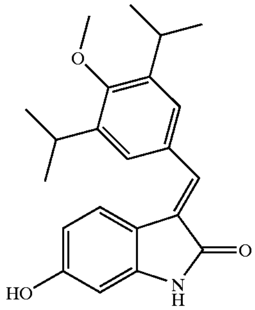 | 3-(3,5-Diisopropyl-4-methoxybenzylidene)-6-hydroxy-1,3-dihydroindol-2-one |
| 5 | 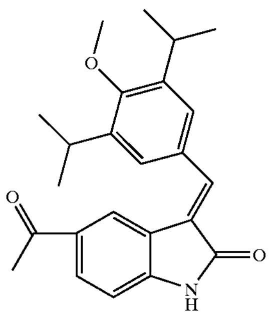 | 5-Acetyl-3-(3,5-diisopropyl-4-methoxybenzylidene)-1,3-dihydroindol-2-one |
| 6 | 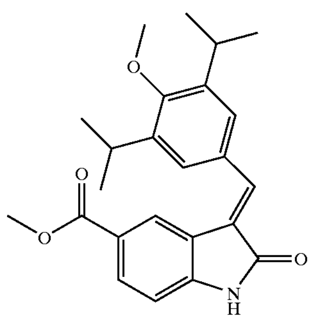 | 3-(3,5-Diisopropyl-4-methoxybenzylidene)-2-oxo-2,3-dihydro-1H-indole-5-carboxylic acid methyl ester |
| 7 | 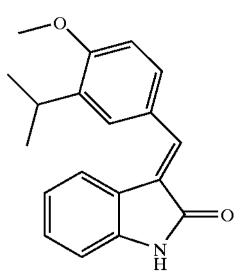 | 3-(3-Isopropyl-4-methoxybenzylidene)-1,3-dihydroindol-2-one |
| 8 | 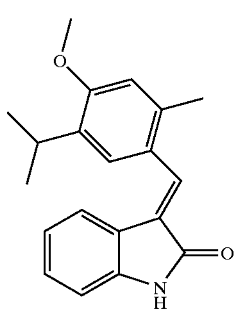 | 3-(5-isopropyl-4-methoxy-2-methylbenzylidene)-1,3-dihydroindol-2-one |

TABLE 1-continued
| Compound | Structures | Names |
|---|---|---|
| 9 | 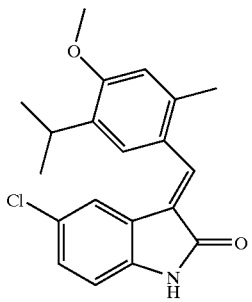 | 5-Chloro-3-(5-isopropyl-4-methoxy-2-methylbenzylidene)-1,3-dihydroindol-2-one |
| 10 | 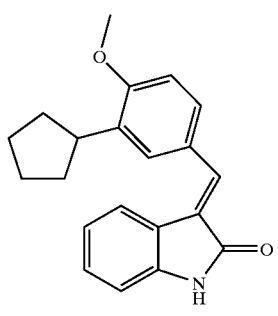 | 3-(3-Cyclopentyl-4-methoxybenzylidene)-1,3-dihydroindol-2-one |
| 11 | 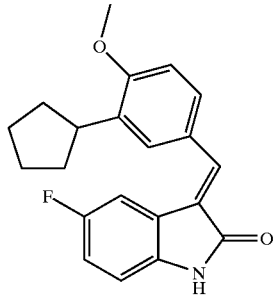 | 3-(3-Cyclopentyl-4-methoxybenzylidene)-5-fluoro-1,3-dihydroindol-2-one |
| 12 | 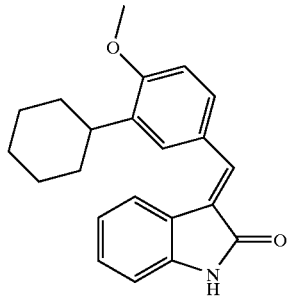 | 3-(3-Cyclohexyl-4-methoxybenzylidene)-1,3-dihydroindol-2-one |
| 13 | 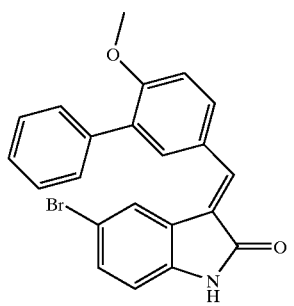 | 5-Bromo-3-(6-methoxybiphenyl-3-ylmethylene)-1,3-dihydroindol-2-one |

TABLE 1-continued

| Compound | Structures | Names |
|---|---|---|
| 14 | 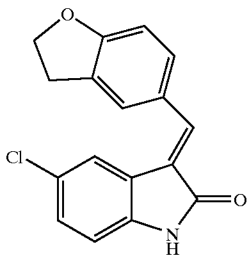 | 5-Chloro-3-(2,3-dihydrobenzofuran-5-ylmethylene)-1,3-dihydroindol-2-one |
| 15 | 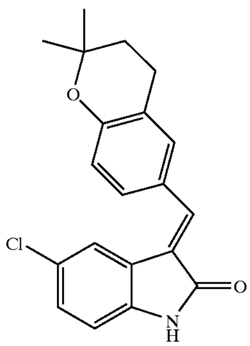 | 5-Chloro-3-(2,2-dimethylchroman-6-ylmethylene)-1,3-dihydroindol-2-one |
| 16 | 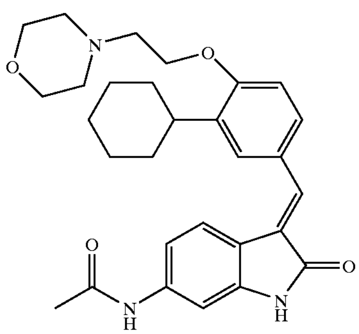 | N-{3-[3-Cyclohexyl-4-(2-morpholin-4-ylethoxy)-benzylidene]-2-oxo-2,3-dihydro-1H-indol-6-yl)-acetamide |
| 17 | 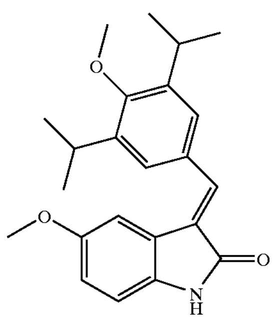 | 3-(3,5-Diisopropyl-4-methoxybenzylidene)-5-methoxy-1,3-dihydroindol-2-one |
| 18 | 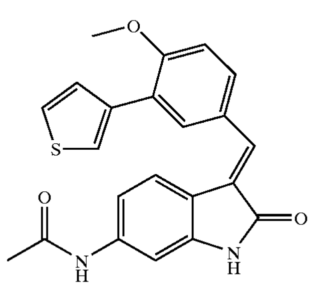 | N-[3-(4-Methoxy-3-thiophen-3-ylbenzylidene)-2-oxo-2,3-dihydro-1H-indol-6-yl]-acetamide |

TABLE 1-continued

| Compound | Structures | Names |
|---|---|---|
| 19 | 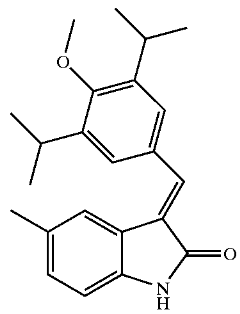 | 3-(3,5-Diisopropyl-4-methoxybenzylidene)-5-methyl-1,3-dihydroindol-2-one |
| 20 | 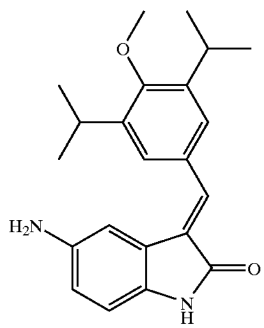 | 5-Amino-3-(3,5-diisopropyl-4-methoxybenzylidene)-1,3-dihydroindol-2-one |
| 21 | 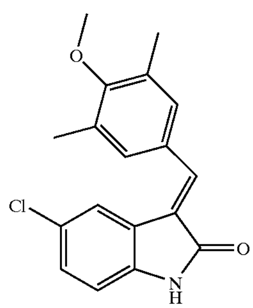 | 5-Chloro-3-(4-methoxy-3,5-dimethylbenzylidene)-1,3-dihydroindol-2-one |
| 22 | 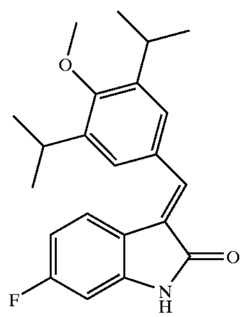 | 3-(3,5-Diisopropyl-4-methoxybenzylidene)-6-fluoro-1,3-dihydroindol-2-one |

TABLE 1-continued
| Compound | Structures | Names |
|---|---|---|
| 23 | 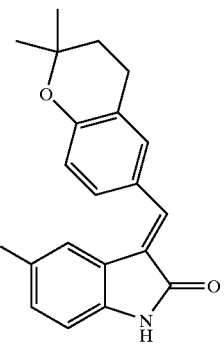 | 3-(2,2-Dimethylchroman-6-ylmethylene)-5-fluoro-1,3-dihydroindol-2-one |
| 24 | 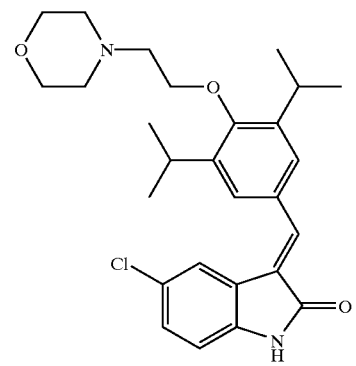 | 5-Chloro-3-[3,5-diisopropyl-4-(2-morpholin-4-ylethoxy)-benzylidene]-1,3-dihydroindol-2-one |
| 25 | 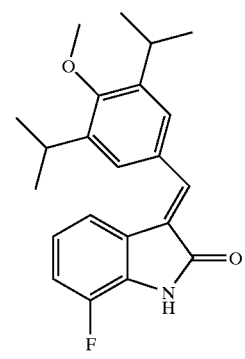 | 3-(3,5-Diisopropyl-4-methoxybenzylidene)-7-fluoro-1,3-dihydroindol-2-one |
| 26 | 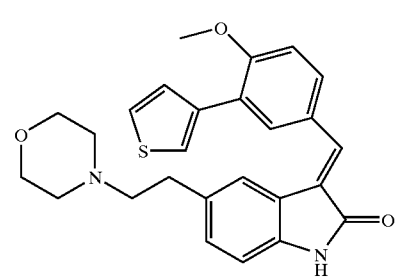 | 3-(4-Methoxy-3-thiophen-3-ylbenzylidene)-5-(2-morpholin-4-ylethyl)-1,3-dihydroindol-2-one |

TABLE 1-continued

| Compound | Structures | Names |
|---|---|---|
| 27 | 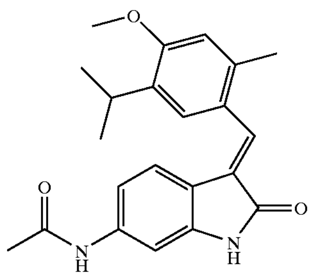 | N-[3-(5-isopropyl-4-methoxy-2-methylbenzylidene)-2-oxo-2,3-dihydro-1H-indol-6-yl]-acetamide |
| 28 | 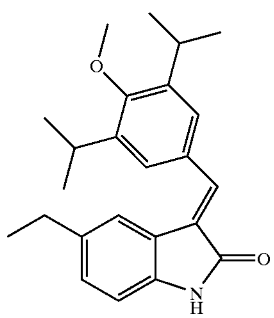 | 3-(3,5-Diisopropyl-4-methoxybenzylidene)-5-ethyl-1,3-dihydroindol-2-one |
| 29 | 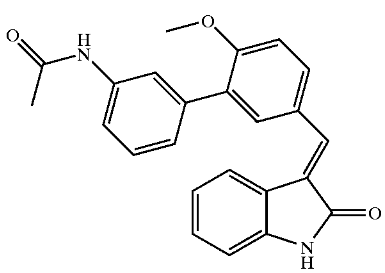 | N-[2'-Methoxy-5'-(2-oxo-1,2-dihydroindol-3-ylidenemethyl)-biphenyl-3-yl]-acetamide |
| 30 | 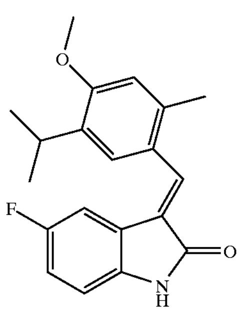 | 5-Fluoro-3-(5-isopropyl-4-methoxy-2-methylbenzylidene)-1,3-dihydroindol-2-one |
| 31 | 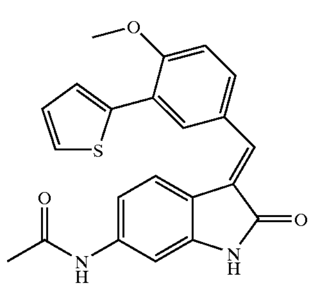 | N-[3-(4-Methoxy-3-thiophen-2-ylbenzylidene)-2-oxo-2,3-dihydro-1H-indol-6-yl]-acetamide |

TABLE 1-continued

| Compound | Structures | Names |
|---|---|---|
| 32 | 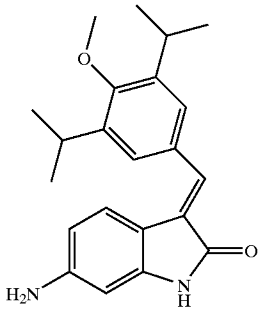 | 6-Amino-3-(3,5-diisopropyl-4-methoxybenzylidene)1,3-dihydroindol-2-one |
| 33 | 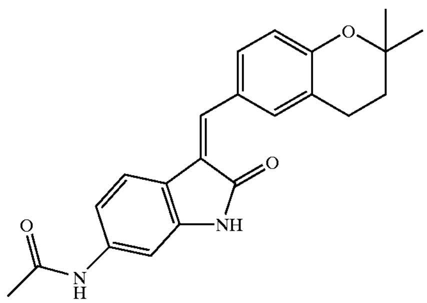 | N-[3-(2,2-Dimethylchroman-6-ylmethylene)-2-oxo-2,3-dihydro-1H-indol-6-yl]-acetamide |
| 34 | 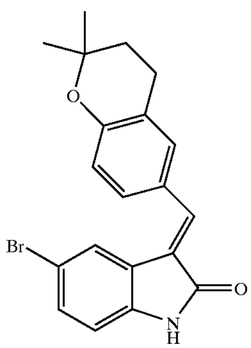 | 5-Bromo-3-(2,2-dimethylchroman-6-ylmethylene)-1,3-dihydroindol-2-one |
| 35 | 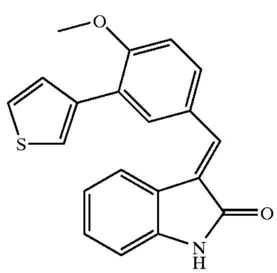 | 3-(4-Methoxy-3-thiophen-3-ylbenzylidene)-1,3-dihydroindol-2-one |
| 36 | 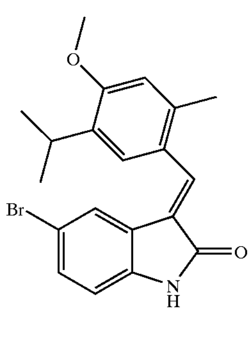 | 5-Bromo-3-(5-isopropyl-4-methoxy-2-methylbenzylidene)-1,3-dihydroindol-2-one |

TABLE 1-continued

| Compound | Structures | Names |
|---|---|---|
| 37 | 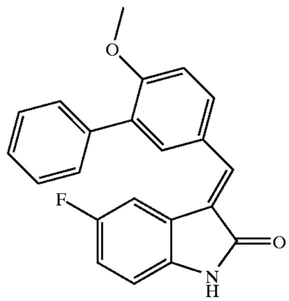 | 5-Fluoro-3-(6-methoxybiphenyl-3-ylmethylene)-1,3-dihydroindol-2-one |
| 38 | 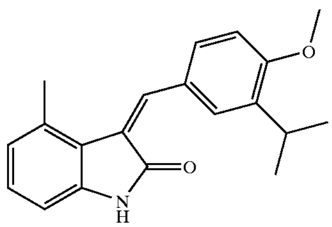 | 3-(3-Isopropyl-4-methoxybenzylidene)-4-methyl-1,3-dihydroindol-2-one |
| 39 | 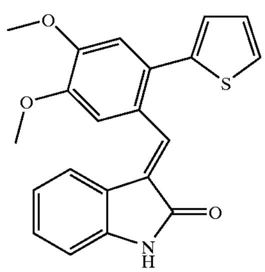 | 3-(4,5-Dimethoxy-2-thiophen-2-ylbenzylidene)-1,3-dihydroindol-2-one |
| 40 | 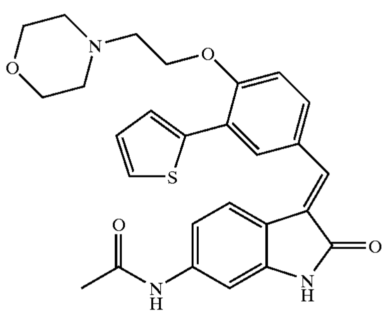 | N-{3-[4-(2-Morpholin-4-ylethoxy)-3-thiophen-2-ylbenzylidene]-2-oxo-2,3-dihydro-1H-indol-6-yl}-acetamide |
| 41 | 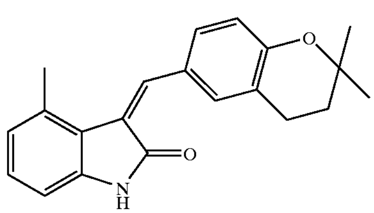 | 3-(2,2-Dimethylchroman-6-ylmethylene)-4-methyl-1,3-dihydroindol-2-one |

TABLE 1-continued

| Compound | Structures | Names |
|---|---|---|
| 42 | 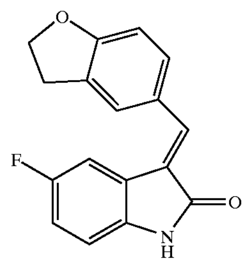 | 3-(2,3-Dihydrobenzofuran-5-ylmethylene)-5-fluoro-1,3-dihydroindol-2-one |
| 43 | 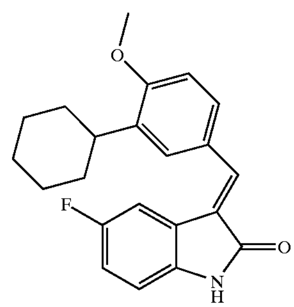 | 3-(3-Cyclohexyl-4-methoxybenzylidene)-5-fluoro-1,3-dihydroindol-2-one |
| 44 | 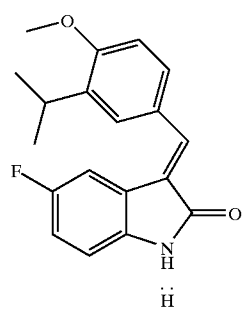 | 5-Fluoro-3-(3-isopropyl-4-methoxybenzylidene)-1,3-dihydroindol-2-one |
| 45 | 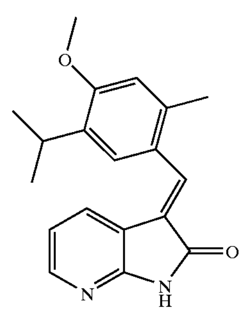 | 3-(5-isopropyl-4-methoxy-2-methylbenzylidene)-1,3-dihydropyrrolo[2,3-b]pyridin-2-one |
| 46 | 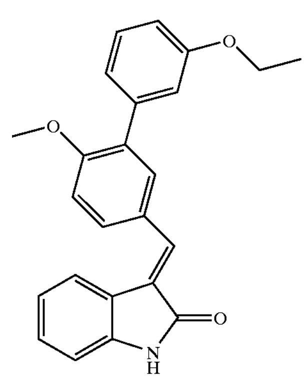 | 3-(3'-Ethoxy-6-methoxybiphenyl-3-ylmethylene)-1,3-dihydroindol-2-one |

TABLE 1-continued

| Compound | Structures | Names |
|---|---|---|
| 47 | 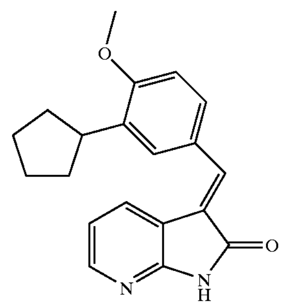 | 3-(3-Cyclopentyl-4-methoxybenzylidene)-1,3-dihydropyrrolo[2,3-b]pyridin-2-one |
| 48 | 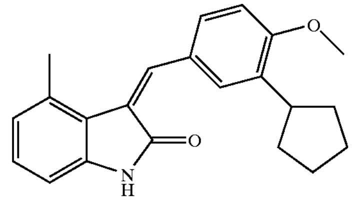 | 3-(3-Cyclopentyl-4-methoxybenzylidene)-4-methyl-1,3-dihydroindol-2-one |
| 49 | 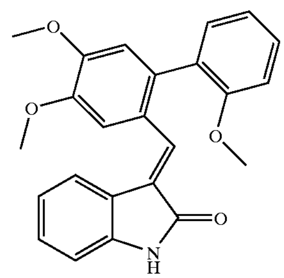 | 3-(4,5,2'-Trimethoxybiphenyl-2-ylmethylene)-1,3-dihydroindol-2-one |
| 50 | 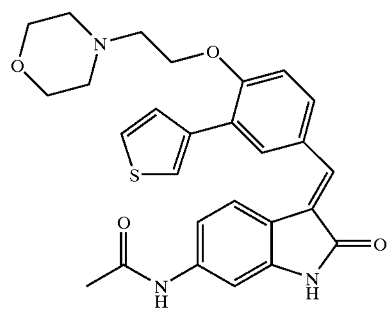 | N-{3-[4-(2-Morpholin-4-ylethoxy)-3-thiophen-3-ylbenzylidene]-2-oxo-2,3-dihydro-1H-indol-6-yl}-acetamide |
| 51 | 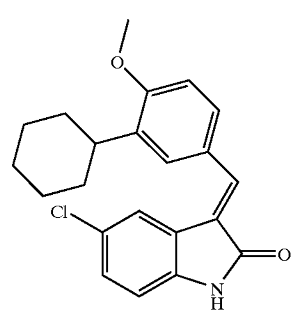 | 5-Chloro-3-(3-cyclohexyl-4-methoxybenzylidene)-1,3-dihydroindol-2-one |

TABLE 1-continued

| Compound | Structures | Names |
|---|---|---|
| 52 | 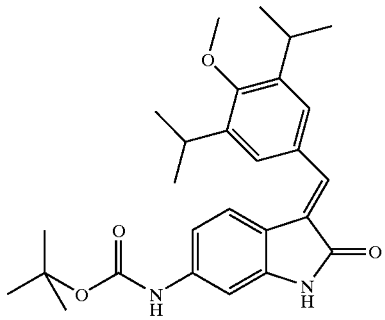 | [3-(3,5-Diisopropyl-4-methoxybenzylidene)-2-oxo-2,3-dihydro-1H-indol-6-yl]-carbamic acid tert-butyl ester |
| 53 | 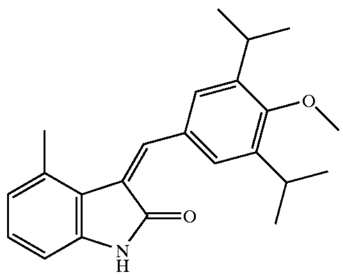 | 3-(3,5-Diisopropyl-4-methoxybenzylidene)-4-methyl-1,3-dihydroindol-2-one |
| 54 | 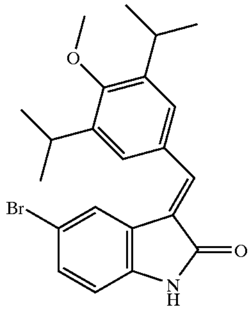 | 5-Bromo-3-(3,5-diisopropyl-4-methoxybenzylidene)-1,3-dihydroindol-2-one |
| 55 | 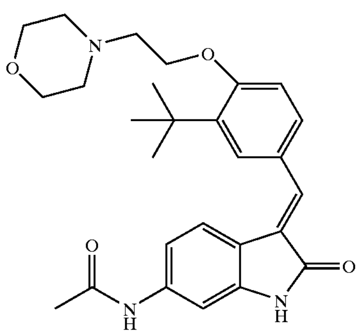 | N-{3-[3-tert-Butyl-4-(2-morpholin-4-ylethoxy)-benzylidene]-2-oxo-2,3-dihydro-1H-indol-6-yl}-acetamide |
| 56 | 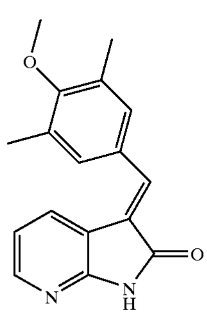 | 3-(4-Methoxy-3,5-dimethylbenzylidene)-1,3-dihydropyrrolo[2,3-b]pyridin-2-one |

TABLE 1-continued
| Compound | Structures | Names |
|---|---|---|
| 57 | 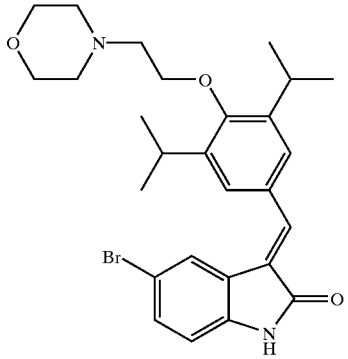 | 5-Bromo-3-[3,5-diisopropyl-4-(2-morpholin-4-ylethoxy)-benzylidene]-1,3-dihydroindol-2-one |
| 58 | 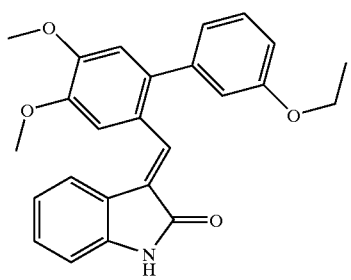 | 3-(3'-Ethoxy-4,5-dimethoxybiphenyl-2-ylmethylene)-1,3-dihydroindol-2-one |
| 59 | 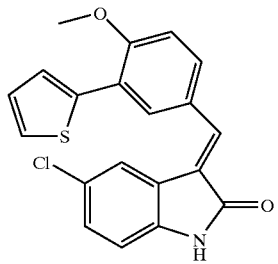 | 5-Chloro-3-(4-methoxy-3-thiophen-2-ylbenzylidene)-1,3-dihydroindol-2-one |
| 60 | 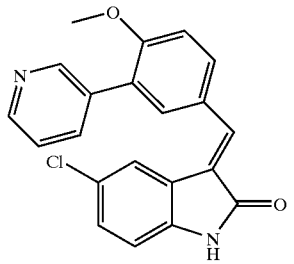 | 5-Chloro-3-(4-methoxy-3-pyridin-3-ylbenzylidene)-1,3-dihydroindol-2-one |
| 61 | 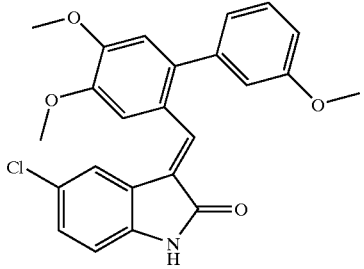 | 5-Chloro-3-(4,5,3'-trimethoxybiphenyl-2-ylmethylene)-1,3-dihydroindol-2-one |

TABLE 1-continued

| Compound | Structures | Names |
|---|---|---|
| 62 | 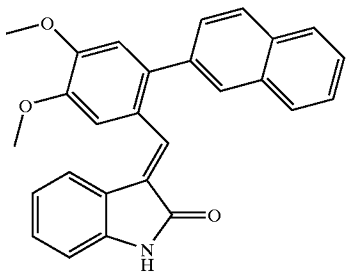 | 3-(4,5-Dimethoxy-2-naphthalen-2-ylbenzylidene)-1,3-dihydroindol-2-one |
| 63 | 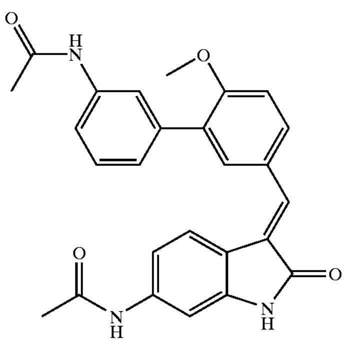 | N-[3-(3'-Acetylamino-6-methoxybiphenyl-3-ylmethylene)-2-oxo-2,3-dihydro-1H-indol-6-yl}-acetamide |
| 64 | 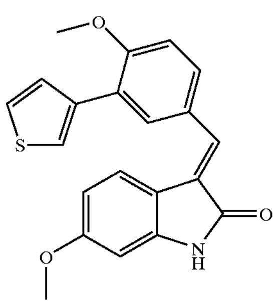 | 6-Methoxy-3-(4-methoxy-3-thiophen-3-ylbenzylidene)-1,3-dihydroindol-2-one |
| 65 | 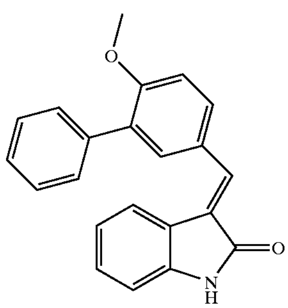 | 3-(6-Methoxybiphenyl-3-ylmethylene)-1,3-dihydroindol-2-one |
| 66 | 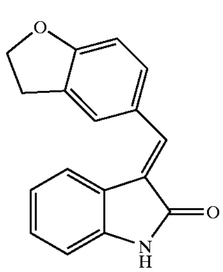 | 3-(2,3-Dihydrobenzofuran-5-ylmethylene)-1,3-dihydroindol-2-one |

TABLE 1-continued

| Compound | Structures | Names |
| --- | --- | --- |
| 67 | 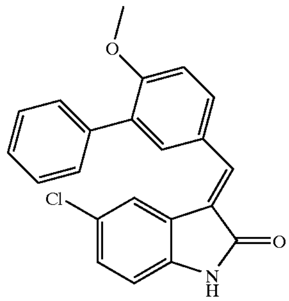 | 5-Chloro-3-(6-methxoybiphenyl-3-ylmethylene)-1,3-dihydroindol-2-one |
| 68 | 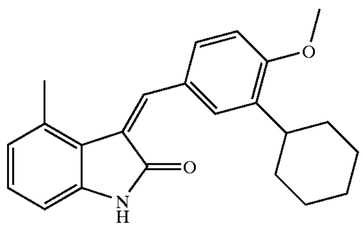 | 3-(3-Cyclohexyl-4-methoxybenzylidene)-4-methyl-1,3-dihydroindol-2-one |
| 69 | 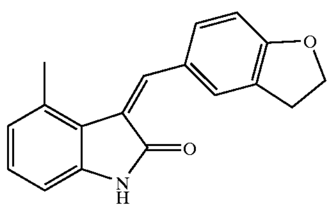 | 3-(2,3-dihydrobenzofuran-5-ylmethylene)-4-methyl-1,3-dihydroindol-2-one |
| 70 | 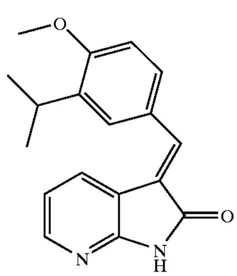 | 3-(3-isopropyl-4-methoxybenzylidene)-1,3-dihydro-pyrrolo[2,3-b]pyridin-2-one |
| 71 | 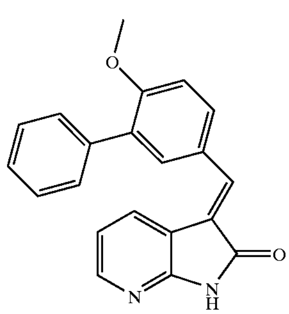 | 3-(6-Methoxybiphenyl-3-ylmethylene)-1,3-dihydro-pyrrolo[2,3-b]pyridin-2-one |

TABLE 1-continued

| Compound | Structures | Names |
|---|---|---|
| 72 | 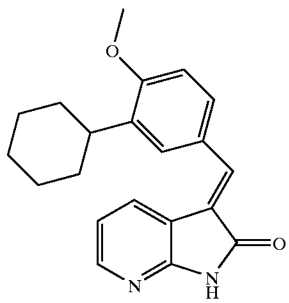 | 3-(3-Cyclohexyl-4-methoxybenzylidene)-1,3-dihydropyrrolo[2,3-b]pyridin-2-one |
| 73 | 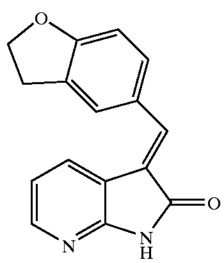 | 3-(2,3-Dihydrobenzofuran-5-ylmethylene)-1,3-dihydropyrrolo[2,3-b]pyridin-2-one |
| 74 | 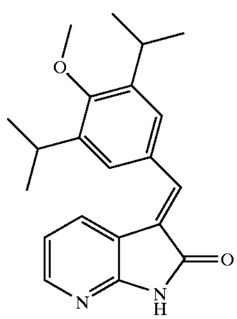 | 3-(3,5-Diisopropyl-4-methoxybenzylidene)-1,3-dihydropyrrolo[2,3-b]pyridin-2-one |
| 75 | 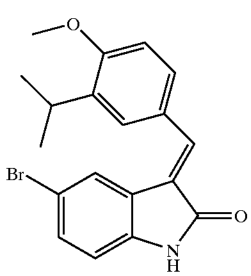 | 5-Bromo-3-(3-isopropyl-4-methxoybenzylidene)-1,3-dihydroindol-2-one |
| 76 | 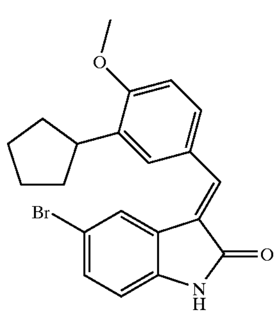 | 5-Bromo-3-(3-cyclopentyl-4-methxoybenzylidene)-1,3-dihydroindol-2-one |

TABLE 1-continued

| Compound | Structures | Names |
|---|---|---|
| 77 | 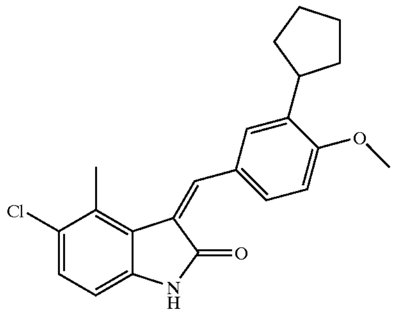 | 5-Chloro-3-(3-cyclopentyl-4-methoxybenzylidene)-4-methyl-1,3-dihydroindol-2-one |
| 78 | 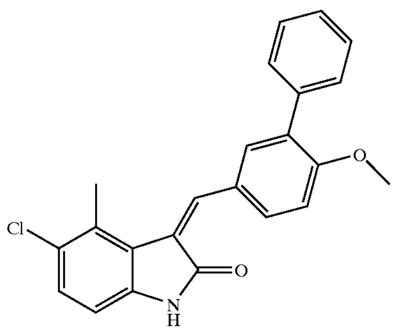 | 5-Chloro-3-(6-methoxybiphenyl-3-ylmethylene)-4-methyl-1,3-dihydroindol-2-one |
| 79 | 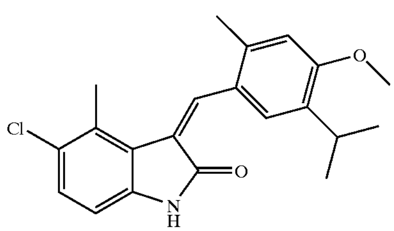 | 5-Chloro-3-(5-isopropyl-4-methoxy-2-methylbenzylidene)-4-methyl-1,3-dihydroindol-2-one |
| 80 | 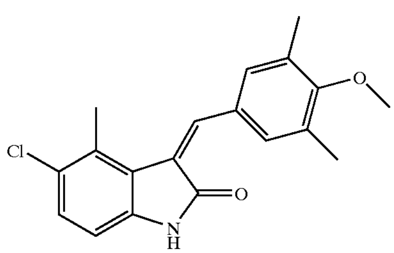 | 5-Chloro-3-(4-methoxy-3,5-dimethylbenzylidene)-4-methyl-1,3-dihydroindol-2-one |
| 81 | 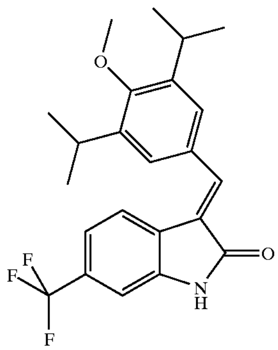 | 3-(3,5-Diisopropyl-4-methoxybenzylidene)-6-trifluoromethyl-1,3-dihydroindol-2-one |

TABLE 1-continued

| Compound | Structures | Names |
|---|---|---|
| 82 | 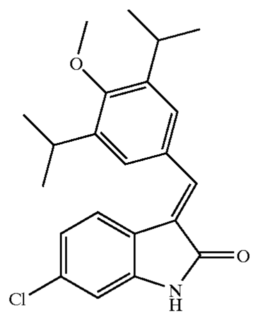 | 6-Chloro-3-(3,5-diisopropyl-4-methoxybenzylidene)-1,3-dihydroindol-2-one |
| 83 | 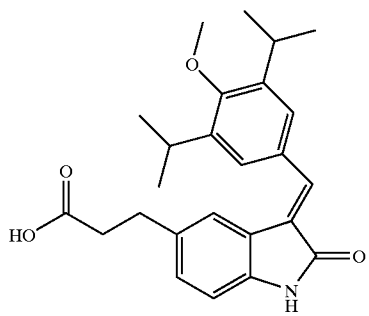 | 3-[3-(3,5-Diisopropyl-4-methoxybenzylidene)-2-oxo-2,3-dihydro-1H-indol-5-yl]-propionic acid |
| 84 | 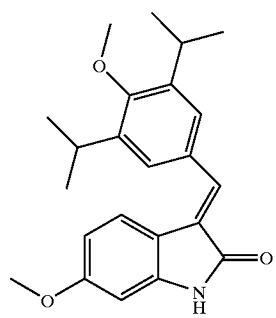 | 3-(3,5-Diisopropyl-4-methoxybenzylidene)-6-methoxy-1,3-dihydroindol-2-one |
| 85 | 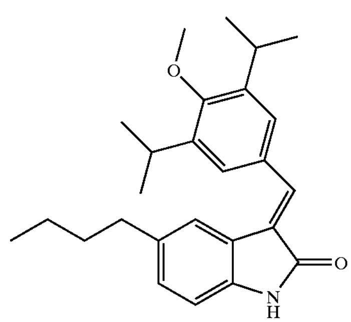 | 5-Butyl-3-(3,5-diisopropyl-4-methoxybenzylidene)-1,3-dihydroindol-2-one |
| 86 | 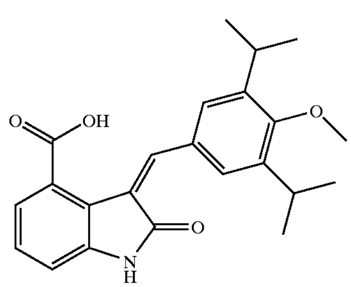 | 3-(3,5-Diisopropyl-4-methoxybenzylidene)-2-oxo-2,3-dihydro-1H-indole-4-carboxylic acid |

TABLE 1-continued

| Compound | Structures | Names |
|---|---|---|
| 87 | 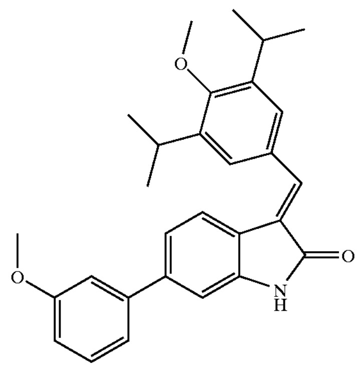 | 3-(3,5-Diisopropyl-4-methxoybenzylidene)-6-(3-methoxyphenyl)-1,3-dihydroindol-2-one |
| 88 | 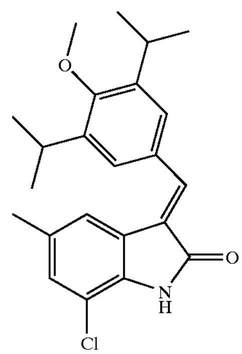 | 7-Chloro-3-(3,5-diisopropyl-4-methoxybenzylidene)-5-methyl-1,3-dihydroindol-2-one |
| 89 | 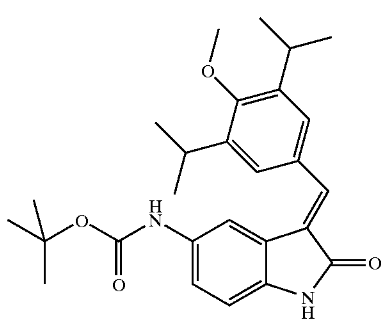 | [3-(3,5-Diisopropyl-4-methoxybenzylidene)-2-oxo-2,3-dihdyro-1H-indol-5-yl]carbamic acid tert-butyl ester |
| 90 | 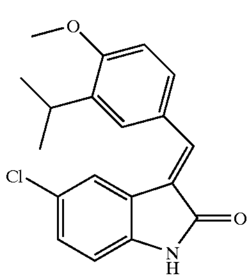 | 5-Chloro-3-(3-iropropyl-4-methoxybenzylidene)-1,3-dihydroindol-2-one |

TABLE 1-continued

| Compound | Structures | Names |
|---|---|---|
| 91 | 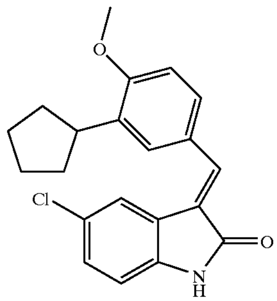 | 5-Chloro-3-(3-cyclopentyl-4-methoxybenzylidene)-1,3-dihydroindol-2-one |
| 92 | 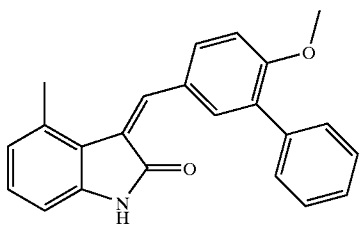 | 3-(6-Methoxybiphenyl-3-ylmethylene)-4-methyl-1,3-dihydroindol-2-one |
| 93 | 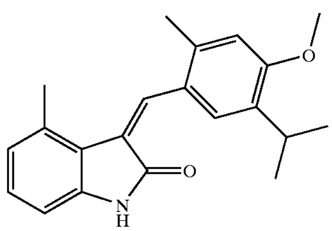 | 3-(5-Isopropyl-4-methoxy-2-methylbenzylidene)-4-methyl-1,3-dihydroindol-2-one |
| 94 | 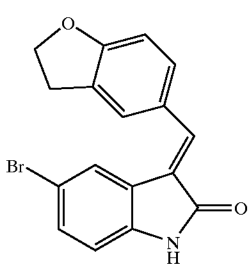 | 5-Bromo-3-(2,3-dihydrobenzofuran-5-ylmethylene)-1,3-dihydroindol-2-one |
| 95 | 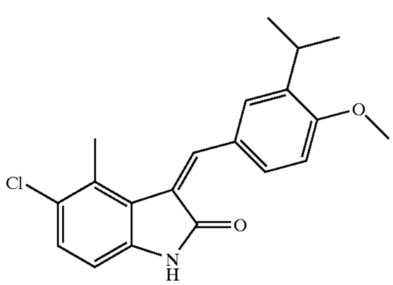 | 5-Chloro-3-(3-isopropyl-4-methoxybenzylidene)-4-methyl-1,3-dihydroindol-2-one |

TABLE 1-continued

| Compound | Structures | Names |
|---|---|---|
| 96 | 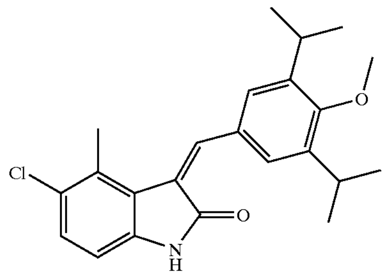 | 5-Chloro-3-(3,5-diisopropyl-4-methoxybenzylidene)-4-methyl-1,3-dihydroindol-2-one |
| 97 | 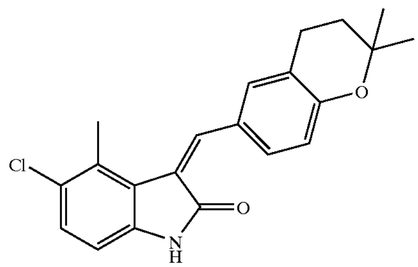 | 5-Chloro-3-(2,2-dimethylchroman-6-ylmethylene)-4-methyl-1,3-dihydroindol-2-one |
| 98 | 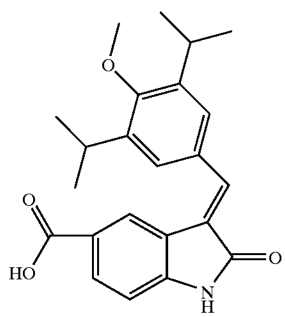 | 3-(3,5-Diisopropyl-4-methoxybenzylidene)-2-oxo-2,3-dihydro-1H-indole-5-carboxylic acid |
| 99 | 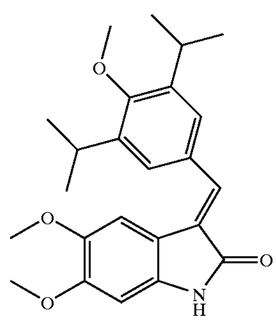 | 3-(3,5-Diisopropyl-4-methoxybenzylidene)-5,6-dimethoxy-1,3-dihydroindol-2-one |
| 100 | 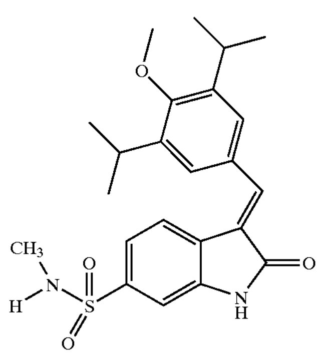 | N-[3-(3,5-Diisopropyl-4-methoxybenzylidene)-2-oxo-2,3-dihydro-1H-indol-6-yl]-methanesulfonamide |

TABLE 1-continued

| Compound | Structures | Names |
|---|---|---|
| 101 | 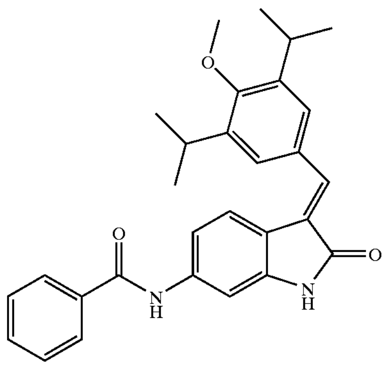 | N-[3-(3,5-Diisopropyl-4-methoxybenzylidene)-2-oxo-2,3-dihydro-1H-indol-6-yl]-benzamide |
| 102 | 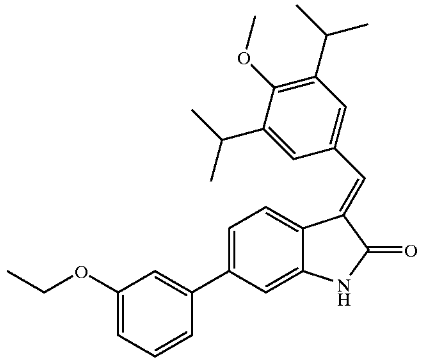 | 3-(3,5-Diisopropyl-4-methoxybenyzylidene)-6-(3-ethoxyphenyl)-1,3-dihydroindol-2-one |
| 103 | 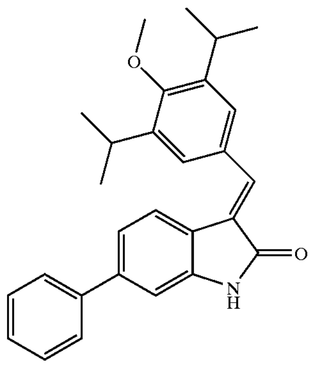 | 3-(3,5-Diisopropyl-4-methoxybenzylidene)-6-phenyl-1,3-dihydroindol-2-one |
| 104 | 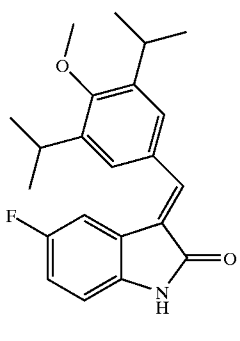 | 3-(3,5-Diisopropyl-4-methoxybenzylidene)-5-fluoro-1,3-dihydroindol-2-one |

TABLE 1-continued

| Compound | Structures | Names |
|---|---|---|
| 105 | 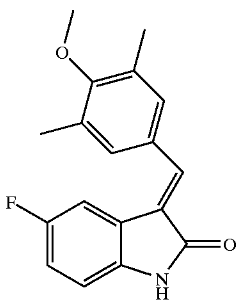 | 5-Fluoro-3-(4-methoxy-3,5-dimethylbenzylidene)-1,3-dihydroindol-2-one |
| 106 | 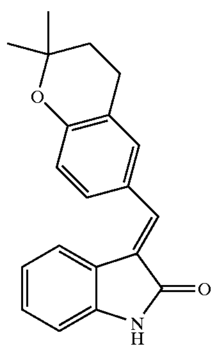 | 3-(2,2-dimethylchroman-6-ylmethylene)-1,3-dihydroindol-2-one |
| 107 | 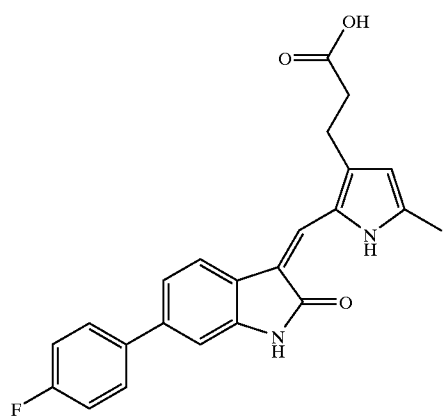 | 3-{2-[6-(4-Fluoro-phenyl)-2-oxo-1,2-dihydroindol-3-ylidenemethyl]-5-methyl-1H-pyrrol-3-yl}-propionic acid |
| 108 | 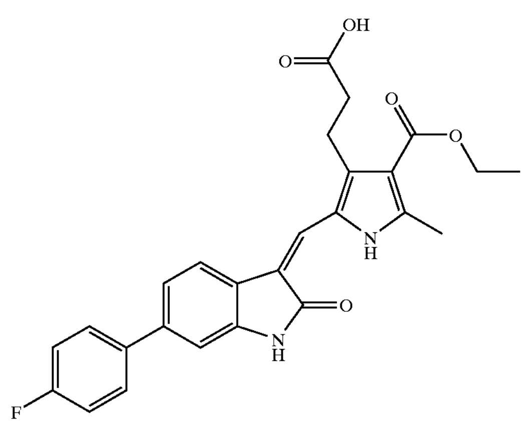 | 4-(2-Carboxy-ethyl)-5-[6-(4-fluoro-phenyl)-2-oxo-1,2-dihydroindol-3-ylidenemethyl]-2-methyl-1H-pyrrole-3-carboxylic acid ethyl ester |

TABLE 1-continued

| Compound | Structures | Names |
|---|---|---|
| 109 | 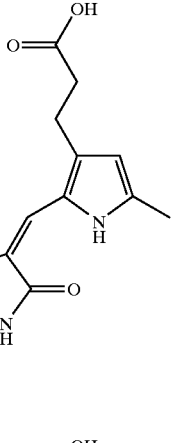 | 3-{2-[6-(2-Methoxy-phenyl)-2-oxo-1,2-dihydroindol-3-ylidenemethyl]-5-methyl-1H-pyrrol-3-yl}-propionic acid |
| 110 | 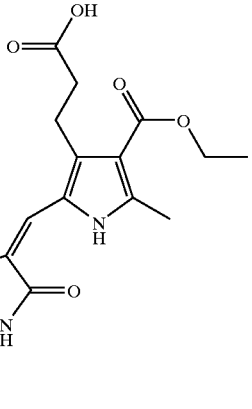 | 4-(2-Carboxy-ethyl)-5-[6-(2-methoxy-phenyl)-2-oxo-1,2-dihydroindol-3-ylidenemethyl]-2-methyl-1H-pyrrole-3-carboxylic acid ethyl ester |
| 111 | 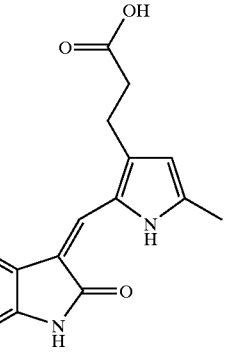 | 3-[2-(5-Chloro-2-oxo-1,2-dihydroindol-3-ylidenemethyl)-5-methyl-1H-pyrrol-3-yl]-propionic acid |
| 112 | 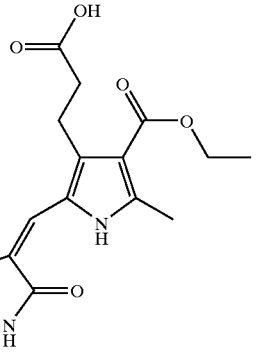 | 4-(2-Carboxy-ethyl)-5-(5-chloro-2-oxo-1,2-dihydroindol-3-ylidenemethyl)-2-methyl-1H-pyrrole-3-carboxylic acid ethyl ester |

TABLE 1-continued

| Compound | Structures | Names |
|---|---|---|
| 113 | 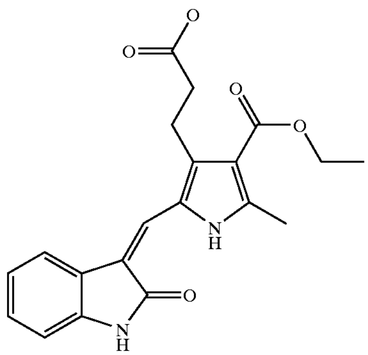 | 4-(2-Carboxy-ethyl)-2-methyl-5-(2-oxo-1,2-dihydroindol-3-ylidenemethyl)-1H-pyrrole-3-carboxylic acid ethyl ester |
| 114 | 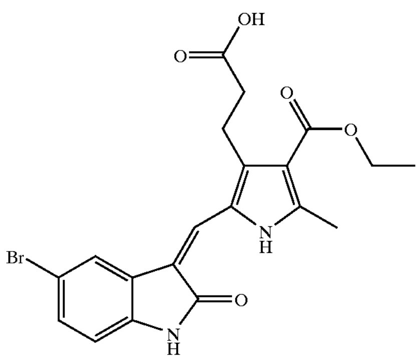 | 5-(5-Bromo-2-oxo-1,2-dihydroindol-3-ylidenemethyl)-4-(2-carboxy-ethyl)-2-methyl-1H-pyrrole-3-carboxylic ethyl ester |
| 115 | 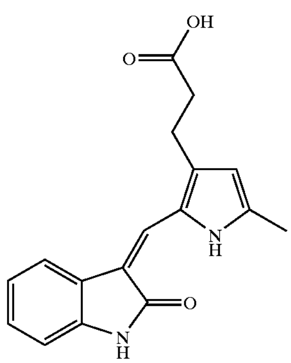 | 3-[5-Methyl-2-(2-oxo-1,2-dihydroindol-3-ylidenemethyl)-1H-pyrrol-3-yl]-propionic acid |
| 116 | 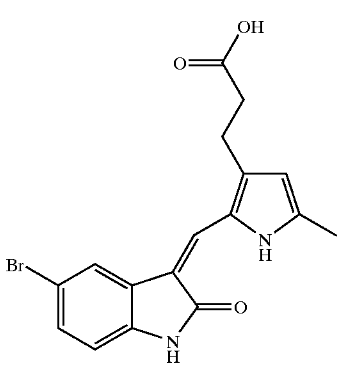 | 3-[2-(5-Bromo-2-oxo-1,2-dihydroindol-3-ylidenemethyl)-5-methyl-1H-pyrrol-3-yl]-propionic acid |

TABLE 1-continued

| Compound | Structures | Names |
|---|---|---|
| 117 | 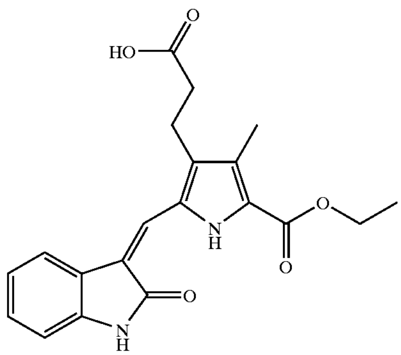 | 4-(2-Carboxy-ethyl)-3-methyl-5-(2-oxo-1,2-dihydroindol-3-ylidenemethyl)-1H-pyrrole-2-carboxylic acid ethyl ester |
| 118 | 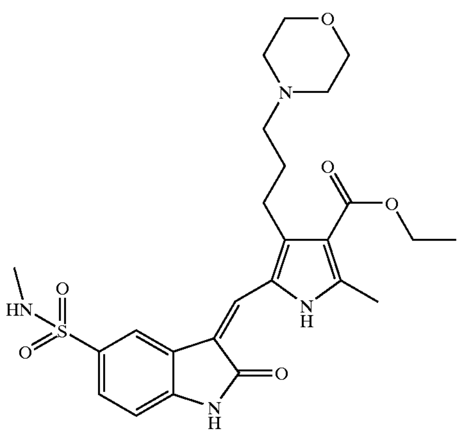 | 2-Methyl-5-(5-methylsulfamoyl-2-oxo-1,2-dihydroindol-3-ylidenemethyl)-4-(3-morpholin-4-yl-propyl)-1H-pyrrole-3-carboxylic acid ethyl ester |
| 119 | 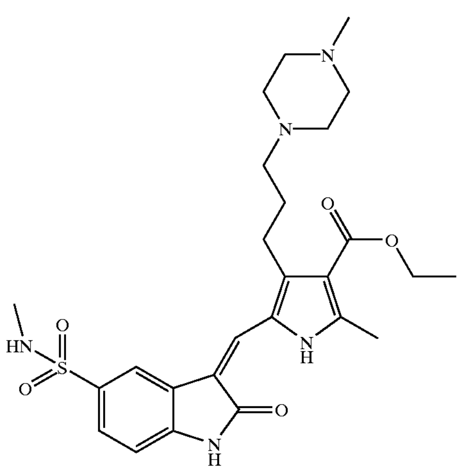 | 2-Methyl-4-[3-(4-methyl-piperazin-1-yl)-propyl]-5-(5-methylsulfamoyl-2-oxo-1,2-dihydroindol-3-ylidenemethyl)-1H-pyrrole-3-carboxylic acid ethyl ester |

TABLE 1-continued

| Compound | Structures | Names |
|---|---|---|
| 120 | 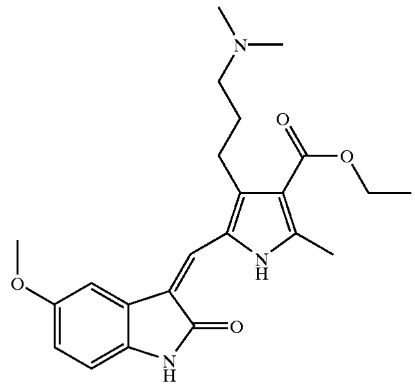 | 4-(3-Dimethylamino-propyl)-5-(5-methoxy-2-oxo-1,2-dihydroindol-3-ylidenemethyl)-2-methyl-1H-pyrrole-3-carboxylic acid ethyl ester |
| 121 | 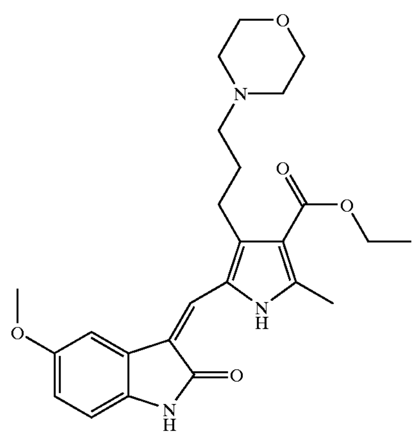 | 5-(5-Methoxy-2-oxo-1,2-dihydroindol-3-ylidenemethyl)-2-methyl-4-(3-morpholin-4-yl-propyl)-1H-pyrrole-3-carboxylic acid ethyl ester |
| 122 | 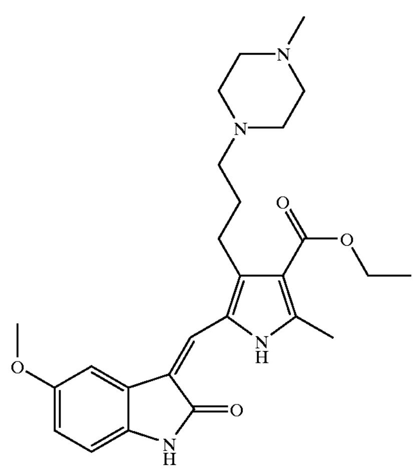 | 5-(5-Methoxy-2-oxo-1,2-dihydroindol-3-ylidenemethyl)-2-methyl-4-[3-(4-methyl-piperazin-1-yl)-propyl]-1H-pyrrole-3-carboxylic acid ethyl ester |

TABLE 1-continued

| Compound | Structures | Names |
|---|---|---|
| 123 | 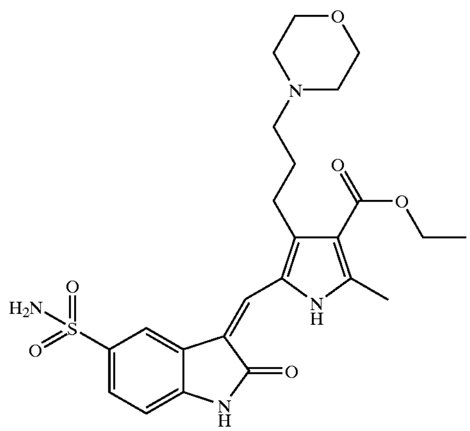 | 2-Methyl-4-(3-morpholin-4-yl-propyl)-5-(2-oxo-5-sulfamoyl-1,2-dihydroindol-3-ylidenemethyl)-1H-pyrrole-3-carboxylic acid ethyl ester |
| 124 | 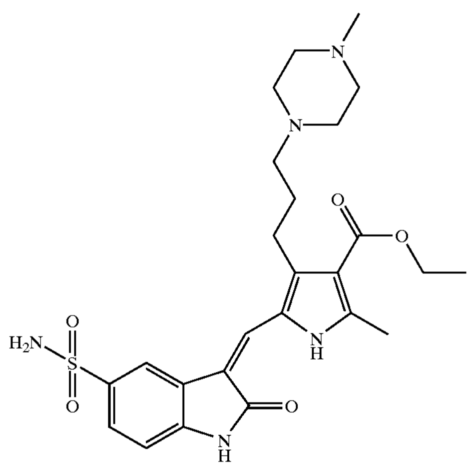 | 2-Methyl-4-[3-(4-methyl-piperazin-1-yl)-propyl]-5-(2-oxo-5-sulfamoyl-1,2-dihydroindol-3-ylidenemethyl)-1H-pyrrole-3-carboxylic acid ethyl ester |
| 125 | 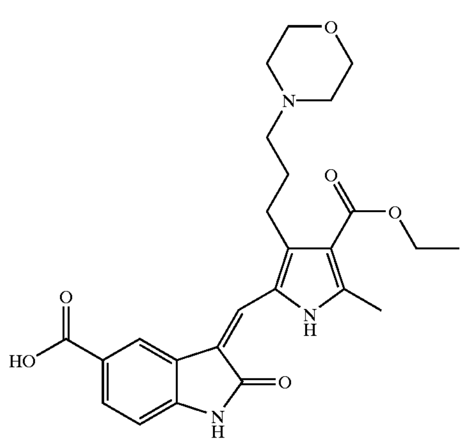 | 3-[4-Ethoxycarbonyl-5-methyl-3-(3-morpholin-4-yl-propyl)-1H-pyrrol-2-ylmethylene]-2-oxo-2,3-dihydro-1H-indole-5-carboxylic acid |

TABLE 1-continued

| Compound | Structures | Names |
|---|---|---|
| 126 | 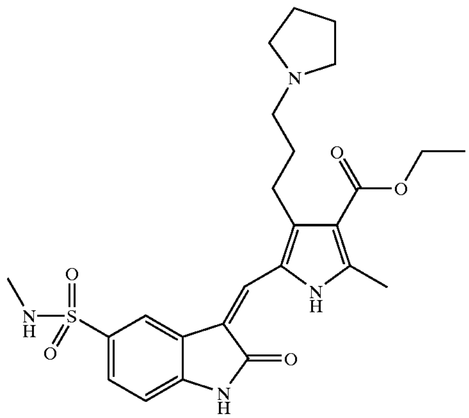 | 2-Methyl-5-(5-methylsulfamoyl-2-oxo-1,2-dihydroindol-3-ylidenemethyl)-4-(3-pyrrolidin-1-yl-propyl)-1H-pyrrole-3-carboxylic acid ethyl ester |
| 127 | 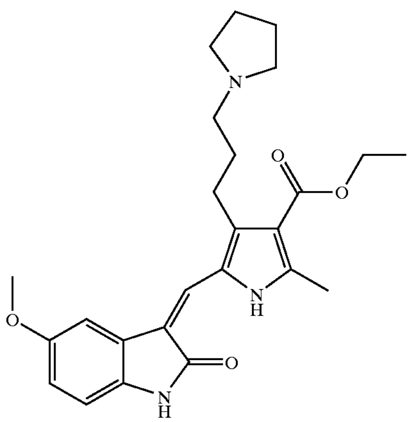 | 5-(5-Methoxy-2-oxo-1,2-dihydroindol-3-ylidenemethyl)-2-methyl-4-(3-pyrrolidin-1-yl-propyl)-1H-pyrrole-3-carboxylic acid ethyl ester |
| 128 | 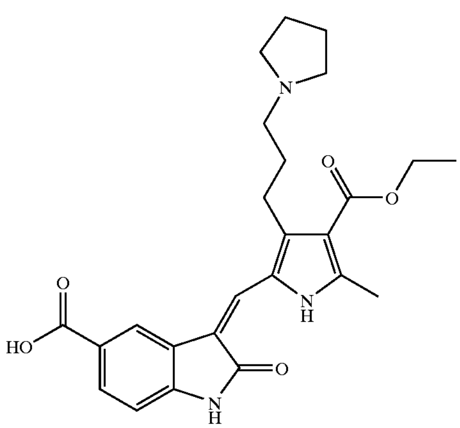 | 3-[4-Ethoxycarbonyl-5-methyl-3-(3-pyrrolidin-1-yl-propyl)-1H-pyrrol-2-ylmethylene]-2-oxo-2,3-dihydro-1H-indole-5-carboxylic acid |

TABLE 1-continued

| Compound | Structures | Names |
|---|---|---|
| 129 | 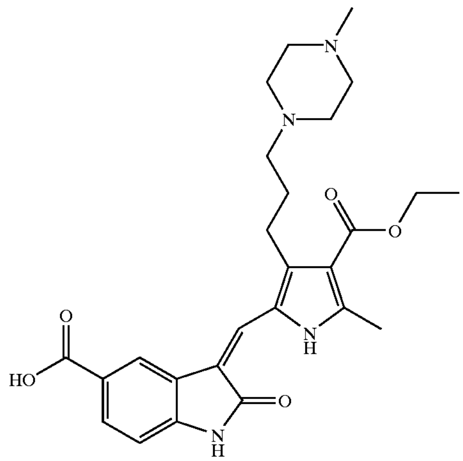 | 3-(4-Ethoxycarbonyl-5-methyl-3-[3-(4-methyl-piperazin-1-yl)-propyl]-1H-pyrrol-2-ylmethylene)-2-oxo-2,3-dihydro-1H-indole-5-carboxylic acid |
| 130 | 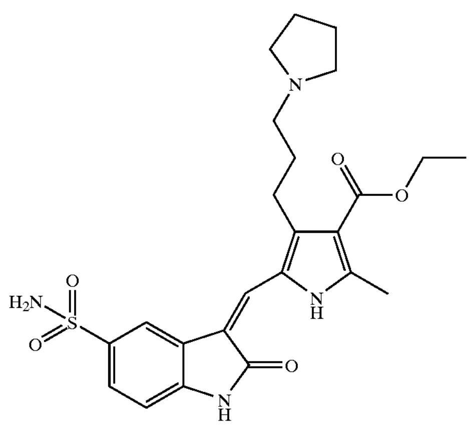 | 2-Methyl-5-[2-oxo-5-sulfamoyl-1,2-dihydroindol-3-ylidenemethyl)-4-(3-pyrrolidin-1-yl-propyl)-1H-pyrrole-3-carboxylic acid ethyl ester |
| 131 | 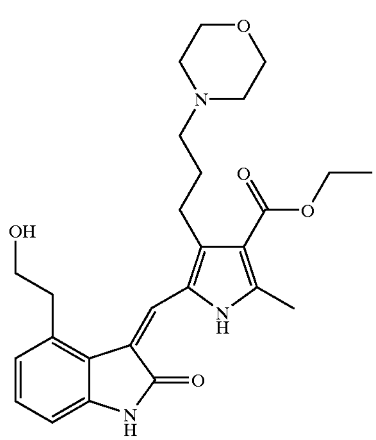 | 5-[4-(2-Hydroxy-ethyl)-2-oxo-1,2-dihydroindol-3-ylidenemethyl]-2-methyl-4-(3-morpholin-4-yl-propyl)-1H-pyrrole-3-carboxylic acid ethyl ester |

TABLE 1-continued

| Compound | Structures | Names |
|---|---|---|
| 132 | 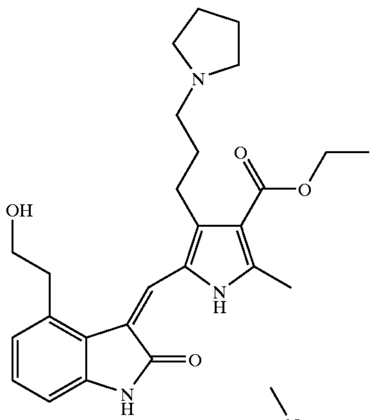 | 5-[4-(2-Hydroxy-ethyl)-2-oxo-1,2-dihydroindol-3-ylidenemethyl]-2-methyl-4-(3-pyrrolidin-1-yl-propyl)-1H-pyrrole-3-carboxylic acid ethyl ester |
| 133 | 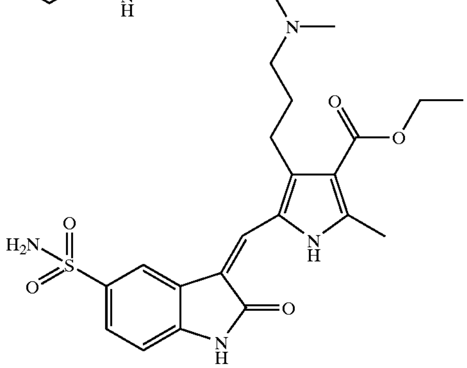 | 4-(3-Dimethylamino-propyl)-2-methyl-5-(2-oxo-5-sulfamoyl-1,2-dihydroindol-3-ylidenemethyl)-1H-pyrrole-3-carboxylic acid ethyl ester |
| 134 | 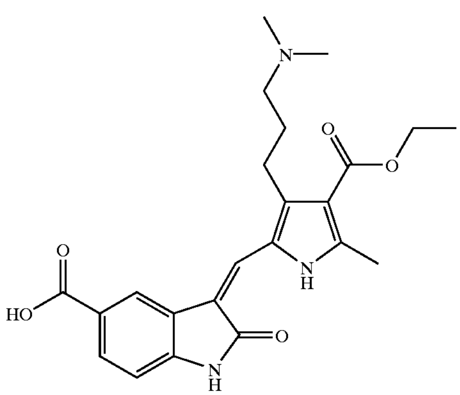 | 3-[3-{3-Dimethylamino-propyl)-4-ethoxycarbonyl-5-methyl-1H-pyrrol-2-ylmethylene]-2-oxo-2,3-dihydro-1H-indole-5-carboxylic acid |
| 135 | 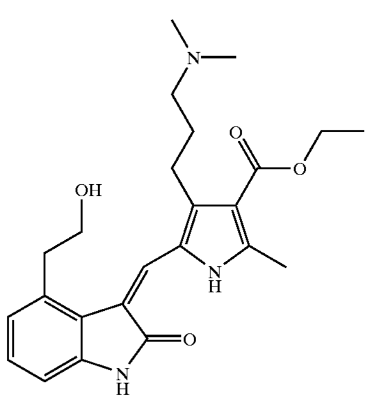 | 4-(3-Dimethylamino-propyl)-5-[4-(2-hydroxy-ethyl)-2-oxo-1,2-dihydroindol-3-ylidenemethyl]-2-methyl-1H-pyrrole-3-carboxylic acid ethyl ester |

TABLE 1-continued

| Compound | Structures | Names |
|---|---|---|
| 136 | 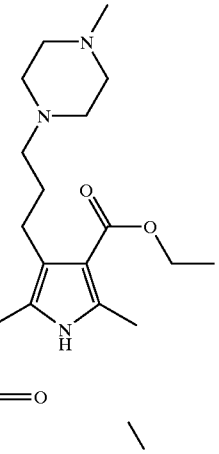 | 5-[4-(2-Hydroxy-ethyl)-2-oxo-1,2-dihydroindol-3-ylidenemethyl]-2-methyl-4-[3-(4-methyl-piperazin-1-yl)-propyl]-1H-pyrrole-3-carboxylic acid ethyl ester |
| 137 | 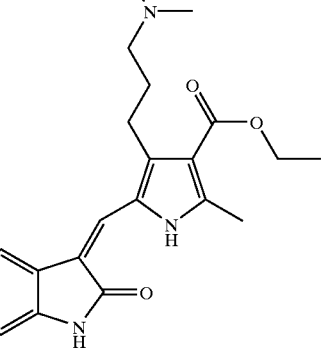 | 4-(3-Dimethylamino-propyl)-2-methyl-5-(5-methyl-sulfamoyl-2-oxo-1,2-dihydroindol-3-ylidenemethyl)-1H-pyrrole-3-carboxylic acid ethyl ester |
| 138 | 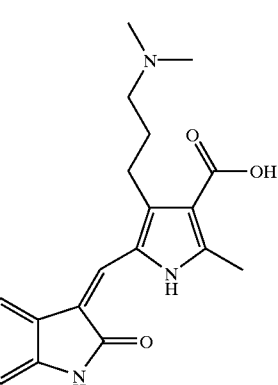 | 4-(3-Dimethylamino-propyl)-2-methyl-5-(5-methyl-sulfamoyl-2-oxo-1,2-dihydroindol-3-ylidenemethyl)-1H-pyrrole-3-carboxylic acid |
| 139 | 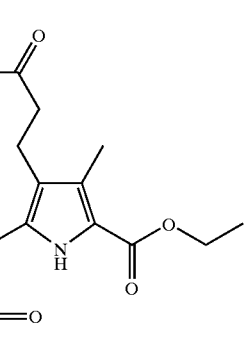 | 4-(2-Carboxy-ethyl)-3-methyl-5-(4-methyl-2-oxo-1,2-dihydroindol-3-ylidenemethyl)-1H-pyrrole-2-carboxylic acid ethyl ester |

TABLE 1-continued

| Compound | Structures | Names |
|---|---|---|
| 140 | 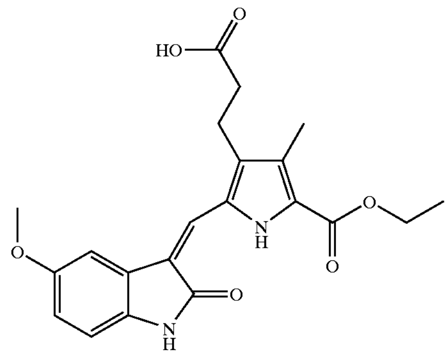 | 4-(2-Carboxy-ethyl)-5-(5-methoxy-2-oxo-1,2-dihydroindol-3-ylidenemethyl)-3-methyl-1H-pyrrole-2-carboxylic acid ethyl ester |
| 141 | 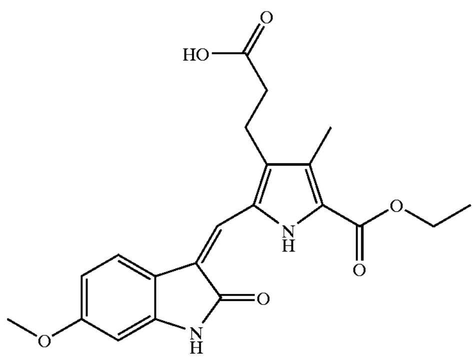 | 4-(2-Carboxy-ethyl)-5-(6-methoxy-2-oxo-1,2-dihydroindol-3-ylidenemethyl)-3-methyl-1H-pyrrole-2-carboxylic acid ethyl ester |
| 142 | 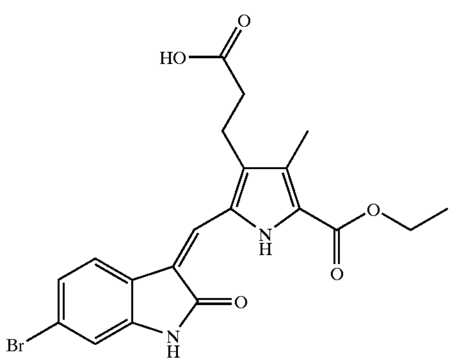 | 5-(5-Bromo-2-oxo-1,2-dihydroindol-3-ylidenemethyl)-4-(2-carboxy-ethyl)-3-methyl-1H-pyrrole-2-carboxylic acid ethyl ester |
| 143 | 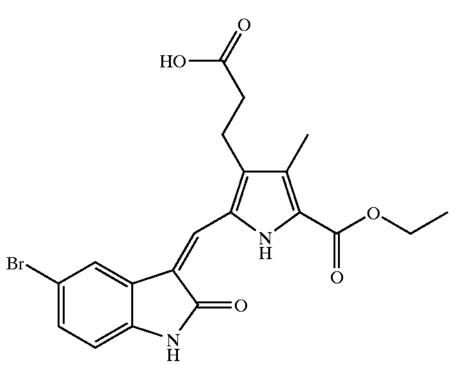 | 5-(5-Bromo-2-oxo-1,2-dihydroindol-3-ylidenemethyl)-4-(2-carboxy-ethyl)-3-methyl-1H-pyrrole-2-carboxylic acid ethyl ester |

TABLE 1-continued

| Compound | Structures | Names |
|---|---|---|
| 144 | 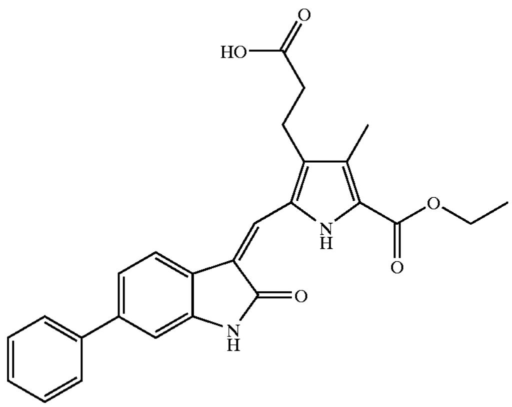 | 4-(2-Carboxy-ethyl)-3-methyl-5-(2-oxo-6-phenyl-1,2-dihydroindol-3-ylidenemethyl)-1H-pyrrole-2-carboxylic acid ethyl ester |
| 145 | 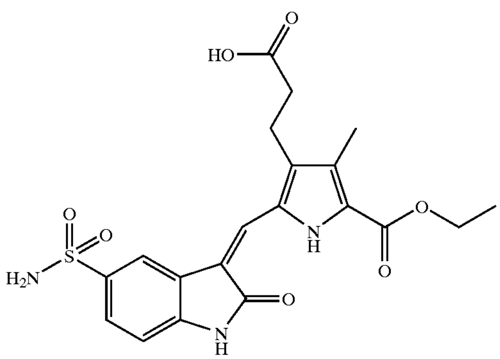 | 4-(2-Carboxy-ethyl)-3-methyl-5-(2-oxo-5-sulfamoyl-1,2-dihydroindol-3-ylidenemethyl)-1H-pyrrole-2-carboxylic acid ethyl ester |
| 146 | 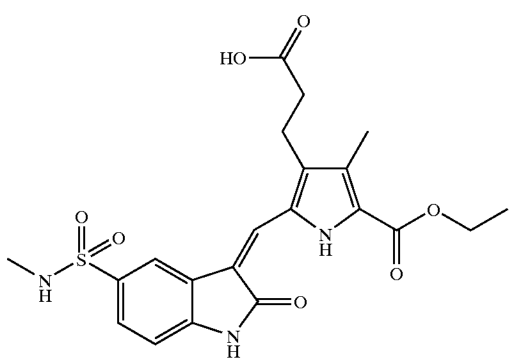 | 4-(2-Carboxy-ethyl)-3-methyl-5-(5-methylsulfamoyl-2-oxo-1,2-dihydroindol-3-ylidenemethyl)-1H-pyrrole-2-carboxylic acid ethyl ester |
| 147 | 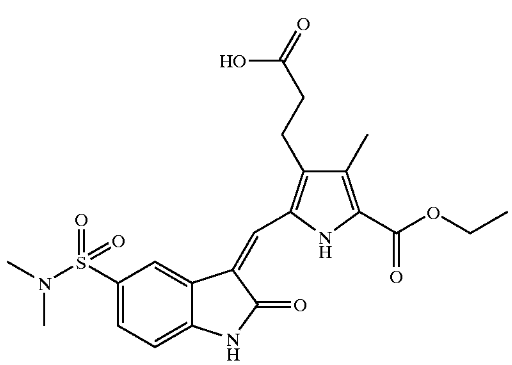 | 4-(2-Carboxy-ethyl)-5-(5-dimethylsulfamoyl-2-oxo-1,2-dihydroindol-3-ylidenemethyl)-3-methyl-1H-pyrrole-2-carboxylic acid ethyl ester |

TABLE 1-continued

| Compound | Structures | Names |
|---|---|---|
| 148 | 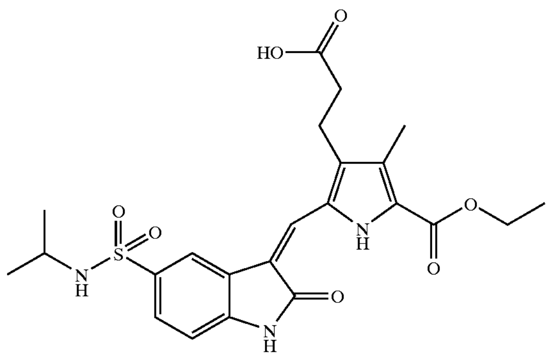 | 4-(2-Carboxy-ethyl)-5-(5-isopropylsulfamoyl-2-oxo-1,2-dihydroindol-3-ylidenemethyl)-3-methyl-1H-pyrrole-2-carboxylic acid ethyl ester |
| 149 | 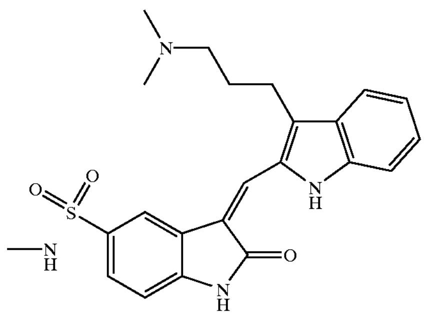 | 3-[3-(3-Dimethylamino-propyl)-1H-indol-2-ylmethylene]-2-oxo-2,3-dihydro-1H-indole-5-sulfonic acid methylamide |
| 150 | 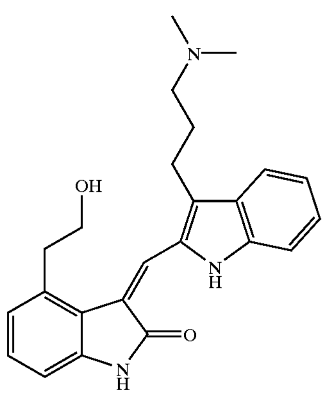 | 3-[3-(3-Dimethylamino-propyl)-1H-indol-2-ylmethylene]-4-(2-hydroxy-ethyl)-1,3-dihydroindol-2-one |
| 151 | 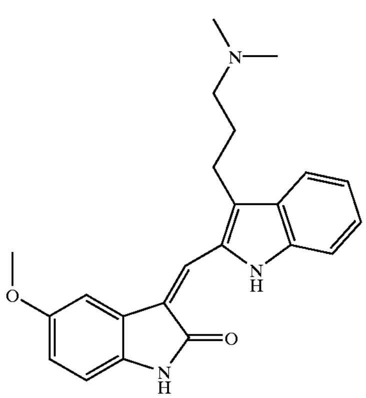 | 3-[3-(3-Dimethylamino-propyl)-1H-indol-2-ylmethylene]-5-methoxy-1,3-dihydroindol-2-one |

TABLE 1-continued

| Compound | Structures | Names |
|---|---|---|
| 152 | 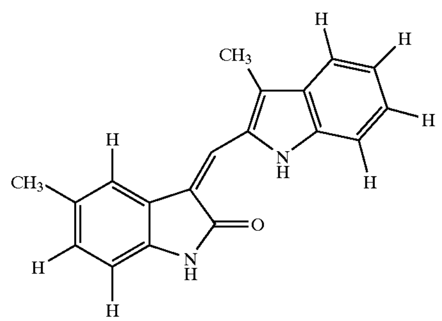 | 5-methyl-3-(3-methyl-1H-indol-2-ylmethylene)-1,3-dihydroindol-2-one |
| 153 | 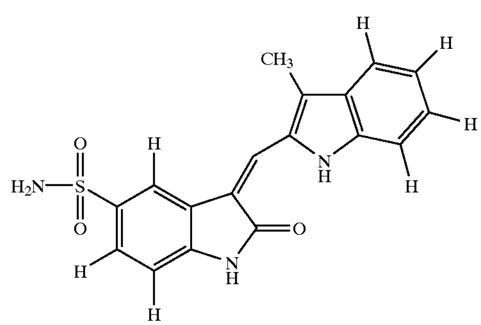 | 3-(3-methyl-1H-indol-2-ylmethylene)-2-oxo-2,3-dihydro-1H-indol-5-sulfonic acid amide |
| 154 | 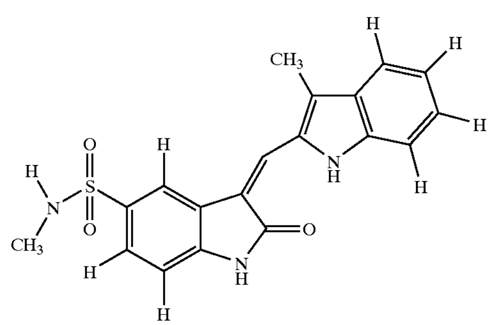 | 3(3-methyl-1H-indol-2-ylmethylene)-2-oxo-2,3-dihydro-1H-indole-5-sulfonic acid methylamide |
| 155 | 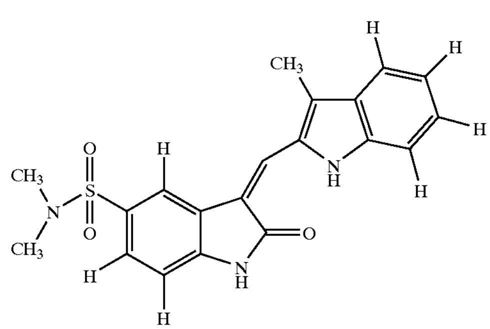 | 3-(3-methyl-1H-indole-2-ylmethylene)-2-oxo-2,3-dihydro-1H-indole-5-sulfonic acid dimethylamide |

TABLE 1-continued

| Compound | Structures | Names |
|---|---|---|
| 156 | 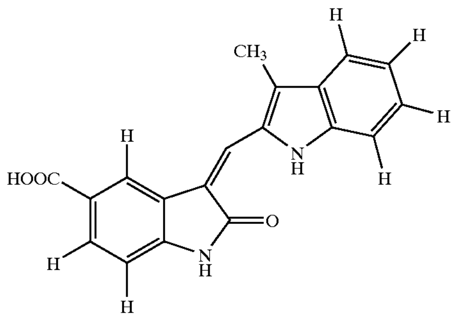 | 3(3-methyl-1H-indol-2-ylmethylene)-2-oxo-2,3-dihydro-1H-indole-5-carboxylic acid |
| 157 | 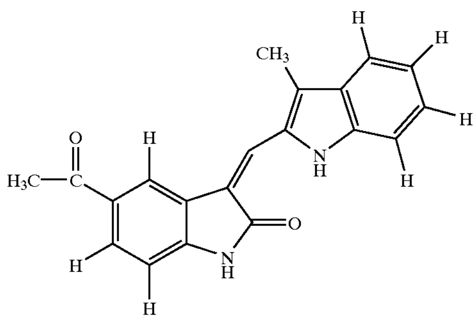 | 5-acetyl-3-(3-methyl-1H-indol-2-ylmethylene)-1,3-dihydroindol-2-one |
| 158 | 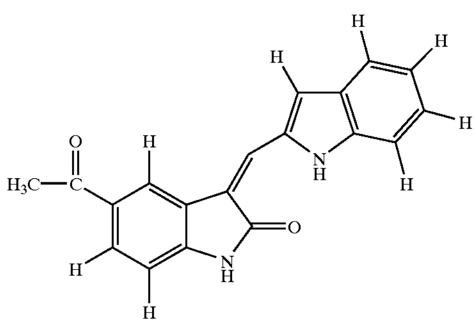 | 5-acetyl-3-(1H-indol-2-ylmethylene)-1,3-dihydroindol-2-one |
| 159 | 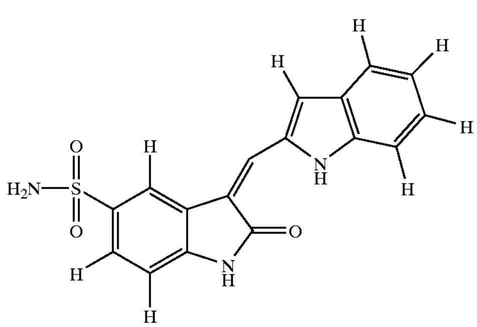 | 3-(1H-indol-2-ylmethylene)-2-oxo-2,3-dihydro-1H-indol-5-sulfonic acid amide |

TABLE 1-continued

| Compound | Structures | Names |
|---|---|---|
| 160 | 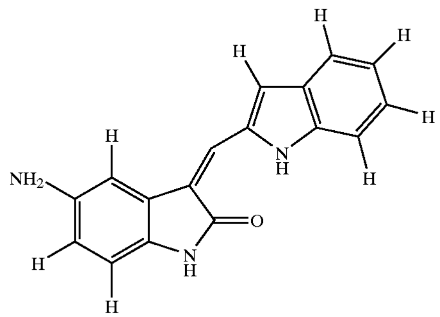 | 5-amino-3-(1H-indol-2-ylmethylene)-1,3-dihydroindol-2-one |
| 161 | 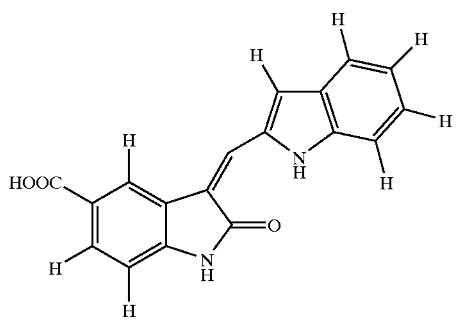 | 3-(1H-indol-2-ylmethylene)-2-oxo-2,3-dihydro-1H-indole-5-carboxylic acid |
| 162 | 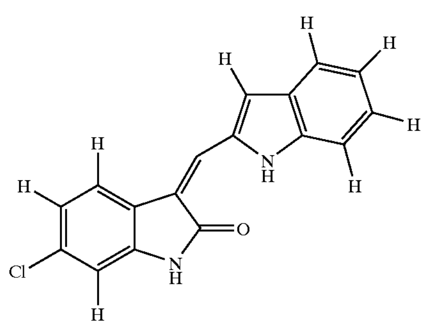 | 6-chloro-3-(1H-indol-2-ylmethylene)-1,3-dihydroindol-2-one |
| 163 | 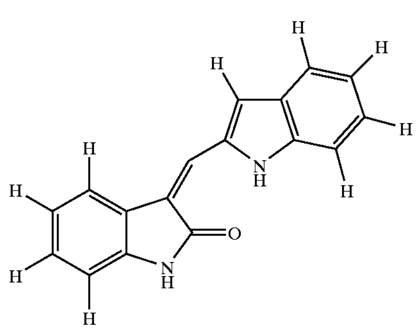 | 3-(1H-indol-2-ylmethylene)-1,3-dihydroindol-2-one |

TABLE 1-continued

| Compound | Structures | Names |
|---|---|---|
| 164 | 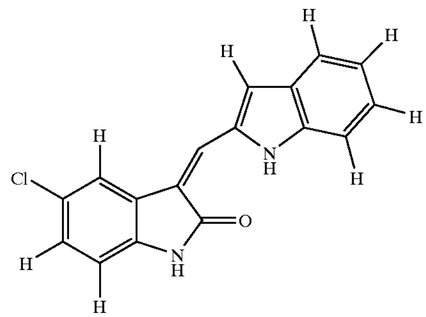 | 5-chloro-3-(1H-indol-2-ylmethylene)-1,3-dihydroindol-2-one |
| 165 | 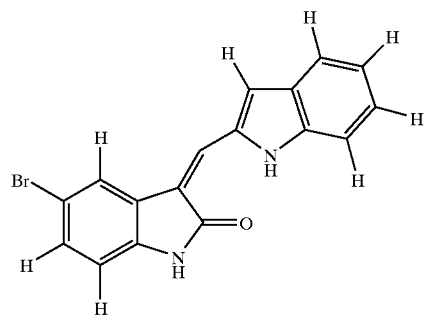 | 5-bromo-3-(1H-indol-2-ylmethylene)-1,3-dihydroindol-2-one |
| 166 | 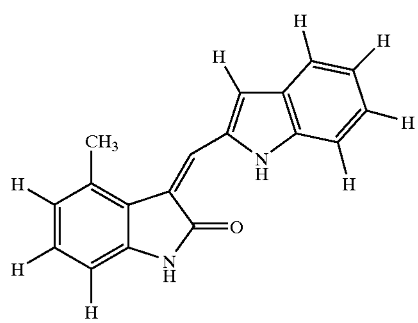 | 3-(1H-indol-2-ylmethylene)-4-methyl-1,3-dihydroindol-2-one |
| 167 | 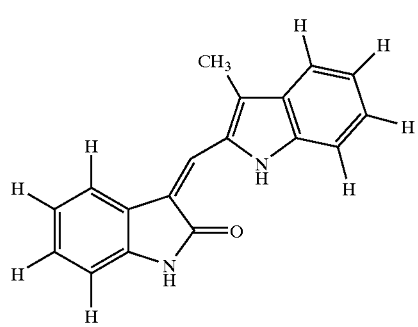 | 3-(3-methyl-1H-indol-2-ylmethylene)-1,3-dihydroindol-2-one |

TABLE 1-continued

| Compound | Structures | Names |
|---|---|---|
| 168 | 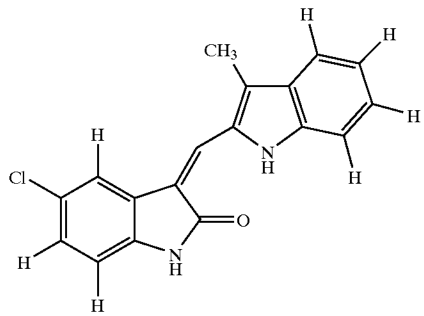 | 5-chloro-3-(3-methyl-1H-indol-2-ylmethylene)-1,3-dihydroindol-2-one |
| 169 | 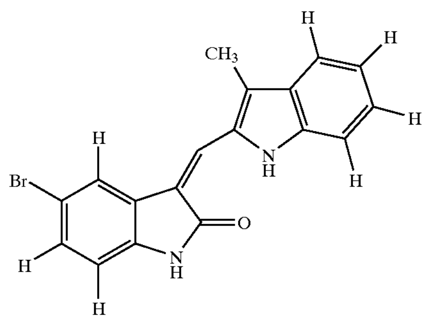 | 5-bromo-3-(3-methyl-1H-indol-2-ylmethylene)-1,3-dihydroindol-2-one |
| 170 | 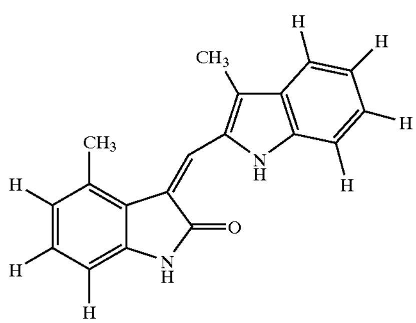 | 4-methyl-3-(3-methyl-1H-indol-2-ylmethylene)-1,3-dihydroindol-2-one |
| 171 | 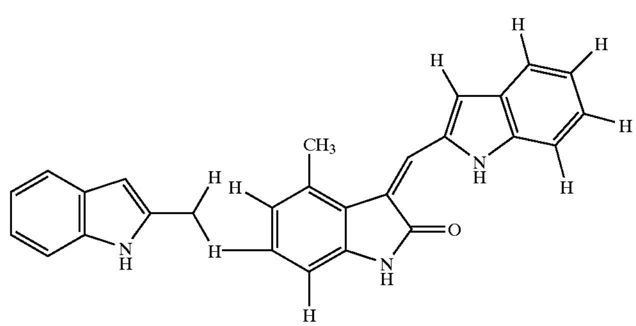 | 3-(1H-indol-2-ylmethylene)-5[(1H-indole-2-ylmethylene)-amino]-1,3-dihydroindol-2-one |
| 172 | 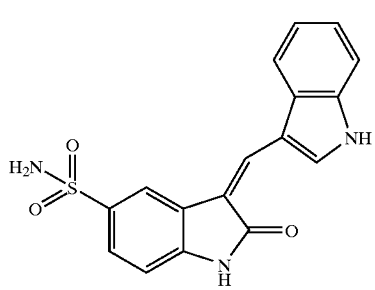 | 3-(1H-indol-3-ylmethylene)-2-oxo-2,3-dihydro-1H-indole-5-sulfonic acid amide |

TABLE 1-continued

| Compound | Structures | Names |
|---|---|---|
| 173 | 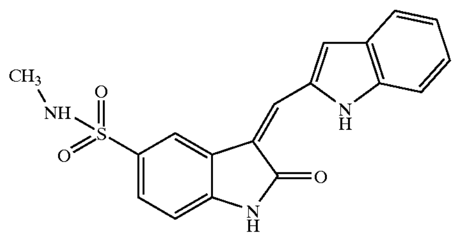 | 3-(1H-indol-2-ylmethylene)-2-oxo-2,3-dihydro-1H-indole-5-sulfonic acid methylamide |
| 174 | 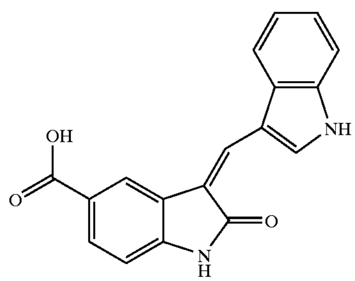 | 3-(1H-indol-3-ylmethylene)-2-oxo-2,3-dihydro-1H-indole-5-carboxylic acid |
| 175 | 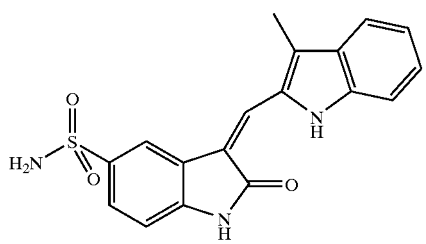 | 3-(3-Methyl-1H-indol-2-ylmethylene)-2-oxo-2,3-dihydro-1H-indole-5-sulfonic acid amide |
| 176 | 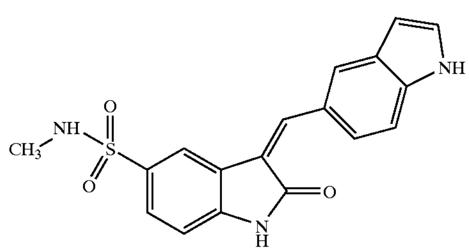 | 3-(1H-Indol-5-ylmethylene)-2-oxo-2,3-dihydro-1H-indole-5-sulfonic acid methylamide |
| 177 | 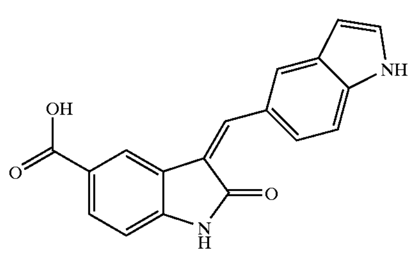 | 3-(1H-Indol-5-ylmethylene)-2-oxo-2,3-dihydro-1H-indole-5-carboxylic acid |
| 178 | 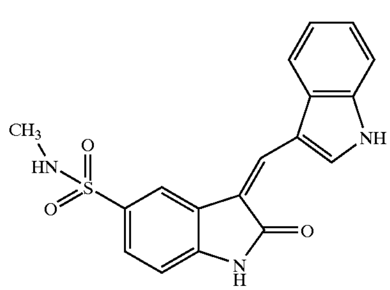 | 3-(1H-Indol-3-ylmethylene)-2-oxo-2,3-dihydro-1H-indole-5-sulfonic acid methylamide |

TABLE 1-continued

| Compound | Structures | Names |
|---|---|---|
| 179 | 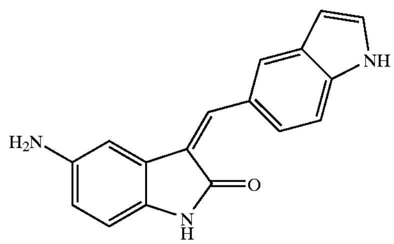 | 5-Amino-3-(1H-indol-5-ylmethylene)-1,3-dihydroindol-2-one |
| 180 | 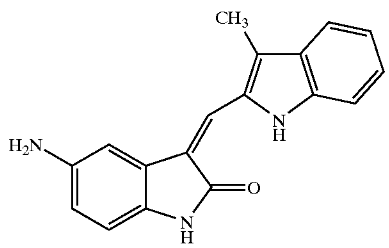 | 5-Amino-3-(3-methyl-1H-indol-2-ylmethylene)-1,3-dihydroindol-2-one |
| 181 | 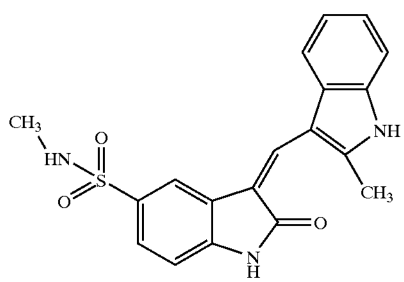 | 3-(2-Methyl-1H-indol-3-ylmethylene)-2-oxo-2,3-dihydro-1H-indole-5-sulfonic acid methylamide |
| 182 | 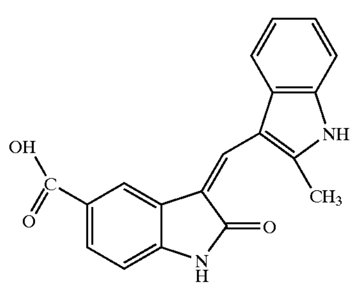 | 3-(2-Methyl-1H-indol-3-ylmethylene)-2-oxo-2,3-dihydro-1H-indole-5-carboxylic acid |
| 183 | 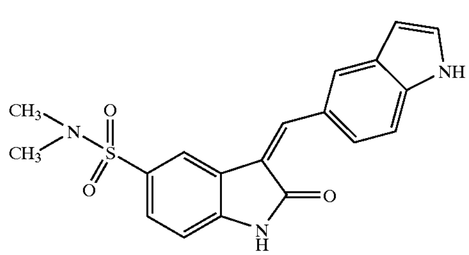 | 3-(1H-Indol-5-ylmethylene)-2-oxo-2,3-dihydro-1H-indole-5-sulfonic acid dimethylamide |

TABLE 1-continued

| Compound | Structures | Names |
|---|---|---|
| 184 | 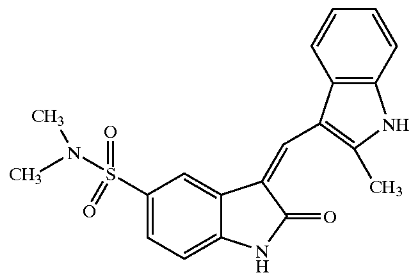 | 3-(2-Methyl-1H-indol-3-ylmethylene)-2-oxo-2,3-dihydro-1H-indole-5-sulfonic acid dimethylamide |
| 185 | 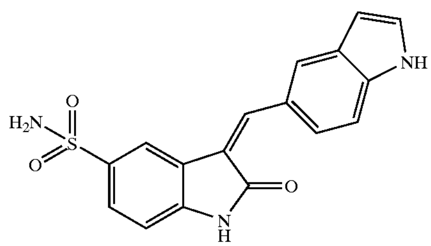 | 3-(1H-Indol-5-ylmethylene)-2-oxo-2,3-dihydro-1H-indole-5-sulfonic acid amide |
| 186 | 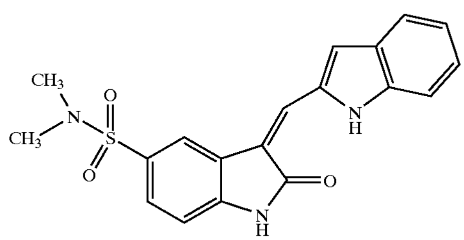 | 3-(1H-Indol-2-ylmethylene)-2-oxo-2,3-dihydro-1H-indole-5-sulfonic acid dimethylamide |
| 187 | 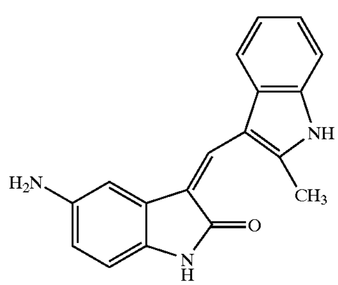 | 5-Amino-3-(2-methyl-1H-indol-3-ylmethylene)-1,3-dihydroindol-2-one |
| 188 | 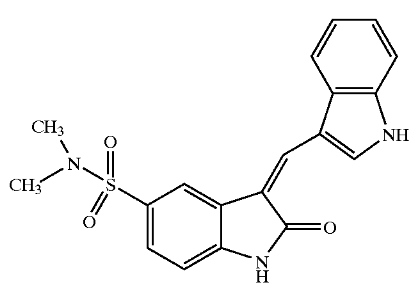 | 3-(1H-Indol-3-ylmethylene)-2-oxo-2,3-dihydro-1H-indole-5-sulfonic acid dimethylamide |

TABLE 1-continued

| Compound | Structures | Names |
|---|---|---|
| 189 | 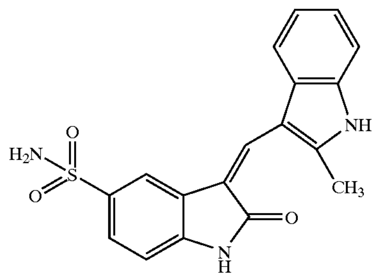 | 3-(2-Methyl-1H-indol-3-ylmethylene)-2-oxo-2,3-dihydro-1H-indole-5-sulfonic acid amide |
| 190 | 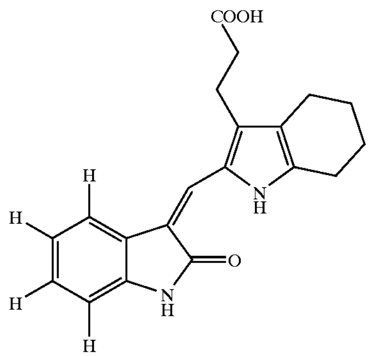 | 3-[2-(2-oxo-1,2-dihydroindol-3-ylidenemethyl)-4,5,6,7-tetrahydro-1H-indol-3-yl]-propionic acid |
| 191 | 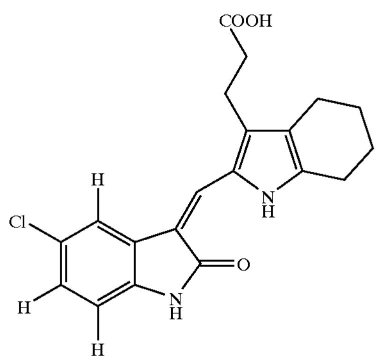 | 3-[2-(5-chloro-2-oxo-1,2-dihydroindol-3-ylidenemethyl)-4,5,6,7-tetrahydro-1H-indol-3-yl]-propionic acid |
| 192 | 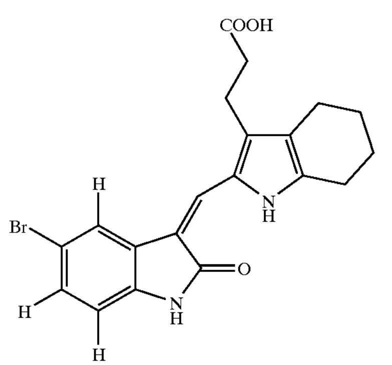 | 3-[2-(5-bromo-2-oxo-1,2-dihydroindol-3-ylidenemethyl)-4,5,6,7-tetrahydro-1H-indol-3-yl]-propionic acid |

TABLE 1-continued

| Compound | Structures | Names |
|---|---|---|
| 193 | 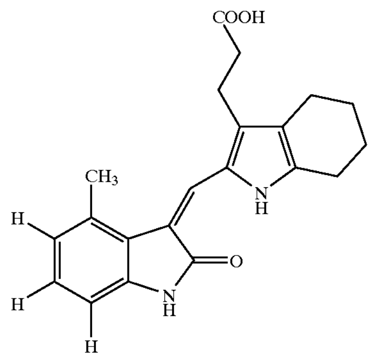 | 3-[2-(4-methyl-2-oxo-1,2-dihydroindol-3-ylidenemethyl)-4,5,6,7-tetrahydro-1H-indol-3-yl]-propionic acid |
| 194 | 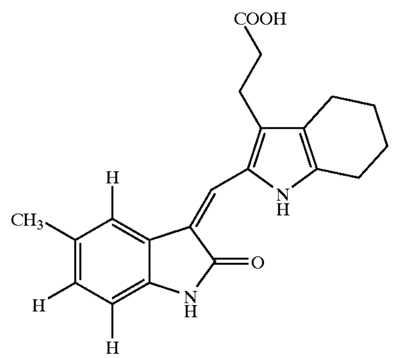 | 3-[2-(5-methyl-2-oxo-1,2-dihydroindol-3-ylidenemethyl)-4,5,6,7-tetrahydro-1H-indol-3-yl]-propionic acid |
| 195 | 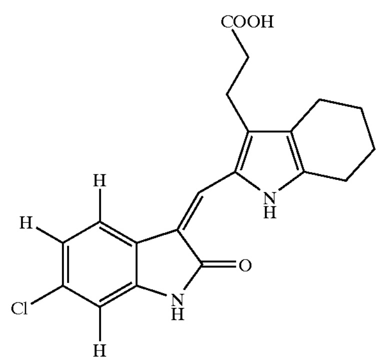 | 3-[2-(6-chloro-2-oxo-1,2-dihydroindol-3-ylidenemethyl)-4,5,6,7-tetrahydro-1H-indol-3-yl]-propionic acid |
| 196 | 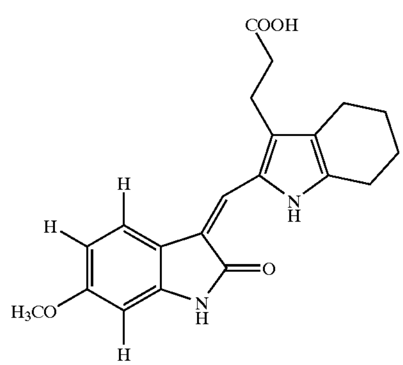 | 3-[2-(6-methoxy-2-oxo-1,2-dihydroindol-3-ylidenemethyl)-4,5,6,7-tetrahydro-1H-indol-3-yl]-propionic acid |

TABLE 1-continued

| Compound | Structures | Names |
|---|---|---|
| 197 | 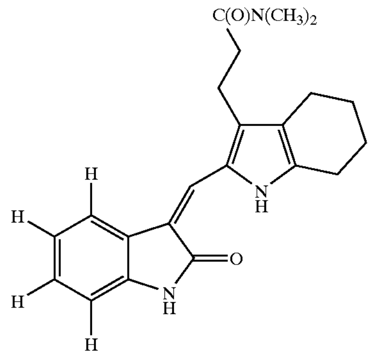 | N,N-dimethyl-3-[2-(2-oxo-1,2-dihydroindol-3-ylidenemethyl)-4,5,6,7-tetrahydro-1H-indol-3-yl]-propionamide |
| 198 | 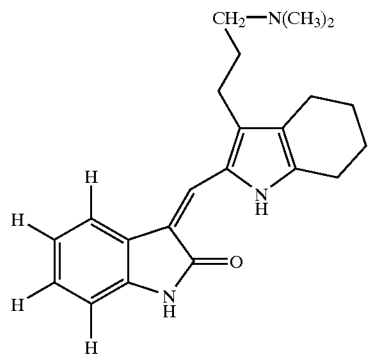 | 3-[3-(3-dimethylamino-propyl)-4,5,6,7-tetrahydro-1H-indol-2-ylmethylene]-1,3-dihydroindol-2-one |
| 199 | 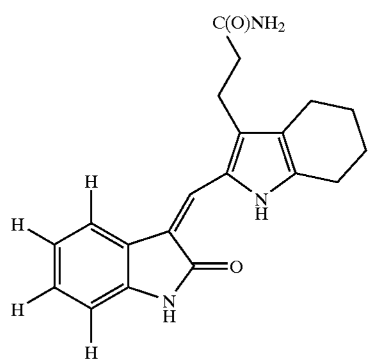 | 3-[2-(2-oxo-1,2-dihydroindol-3-ylidenemethyl)-4,5,6,7-tetrahydro-1H-indol-3-yl]-propionamide |
| 200 | 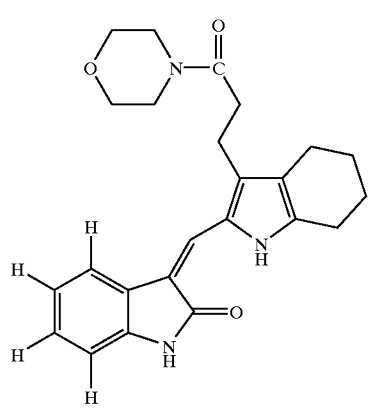 | 3-[3-(3-morpholin-4-yl-3-oxo-propyl)-4,5,6,7-tetrahydro-1H-indol-2-ylmethylene]-1,3-dihydroindol-2-one |

TABLE 1-continued

| Compound | Structures | Names |
|---|---|---|
| 201 | 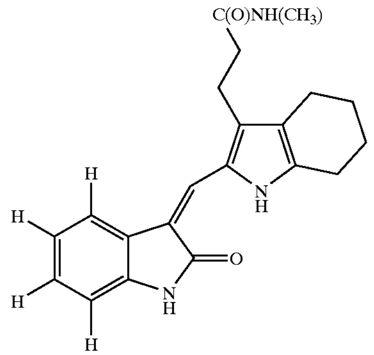 | N-methyl-3-[2-(2-oxo-1,2-dihydroindol-3-ylidenemethyl)-4,5,6,7-tetrahydro-1H-indol-3-yl]-propionamide |
| 202 | 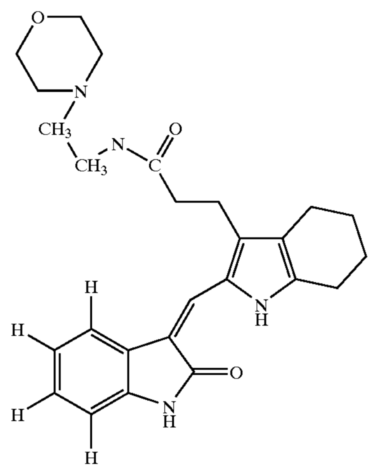 | N-(2-morpholin-4-yl-ethyl)-3-[2-(2-oxo-1,2-dihydroindol-3-ylidenemethyl)-4,5,6,7-tetrahydro-1H-indol-3-yl]-propionamide |
| 203 | 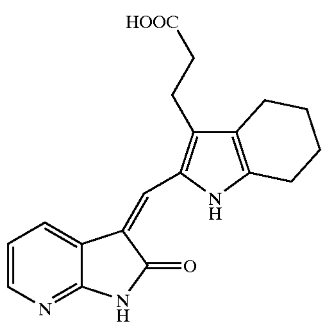 | 3-[2-(2-oxo-1,2-dihydro-pyrrolo[2,3-b]pyridin-3-ylidenemethyl)-4,5,6,7-tetrahydro-1H-indol-3-yl]-propionic acid |
| 204 | 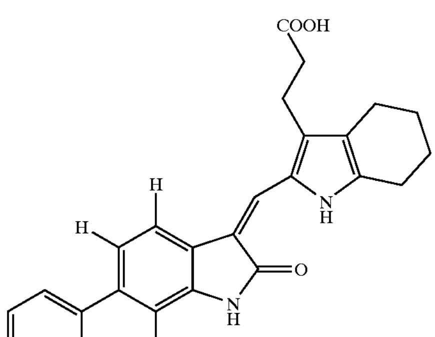 | 3-{2-[6-(3-methoxyphenyl)-2-oxo-1,2-dihydroindol-3-ylidenemethyl]-4,5,6,7-tetrahydro-1H-indol-3-yl}-propionic acid |

TABLE 1-continued

| Compound | Structures | Names |
|---|---|---|
| 205 | 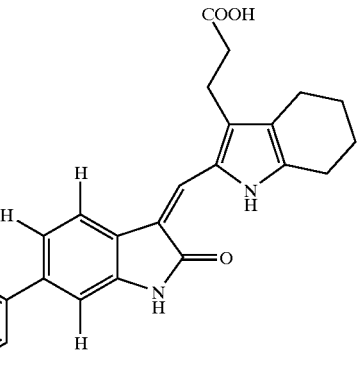 | 3-{2-[6-(4-methoxyphenyl)-2-oxo-1,2-dihydroindol-3-ylidenemethyl]-4,5,6,7-tetrahydro-1H-indol-3-yl}-propionic acid |
| 206 | 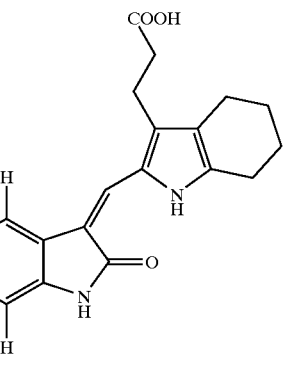 | 3-[2-(2-oxo-6-phenyl-1,2-dihydroindol-3-ylidenemethyl)-4,5,6,7-tetrahydro-1H-indol-3-yl]-propionic acid |
| 207 | 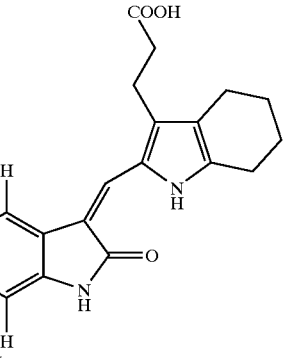 | 3-{2-[6-(2-methoxyphenyl)-2-oxo-1,2-dihydroindol-3-ylidenemethyl]-4,5,6,7-tetrahydro-1H-indol-3-yl}-propionic acid |
| 208 | 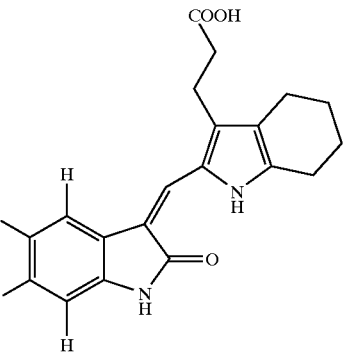 | 3-[2-(5-isopropylaminosulfonyl-2-oxo-1,2-dihydroindol-3-ylidenemethyl)-4,5,6,7-tetrahydro-1H-indol-3-yl]-propionic acid |

TABLE 1-continued

| Compound | Structures | Names |
|---|---|---|
| 209 | 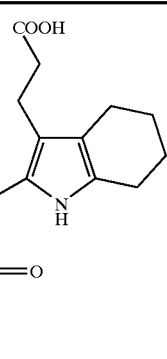 | 3-[2-(6-morpholin-4-yl-2-oxo-1,2-dihydroindol-3-ylidenemethyl)-4,5,6,7-tetrahydro-1H-indol-3-yl}-propionic acid |
| 210 | 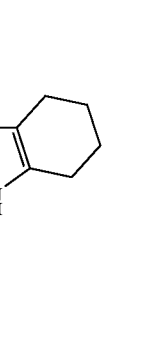 | 3-[2-(5-chloro-4-methyl-2-oxo-1,2-dihydroindol-3-ylidenemethyl)-4,5,6,7-tetrahydro-1H-indol-3-yl]-propionic acid |
| 211 | 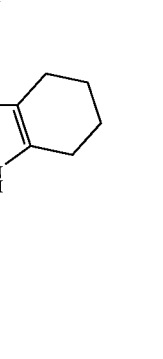 | 3-[2-(5-bromo-4-methyl-2-oxo-1,2-dihydroindol-3-ylidenemethyl)-4,5,6,7-tetrahydro-1H-indol-3-yl]-propionic acid |
| 212 | 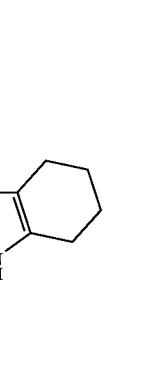 | 3-[2-(5-bromo-2-oxo-1,2-dihydroindol-3-ylidenemethyl-4,5,6,7-tetrahydro-1H-indol-3-yl]-N-(2-morpholin-4-yl-ethyl)-propionamide |

TABLE 1-continued
| Compound | Structures | Names |
|---|---|---|
| 213 | 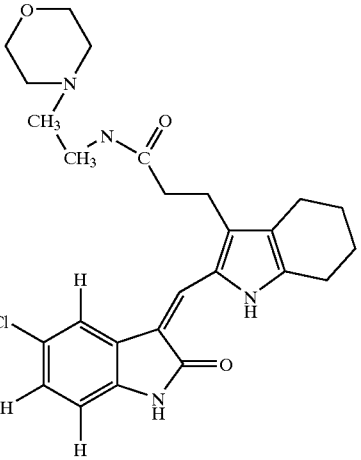 | 3-[2-(5-chloro-2-oxo-1,2-dihydroindol-3-ylidenemethyl)-4,5,6,7-tetrahydro-1H-indol-3-yl]-N-(2-morpholin-4-yl-ethyl)-propionamide |
| 214 | 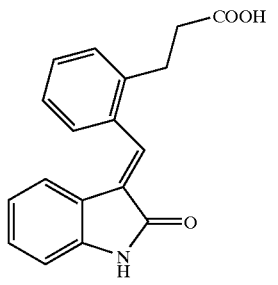 | 3-[2-(2-oxo-1,2-dihydroindol-3-ylidenemethyl)-phenyl]-propionic acid |
| 215 | 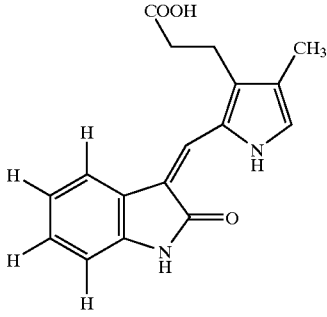 | 3-[4-Methyl-2-(2-oxo-1,2-dihydroindol-3-ylidenemethyl)-1H-pyrrol-3-yl]propionic acid |
| 216 | 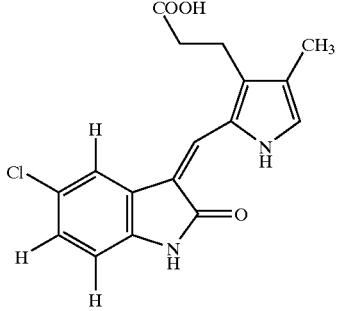 | 3-[2-(5-Chloro-2-oxo-1,2-dihydroindol-3-ylidenemethyl)-4-methyl-1H-pyrrol-3-yl]-propionic acid |

TABLE 1-continued
| Compound | Structures | Names |
|---|---|---|
| 217 | 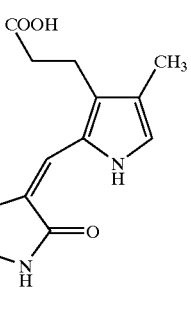 | 3-[2-(6-Methoxy-2-oxo-1,2-dihydroindol-3-ylidenemethyl)-4-methyl-1H-pyrrol-3-yl]-propionic acid |
| 218 | 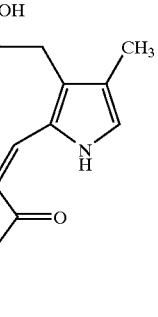 | 3-[2-(4-Methyl-2oxo-1,2-dihydroindol-3-ylidenemethyl)-4-methyl-1H-pyrrol-3-yl]-propionic acid |
| 219 | 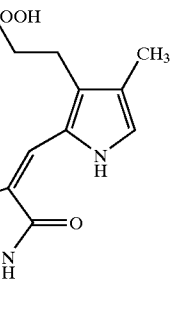 | 3-[2-(6-Chloro-2-oxo-1,2-dihydroindol-3-ylidenemethyl)-4-methyl-1H-pyrrol-3-yl]-propionic acid |
| 220 | 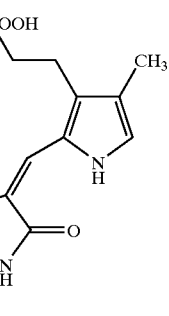 | 3-[2-(5-Bromo-2-oxo-1,2-dihydroindol-3-ylidenemethyl)-4-methyl-1H-pyrrol-3-yl]-propionic acid |

TABLE 1-continued

| Compound | Structures | Names |
|---|---|---|
| 221 | 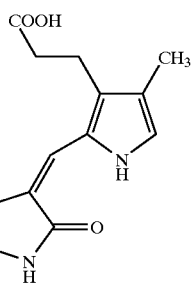 | 3-[2-(5-Methyl-2-oxo-1,2-dihydroindol-3-ylidenemethyl)-4-methyl-1H-pyrrol-3-yl]-propionic acid |
| 222 | 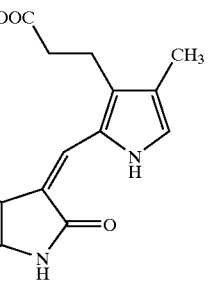 | 3-[2-(5-Methoxy-2-oxo-1,2-dihydroindol-3-ylidenemethyl)-4-methyl-1H-pyrrol-3-yl]-propionic acid |
| 223 | 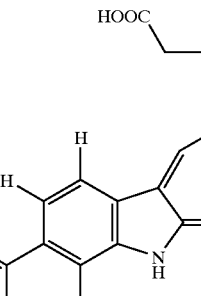 | 3-{2-[6-(3-Methoxyphenyl)-2-oxo-1,2-dihydroindol-3-ylidenemethyl]-4-methyl-1H-pyrrol-3-yl}-propionic acid |
| 224 | 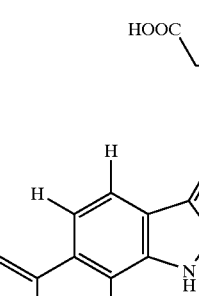 | 3-{2-[6-(3-Ethoxyphenyl)-2-oxo-1,2-dihydroindol-3-ylidenemethyl]-4-methyl-1H-pyrrol-3-yl}-propionic acid |

3. Biochemistry/Pharmacotherapy

Another aspect of this invention relates to a method for the modulation of the catalytic activity of a PK by contacting a PK with a compound of this invention or a physiologically acceptable salt or prodrug thereof.

As used herein, "PK" refers to receptor protein tyrosine kinase (RTKs), non-receptor or "cellular" tyrosine kinase (CTKs) and serine-threonine kinases (STKs).

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK cr STK is exposed or, more preferably, the inhibition of the catalytic activity of RTKs, CTKs and STKS.

The term "catalytic activity" as used herein refers to the rate of phosphorylation of tyrosine under the influence, direct or indirect, of RTKs and/or CTKs or the phosphorylation of serine and threonine under the influence, direct or indirect, of STKs.

The term "contacting" as used herein refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

A further aspect of this invention is that the modulation of the catalytic activity of PKs using a compound of this invention may be carried out in vitro or in vivo.

"In vitro" refers to procedures performed in an artificial environment such as, e.g., without limitation, in a test tube or culture medium.

As used herein, "in vivo" refers to procedures performed within a living organism such as, without limitation, a mouse, rat, rabbit ot human being.

A still further aspect of this invention is that the protein kinase whose catalytic activity is being modulated by a compound of this invention is selected from the group consisting of receptor protein tyrosine kinases, a cellular (or non-receptor) tyrosine kinases and serine-threonine kinases.

It is an aspect of this invention that the receptor protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R.

In addition, it is an aspect of this invention that the cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk.

Another aspect of this invention is that the serine-threonine protein kinase whose catalytic activity is modulated by a compound of this invention is selected from the group consisting of CDK2 and Raf.

A pharmaceutical composition of a compound of this invention with a pharmaceutically acceptable carrier or excipient is yet another aspect of this invention. Such pharmaceutical composition may contain both carriers and excipients as well as other components generally known to those skilled in the formulation of pharmaceutical compositions.

A method for treating or preventing a protein kinase related disorder in an organism comprising administering a therapeutically effective amount of a compound, salt or prodrug of this invention to an organism in need of such treatment is another aspect of this invention.

As used herein, "PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

As used herein, the terms "prevent", "preventing" and "prevention" refer to a method for barring an organism from acquiring a PK related disorder in the first place.

As used herein, the terms "treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukariotic cell or as complex as a mammal, including a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

It is an aspect of this invention that the above-referenced protein kinase related disorder is selected from the group consisting of a receptor protein tyrosine kinase related disorder, a cellular tyrosine kinase disorder and a serine-threonine kinase related disorder.

In yet another aspect of this invention, the above referenced protein kinase related disorder is selected from the group consisting of an EGFR related disorder, a PDGFR related disorder, an IGFR related disorder and a flk related disorder.

The above referenced protein kinase related disorder is a cancer selected from the group consisting of squamous cell carcinoma, sarcomas such as Kaposi's sarcoma, astrocytoma, glioblastoma, lung cancer, bladder cancer, colorectal cancer, gastrointestinal cancer, head and neck cancer, melanoma, ovarian cancer, prostate cancer, breast cancer, small-cell lung cancer and glioma in a further aspect of this invention.

The above referenced protein kinase related disorder is selected from the group consisting of diabetes, an autoimmune disorder, a hyperproliferation disorder, von Hippel-Lindau disease, restenosis, fibrosis, psoriasis, osteoarthritis, rheumatoid arthritis, an inflammatory disorder and angiogenesis in yet another aspect of this invention.

Additional disorders which may be treated or prevented using the compounds of this invention are immunological disorders such as autoimmune disease (AIDS) and cardiovasular disorders such as atherosclerosis.

It is as aspect of this invention that a chemical compound that modulates the catalytic activity of a protein kinase may be identified by contacting cells expressing said protein kinase with a compound, salt or prodrug of the present invention and then monitoring said cells for an effect.

By "monitoring" is meant observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

It is also an aspect of this invention that a compound described herein, or its salt or prodrug, might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidin analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound, salt or prodrug of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound, salt or prodrug of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound, salt or prodrug of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole).

Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia.

DETAILED DESCRIPTION OF THE INVENTION

1. Brief Description of the Tables

TABLE 1 shows the chemical structures of some exemplary compounds of this invention. The compound numbers correspond to the Example numbers in the Examples section. That is, the synthesis of Compound 1 in Table 1 is described in Example 1. The compounds presented in Table 1 are exemplary only and are not to be construed as limiting the scope of this invention in any manner.

TABLE 2 shows the results of biological testing of some exemplary compounds of this invention. The results are reported in terms of $IC_{50}$, the micromolar ($\mu M$) concentration of the compound being tested which causes a 50% change in the activity of the target PKT compared to the activity of the PTK in a control to which no test compound has been added. Specifically, the results shown indicate the concentration of a test compound needed to cause a 50% reduction of the activity of the target PTK. The bioassays used are described in detail below.

2. Indications/Target Diseases

The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transductions is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, *Neuron* 9:303–391.

It has been shown that tyrosine phosphorylation sites on growth factor receptors function as high-affinity binding sites for SH2 (src homology) domains of signaling molecules. Fantl et al., 1992, *Cell* 69:413–423, Songyang et al., 1994, *Mol. Cell. Biol.* 14:2777–2785), Songyang et al., 1993, *Cell* 72:767–778, and Koch et al., 1991, *Science* 252:668–678. Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. More specifically, it is thought that the 2-indolinone component of the compounds of this invention binds in the general space normally occupied by the adenine ring of ATP. Specificity of a particular molecule for a particular PK may then arise as the result of additional interactions between the various substituents on the 2-indolinone core and the amino acid domains specific to particular PKs. Thus, different indolinone substituents may contribute to preferential binding to particular PKs. The ability to select compounds active at different ATP (or other nucleotide) binding sites makes the compounds of this invention useful for targeting any protein with such a site. The compounds disclosed herein may thus have utility as in vitro assays for such proteins as well as exhibiting in vivo therapeutic effects through interaction with such proteins.

In another aspect, the protein kinase, the catalytic activity of which is modulated by contact with a compound of this invention, is a protein tyrosine kinase, more particularly, a receptor protein tyrosine kinase. Among the receptor protein tyrosine kinases whose catalytic activity can be modulated with a compound of this invention, or salt thereof, are, without limitation, EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R.

The protein tyrosine kinase whose catalytic activity is modulated by contact with a compound of this invention, or a salt or a prodrug thereof, can also be a non-receptor or cellular protein tyrosine kinase (CTK). Thus, the catalytic activity of CTKs such as, without limitation, Src, Frk, Btk, Csk, Abl, ZAP70, Fes, Fps, Fak, Jak, Ack, Yes, Fyn, Lyn, Lck, Blk, Hck, Fgr and Yrk, may be modulated by contact with a compound or salt of this invention.

Still another group of PKs which may have their catalytic activity modulated by contact with a compound of this invention are the serine-threonine protein kinases such as, without limitation, CDK2 and Raf.

In another aspect, this invention relates to a method for treating or preventing a PK related disorder by administering a therapeutically effective amount of a compound of this invention, or a salt or a prodrug thereof, to an organism.

It is also an aspect of this invention that a pharmaceutical composition containing a compound of this invention or a salt or prodrug thereof is administered to an organism for the purpose of preventing or treating a PK related disorder.

This invention is therefore directed to compounds that modulate PK signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders and metabolic disorders.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (fit-1) receptor (Shibuya et al., 1990, *Oncogene*, 5:519–524; De Vries et al., 1992, *Science*, 255:989–991) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, 1989, *Biochein. Biophys. Res. Comm.*, 161:851–858; Vaisman et al., 1990, *J. Biol. Chem.*, 265:19461–19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, 1993, *Current Biology*, 3(10)699–702; Houck, et al., 1992, *J. Biol. Chem.*, 267:26031–26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, *J. Biolocical Chem.*, 267(16) :10931–34. Uncontrolled vasculogenesis and/or angiogenesis has been associated with diseases such as diabetes as well as with malignant solid tumors that rely on vascularization for growth. Klagsburn & Soker, 1993, *Current Biology*, 3(10) :699–702; Folkham, 1991, *J. Natl. Cancer Inst.*, 82:4–6; Weidner, et al., 1991, *New Engl. J. Med.*, 324:1–5.

The surmised role of VEGF in endothelial cell proliferation and migration during angiogenesis and vasculogenesis indicates an important role for the KDR/FLK-1 receptor in these processes. Diseases such as diabetes mellitus (Folkman, 198, in *XIth Congress of Thrombosis and Haemostasis* (Verstraeta, et al., eds.), pp. 583–596, Leuven University Press, Leuven) and arthritis, as well as malignant tumor growth may result from uncontrolled angiogenesis. See e.g., Folkman, 1971, *N. Engl. J. Med.*, 285:1182–1186. The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., 1994, *DN&P*, 7(6):334–339. More particularly, the KDR/FLK-1 receptor's highly specific role in neovascularization make it a choice target for therapeutic approaches to the treatment of cancer and other diseases which involve the uncontrolled formation of blood vessels.

Thus, one aspect of the present invention relates to compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other component along the tyrosine kinase signal transduction pathway, they may also act directly on the tumor cells that result from uncontrolled angiogenesis.

Although the nomenclature of the human and murine counterparts of the generic "flk-I" receptor differ, they are, in many respects, interchangeable. The murine receptor, Flk-1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., 1993, *Cell*, 72:835–846; Quinn et al., 1993, *Proc. Natl. Acad. Sci. USA*, 90:7533–7537. FLK-1 also associates with and subsequently tyrosine phosphorylates human RTK substrates (e.g., PLC-γ or p85) when co-expressed in 293 cells (human embryonal kidney fibroblasts).

Models which rely upon the FLK-1 receptor therefore are directly applicable to understanding the KDR receptor. For example, use of the murine FLK-1 receptor in methods which identify compounds that regulate the murine signal transduction pathway are directly applicable to the identification of compounds which may be used to regulate the human signal transduction pathway, that is, which regulate activity related to the KDR receptor. Thus, chemical compounds identified as inhibitors of KDR/FLK-1 in vitro, can be confirmed in suitable in vivo models. Both in vivo mouse and rat animal models have been demonstrated to be of excellent value for the examination of the clinical potential of agents acting on the KDR/FLK-1 induced signal transduction pathway.

Thus, in one aspect, this invention is directed to compounds that regulate, modulate and/or inhibit vasculogenesis and/or angiogenesis by affecting the enzymatic activity of the KDR/FLK-1 receptor and interfering with the signal transduced by KDR/FLK-1. In another aspect, the present invention is directed to compounds which regulate, modulate and/or inhibit the KDR/FLK-1 mediated signal transduction pathway as a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggest the administration of compounds which inhibit the KDR/Flk-1 mediated signal transduction pathway may also be used in the treatment of hemangioma, restenois and diabetic retinopathy.

A further aspect of this invention relates to the inhibition of vasculogenesis and angiogenesis by other receptor-mediated pathways, including the pathway comprising the flt-1 receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signalling molecules that facilitate the appropriate cellular response, e.g., cell division and metabolic effects to the extracellular microenvironment. See, Schlessinger and Ullrich, 1992, *Neuron,* 9:1–20.

The close homology of the intracellular regions of KDR/FLK-1 with that of the PDGF-β receptor (50.3% homology) and/or the related flt-1 receptor indicates the induction of overlapping signal transduction pathways. For example, for the PDGF-β receptor, members of the src family (Twamley et al., 1993, *Proc. Natl. Acad. Sci. USA,* 90:7696–7700), phosphatidylinositol-3'-kinase (Hu et al., 1992, *Mol. Cell. Biol.,* 12:981–990), phospholipase cγ (Kashishian & Cooper, 1993, *Mol. Cell. Biol.,* 4:49–51), ras-GTPase-activating protein, (Kashishian et al., 1992, *EMBO J.,* 11:1373–1382), PTP-ID/syp (Kazlauskas et al., 1993, *Proc. Natl. Acad. Sci. USA,* 10 90:6939–6943), Grb2 (Arvidsson et al., 1994, *Mol. Cell. Biol.,* 14:6715–6726), and the adapter molecules Shc and Nck (Nishimura et al., 1993, *Mol. Cell. Biol.,* 13:6889–6896), have been shown to bind to regions involving different autophosphorylation sites. See generally, Claesson-Welsh, 1994, *Prog. Growth Factor Res.,* 5:37–54. Thus, it is likely that signal transduction pathways activated by KDR/FLK-1 include the ras pathway (Rozakis et al., 1992, *Nature,* 360:689–692), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, *Kidney International* 43:47S–54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, *Br. J. Cancer* 63:227–233, Torp et al., 1992, *APMIS* 100:713–719) HER2/neu (Slamon et al., 1989, *Science* 244:707–712) and PDGF-R (Kumabe et al., 1992, *Oncogene,* 7:627–633) are over-expressed in many tumors and/or persistently activated by autocrine loops. In fact, in the most common and severe cancers these receptor over-expressions (Akbasak and Suner-Akbasak et al., 1992, *J. Neurol. Sci.,* 111:119–133, Dickson et al., 1992, *Cancer Treatment Res.* 61:249–273, Korc et al., 1992, *J. Clin. Invest.* 90:1352–1360) and autocrine loops (Lee and Donoghue, 1992, *J. Cell. Biol.,* 118:1057–1070, Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.,* 50:2511–2517). In addition, IGF-I, while integrally involved in the normal growth and differentiation of the nervous system, also appears to be an autocrine stimulator of human gliomas. Sandberg-Nordqvist et al., 1993, *Cancer Res.* 53:2475–2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, *Eukarvotic Gene Expression,*1:301–326. In a series of recent publications, Baserga suggests that IGF-IR plays a central role in the mechanism of transformation and, as such, could be a preferred target for therapeutic interventions for a broad spectrum of human malignancies. Baserga, 1995, *Cancer Res.,* 55:249–252, Baserga, 1994, *Cell* 79:927–930, Coppola et al., 1994, *Mol. Cell. Biol.,* 14:4588–4595.

STKs have been implicated in many types of cancer including, notably, breast cancer (Cance, et al., *Int. J. Cancer,* 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-LR are indicated in type-II diabetes mellitus. A more complete correlation between specific RTKs and their therapeutic indications is set forth in Plowman et al., 1994, *DN&P* 7:334–339.

As noted previously, not only RTKs but CTKs including, but not limited to, src, abl, fps, yes, fyn, lyn, lck, blk, hck, fgr and yrk (reviewed by Bolen et al., 1992, *FASEB J.,* 6:3403–3409) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v-src}$) in chicken. Moreover, its cellular homolog, the proto-oncogene $pp60^{c-src}$ transmits oncogenic signals of many receptors. Over-expression of EGFR or HER2/neu in tumors leads to the constitutive activation of $pp60^{c\text{-}src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflamation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents.

Finally, both RTKs and CTKs are currently suspected as being involved in hyperimmune disorders.

A method for identifying a chemical compound that modulates the catalytic activity of one or more of the above discussed protein kinases is another aspect of this invention. The method involves contacting cells expressing the desired protein kinase with a compound of this invention (or its salt or prodrug) and monitoring the cells for any effect that the compound has on them. The effect may be any observable, either to the naked eye or through the use of instrumentation, change or absence of change in a cell phenotype. The change or absence of change in the cell phenotype monitored may be, for example, without limitation, a change or absence of change in the catalytic activity of the protein kinase in the cells or a change or absence of change in the interaction of the protein kinase with a natural binding partner.

Examples of the effect of a number of exemplary compounds of this invention on several PTKs are shown in Table 2. The compounds and data presented are not to be construed as limiting the scope of this invention in any manner whatsoever.

3. Pharmaceutical Compositions and Use

A compound of the present invention, a prodrug thereof or a physiologically acceptable salt of either the compound or its prodrug, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

As used herein, "administer" or "administration" refers to the delivery of a compound, salt or prodrug of the present invention or of a pharmaceutical composition containing a compound, salt or prodrug of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration ary oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired; to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PvP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the fomulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharamcologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80™, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addtion, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide (Ca(OH)$_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the IC$_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the IC$_{50}$ and the LD$_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

4. Synthesis

The compounds of this invention, as well as the precursor oxindoles and aldehydes, may be readily synthesized using techniques well known in the chemical arts. It will be appreciated by those skilled in the art that other synthetic pathways for forming the compounds of the invention are available and that the following is offered by way of example and not limitation.

General synthetic procedures.

The following general methodologies may be used to prepare intermediates to and compounds of this invention.

Preparation of substituted oxindoles

5-Amino-2-oxindole

5-Nitro-2-oxindole (6.3 g) was hydrogenated in methanol over 10% palladium on carbon to give 3.0 g (60% yield) of the title compound as a white solid.

5-Bromo-2-oxindole

2-Oxindole (1.3 g) in 20 mL acetonitrile was cooled to −10° C. and 2.0 g N-bromosuccinimide was slowly added with stirring. The reaction was stirred for 1 hour at −10° C. and 2 hours at 0° C. The precipitate was collected, washed with water and dried to give 1.9 g (90% yield) of the title compound.

4-Methyl-2-oxindole

Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6N hydrochloric acid. The resulting precipitate was collected by vacuum filtration, washed with water, and dried under vacuum to give 9.8 g (45% yield) of 2-methyl-6-nitrophenylacetic acid as an off-white solid. The solid was hydrogenated in methanol over 10% palladium on carbon to give 9.04 g of the title compound as a white solid.

7-Bromo-5-chloro-2-oxindole

5-Chloro-2-oxindole (16.8 g) and 19.6 g of N-bromosuccinimide were suspended in 140 mL of acetonitrile and refluxed for 3 hours. Thin layer chromatography (silica, ethyl acetate) at 2 hours of reflux showed 5-chloro-2-oxindole or N-bromosuccinimide (Rf 0.8), product (Rf 0.85) and a second product (Rf 0.9) whose proportions did not change after another hour of reflux. The mixture was cooled to 10° C., the precipitate was collected by vacuum filtration, washed with 25 mL of ethanol and sucked dry for 20 minutes in the funnel to give 14.1 g of wet product (56% yield). The solid was suspended in 200 mL of denatured ethanol and slurry-washed by stirring and refluxing for 10 minutes. The mixture was cooled in an ice bath to 10° C. The solid product was collected by vacuum filtration, washed with 25 mL of ethanol and dried under vacuum at 40° C. to give 12.7 g (51% yield) of 7-bromo-5-chloro-2-oxindole.

5-Fluoro-2-oxindole

5-Fluoroisatin (8.2 g) was dissolved in 50 mL of hydrazine hydrate and refluxed for 1.0 hr. The reaction mixtures were then poured in ice water. The precipitate was then filtered, washed with water and dried in a vacuum oven to afford the title compound.

5-Nitro-2-oxindole

2-Oxindole (6.5 g) was dissolved in 25 mL concentrated sulfuric acid and the mixture maintained at −10 to −15° C. while 2.1 mL of fuming nitric acid was added dropwise. After the addition of the nitric acid the reaction mixture was stirred at 0° C. for 0.5 hr and poured into ice-water. The precipitate was collected by filtration, washed with water and crystallized from 50% acetic acid. The crystalline product was then filtered, washed with water and dried under vacuum to give 6.3 g (70%) of 5-nitro-2-oxindole.

5-Aminosulfonyl-2-oxindole

To a 100 mL flask charged with 27 mL of chlorosulfonic acid was added slowly 13.3 g of 2-oxindole. The reaction temperature was maintained below 30° C. during the addition. After the addition, the reaction mixture was stirred at room temperature for 1.5 hr, heated to 68° C. for 1 hr, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of the title compound as an off-white solid.

5-Methylaminosulfonyl-2-oxindole

A suspension of 3.38 g of 5-chlorosulfonyl-2-oxindole in 10 mL 2M methylamine in tetrahydrofuran was stirred at room temperature for 4 hours during which time a white solid formed. The precipitate was collected by vacuum filtration, washed twice with 5 mL of water and dried under vacuum at 40° C. overnight to give 3.0 g (88% yield) of 5-methylaminosulfonyl-2-oxindole.

5-(4-Trifluoromethylphenylaminosulfonyl)-2-oxindole

A suspension of 2.1 g of 5-chlorosulfonyl-2-oxindole, 1.6 g of 4-trifluoromethylaniline and 1.4 g of pyridine in 20 mL of dichloromethane was stirred at room temperature for 4 hours. The precipitate which formed was collected by vacuum filtration, washed twice with 5 mL of water and dried under vacuum at 40° C. overnight to give 2.4 g of crude product containing some impurities by thin layer chromatography. The crude product was chromatographed on silica gel eluting with ethyl acetate:hexane (1:2) to give 1.2 g (37% yield) of 5-(4-trifluoromethylphenyl-aminosulfonyl)-2-oxindole.

5-(Morpholinosulfonyl)-2-oxindole

A suspension of 2.3 g of 5-chlorosulfonyl-2-oxindole and 2.2 g of morpholine in 50 mL of dichloromethane was stirred at room temperature for 3 hours. The white precipitate was collected by vacuum filtration, washed with ethyl acetate and hexane and dried under vacuum at 40° C. overnight to give 2.1 g (74% yield) of 5-(morpholinosulfonyl)-2-oxindole.

6-Trifluoromethyl-2-oxindole

Dimethylsulfoxide (330 mL) was added to 7.9 g of sodium hydride followed by dropwise addition of 43.6 g of diethyloxalate. The mixture was heated to 100° C. for 1.0 hour and cooled to room temperature. 2-Nitro-4-trifluoromethyltoluene (31.3 g) was added, the reaction stirred for 30 minutes at room temperature and then heated to 100° C. for 1 hour. The reaction was cooled and poured into a mixture of saturated aqueous ammonium chloride, ethyl acetate and hexane. The organic layer was washed with saturated ammonium chloride, water and brine, dried, and concentrated to give dimethyl 2-(2-nitro-4-trifluoromethylphenyl)malonate.

The diester was dissolved in a mixture of 6.4 g of lithium chloride and 2.7 mL of water in 100 mL of dimethylsulfoxide and heated to 100° C. for 3 hours. The reaction was cooled and poured into a mixture of ethyl acetate and brine. The organic phase was washed with brine, dried with sodium sulfate, concentrated and chromatographed on silica gel (10% ethyl acetate in hexane). The fractions containing product were evaporated to give 25.7 g of methyl 2-nitro-4-trifluoromethylphenylacetate.

Methyl 2-nitro-4-trifluoromethylphenylacetate (26 mg) was hydrogenated over 10% palladium on carbon and then heated at 100° C. for 3 hours. The catalyst was removed by filtration and the solvent evaporated to give the title compound.

4-Carboxy-2-oxindole

A solution of trimethylsilyldiazomethane in hexane (2M) was added dropwise to a solution of 2.01 g of 2-chloro-3-carboxy-nitrobenzene in 20 mL methanol at room temperature until no further gas evolution occurred. The excess trimethylsilyldiazo-methane was quenched with acetic acid. The reaction mixture was dried by rotary pump and the residue was further dried in a vacuum oven overnight. The product (2-chloro-3-methoxycarbonyl-nitrobenzene) was pure enough for the following reaction.

Dimethyl malonate (6.0 mL) was added to an ice-cold suspension of 2.1 g of sodium hydride in 15 mL of DMSO. The reaction mixture was then stirred at 100° C. for 1.0 h and then cooled to room temperature. 2-Chloro-3-methoxycarbonyl-nitrobenzene (2.15 g) was added to the above mixture in one portion and the mixture was heated to 100° C. for 1.5 h. The reaction mixture was then cooled to room temperature and poured into ice water, acidified to pH 5, and extracted with ethyl acetate. The organic layer was washed with brine, dried over anhydrous sodium sulfate and concentrated to give 3.0 g of the dimethyl 2-methoxycarbonyl-6-nitrophenylmalonate.

Dimethyl 2-methoxycarbonyl-6-nitrophenylmalonate (3.0 g) was refluxed in 50 mL of 6 N hydrochloric acid overnight. The mixture was concentrated to dryness and refluxed for 2 hours with 1.1 g of tin(II) chloride in 20 mL of ethanol. The mixture was filtered through Celite, concentrated and chromatographed on silica gel (ethyl acetate-:hexane:acetic acid) to give 0.65 g (37% yield) of 4-carboxy-2-oxindole as a white solid.

5-Carboxyethyl-2-oxindole

5-Cyanoethyl-2-oxindole (4.02 g) in 10 mL of water containing 25 mL of concentrated hydrochloric acid was refluxed for 4 hours. The mixture was cooled, water added and the resulting solid collected by vacuum filtration, washed with water and dried to give 1.9 g (44% yield) of the title compound as a yellow solid.

5-(Morpholin-4-ethyl)-2-oxindole

5-Chloroethyl-2-oxindole (2.3 g), 1.2 mL of morpholine and 1.2 mL of diisopropylethylamine were heated overnight at 100° C. in 10 mL of dimethylsulfoxide. The mixture ws cooled, poured into water and extacted with ethyl acetate. The organic layer was washed with brine, dried and evaporated. The residue was chromatographed on silica gel (5% methanol in chloroform) to give 0.9 g (31%) of the title compound as a white solid.

5-(4-Methoxycarbonylbenzamido)-2-oxindole

A mixture of 82.0 mg 5-amino-2-oxindole and 131.0 mg 4methoxycarbonylbenzoyl chloride in pyridine was stirred at room temperature for 3 hr and poured into ice water. The precipitate was filtered, washed with water and dried in a vacuum oven to give 138.0 mg of 5-(4-methoxycarbonylbenzamido)-2-oxindole (81% yield).

5-Methoxy-2-oxindole

Chloral hydrate (9.6 g) was dissolved in 200 mL of water containing 83 g of sodium sulfate. The solution was warmed to 60° C., a solution of 11.4 g of hydroxylamine hydrochloride in 50 mL of water was added and the mixture was held at 60° C. In a separate flask, 6.4 g of 4-anisidine and 4.3 mL of concentrated hydrochloric acid in 80 mL of water was warmed to 80° C. The first solution was added to the second and the mixture refluxed for 2 minutes after which it was cooled slowly to room temperature and then cooled in an ice bath. The tan precipitate was collected by vacuum filtration, washed with water and dried under vacuum to give 8.6 g (85% yield) of N-(2-hydroximinoacetyl)anisidine.

Concentrated sulfuric acid (45 mL) containing 5 mL of water was warmed to 60° C. and 8.6 g of N-(2-hydroximinoacetyl)anisidine was added in one portion. The stirred mixture was heated to 93° C. for 10 minutes and then allowed to cool to room temperature. The mixture was poured into 500 g of ice and extracted 3 times with ethyl acetate. The combined extracts were dried over anhydrous sodium sulfate and concentrated to give 5.1 g (65% yield) of 5-methoxyisatin as a dark red solid. 5-Methoxyisatin (5.0 g) and 30 mL of hydrazine hydrate were heated to reflux for 15 minutes. The reaction mixture was cooled to room temperature and 50 mL of water was added. The mixture was extracted 3 times with 25 mL of ethyl acetate each time, the organic layers combined, dried over anhydrous sodium sulfate and concentrated to give a yellow solid. The solid was stirred in ethyl acetate and 1.1 g of insoluble material was removed by vacuum filtration and saved. This material proved to be 2-hydrazinocarbonylmethyl-4-anisidine. The filtrate was concentrated and chromatographed on silica gel eluting with ethyl acetate:hexane (1:1) to give 0.7 g of 5-methoxy-2-oxindole as a yellow solid. The 1.1 g of 2-hydrazino-carbonylmethyl-4-anisidine was refluxed for 1 hour in 20 mL of 1N sodium hydroxide. The mixture was cooled, acidified to pH 2 with concentrated hydrochloric acid and extracted 3 times with 25 mL of ethyl acetate each time. The organic extracts were combined, washed with brine, dried over anhydrous sodium sulfate and concentrated to give 0.8 g of 5-methoxy-2-oxindole as a yellow solid. The combined yield was 1.5 g or 33%.

7-Azaoxindole 3,3-Dibromo-7-azaoxindole (2.9 g) was dissolved in a mixture of 20 mL of acetic acid and 30 mL of acetonitrile. To the solution was added 6.5 g of zinc dust. The mixture was stirred for 2 hrs at room temperature. The solid was filtered from the mixture and the solvent evaporated. The residue was slurried with ethyl acetate. The ethyl acetate solution containing insoluble solid was passed through a short column of silica gel. The collected ethyl acetate solution was evaporated and the residue dried under vacuum to give 1.8 g (yield 91%) of 7-azaoxindole acetic acid salt.

5-Dimethylaminosulfonyl-2-oxindole

A suspension of 2.3 g 5-chlorosulfonyl-2-oxindole in 10 mL 2M dimethylamine in methanol was stirred at room temperature for 4 hours at which time a white solid formed. The precipitate was collected by vacuum filtration, washed with 5 mL of 1N sodium hydroxide and 5 mL of 1N hydrochloric acid and dried under vacuum at 40° C. overnight to give 1.9 g (79% yield) of 5-dimethylaminosulfonyl-2-oxindole.

6-Phenyl-2-oxindole

Dimethyl malonate (10 mL) in 25 mL of dimethylsulfoxide was added dropwise to 3.5 g sodium hydride suspended in 25 mL dimethylsulfoxide and the mixture heated at 100° C. for 10 minutes. The mixture was cooled to room temperature and 4.7 g of 4-fluoro-3-nitrobiphenyl in 25 mL dimethylsulfoxide was added. The mixture was heated at 100° C. for 2 hours, cooled and quenched with 300 mL of saturated ammonium chloride solution. The mixture was extracted three times with ethyl acetate and the combined organic layers washed with water and brine and evaporated to give, as a yellow oil, crude dimethyl-3-nitrobiphenyl-4-malonate.

Crude dimethyl-3-nitrobiphenyl-4-malonate was refluxed in 30 mL of 6 N hydrochloric acid for 24 hours. The precipitate was collected by filtration, washed with water and dried to give 4.5 g of 3-nitrobiphenyl-4-acetic acid as a cream colored solid.

Iron powder (2.6 g) was added all at once to 4.5 g of 3-nitrobiphenyl-4-acetic acid in 40 mL of acetic acid. The mixture was refluxed for 2 hours, concentrated to dryness and taken up in ethyl acetate. The solids were removed by filtration and the filtrate washed twice with 1N hydrochloric acid and brine and dried over anhydrous sodium sulfate. The filtrate was concentrated to give 3.4 g (93% yield) of 6-phenyl-2-oxindole as a light brown solid.

6-(3-Methoxyphenyl)-2-oxindole

Tetrakis(triphenylphosphine)palladium (0.8 g) was added to a mixture of 5 g 3-methoxyphenylboronic acid, 5 g 5-bromo-2-fluoro-nitrobenzene and 11 mL of 2 M sodium carbonate solution in 100 mL of toluene. The mixture was refluxed for 2 hours, diluted with water and extracted with ethyl acetate. The ethyl acetate was washed with saturated sodium bicarbonate and brine and then dried and concentrated to give an oily solid. The solid was chromatographed on silica gel (ethyl acetate:hexane (1:6)) to give 4.3 g (77% yield) of 4-fluoro-3'-methoxy-3-nitrobiphenyl.

Dimethyl malonate (9.7 mL) was added dropwise to 2.0 g sodium hydride suspended in 50 mL dimethylsulfoxide. The mixture was heated to 100° C. for 35 minutes and cooled to room temperature. 4-Fluoro-2'-methoxy-3-nitrobiphenyl (4.2 g) in 50 mL dimethylsulfoxide was added and the mixture was heated at 100° C. for 1 hour. The reaction mixture was cooled and quenched with 300 mL of saturated ammonium chloride solution and extracted twice with ethyl acetate. The extracts were combined, washed with brine, dried over anhydrous sodium sulfate and concentrated to give crude dimethyl 3'-methoxy-3-nitrobiphenyl-4-malonate as a pale yellow solid.

Crude dimethyl 3'-methoxy-3-nitrobiphenyl-4-malonate was heated at 110° C. in 45 mL 6N hydrochloric acid for 4 days and then cooled. The precipitate was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g of 10% palladium on carbon for 3 hours at room temperature. The catalyst was removed by filtration, washed with methanol and the filtrates combined and concentrated to give a brown solid. The solid was chromatographed on silica gel in ethyl acetate:hexane:acetic acid (33:66:1) to give 3.0 g of 6-(3-methoxypheny)-2-oxindole as a pink solid.

5-Acetyl-2-oxindole

2-Oxindole (3 g) was suspended in 1,2-dichloroethane and 3.2 mL acetyl chloride were slowly added. The resulting suspension was heated to 50° C. for 5 hours, cooled, and poured into water. The resulting precipitate was collected by vacuum filtration, washed copiously with water and dried under vacuum to give 2.9 g (73% yield) of the title compound as a brown solid.

5-Cyanoethyl-2-oxindole

Potassium cyanide (2.0 g) was added to 15 mL of dimethyl-sulfoxide and heated to 90° C. 5-Chloroethyl-2-oxindole (3.0 g) dissolved in 5 mL dimethyl sulfoxide was added slowly with stirring, and the reaction heated to 150° C. for 2 hours. The mixture was cooled, poured into ice water and the precipitate collected by vacuum filtration, washed with water, dried and then chromatographed on silica gel (5% methanol in chloroform) to give 1.2 g (42% yield) of the title compound.

6-(Morpholin-4-yl)-2-oxindole

6-Amino-2-oxindole (2.2 g), 4.0 g 2,2'-dibromoethyl ether and 7.9 g sodium carbonate were refluxed in 20 ml ethanol overnight, concentrated and diluted with 50 ml of water. The mixture was extracted three times with 50 ml of ethyl acetate and the organic extracts combined, washed with 20 ml of brine, dried over anhydrous sodium sulfate and concentrated to dryness. The solid was chromatographed on a column of silica gel (ethyl acetate:hexane (1:1) containing 0.7% acetic acid) to give 1.2 g (37% yield) of the title compound as a beige solid.

Methylation of phenols

An appropriate phenol (1 equivalent) is stirred overnight at room temperature with an equal volume of dimethylformamide containing 1.3 equivalents of methyl iodide and 1.3 equivalents of potassium carbonate. The mixture is diluted with water and extracted with ethyl acetate. The ethyl acetate layer is washed with water and brine. The organic layer is separated, dried over anhydrous sodium sulfate and evaporated to dryness to give the anisole derivative.

Formylation of anisoles

The anisole (1 equivalent), dimethylformamide (1–3 equivalents) and phosphorus oxychloride (1–3 equivalents) are heated to 100° C. for 1–3 hours. The reaction mixture is cooled to room temperature and dichloromethane is added. The mixture is cooled in ice and water is then added, followed by 4–12 equivalents of concentrated sodium hydroxide until a pH of 9–10 is reached. The organic layer is separated and washed with water and then with brine, dried over anhydrous sodium sulfate and evaporated to give the crude aldehyde. The crude aledehyde is dissolved in boiling hexane containing activated carbon and the hexane solution is decanted and filtered hot through a layer of silica gel. The filtrate is evaporated to dryness to give the benzaldehyde derivative.

Formylation of pyrroles $POCl_3$ (1.1 equiv.) is added dropwise to dimethylformamide (3 equiv.) in dichloromethane at −10° C. followed by the appropriate pyrrole. After stirring for two hours, the reaction mixture is diluted with $H_2O$ and basified to pH 11 with 10 N KOH. The precipitate which forms is collected by filtration, washed with $H_2O$ and dried in a vacuum oven to give the desired aldehyde.

Saponification of pyrrolecarboxylic acid esters

A mixture of a pyrrolecarboxylic acid ester and KOH (2–4 equiv.) in EtOH is refluxed until reaction completion is indicated by thin layer chromatography (TLC). The cooled reaction mixtrue is acidified to pH 3 with 1 N HCl. The precipitate which forms is collected by filtration, washed with $H_2O$ and dried in a vacuum oven to give the desired pyrrolecarboxylic acid.

Amidation of pyrrolecarboxylic acids

To a stirred solution of a pyrrolecarboxylic acid dissolved in dimethylformamide(0.3M) is added 1-ethyl-3-(3-dimethylaminopropyl)carboiimide (1.2 equiv.), 1-hydroxybenzotriazole (1.2 equiv.), and triethylamine (2 equiv.). The appropriate amine is added (1 equiv.) and the reaction stirred until completion is indicated by TLC. The reaction is diluted with saturated $NaHCO_3$ and brine (with extra salt), dried over anhydrous $MgSO_4$ and concentrated to afford the desired amide.

Preparation of pyrrole and indole carbaldehydes

3-(2-Formyl-5-methyl-1N-pyrrol-3-yl)propionic acid 4-(2-Carboxyethyl)-3-ethoxycarbonyl-2-methylpyrrole (Bulter, A. R., and George, S. D. (1993) Tetrahedron 49: 7017–7026) was hydrolyzed using potassium hydroxide (KOH) in ethanol (EtOH) to give 4-(2-carboxyethyl)-2-methyl-1H-pyrrole-3-carboxylic acid (64%).

$^1$HNMR (DMSO-$d_6$) δ11.63 (s, 1H, COOH), 10.81 (s, 1H, NH), 6.36 (s, 1H, CH), 2.78, 2.45 (2×t, 4H, $CH_2CH_2$), 2.34(s, 3H, $CH_3$).

MS m/z 225 [M+2].

4-(2-Carboxyethyl)-2-methyl-1H-pyrrole-3-carboxylic acid was decarboxylated by heating for one hour at 200° C. to give 3-(5-methyl-1H-pyrrole-3-yl)propionic acid.

$^1$HNMR (DMSO-$d_6$) δ10.07 (s, 1H, NH), 9.60 (br s, 1H, COOH), 6.30 (s, 1H, CH), 5.56 (s, 1H, CH), 2.51, 2.36 (2×t, 4H, $CH_2CH_2$), 2.10(s, 3H, $CH_3$).

MS m/z 154 [M+1].

3-(5-Methyl-1H-pyrrol-3-yl)propionic acid was formylated using phosphorus oxycloride ($POCl_3$) and N,N-dimethylformamide (DMF) to give 3-(2-formyl-5-methyl-1H-pyrrole-3-yl)propionic acid.

$^1$HNMR (300 MHz, DMSO-$d_6$) δ12.09 (br s, 1H, COOH), 11.54 (br s, 1H, NH), 9.44 (s, 1H, CHO), 5.86 (d, J=1.8 Hz, 1H), 2.87 (t, J=7.5 Hz, 2H, $CH_2$), 2.47 (t, J=7.5 Hz, 2H, $CH_2$), 2.16 (s, 3H, $CH_3$).

MS–EI m/z 181 [M$^+$].

4-(2-Carboxyethyl)-5-formyl-3-methyl-1H-pyrrole-2-carboxylic acid ethyl ester To a suspension of 10 g (38.9 mmol) ethyl 2,4-dimethyl-5-(ethoxycarbonyl)-3-pyrrolepropionate (commercially available) in a mixture of water (250 mL) and methanol (MeOH) (50 mL) was added 3.0 g of KOH in 50 mL of water. The mixture was stirred at 70° C. for 4 hr. The reaction mixture was cooled and the methanol was stripped from the mixture under vacuum. The remaining solution was filtered and the filtrate was then acidified with 6N hydrochloric acid to pH 3. The precipitate which formed was collected by filtration, washed with a 2:1 mixture of water and ethanol and dried under vacuum to give 7.5 g of 4-(2-carboxy-ethyl)-3,5-dimethyl-1H-pyrrole-2-carboxylic acid ethyl ester as a white solid.

$^1$HNMR (360 MHz, DMSO-$d_2$) δ12.03 (br s, 1H, COOH), 11.02 (br s, 1H, NH), 4.16 (q, J=7.2 Hz, 2H, $OCH_2CH_3$). 2.53 (t, J=7.8 Hz, 2H, $CH_2CH_2$), 2.25 (t, J=7.8 Hz, 2H, $CH_2CH_2$), 2.16 (s, 3H, $CH_3$), 2.11 (s, 3H, $CH_3$), 1.25 (t, J=7.2 Hz, 3H, $OCH_2CH_3$).

MS–EI m/z 239 [M$^+$].

To a mixture of 7 g 4-(2-carboxyethyl)-3,5-dimethyl-1H-pyrrole-2-carboxylic acid ethyl ester in 35 mL each of tetrahydrofuran (THF), acetic acid (AcOH) and water at −10° C. was added 70 g of ceric ammonium nitrate in portion over 20 minutes, the reaction temperature being maintained at about 5° C. The resulting mixture was them cooled to 0° C., stirred for another 2 hr and then diluted with 250 mL of brine. The mixture was then extracted with 2×300 mL 10% MeOH in dichloromethane (DCM). The organic extracts were combined and dried over anhydrous magnesium sulfate ($MgSO_4$), filtered and concentrated. The residue was purified on silica gel column with hexanes(hex)/ethyl acetate (EtOAc)/AcOH (6:4:0.05) followed by crystallization in EtOAc to give 1.5 g of 4-(2-carboxyethyl)-5-formyl-3-methyl-1H-pyrrole-2-carboxylic acid ethyl ester as a white solid.

$^1$HNMR (360 MHz, DMSO-$d_6$) δ12.36 (br s, 1H, COOH), 12.01 (br s, 1H, NH), 9.77 (s, 1H, CHO), 4.27 (q, J=7.1 Hz, 2H, $OCH_2CH_3$), 2.89 (t, J=7.6 Hz, 2H, $CH_2CH_2$), 2.37 (t, J=7.6 Hz, 2H, $CH_2CH_2$), 2.21 (s, 3H, $CH_3$), 1.30 (t, J=7.1 Hz, 3H, $OCH_2CH_3$).

MS–EI m/z 253 [M$^+$].

4-(3-Dimethylaminopropyl)-5-formyl-2-methyl-1H-pyrrole-3-carboxylic acid ethyl ester To a suspension of 4-(2-carboxyethyl)-3-ethoxycarbonyl-2-methylpyrrole (2 g, 8.88 mmol) (Bulter, A. R., and George, S. D. (1993) Tetrahedron 49: 7017–7026) in 18 mL of DMF was added 1.73 g (10.65 mmol) 1,1'-carbonyldiimidazole (CDI) followed by the dropwise addition of 8.9 mL (17.76 mmol) of 2M dimethylamine in THF. After stirring for 2 hr, the reaction was diluted with water (200 mL) and cooled. The precipitate which formed was collected by filtration, washed with water and dried to give 1.0 g of the product as a white crystalline solid. The filtrate was extracted with EtOAc, the organic layer was washed with brine, dried and concentrated to obtain an additional 0.9 g of the product for a total of 1.9 g of 4-(2-dimethylcarbamoyl-ethyl)-2-methyl-1H-pyrrole-3-carboxylic acid ethyl ester (85%).

$^1$HNMR (360 MHz, DMSO-$d_6$) δ10.89 (br s, 1H, NH), 6.40 (d, J=2.5 Hz, 1H), 4.13 (q, J=7.1 Hz, 2H, $OCH_2CH_3$), 2.92 (s, 3H, $NCH_3$), 2.79 (s, 3H, $NCH_3$), 2.75 (m, 2H, $CH_2CH_2$), 2.45 (m, 2H, $CH_2CH_2$), 2.35 (s, 3H, $CH_3$), 1.23 (t, J=7.1 Hz, 3H, $OCH_2CH_3$).

MS–EI m/z 252 [M$^+$].

To a heterogeneous mixture of 4-(2-dimethylcarbamoyl-ethyl)-2-methyl-1H-pyrrole-3-carboxylic acid ethyl ester (1.01 g, 4 mmol) in THF (9 mL) was added dropwise 8 mL of borane-tetrahydrofuran complex (1M in THF). The mixture was refluxed overnight. Then 9.0 mL of MeOH was added slowly to the reaction and refluxing was continued for another 2 hr. The reaction mixture was cooled, quenched with 1N HCl and extracted with EtOAc. The aqueous layer was basified with aqueous KOH and extracted with EtOAc. The EtOAc extract was washed with brine, dried and concentrated to give 616 mg (65%) of 4-(3-dimethylaminopropyl)-2-methyl-1H-pyrrole-3-carboxylic acid ethyl ester as a faint orange oil.

$^1$HNMR (360 MHz, DMSO-$d_6$) δ10.84 (br s, 1H, NH), 6.36 (d, J=2.5 Hz, 1H), 4.12 (q, J=7.1 Hz, 2H, $OCH_2CH_3$), 2.52 (m, 2H, $CH_2$), 2.34 (s, 3H, $CH_3$), 2.17 (m, 2H, $CH_2$), 2.08 (s, 6H, $N(CH_3)_2$), 1.57 (m, 2H, $CH_2CH_2$), 1.23 (t, J=7.1 Hz, 3H, $OCH_2CH_3$).

MS–EI m/z 238 [M$^+$].

4-(3-Dimethylaminopropyl)-2-methyl-1H-pyrrole-3-carboxylic acid ethyl ester (600 mg, 2.5 mmol) was formylated using $POCl_3$ and DMF to give 645 mg (96%) of 4-(3-dimethylamino-propyl)-5-formyl-2-methyl-1H-pyrrole-3-carboxylic acid ethyl ester.

$^1$HNMR (360 MHz, DMSO-$d_6$) δ12.15 (br s, 1H, NH), 9.59 (s, 1H, CHO), 4.19 (q, J=7.2 Hz, 2H, $OCH_2CH_3$), 2.93 (m, 2H, $CH_2$), 2.41 (s, 3H, $CH_3$), 2.18 (m, 2H, $CH_2$), 2.09 (s, 6H, $N(CH_3)_2$), 1.63 (m, 2H, $CH_2CH_2 CH_2$), 1.27 (t, J=7.2 Hz, 3H, $OCH_2CH_3$).

MS–EI m/z 266 [M$^+$].

3-(3-Dimethylaminopropyl)-1H-indole-2-carbaldehyde

Ethyl indole-2-carboxylate (10 g, 52.8 mmol) was formylated using $POCl_3$ (1.3 equiv.) and DMF (1.3 equiv.) as above to give 3-formyl-1H-indole-2-carboxylic acid ethyl ester as a white solid.

$^1$HNMR (360 MHz, DMSO-$d_6$) δ12.0 (br s, 1H, NH), 10.6 (s, 1H, CHO), 8.24 (dd, J=0.7 & 8.0 Hz, 1H), 7.57 (d, 1H), 7.38 (m, 1H), 7.26 (m, 1H), 4.44 (q, J=7.12 Hz, 2H, $OCH_2CH_3$), 1.39 (t, J=7.12 Hz, 3H, $OCH_2CH_3$).

MS–EI m/z 217 [M$^+$].

Butyllithium (1.1 equiv.) was added to a suspension of (2-dimethylaminoethyl)triphenylphosphonium bromide in THF (0.2 M) at 0° C. After stirring for 30 minutes, lithium diethylamine (1.1 equiv.) was added dropwise followed by the cold suspension of 3-formyl-1H-indole-2-carboxylic acid ethyl ester (3.96 g, 18.2 mmol) in THF. The resulting orange suspension was stirred for 18 hours. The reaction was then quenched with saturated ammonium chloride and extracted with 10% MeOH in DCM. The organic layer was washed with saturated sodium bicarbonate, dried and concentrated to give 3-(3-dimethylaminopropenyl)-1H-indole-2-carboxylic acid ethyl ester as a brownish-red waxy solid.

$^1$HNMR (360 MHz, DMSO-$d_6$) δ11.8 (br s, 1H, NH), 7.93 (d, 1H), 7.49 (d, 1H), 7.41 (d, 1H), 7.3 (t, 1H), 7.14 (t, 1H), 6.33–6.42 (m, 1H), 4.36 (q, 2H, $OCH_2CH_3$), 3.38 (d, 2H, $CH_2$), 2.44 (s, 6H, 2×$CH_3$), 1.36 (t, 3H, $OCH_2CH_3$).

MS–EI m/z 272 [M$^+$].

3-(3-Dimethylaminopropenyl)-1H-indole-2-carboxylic acid ethyl ester was hydrogenated using 10% palladium over carbon to reduce the double bond followed by a lithium aluminum hydride (LAH) reduction of the ester group to an alcohol resulting in the formation of [3-(3-dimethylaminopropyl)-1H-indol-2-yl]methanol as an orange oil.

Manganese dioxide (10 equiv.) was added to a solution of [3-(3-dimethylaminopropyl)-1H-indol-2-yl]methanol (2.2 g) in DCM. The mixture was stirred at room temperature for 18 hr. Insoluble materials were removed by filtration and the filtrate was concentrated. The residue was column chromatographed to give 3-(3-dimethylaminopropyl)-1H-indole-2-carbaldehyde as a cream-colored solid.

$^1$HNMR (300 MHz, DMSO-$d_6$) δ11.58 (br s, 1H, NH), 10.0 (s, 1H, CHO), 7.72 (d, 1H), 7.39 (d, 1H), 7.29 (t, 1H), 7.07 (t, 1H), 3.08 (t, 2H, $CH_2$), 2.20 (t, 2H), 2.12 (s, 6H, 2×$CH_3$), 1.73 (t, 2H, $CH_2$).

MS–EI m/z 230 [M$^+$].

Preparation of aminotetrahydoindolecarbaldehydes

A mixture of 5-aminolevulinic acid hydrochloride (1 equiv.), 1,3-cyclohexanedione (1 equiv.) and sodium acetate (2 equiv.) in water (1M) is stirred at 110° C. for 4–12 hr and then cooled. The precipitate which forms is collected by vacuum filtration, washed with 30% ethanol in water and dried under vacuum to give the amido-keto-tetrahydroindole in 50–70% yield.

Lithium aluminum hydride (LAH, 4 equiv.)is added dropwise to a suspension of the appropriate amido-keto-tetrahydroindole (1 equiv.) in THF (0.5 M). The mixture is refluxed overnight. The mixture is then cooled and water is added carefully until no more gas is generated, then a few drops of 15% NaOH/water is added. The mixture is then stirred at room temperature for 0.5 hr and filtered to remove insoluble materials. The filtrate is concentrated to give the amino-tetrahydroindole.

Examples of syntheses of aminotetrahydroindolecarbaldehydes

The following syntheses of aminotetrahydroindolecarbaldehydes are shown by way of example only and are not to be construed as limiting the scope of this invention in any manner whatsoever.

3-[3-(4-methylpiperazin-1-yl)propyl]-4,5,6,7-tetrahydro-1H-indole-2-carbaldehyde Step 1: A mixture of 5-aminolevulinic acid hydrochloride (1.68 g, 10 mmol), 1,3-cyclohexanedione (1.12 g, 10 mmol) and sodium acetate (1.64 g, 20 mmol) in water (10 mL) was stirred at 110° C. for 4 hr and then cooled. The precipitate which formed was collected by vacuum filtration, washed with 30% of ethanol in water and dried under vacuum to give 1.7 g (82%) of 3-(4-oxo-4,5,6,7-tetrahydro-1H-indol-3-yl)-propionic acid.

$^1$HNMR (360 MHz, DMSO-d6) δ11.91 (br s, 1H, COOH), 10.99 (br s, 1H, NH), 6.45 (d, J=1.4 Hz, 1H), 2.76 (t, 2H, $CH_2$), 2.69 (t, 2H, $CH_2$), 2.44 (t, 2H, $CH_2$), 2.26 (t, 2H, $CH_2$), 1.96 (m, 2H, $CH_2$).

MS–EI m/z 207 [M$^+$].

Step 2: To a suspension of 10 g of the product of step 1 (48 mmol) in dichloromethane(60 mL) was added 9.3 g (57.6 mmol) of 1,1'-carbonyldiimidazole. The mixture was stirred at room temperature for 2 hours and then 5.3 mL (48 mmol) 1-methylpiperazine and 8.4 mL (48 mmol) N,N-diisopropylethylamine was added. The dark red reaction mixture was then stirred at room temperature overnight. The reaction was then poured into water, the organic layer separated and washed with brine, dried and concentrated to give 8 g (57%) of 3-[3-(4-methylpiperazin-1-yl)-3-oxo-propyl]-1,5,6,7-tetrahydroindol-4-one.

$^1$HNMR (360 MHz, DMSO-d6) δ10.97 (br s, 1H, NH), 6.47 (d, J=2.0 Hz, 1H), 3.43 (m, 4H, 2×$CH_2$), 2.67–2.75 (m, 4H, 2×$CH_2$), 2.51 (m, 2H, $CH_2$), 2.27 (m, 2H, $CH_2$), 2.20 (m, 4H, 2×$CH_2$), 2.15 (s, 3H, $CH_3$), 1.97 (m, 2H, $CH_2$).

MS–EI m/z 289 [M$^+$].

Step 3: LAH (2.6 g, 68 mmol) was added dropwise to a suspension of 3-[3-(4-methylpiperazin-1-yl)-3-oxo-propyl]-1,5,6,7-tetrahydroindol-4-one (5 g, 17 mmol) in THF (300 mL). The mixture was then refluxed overnight. The mixture was then cooled and 2.6 mL each of water followed by a few drops of 15% NaOH was added. The reaction was stirred at room temperature for 30 min and then filtered to remove insolubles. The filtrate was concentrated to give 4.5 g (100%) of 3-[3-(4-methylpiperazin-1-yl)propyl]-4,5,6,7-tetrahydro-1H-indole.

$^1$HNMR (360 MHz, DMSO-d6) δ9.79 (br s, 1H, NH), 6.22 (d, J=2.0 Hz, 1H), 2.44 (m, 2H, $CH_2$), 2.21–2.3 (m, 14H, 7×$CH_2$), 2.12 (s, 3H, $CH_3$), 1.65 (m, 4H, 2×$CH_2$), 1.53 (m, 2H, $CH_2$).

MS–EI m/z 261 [M$^+$].

Step 4: POCl$_3$ (1.8 mL, 18.9 mmol) was added dropwise to N,N-dimethylformamide(DMF, 3.8 mL, 51.6 mmol) at −5° C. The mixture was then allowed to come to room temperature and then stirred for 30 minutes after which it was again cooled to −5° C. A solution of 3-[3-(4-methylpiperazin-1-yl)-propyl]-4,5,6,7-tetrahydro-1H-indole (4.5 g, 17.2 mmol) in DMF (9 mL) was added dropwise. The mixture was again allowed to come to room temperature and then stirred at that temperature overnight. The reaction was then quenched with ice, followed by 10 N NaOH to adjust the pH to 10–11. After stirring at room temperature for 1 hr, the reaction was extracted with ethyl acetate (EtOAc), the organic layer separated, washed with brine, dried and concentrated to give 3.1 g (62%) of 3-[3-(4-methylpiperazin-1-yl)-propyl]-4,5,6,7-tetrahydro-1H-indole-2-carbaldehyde.

$^1$HNMR (360 MHz, DMSO-d6) δ11.24 (br, s, 1H, NH), 9.42 (s, 1H, CHO), 2.60 (t, 2H, $CH_2$), 2.51 (m, 2H, $CH_2$), 2.35 (m, 2H, $CH_2$), 2.28 (m, 8H, 4×$CH_2$), 2.21 (m, 2H, $CH_2$), 2.12 (s, 3H, $CH_3$), 1.57–1.68 (m, 6H, 3×$CH_2$).

MS–EI m/z 289 [M$^+$].

3-(3-dimethylaminopropyl)-4,5,6,7-tetrahydro-1H-indole-2-carbaldehyde

The procedure was the same as that employed in Example A except that the amine in Step 2 was dimethylamine (2.0M solution in tetrahydrofuran).

Step 2:

N,N-Dimethyl-3-(4-oxo-4,5,6,7-tetrahydro-1H-indol-3-yl)-propionamide $^1$HNMR (300 MHz, DMSO-d6) δ11.0 (br s, 1H, NH), 6.48 (d, J=1.6 Hz, 1H), 2.95 (s, 3H, $CH_3$), 2.79 (s, 3H, $CH_3$), 2.71 (m, 4H, 2×$CH_2$), 2.47 (m, 2H, $CH_2$), 2.27 (t, 2H, $CH_2$), 1.96 (m, 2H, $CH_2$).

MS–EI m/z 234 [M$^+$].

Step 3:

Dimethyl-[3-(4,5,6,7-tetrahydro-1H-indol-3-yl)propyl]-amine $^1$HNMR (300 MHz, DMSO-d6) δ9.83 (br s, 1H, NH), 6.22 (d, J=2.3 Hz, 1H), 2.43 (m, 2H, $CH_2$), 2.28 (m, 2H, $CH_2$), 2.14–2.25 (m, 4H, $CH_2$), 2.08 (s, 6H, $N(CH_3)_2$), 1.64 (m, 4H, 2×$CH_2$), 1.53 (m, 2H, $CH_2$).

MS–EI m/z 206 [M$^+$].

Step 4:

3-(3-Dimethylaminopropyl)-4,5,6,7-tetrahydro-1H-indole-2-carbaldehyde $^1$HNMR (300 MHz, DMSO-d6) δ11.29 (br, s, 1H, NH), 9.40 (s, 1H, CHO), 2.59 (t, 2H, $CH_2$), 2.5 (m, 2H, $CH_2$), 2.34 (m, 2H, $CH_2$), 2.16 (m, 2H, $CH_2$), 2.08 (s, 6H, $N(CH_3)_2$), 1.67 (m, 4H, 2×$CH_2$), 1.56 (m, 2H, $CH_2$).

MS–EI m/z 234 [M$^+$].

3-(3-pyrrolidin-1-ylpropyl)-4,5,6,7-tetrahydro-1H-indole-2-carbaldehyde

The procedure employed was that same as that in Example A except that the amine used in Step 2 was pyrrolidine.

Step 2:

3-(3-Oxo-3-pyrrolidin-1-ylpropyl)-1,5,6,7-tetrahydroindol-4-one $^1$HNMR (300 MHz, DMSO-d6) δ11.05 (br s, 1H, NH), 6.46 (d, J=1.5 Hz, 1H), 3.35 (m, 2H, $CH_2$), 2.24 (m, 2H, $CH_2$), 2.66–2.73 (m, 4H, 2×$CH_2$), 2.44 (m, 2H, $CH_2$), 2.26 (m, 2H, $CH_2$), 1.96 (m, 2H, $CH_2$), 1.82 (m, 2H, $CH_2$), 1.73 (m, 2H, $CH_2$).

MS–EI m/z 260 [M$^+$].

Step 3:

3-(3-Pyrrolidin-1-ylpropyl)-4,5,6,7-tetrahydro-1H-indole $^1$HNMR (300 MHz, DMSO-d6) δ9.82 (br s, 1H, NH), 6.22 (s, 1H), 2.2–2.5 (m, 12H, 6×CH$_2$), 1.5–1.64(m, 10H, 5×CH$_2$).

MS–EI m/z 232 [M$^+$].

Step 4:

3-(3-Pyrrolidin-1-ylpropyl)-4,5,6,7-tetrahydro-1H-indole-2-carbaldehyde $^1$HNMR (300 MHz, DMSO-d6) δ11.28 (br, s, 1H, NH), 9.38 (s, 1H, CHO), 2.59 (t, 2H, CH$_2$), 2.46 (m, 2H, CH$_2$), 2.3–2.44 (m, 8H, 4×CH$_2$), 1.55–1.65 (m, 10H, 5×CH$_2$).

MS–EI m/z 260 [M$^+$].

3-(3-diethylamino-propyl)-4,5,6,7-tetrahydro-1H-indole-2-carbaldehyde

The procedure used was the same as that in Example A except that the amine used was diethylamine.

Step 2:

N,N-Diethyl-3-(4-oxo-4,5,6,7-tetrahydro-1H-indol-3-yl)-propionamide $^1$HNMR (300 MHz, DMSO-d6) δ11.0 (br s, 1H, NH), 6.47 (d, J=2.0 Hz, 1H), 3.24 (m, 4H, N(CH$_2$CH$_3$)$_2$), 2.69 (m, 4H, 2×CH$_2$), 2.46 (m, 2H, CH$_2$), 2.27 (m, 2H, CH$_2$), 1.96 (m, 2H, CH$_2$), 1.04 (t, J=7.0 Hz, 3H, NCH$_2$CH$_3$), 0.98 (t, J=7.0 Hz, 3H, NCH$_2$CH$_3$).

Step 3:

Diethyl-[3-(4,5,6,7-tetrahydro-1H-indol-3-yl)-propyl]-amine $^1$HNMR (300 MHz, DMSO-d6) δ9.83 (br s, 1H, NH), 6.22 (d, J=2.0 Hz, 1H), 2.19–2.44 (m, 12H, 6×CH$_2$), 1.64(m, 4H, 2×CH$_2$), 1.51 (m, 2H, CH$_2$), 0.90 (t, J=7.0 Hz, 6H, N(CH$_2$CH$_3$)$_2$).

MS–EI m/z 234 [M$^+$].

Step 4:

3-(3-Diethylaminopropyl)-4,5,6,7-tetrahydro-1H-indole-2-carbaldehyde $^1$HNMR (360 MHz, DMSO-d6) δ11.24 (br, s, 1H, NH), 9.42 (s, 1H, CHO), 2.59 (t, 2H, CH$_2$), 2.34–2.53 (m, 10H, 5×CH$_2$), 1.67 (m, 4H, 2×CH$_2$), 1.57 (m, 2H, CH$_2$), 0.91 (t, J=7.0 Hz, 6H, N(CH$_2$CH$_3$)$_2$).

MS–EI m/z 262 [M$^+$].

3-(3-Diethylaminopropyl)-6,6-dimethyl-4,5,6,7-tetrahydro-1H-indole-2-carbaldehyde Step 1: A mixture of 5-aminolevulinic acid hydrochloride (1.68 g, 10 mmol), 5,5-dimethyl-1,3-cyclohexandione (1.4 g, 10 mmol) and sodium acetate (1.64 g, 20 mmol) in water (10 mL) was stirred at 110° C. for 4 hr and then cooled. The precipitate which formed was collected by vacuum filtration, washed with 30% of ethanol (EtOH) in water and dried under vacuum to give 1.6 g (68%) of 3-(4-oxo-6-dimethyl-4,5,6,7-tetrahydro-1H-indol-3-yl)propionic acid.

$^1$HNMR (360 MHz, DMSO-d6) δ11.89 (br s, 1H, COOH), 10.94 (br s, 1H, NH), 6.45 (d, J=1.4 Hz, 1H), 2.76 (t, 2H, CH$_2$), 2.57 (s, 2H, CH$_2$), 2.44 (t, 2H, CH$_2$), 2.16 (s, 2H, CH$_2$), 0.99 (s, 6H, 2×CH$_3$).

MS–EI m/z 235 [M$^+$].

Step 2: To a suspension of 1.18 g (5 mmol) of the product of step 1 in dichloromethane (25 mL) was added 0.97 g (6 mmol) of CDI. After stirring at room temperature for 2 hr, 2.1 mL (20 mmol) diethylamine was added. The mixture was stirred at room temperature overnight. The reaction was concentrate and the residue was dissolved in dichloromethane, washed with brine, dried and concentrated to give 1.2 g (83%) of 3-(6,6-dimethyl-4-oxo-4,5,6,7-tetrahydro-1H-indol-3-yl)-N,N-diethylpropionamide as a white solid.

$^1$HNMR (360 MHz, DMSO-d6) δ10.91 (br s, 1H, NH), 6.46 (s, 1H), 3.20–3.29 (m, 4H, 2×CH$_2$), 2.72–2.76 (m, 2H, CH$_2$), 2.57 (s, 2H, CH$_2$), 2.45 (m, 2H, CH$_2$), 2.17 (s, 2H, CH$_2$), 0.96–1.06 (m, 12H, 4×CH$_3$).

MS–EI m/z 290 [M$^+$].

Step 3: LAH (0.57 g, 15.1 mmol) was added dropwise to a suspension of 3-(6,6-dimethyl-4-oxo-4,5,6,7-tetrahydro-1H-indol-3-yl)-N,N-diethylpropionamide (1.1 g, 3.8 mmol) in THF (80 mL). The mixture was refluxed overnight. The reaction was cooled and ice was added until no more gas was generated. A few drops of 15% NaOH in water was then added. The mixture was stirred at room temperature for 30 minutes and then filtered to remove insolubles. The filtrate was concentrated to give 0.9 g of [3-(6,6-dimethyl-4,5,6,7-tetrahydro-1H-indol-3-yl)-propyl]-diethylamine as a light yellow oil.

$^1$HNMR (360 MHz, DMSO-d6) δ9.75 (br s, 1H, NH), 6.24 (s, 1H), 2.19–2.44 (m, 14H, 7×CH$_2$), 1.53 (m, 2H, CH$_2$), 1.40 (m, 2H, CH$_2$), 0.88–0.92 (m, 12H, 4×CH$_3$).

MS–EI m/z 262 [M$^+$].

Step 4: POCl$_3$ (0.35 mL, 3.74 mmol) was added dropwise to DMF (0.8 mL, 10.3 mmol) at −5° C. After stirring at room temperature for 30 min, the mixture was cooled to −5° C. A solution of [3-(6,6-dimethyl-4,5,6,7-tetrahydro-1H-indol-3-yl)-propyl]-diethylamine (0.9 g, 3.4 mmol) in DMF (2 mL) was then added dropwise. The mixture was stirred at room temperature for 3 hours and then quenched with ice, followed by 10 N KOH to adjust pH to 10–11. After stirring at room temperature for 1 hour, the mixture was extracted with EtOAc, washed with brine, dried and concentrated to give 0.55 g 3-(3-diethylaminopropyl)-6,6-dimethyl-4,5,6,7-tetrahydro-1H-indole-2-carbaldehyde.

$^1$HNMR (360 MHz, DMSO-d6) δ11.23 (br, s, 1H, NH), 9.41 (s, 1H, CHO), 2.61 (t, 2H, CH$_2$), 2.30–2.43 (m, 10 H, 5×CH$_2$), 1.58 (m, 2H, CH$_2$), 1.45 (t, 2H, CH$_2$), 0.93 (s, 6H, 2×CH$_3$), 0.89 (t, 6H, N(CH$_2$CH$_3$)$_2$).

MS–EI m/z 290 [M$^+$].

6,6-Dimethyl-3-(3-pyrrolidin-1-ylpropyl)-4,5,6,7-tetrahydro-1H-indole-2-carbaldehyde The procedure employed was the same as that in Example E except that the amine in Step 2 was pyrrolidine.

Step 2:

6,6-Dimethyl-3-(3-oxo-3-pyrrolidin-1-ylpropyl)-1,5,6,7-tetrahydroindol-4-one $^1$HNMR (360 MHz, DMSO-d6) δ10.90 (br s, 1H, NH), 6.46 (s, 1H), 3.34 (t, 2H, CH$_2$), 3.25 (t, 2H, CH$_2$), 2.76 (m, 2H, CH$_2$), 2.58 (s, 2H, CH$_2$), 2.43 (m, 2H, CH$_2$), 2.17 (s, 2H, CH$_2$), 1.74–1–1.74 (m, 4H, 2×CH$_2$), 1.00 (s, 6H, 2×CH$_3$).

MS–EI m/z 288 [M$^+$].

Step 3:

6,6-Dimethyl-3-(3-pyrrolidin-1-ylpropyl)-4,5,6,7-tetrahydro-1H-indole

¹HNMR (360 MHz, DMSO-d6) δ9.75 (br s, 1H, NH), 6.23 (d, 1H), 2.22–2.37 (m, 12H, 6×CH₂), 1.55–1.66 (m, 6H, 3×CH₂), 1.40 (m, 2H, CH₂), 0.92 (s, 6H, 2×CH₃).
MS–EI m/z 260 [M⁺].
Step 4:

6,6-Dimethyl-3-(3-pyrrolidin-1-ylypropyl)-4,5,6,7-tetrahydro-1H-indole-2-carbaldehyde ¹HNMR (360 MHz, DMSO-d6) δ11.25 (br, s, 1H, NH), 9.41 (s, 1H, CHO), 2.64 (t, 2H, CH₂), 2.31–2.38 (m, 10 H, 5×CH₂), 1.59–1.67 (m, 6H, 3×CH₂), 1.46 (t, 2H, CH₂), 0.93 (s, 6H, 2×CH₃).
MS–EI m/z 288 [M⁺].

6,6-Dimethyl-3-[3-(4-methylpiperazin-1-yl)-propyl]-4,5,6,7-tetrahydro-1H-indole-2-carbaldehyde The procedure used was that same as that in Example E except that the amine in Step 2 was 1-methylpiperazine.
Step 2:

6,6-Dimethyl-3-[3-(4-methylpiperazin-1-yl)-3-oxopropyl]-1,5,6,7-tetrahydroindol-4-one ¹HNMR (360 MHz, DMSO-d6) δ10.93 (br s, 1H, NH), 6.48 (s, 1H), 3.42 (m, 4H, 2×CH₂), 3.73 (m, 2H, CH₂), 2.57 (s, 2H, CH₂), 2.48 (m, 2H, CH₂), 2.21 (m, 4H, 2×CH₂), 2.17 (s, 2H, CH₂), 2.15 (s, 3H, CH₃), 1.00 (s, 6H, 2×CH₃).
MS–EI m/z 317 [M⁺].
Step 3:

6,6-Dimethyl-3-[3-(4-methylpiperazin-1-yl)-propyl]-4,5,6,7-tetrahydro-1H-indole ¹HNMR (360 MHz, DMSO-d6) δ9.74 (br s, 1H, NH), 6.24 (s, 1H), 2.21–2.30 (m, 16H, 8×CH₂), 2.12 (s, 3H, CH₃), 1.56 (m, 2H, CH₂), 1.40 (m, 2H, CH₂), 0.92 (s, 6H, 2×CH₃).
MS–EI m/z 289 [M⁺].
Step 4:

6,6-Dimethyl-3-[3-(4-methylpiperazin-1-yl)-propyl]-4,5,6,7-tetrahydro-1H-indole-2-carbaldehyde ¹HNMR (360 MHz, DMSO-d6) δ11.21 (br, s, 1H, NH), 9.42 (s, 1H, CHO), 2.62 (t, 2H, CH₂), 2.18–2.37 (m, 14 H, 7×CH₂), 2.12 (s, 3H, CH₃), 1.61 (m, 2H, CH₂), 1.45 (t, 2H, CH₂), 0.93 (s, 6H, 2×CH₃).
MS–EI m/z 317 [M⁺].

6,6-Dimethyl-3-(3-morpholin-4-ylpropyl)-4,5,6,7-tetrahydro-1H-indole-2-carbaldehyde The procedure used was the same as that in Example E except that the amine used was morpholine.
Step 2:

6,6-Dimethyl-3-(3-morpholin-4-yl-3-oxopropyl)-1,5,6,7-tetrahydroindol-4-one

¹HNMR (360 MHz, DMSO-d6) δ10.94 (br s, 1H, NH), 6.49 (s, 1H), 3.42–3.50 (m, 8H, 4×CH₂), 2.74 (m, 2H, CH₂), 2.57 (s, 2H, CH₂), 2.48 (m, 2H, CH₂), 2.17 (s, 2H, CH₂), 1.00 (s, 6H, 2×CH₃).
MS–EI m/z 304 [M⁺].

Step 3:

6,6-Dimethyl-3-(3-morpholin-4-ylpropyl)-4,5,6,7-tetrahydro-1H-indole

¹HNMR (360 MHz, DMSO-d6) δ9.75 (br s, 1H, NH), 6.24 (s, 1H), 3.54 (m, 4H, 2×CH₂), 2.23–2.31 (m, 12H, 6×CH₂), 1.58 (m, 2H, CH₂), 1.40 (m, 2H, CH₂), 0.92 (s, 6H, 2×CH₃).
MS–EI m/z 276 [M⁺].
Step 4:

6,6-Dimethyl-3-(3-morpholin-4-ylpropyl)-4,5,6,7-tetrahydro-1H-indole-2-carbaldehyde ¹HNMR (360 MHz, DMSO-d6) δ11.25 (br, s, 1H, NH), 9.43 (s, 1H, CHO), 3.54 (m, 4H, 2×CH₂), 2.63 (t, 2H, CH₂), 2.20–2.37 (m, 10 H, 5×CH₂), 1.62 (m, 2H, CH₂), 1.45 (t, 2H, CH₂), 0.93 (s, 6H, 2×CH₃).
MS–EI m/z 304 [M⁺].

3-(3-Dimethylaminopropyl)-6,6-dimethyl-4,5,6,7-tetrahydro-1H-indole-2-carbaldehyde The procedure was the same as that in Example E except that the amine used was dimethylamine.
Step 2:

3-(6,6-Dimethyl-4-oxo-4,5,6,7-tetrahydro-1H-indol-3-yl)-N,N-dimethylpropionamide ¹HNMR (360 MHz, DMSO-d6) δ10.93 (br s, 1H, NH), 6.48 (s, 1H), 2.94 (s, 3H, CH₃), 2.79 (s, 3H, CH₃), 2.72 (m, 2H, CH₂), 2.57 (s, 2H, CH₂), 2.48 (m, 2H, CH₂), 2.17 (s, 2H, CH₂), 1.00 (m, 6H, 2×CH₃).
MS–EI m/z 262 [M⁺].
Step 3:

[3-(6,6-Dimethyl-4,5,6,7-tetrahydro-1H-indol-3-yl)-propyl]dimethylamine

¹HNMR (360 MHz, DMSO-d6) δ9.75 (br s, 1H, NH), 6.24 (s, 1H), 3.36 (m, 2H, CH₂), 2.07–2.3 (m, 14H, 7×CH₂), 1.53 (m, 2H, CH₂), 1.40 (m, 2H, CH₂), 0.92 (s, 6H, 2×CH₃).
MS–EI m/z 234 [M⁺].
Step 4:

3-(3-Dimethylaminopropyl)-6,6-dimethyl-4,5,6,7-tetrahydro-1H-indole-2-carbaldehyde ¹HNMR (360 MHz, DMSO-d6) δ11.25 (br s, 1H, NH), 9.41 (s, 1H, CHO), 2.62 (t, 2H, CH₂), 2.36 (t, 2H, CH₂), 2.30 (s, 2H, CH₂), 2.21 (t, 2H, CH₂), 2.12 (s, 6H, 2×CH₃), 1.60 (m, 2H, CH₂), 1.46 (t, 2H, CH₂), 0.93 (s, 6H, 2×CH₃).
MS–EI m/z 262 [M⁺].

Condensation of aldehydes and oxindoles containing carboxylic acid substituents

A mixture of the appropriate oxindole (1 equivalent), 1 equivalent of the appropriate aldehyde and 1–3 equivalents of piperidine (or pyrrolidine) in ethanol (0.4 M) is stirred at 90–100° C. until the reaction complete as indicated by thin layer chromatography. The mixture is then concentrated and the residue is triturated with dilute hydrochloric acid. The resulting precipitate is collected by vacuum filtration, washed with water and ethanol and dried to give the product.

Condensation of aldehyde and oxindole not containing carboxylic acid substituents A mixture of the appropriate oxindole (1 equivalent), 1 equivalent of the appropriate aldehyde and 1–3 equivalents of piperidine (or pyrrolidine) in ethanol (0.4 M) is stirred at 90–100° C. until the reaction complete as indicated by thin layer chromatography. The mixture is cooled to room temperature and the precipitate which forms is collected by vacuum filtration, washed with ethanol and dried to give the product. Where a precipitate does not form, the mixture is concentrated and the product isolated by column chromatography.

Condensation of aldehyde and oxindole containing amino substituents

The aminooxindole is first protected with a BOC-group. After the condensation with the appropriate aldehyde, the solid which forms is deprotected using trifluoroacetic acid to yield the desired product.

C. EXAMPLES

Synthesis of 3-methylidenyl-2-indolinones of this invention

The following syntheses of representative compounds of this invention are shown by way of example only and are not to be construed as limiting the scope of this invention in any manner whatsoever.

Example 1

3-(3,5-Diisopropyl-4-methoxybenzylidene)-1,3-dihydroindol-2-one 3,5-Diisopropyl-4-hydroxybenzaldehyde was methylated to give 3,5-diisopropyl-4-methoxybenzaldehyde.

$^1$HNMR (d$_6$-DMSO) δ: 10.1 (s, 1H, CHO), 6.9 (s, 2H, aromatic), 3.9 (s, 3H, OCH$_3$), 3.2 (m, 2H, 2×CH), 1.2 (d, 12H, 4×CH$_3$).

3,5-Diisopropyl-4-methoxybenzaldehyde was then condensed with 2-oxindole to give 0.25 g of 3-(3,5-Diisopropyl-4-methoxybenzylidene)-1,3-dihydroindol-2-one as a yellow-orange solid.

$^1$HNMR (d$_6$-DMSO) δ: 10.54 (s, 1H, CONH), 7.6, 7.59, 7.49, 7.21, 6.81–6.88 (multiplets, 7H, =CH—, aromatic), 3.73 (s, 3H, OCH$_3$), 3.26–3.33 (m, 2H, 2×—CH), 1.2 (d, J=7.23 Hz, 12H, 4×CH$_3$).

MS m/z 336.

Example 2

5-Chloro-3-(3,5-diisopropl-4-methoxybenzylidene)-1,3-dihydroindol-2-one 3,5-Diisopropyl-4-methoxybenzaldehyde was condensed with 5-chloro-2-oxindole to give 0.3 g of 5-chloro-3-(3,5-diisopropyl-4-methoxybenzylidene)-1,3-dihydroindol-2-one as a yellow-orange solid.

$^1$HNMR (d$_6$-DMSO) δ: 10.69 (s, 1H, CONH), 7.67 (s, 1H, =CH—), 7.6 (d, J=1.85 Hz, 1H, H-4), 7.51 (s, 2H, aromatic), 7.26 (dd, J=1.85, 8.3 Hz, 1H, H-6), 6.89 (d, J=8.3 Hz, 1H, H-7), 3.74 (s, 3H, OCH$_3$), 3.27–3.34 (m, 2H, 2×—CH), 1.22 (d, J=6.7 Hz, 12H, 4×CH$_3$).

Example 3

N-[3-(3,5-Diisopropyl-4-methoxybenzylidene)-2-oxo-2,3-dihydro-1H-indol-6-yl]-acetamide Tin chloride dihydrate (225 g) was added to a solution of 2,4-dinitrophenylacetic acid (22.6 g) in ethanol (450 ml). The mixture was heated at 90° C. for 10 hours. The reaction mixture was cooled and adjusted to pH 11 with 12M sodium hydroxide. The solids were removed by filtration and the filtrate was concentrated. The residue was treated with ethanol (300 ml). Insoluble materials were removed by filtration and washed with ethanol (5×60 ml). The combined ethanol solutions were evaporated and the solid obtained was dried under vacuum to give 15 g of 6-amino-2-oxindole as a brown powder.

$^1$HNMR (360 MHz, DMSO-d6) δ: 10.03 (s, br, NH), 6.78 (d, J=8.55 Hz, 1H, H-4), 6.09–6.11 (m, 2H), 4.95 (s, br, 2H, NH2), 3.22 (s, 2H, H-3).MS (+APCI) m/z (relative intensity, %)

MS m/z 147 ([M−1]$^+$, 100).

To a mixture of 6-amino-2-oxindole (1 g) and acetyl chloride (0.79 g) in 10 ml of dichloromethane at 0° C. was added triethylamine (1 g). The mixture was brought to room temperature and stirred for 4 hours protected from atmospheric moisture with a dry-tube. The solvent was then evaporated and the residue was recrystallized from methanol to give 0.98 g (77%) of 6-acetylamnino-2-oxindole as a beige solid.

1HNMR (360 MHz, DMSO-d6) δ: 10.28 (s, br, NH), 9.83 (s, br, NH), 7.34 (d, J=1.4 Hz, 1H, H-7), 7.06 (d, J=7.9 Hz, 1H, H-4), 6.97 (dd, J=1.4, 7.9 Hz, 1H, H-5), 3.37 (s, 2H, H-3), 2.01 (s, 3H, CH$_3$).

3,5-Diisopropyl-4-methoxybenzaldehyde was condensed with 6-acetamido-2-oxindole to give 0.3 g of N-[3-(3,5-diisopropyl-4-methoxybenzylidene)-2-oxo-2,3-dihydro-1H-indol-6-yl]-acetamide as a yellow-orange solid.

$^1$HNMR (d$_6$-DMSO) δ: 10.48 (s, 1H, CONH), 9.99 (s, 1H, CONH), 7.51 (d, J=8 Hz, 1H, H-4), 7.46 (s, 2H, aromatic), 7.44 (s, 1H, =CH—), 7.41 (d, J=2 Hz, 1H, H-7), 6.91 (dd, J=2.8 Hz, 1H, H-5), 3.73 (s, 3H, OCH$_3$), 3.26–3.34 (m, 2H), 2.03 (s, 3H, CH$_3$), 1.21 (d, J=7 Hz, 12H, 4×CH$_3$).

MS m/z 392.

Example 4

3-(3,5-Diisopropyl-4-methoxybenzylidene)-6-hydroxy-1,3-dihydroindol-2-one 3,5-Diisopropyl-4-methoxybenzaldehyde was condensed with 6-hydroxy-2-oxindole to give 0.3 g of 3-(3,5-Diisopropyl-4-methoxybenzylidene)-6-hydroxy-1,3-dihydroindol-2-one as a yellow-orange solid.

$^1$HNR (d$_6$-DMSO) δ: 10.34 (s, 1H, CONH), 9.79 (s, 1H, OH), 7.42 (d, J=8 Hz, 1H, H-4), 7.43 (s, 2H, aromatic), 7.33 (s, 1H, =CH—), 6.32 (d, J=2 Hz, 1H, H-7), 6.21 (dd, J=2.8 Hz, 1H, H-5), 3.72 (s, 3H, OCH$_3$), 3.25–3.33 (m, 2H), 1.2 (d, J=7 Hz, 12H, 4×CH$_3$).

MS m/z 351.

Example 5

5-Acetyl-3-(3,5-diisopropyl-4-methoxybenzylidene)-1,3-dihydroindol-2-one

2-Oxindole (3 g) was suspended in 1,2-dichloroethane and slowly treated with 3.2 ml of acetyl chloride. The resulting suspension was heated at 50° C. for 5 hours, cooled, and poured into water. The resulting precipitate was collected by vacuum filtration, washed copiously with water and dried under vacuum to give 2.9 g (73% yield) of 5-acetyl-2-oxindole as a brown solid.

$^1$HNMR (360 MHz, DMSO-d6) δ: 10.75 (s, br, NH), 7.83 (d, J=8.23 Hz, 1H), 7.78 (s, 1H, H-4), 6.88 (d, J=8.23 Hz, 1H), 3.53 (s, 2H, CH2), 2.49 (s, 3H, CH3).

3,5-Diisopropyl-4-methoxybenzaldehyde was condensed with 5-acetyl-2-oxindole to give 0.3 g of 5-Acetyl-3-(3,5-diisopropyl-4-methoxybenzylidene)-1,3-dihydroindol-2-one as a yellow-orange solid.

$^1$HNMR (d$_6$-DMSO) δ: 10.95 (s, 1H, CONH), 8.22 (d, J=2 Hz, 1H, H-4), 7.93 (dd, J=2.8 Hz, 1H, H-6), 7.69 (s, 1H, =CH—), 7.53 (s, 2H, aromatic), 6.97 (d, J=8 Hz, 1H, H-7), 3.75 (s, 3H, OCH$_3$), 3.24–3.34 (m, 2H), 2.48 (s, 3H, CH$_3$), 1.24 (d, J=7 Hz, 12H, 4×CH$_3$).

MS m/z 377.

Example 6

3-(3,5-Diisopropyl-4-methoxybenzylidene)-2-oxo-2,3-dihydro-1H-indole-5-carboxylic acid methyl ester 2-Oxindole (82.9 g) was suspended in 630 ml of acetic acid in a reaction vessel equipped with mechanical stirring and the mixture cooled to 10° C. in an ice water bath. Solid N-iodosuccinimide (175 g) was added in portions over 10 minutes. After the addition was complete the mixture was stirred for 1 hour at 10° C. The suspended solid which was always present became very thick at this time. The solid was collected by vacuum filtration, washed with 100 ml of 50% acetic acid in water and then with 200 ml of water and subjected to vacuum filtration for 20 minutes to partially air dry it. The product was then dried under vacuum to give 93.5 g (36%) of 5-iodo-2-oxindole containing about 5% 2-oxindole by proton NMR.

$^1$HNMR (360 MHz, DMSO-d6) δ: 10.45 (s, 1H, NH-1), 7.49 (s, 1H, H-4), 7.48 (d, J=8.10 Hz, 1H, H-6), 6.64 (d, J=8.10 Hz, 1H, H-7), and 3.46 (s, 2H, CH$_2$-3).

MS (m/z (relative intensity, %)) 258 ([M−1]$^+$, 13).

5-Iodo-2-oxindole (17 g) was refluxed with 2 g of palladium diacetate, 18.2 g of triethylamine, 150 ml of methanol, 15 ml of dimethylsulfoxide and 2.6 g of DPPP in an atmosphere saturated with carbon monoxide. After 24 hours, the reaction was filtered to remove the catalyst and the filtrate was concentrated. The concentrate was chromatographed on silica gel using 30% ethyl acetate/hexane as the eluent. The fractions containing product were concentrated and allowed to stand. The precipitated product was collected by vacuum filtration to give 0.8 g (7%) of 5-methoxycarbonyl-2-oxindole as an off-white solid.

$^1$HNMR (360 MHz, DMSO-d6) δ: 10.70 (s, br, 1H, NH-1), 7.83 (dd, J=1.77, 8.29 Hz, 1H, H-6), 7.77 (s, br, 1H, H-4), 6.89 (d, J=8.29 (Hz, 1H, H-7), 3.80 (s, 3H, COOCH$_3$-5), 3.51 (s, 2H, CH$_2$-3).

3,5-Diisopropyl-4-methoxybenzaldehyde was condensed with 5-methoxycarbonyl-2-oxindole to give 0.25 g of 3-(3,5-Diisopropyl-4-methoxybenzylidene)-2-oxo-2,3-dihydro-1H-indole-5-carboxylic acid methyl ester as a yellow-orange solid.

$^1$HNMR (d$_6$-DMSO) δ: 10.96 (s, 1H, CONH), 8.29 (d, J=1 Hz, 1H, H-4), 7.88 (dd, J=1.8 Hz, 1H, H-6), 7.7 (s, 1H, =CH—), 7.55 (s, 2H, aromatic), 7.0 (d, J=8 Hz, 1H, H-7), 3.76 (s, 3H, OCH$_3$), 3.73 (s, 3H, OCH$_3$), 3.26–3.35 (m, 2H), 1.23 (d, J=7 Hz, 12H, 4×CH$_3$).

MS m/z 393.

Example 7

3-(3-Isopropyl-4-methoxybenzylidene)-1,3-dihydroindol-2-one

2-Isopropylphenol was methylated and then formylated to give 3-isopropyl-4-methoxybenzaldehyde. 3-Isopropyl-4-methoxybenzaldehyde was condensed with 2-oxindole to give 0.3 g of 3-(3-isopropyl-4-methoxybenzylidene)-1,3-dihydroindol-2-one as a yellow-orange solid.

$^1$HNMR (d$_6$-DMSO) δ: 10.5 (s, 1H, CONH), 7.7, 7.6, 7.2, 7.1, 6.8 (multiplets, 8H, aromatic, =CH—), 3.9 (s, 3H, OCH$_3$), 3.2 (m, 1H, CH), 1.2 (d, 6H, 2×CH$_3$).

Example 8

3-(5-Isoporpyl-4-methoxy-2-methylbenzylidene)-1,3-dihydroindol-2-one

5-Isopropyl-4-methoxy-2-methylbenzaldehyde was condensed with 2-oxindole to give 0.25 g of 3-(5-Isopropyl-4-methoxy-2-methylbenzylidene)-1,3-dihydroindol-2-one as a yellow-orange solid.

1HNMR (d$_6$-DMSO) δ: 10.5 (s, 1H, CONH), 7.6, 7.4, 7.3, 7.2, 6.9, 6.8, 6.8 (multiplets, 7H, aromatic, =CH—), 3.9 (s, 3H, OCH$_3$), 3.2 (m, 1H, CH), 2.3 (s, 3H, CH$_3$), 1.2 (d, 6H, 2×CH$_3$).

Example 9

5-Chloro-3-(5-isopropyl-4-methoxy-2-methylbenzylidene)-1,3-dihydroindol-2-one

2-Isopropyl-5-methylphenol was methylated and then formylated to give 5-isopropyl-4-methoxy-2-methylbenzaldehyde.

$^1$HNMR (d$_6$-DMSO) δ: 10.1 (s, 1H, CHO), 7.6, 6.9 (2×s, 2H, aromatic), 3.9 (s, 3H, OCH$_3$), 3.2 (m, 1H, CH), 2.6 (s, 3H, CH$_3$), 1.2 (d, 6H, 2×CH$_3$).

5-Isopropyl-4-methoxy-2-methylbenzaldehyde was condensed with 5-chloro-2-oxindole to give 0.3 g of 5-Chloro-3-(5-isopropyl-4-methoxy-2-methylbenzylidene)-1,3-dihydroindol-2-one as a yellow-orange solid.

$^1$HNMR (d$_6$-DMSO) δ: 10.65 (s, 1H, CONH), 7.73 (s, 1H,), 7.49 (s, 1H,), 7.4 (d, J=2 Hz, 1H, H-4), 7.23 (dd, J=2.8 Hz, 1H, H-6), 6.98 (s, 1H), 6.86 (d, J=8 Hz, 1H, H-7), 3.86 (s, 3H, OCH$_3$), 3.23–3.3 (m, 2H), 2.33 (s, 3H, CH$_3$), 1.15 (d, J=7 Hz, 6H, 2×CH$_3$).

MS m/z 341.

Example 10

3-(3-Cyclopentyl-4-methoxybenzylidene)-1,3-dihydroindol-2-one

3-Cyclopentyl-4-methoxybenzaldehyde was condensed with 2-oxindole to give 0.25 g of 3-(3-Cyclopentyl-4-methoxybenzylidene)-1,3-dihydro-indol-2-one as a yellow-orange solid.

$^1$HNMR (d$_6$-DMSO) δ: 10.5 (s, 1H, CONH), 7.6, 7.5, 7.2, 7.1, 6.8 (multiplets, 8H, aromatic, =CH—), 3.9 (s, 3H, OCH$_3$), 3.2 (m, 1H, CH), 1.8 (multiplets, 8H, 4×CH$_2$).

Example 11

3-(3-Cyclopentyl-4-methoxybenzylidene)-5-fluoro-1,3-dihydroindol-2-one

2-Cyclopentylphenol was methylated and then formylated to give 3-cyclopentyl-4-methoxybenzaldehyde.

$^1$HNMR (d$_6$-DMSO) δ: 9.9 (s, 1H, CHO), 7.8, 7.7, 7.2 (multiplets, 3H, aromatic), 3.9 (s, 3H, OCH$_3$), 3.2 (m, 1H, CH), 1.2 (multiplets, 8H, 4×CH$_2$).

3-Cyclopentyl-4-methoxybenzaldehyde was condensed with 5-fluoro-2-oxindole to give 0.25 g of 3-(3-cyclopentyl- 4-methoxybenzylidene)-5-fluoro-1,3-dihydroindol-2-one as a yellow-orange solid.

$^1$HNMR (d$_6$-DMSO) δ: 10.5 (s, 1H, CONH), 7.6, 7.6, 7.6, 7.4, 7.1, 7.0, 6.8 (multiplets, 7H, aromatic, vinyl CH), 3.9 (s, 3H, CH$_3$), 3.3 (m, 1H, CH), 2.0–1.5 (multiplets, 8H, 4×CH$_2$).

MS m/z 337.

Example 12

3-(3-Cyclohexyl-4-methoxybenzylidene)-1,3-dihydroindol-2-one

2-Cyclohexylphenol was methylated and then formylated. The aldehyde was condensed with oxindole to give 0.3 g of 3-(3-Cyclohexyl-4-methoxybenzylidene)-1,3-dihydroindol-2-one as a yellow-orange solid.

$^1$HNMR (d$_6$-DMSO) δ: 10.5 (s, 1H, CONH), 7.7, 7.6, 7.6, 7.2, 7.1, 6.8, 6.8 (multiplets, 7H, aromatic, =CH—), 3.9 (s, 3H, OCH$_3$), 3.0 (m, 1H, CH), 1.8, 1.4 (multiplets, 10H, 5×CH$_2$).

Example 13

5-Bromo-3-(6-methoxybiphenyl-3-ylmethylene)-1,3-dihydroindol-2-one

2-Phenylanisole was formylated to give 4-methoxy-3-phenylbenzaldehyde.

$^1$HNMR (d$_6$-DMSO) δ: 9.9 (s, 1H, CHO), 7.9, 7.8, 7.5, 7.4, 7.4, 7.3 (multiplets, 8H, aromatic), 3.9 (s, 3H, OCH$_3$.

MS m/z 213.

4-Methoxy-3-phenylbenzaldehyde was condensed with 5-bromo-2-oxindole to give 0.3 g of 5-Bromo-3-(6-methoxybiphenyl-3-ylmethylene)-1,3-dihydroindol-2-one as a yellow-orange solid.

$^1$HNMR (d$_6$-DMSO) δ: 10.6 (s, 1H, CONH), 7.8–6.8 (multiplets, 12H, aromatic, =CH—), 3.9 (s, 3H, OCH$_3$).

Example 14

5-Chloro-3-(2,3-dihydro-benzofuran-5-ylmethylene)-1,3-dihydroindol-2-one 2,3-Dihydro-5-formylbenzofuran was condensed with 5-chloro-2-oxindole to give 0.25 g of 5-Chloro-3-(2,3-dihydro-benzofuran-5-ylmethylene)-1,3-dihydroindol-2-one as a yellow-orange solid.

$^1$HNMR (d$_6$-DMSO) δ: 10.6 (s, 1H, CONH), 8.6, 8.2, 7.7, 7.6, 7.2, 6.9, 6.8 (multiplets, 7H, aromatic, =CH—), 4.6 (t, 2H, OCH$_2$), 3.2 (t, 2H, OCH$_2$).

Example 15

5-Chloro-3-(2,2-dimethyl-chroman-6-ylmethylene)-1,3-dihydroindol-2-one 2,2-Dimethyl-6-formylchromane was condensed with 5-chloro-2-oxindole to give 0.3 g of 5-Chloro-3-(2,2-dimethylchroman-6-ylmethylene)-1,3-dihydroindol-2-one as a yellow-orange solid.

$^1$HNMR (d$_6$-DMSO) δ: 10.61 (s, 1H, CONH), 8.31, 8.27, 7.76, 7.17, 6.79 (multiplets, 6H, aromatic), 7.8 (s, 1H, =CH—), 2.78 (t, 2H, CH$_2$), 1.81 (t, 2H, CH$_2$), 1.31 (s, 6H, 2×CH$_3$).

MS m/z 340.5 (M+1).

Example 16

N-{3-[3-Cyclohexyl-4-(2-morpholin-4-ylethoxy)-benzylidene]-2-oxo-2,3-dihydro-1H-indol-6-yl}-acetamide Triphenylphosphine (7.47 g, 19.58 mmol) was added to a solution of 2-cyclohexyl-4-chlorophenol (6 g, 28.48 mmol) and 2-hydroxyethylmorpholine (3.5 g, 28.48 mmol) in tetrahydrofuran (50 ml), followed by the dropwise addition of diethylazodicarboxylate (4.5 ml, 28.48 mmol). The mixture stirred at room temperature for 12 hours. The reaction mixture was concentrated under reduced pressure and triturated with dichloromethane/hexanes and then washed with more hexanes. Chromatography (silica, 10–20–30% ethyl acetate/hexanes) afforded 8.4 g (95%) of 3-cyclohexyl-4-morpholinoethoxy-chlorobenzene as a yellowish oil.

$^1$HNMR (360 MHz, DMSO-d6) δ: 7.12 (m, 2H, 2×Ar—H), 6.93 (d, J=9 Hz, 1H, Ar—H), 4.04 (m, 2H, O—CH$_2$CH$_2$), 3.55 (m, 4H, 2× ringO—CH$_2$CH$_2$), 2.84 (m, 1H, CHcyclohexyl), 2.68 (m, 2H, N—CH$_2$CH$_2$), 2.47 (m, 4H, 2× ringN—CH$_2$CH$_2$), 1.7 (m, 5H, cyclohexyl), 1.3 (m, 5H, cyclohexyl).

MS m/z 324.4 and 325.4, [M+1]$^+$ and [M+3]$^+$.

Naphthalene (3.48 g, 27.2 mmol) was added to a suspension of 30% lithium dispersion (3.2 g, 138 mmol, prewashed with tetrahydrofuran) in tetrahydrofuran (80 ml). The suspension was stirred until a green color appeared (approximately 1 hour). The reaction was cooled to −78° C., and a solution of the 3-cyclohexyl-4-morpholinoethoxy-chlorobenzene (8 g, 24.7 mmol) in tetrahydrofuran (20 ml) was added. After 1 hour, the reaction was warmed to 0° C. and stirred for an additional hour. Dimethylformamide (9.6 ml, 123.5 mmol) was added, the reaction was stirred at 0° C. for one more hour and then warmed to room temperature and stirred for another hour. The reaction was quenched with methanol (30 ml), added to 1N hydrochloric acid (300 ml) and extracted with ethyl acetate (400 ml). The organic layer was washed with water (300 ml), saturated sodium bicarbonate solution (300 ml) and brine (300 ml), dried over magnesium sulfate and concentrated. Chromatography (silica, 40–60% ethyl acetate/hexanes) afforded 3 g (34%) of 3-cyclohexyl-4-morpholinoethoxybenzaldehyde as a light yellow oil.

$^1$HNMR (360 MHz, DMSO-d6) δ: 9.83 (s, 1H, CHO), 7.12 (m, 2H, 2×Ar—H), 7.13 (d, J=8 Hz, 1H, Ar—H), 4.19 (m, 2H, O—CH$_2$CH$_2$), 3.55 (m, 4H, 2× ringO—CH$_2$CH$_2$), 2.88 (m, 1H, CHcyclohexyl), 2.74 (m, 2H, N—CH$_2$CH$_2$), 2.49 (m, 4H, 2× ringN—CH$_2$CH$_2$), 1.7 (m, 5H, cyclohexyl), 1.3 (m, 5H, cyclohexyl).

MS m/z 318.4 [M+1]$^+$.

A mixture of 3-cyclohexyl-4-morpholinoethoxybenzaldehyde (3 g, 9.45 mmol), 6-acetamido-2-oxindole (3.5 g, 18.9 mmol) and piperidine (5 ml, 50 mmol) in ethanol (35 ml) was held in a sealed tube at 100° C. for 6 hours. The reaction mixture was cooled, diluted with ethyl acetate (500 ml) and filtered to remove excess 6-acetamido-2-oxindole. The filtrate was extracted with 0.5N hydrochloric acid (200 ml) and brine (2×200 ml). The acid wash was basified with solid sodium bicarbonate to pH 9 and extracted with ethyl acetate (2×200 ml). The combined organic layers were washed with brine (200 ml), dried over magnesium sulfate and concentrated. The combined solids were dissolved in dichloromethane (25 ml) and precipitated with diethyl ether (500 ml) to afford 1.6 g of a mustard yellow solid. The solid was dissolved in methanol (100 ml) and filtered, affording a yellow solid (which was set aside) and then precipitated with water (400 ml) and filtered. The solid residue was redissolved in methanol and concentrated to a solid. This process was repeated twice to afford ~82% pure isomer 1 by HPLC. The filtered yellow solid was 77% isomer 2 by HPLC.

¹HNMR (360 MHz, DMSO-d6) δ: 10.45 (s, 1H, NH), 10.0 (s, 1H, NHAc), 7.55 (m, 3H, Ar—H), 7.44 (m, 2H, Ar—H and Ar—CH=C), 7.07 (d, 1H, J=8 Hz, Ar—H), 6.89 (dd, 1H, J=2 and 8 Hz, Ar—H), 4.16 (m, 2H, Ar—OCH$_2$), 3.57 (m, 4H, OCH$_2$CH$_2$N), 2.92 (m, 1H, chexCH), 2.75 (m, 2H, ArOCH$_2$—CH$_2$N), 2.51 (m, 4H, NCH$_2$CH$_2$O), 2.02 (s, 3H, NHCOCH$_3$), 1.8 (m, 5H, chexCH$_2$), 1.38 (m, 5H, chexCH$_2$). 20% isomer 1; 77% isomer 2

¹HNMR (360 MHz, DMSO-d6) δ: 10.39 (s, 1H, NH), 9.92 (s, 1H, NHAc), 8.37 (d, 1H, J=2 Hz, Ar—H), 8.24 (m, 1H, Ar—H), 7.55 (s, 1H, Ar—CH=C), 7.52 (d, 1H, J=8 Hz, Ar—H), 7.36 (m, 1H, Ar—H), 7.03 (m, 2H, Ar—H), 4.16 (m, 2H, Ar—OCH$_2$), 3.57 (m, 4H, OCH$_2$CH$_2$N), 2.88 (m, 1H, chexCH), 2.74 (m, 2H, ArOCH$_2$—CH$_2$N), 2.51 (m, 4H, NCH$_2$CH$_2$O), 2.03 (s, 3H, NHCOCH$_3$), 1.8 (m, 5H, chex CH$_2$), 1.38 (m, 5H, chexCH$_2$).

Example 17

3-(3,5-Diisopropyl-4-methoxybenzylidene)-5-methoxy-1,3-dihydroindol-2-one 3,5-Diisopropyl-4-hydroxybenzaldehyde was methylated to give 3, 5-diisopropyl-4-methoxybenzaldehyde.

¹HNMR (360 MHz, DMSO-d6) δ: 10.1 (s, 1H, CHO), 6.9 (s, 2H, aromatic), 3.9 (s, 3H, OCH$_3$), 3.2 (m, 2H, 2×CH), 1.2 (d, 12H, 4×CH$_3$).

A solution of 11.4 g of hydroxylamine hydrochloride in water (50 ml) was added to a solution of chloral hydrate (9.6 g) and sodium sulfate (83 g) in water (200 ml) at 60° C. The mixture was held at 60° C. while, in a separate flask, a solution of 4-anisidine (6.4 g) and concentrated hydrochloric acid (4.3 ml) in water (80 ml) was warmed to 80° C. The first solution was then added to the second and the reaction was refluxed for 2 minutes, cooled slowly to room temperature and then cooled in an ice bath. The tan precipitate which formed was collected by vacuum filtration, washed with water and dried under vacuum to give 8.6 g (85% yield) of N-(2-hydroximinoacetyl)-anisidine.

Concentrated sulfuric acid (45 ml) containing water (5 ml) was warmed to 60° C. and 8.6 g of N-(2-hydroximinoacetyl)-anisidine was added in one portion. The mixture was stirred at 93° C. for 10 minutes and then allowed to cool to room temperature. The mixture was poured into 500 g of ice and extracted 3 times with ethyl acetate. The combined extracts were dried over anhydrous sodium sulfate and concentrated to give 5.1 g (65% yield) of 5-methoxyisatin as a dark red solid.

A mixture of 5-methoxyisatin (5.0 g) and 30 ml of hydrazine hydrate was refluxed for 15 minutes. The reaction mixture was cooled to room temperature and 50 ml of water was added. The mixture was extracted 3 times with 25 ml of ethyl acetate, the organic layers combined, dried over anhydrous sodium sulfate and concentrated to give a yellow solid. The solid was stirred in ethyl acetate and 1.1 g of insoluble material removed by vacuum filtration and saved. This material proved to be 2-hydrazinocarbonyl-methyl-4-anisidine. The filtrate was concentrated and chromatographed on silica gel eluting with ethyl acetate:hexane 1:1 to give 0.7 g of 5-methoxy-2-oxindole as a dirty yellow solid. The 1.1 g of 2-hydrazinocarbonyl-methyl-4-anisidine was refluxed for 1 hour in 20 ml of 1 N sodium hydroxide. The mixture was cooled, acidified to pH 2 with concentrated hydrochloric acid and extracted 3 times with 25 ml of ethyl acetate. The organic extracts were combined, washed with brine, dried over anhydrous sodium sulfate and concentrated to give 0.8 g of 5-methoxy-2-oxindole as a dirty yellow solid. The combined yield was 1.5 g or 33%.

¹HNMR (360 MHz, DMSO-d6) δ: 10.13 (s, 1H, NH-1), 6.84 (s, 1H, H-4), 6.72 (d, J=9 Hz, 1H, H-6), 6.69 (d, J=9 Hz, 1H, H-7), 3.68 (s, 3H, OCH$_3$-5), 3.41 (s, 2H, CH$_2$-3).

MS m/z 163 [M+1]$^+$.

3,5-Diisopropyl-4-methoxybenzaldehyde was condensed with 5-methoxy-2-oxindole to give 0.3 g of 3-(3,5-Diisopropyl-4-methoxybenzylidene)-5-methoxy-1,3-dihydroindol-2-one as a yellow-orange solid.

¹HNMR (360 MHz, DMSO-d6) δ: 10.34 (s, 1H, NH), 7.59 (s, 2H), 7.47 (s, 2H), 7.15 (d, J=2 Hz, 1H), 6.85 (dd, J=2, 8 Hz, 1H), 6.58 (d, J=8 Hz, 1H), 3.73 (s, 3H, OCH$_3$), 3.63 (s, 3H, OCH$_3$), 3.25–3.39 (m, 2H, 2×(CH$_3$)$_2$CH), 1.2 (d, 12H, 2×(CH$_3$)$_2$CH).

MS APCI m/z 366.1 [M+1]$^+$.

Example 18

N-[3-(4-Methoxy-3-thiophene-3-ylbenzylidene)-2-oxo-2,3-dihydro-1H-indol-6-yl]-acetamide Tetrakis(triphenylphosphine)palladium(0) (1.35 g) was added to a solution of 4-methoxy-3-bromobenzaldehyde (6.72 g) in toluene (45 ml) and ethanol (45 ml), followed by addition of 2M aqueous sodium carbonate (80 ml). To this mixture was added thiophene-3-boronic acid (5 g). The mixture was then refluxed for 12 hours. The reaction mixture was poured into water (200 ml) and extracted into ethyl acetate (2×150 ml). The organic layer was washed with saturated aqueous sodium bicarbonate (150 ml) and brine (150 ml), dried over magnesium sulfate and concentrated. Chromatography (silica, 20% ethyl-acetate/hexanes) afforded 6 g (88%) of 3(3-thiophene)-4-methoxybenzaldehyde as a yellow oil.

¹HNMR (360 MHz, DMSO-d6) δ: 9.92 (s, 1H, CHO), 8.04 (d, 1H, J=2 Hz, 1×Ar—H), 7.8 (m, 2H, Ar—H), 7.58 (dd, 1H, J=3 and 5 Hz, thiophene and Ar—H), 7.50 (dd, 1H, J=2 and 5 Hz, Ar—H), 7.28 (d, 1H, J=9 Hz, thiophene), 3.94 (s, 3H, OCH$_3$).

MS m/z 219.2 [M+1]$^+$.

A mixture of 3(3-thiophene)-4-methoxybenzaldehyde (1.72 g), 6-acetamido-2-oxindole (1.5 g) and piperidine (4 ml) in ethanol (26 ml) was held in a sealed tube for 12 hours at 100° C. The reaction was cooled and poured into diethyl ether. The precipitate which formed was removed by filtration, washed with diethyl ether and then hexanes and dried to afford 0.9 g (29%) of N-[3-(4-methoxy-3-thiophene-3-ylbenzylidene)-2-oxo-2,3-dihydro-1H-indol-6-yl]-acetamide as a tan solid.

¹HNMR 360 MHz, DMSO-d6) δ: 10.52 (s, 1H, NH), 10.22 (s, 1H, NHAc), 7.85 (m, 2H, 2×Ar—H), 7.7 (dd, J=2 and 9 Hz, 1H, Ar—H), 7.6 (m, 2H, 2×Ar—H), 7.5 (dd, 1H, J=1 and 5 Hz, Ar—H), 7.47 (s, 2H, Ar—H and Ar—CH=C), 7.25 (d, 1H, J=9 Hz, Ar—H), 6.96 (dd, 1H, J=2 and 9 Hz, Ar—H), 3.92 (s, 3H, OCH$_3$), 2.04 (s, 3H, NHCOCH$_3$).

MS m/z 391.2 [M+1]$^+$.

Example 19

3-(3,5-Diisopropyl-4-methoxybenzylidene)-5-methyl-1,3-dihydroindol-2-one

A mixture of 5-methylisatin (15.0 g) and 60 ml of hydrazine hydrate was stirred at 140–160° C. for 4 hours. The reaction mixture was cooled to room temperature, poured into 300 ml of ice water and acidified to pH 2 with 6 N hydrochloric acid. After standing at room temperature for 2 days, a precipitate formed which was collected by vacuum filtration, washed with water and dried under vacuum to give 6.5 g (47% yield) of 5-methyl-2-oxindole.

$^1$HNMR (360 MHz, DMSO-d6) δ: 10.20 (s, br, 1H, NH-1), 6.99 (s, 1H, H-4), 6.94 (d, J=8 Hz, 1H, H-6), 6.68 (d, J=8 Hz, 1H, H-7), 3.39 (s, 2H, CH$_2$-3), and 2.22 (s, 3H, CH$_3$-5).

3,5-Diisopropyl-4-methoxybenzaldehyde was condensed with 5-methyl-2-oxindole to give 0.3 g of 3-(3,5-diisopropyl-4-methoxybenzylidene)-5-methyl-1,3-dihydroindol-2-one as a yellow-orange solid.

$^1$HNMR (360 MHz, DMSO-d6) δ: 10.41 (s, br, 1H, NH), 7.56 (s, 1H), 7.51 (s, 2H), 7.50 (s, br, 1H), 7.03 (d, br, J=8 Hz, 1H), 6.76 (d, J=8 Hz, 1H), 3.74 (s, 3H, OCH$_3$), 3.26–3.35 (m, 2H, 2×(CH$_3$)$_2$CH), 2.15 (s, 3H, CH$_3$), 1.22 (d, J=7 Hz, 12H, 2×(CH$_3$)$_2$CH).

MS APCI m/z 350.2 [M+1]$^+$.

Example 20

5-Amino-3-(3,5-diisoproryl-4-methoxy-benzylidene)-1,3-dihydroindol-2-one

2-Oxindole (6.5 g) was dissolved in concentrated sulfuric acid (25 ml) and the mixture maintained at −10 to 15° C. while fuming nitric acid (2.1 ml) was added dropwise. After the addition of the nitric acid the reaction mixture was stirred at 0° C. for 0.5 hour and poured into ice-water. The precipitate which formed was collected by filtration, washed with water and crystallized from 50% acetic acid. The final crystalline product was then filtered, washed with water and dried under vacuum to give 6.3 g (70%) of 5-nitro-2-oxindole.

5-Nitro-2-oxindole (6.3 g) was hydrogenated in methanol over 10% palladium on carbon to give 3.0 g (60% yield) of 5-amino-2-oxindole as a white solid.

3,5-Diisopropyl-4-methoxybenzaldehyde was condensed with 5-amino-2-oxindole to give 0.3 g of 5-Amino-3-(3,5-diisopropyl-4-methoxybenzylidene)-1,3-dihydroindol-2-one as a yellow-orange solid.

$^1$HNMR (360 MHz, DMSO-d6) δ: 10.62 (br s, 1H, NH), 8.31 (s, 2H), 7.8 (s, 1H), 7.65 (s, 1H), 7.55 (d, 1H), 7.47 (s, 1H), 7.09 (dd, J=2, 8 Hz, 1H), 6.88 (d, J=8 Hz, 1H), 3.72 (3H, OCH$_3$), 3.24–3.32 (m, 2H, 2×(CH$_3$)$_2$CH), 1.23 (d, J=6.5 Hz, 12H, 2×(CH$_3$)2CH).

Example 21

5-Chloro-3-(4-methoxy-3,5-dimethylbenzylidene)-1,3-dihydroindol-2-one 2,6-Dimethylphenol was methylated and then formylated.

$^1$HNMR (d$_6$-DMSO) δ: 10.1(s, 1H, CHO), 6.9(s, 2H, aromatic), 3.9(s, 3H, OCH$_3$), 2.6(s, 6H, 2×CH$_3$).

3,5-Dimethyl-4-methoxybenzaldehyde was condensed with 5-chloro-2-oxindole to give 0.3 g of 5-chloro-3-(4-methoxy-3,5-dimethylbenzylidene)-1,3-dihydroindol-2-one as a yellow-orange solid.

Example 22

3-(3,5-Diisopropyl-4-methoxybenzylidene)-6-fluoro-1,3-dihydroindol-2-one

A suspension of sodium hydride (2.6 g) and dimethylmalonate (14.5 g) in dimethylsulfoxide (160 ml) was stirred at 100° C. for 1 hour. The mixture was cooled to room temperature and 7.95 g of 2,5-difluoronitrobenzene was added and stirring was continued for 30 minutes. The mixture was then heated to 100° C. and stirred for 1 additional hour, then cooled to room temperature and poured into 400 ml of saturated ammonium chloride. The mixture was extracted with ethyl acetate (200 ml) and the organic layer washed with brine, dried over anhydrous sodium sulfate and concentrated under vacuum. The residue was crystallized from methanol to give 24.4 g (80% yield) of dimethyl 4-fluoro-2-nitrophenylmalonate as a white solid. The filtrate was concentrated and chromatographed on a column of silica gel (ethyl acetate:hexane 1:8) to give 5.03 g of dimethyl 4-fluoro-2-nitrophenylmalonate, for a total of 29.5 g (96% yield).

Dimethyl 4-fluoro-2-nitrophenylmalonate (5.0 g) was refluxed in 20 ml of 6 N hydrochloric acid for 24 hours. The reaction was cooled and the white solid which formed was collected by vacuum filtration, washed with water and dried to give 3.3 g (87% yield) of 4-fluoro-2-nitrophenylacetic acid.

4-Fluoro-2-nitrophenylacetatic acid (3.3 g) dissolved in acetic acid (15 ml) was hydrogenated over 0.45 g of 10% palladium on carbon under 60 psi for 2 hours. The catalyst was removed by filtration and washed with 15 ml of methanol. The combined filtrates were concentrated and diluted with water. The precipitate was collected by vacuum filtration, washed with water and dried to give 1.6 g (70% yield) of 6-fluoro-2-oxindole. The filtrate was concentrated to give a purple solid with an NMR spectrum similar to the first crop. Chromatography of the purple solid (ethyl acetate:hexane 1:2, silica gel) gave a second crop of 6-fluoro-2-oxindole as a white solid.

$^1$HNMR (360 MHz, DMSO-d6) δ: 10.43 (s, 1H, NH-1), 7.17 (t, J=8 Hz, H-4), 6.69 (ddd, J=2, 8, 10 Hz, 1H, H-5), 6.6 (dd, J=2, 9 Hz, 1H, H-7), and 3.42 (s, 2H, CH$_2$-3).

MS m/z 152.8 [M+1]$^+$.

3,5-Diisopropyl-4-methoxybenzaldehyde was condensed with 6-fluoro-2-oxindole to give 0.3 g of 3-(3,5-diisopropyl-4-methoxybenzylidene)-6-fluoro-1,3-dihydroindol-2-one as a yellow-orange solid.

$^1$HNMR (360 MHz, DMSO-d6) δ: 10.69 (s, br, 1H, NH), 7.58 (s, 1H, vinyl), 7.55–7.59 (m, 1H), 7.47 (s, 2H), 6.68 (m, 2H), 3.73 (s, 3H, OCH$_3$), 3.25–3.34 (m, 2H, 2×(CH$_3$)$_2$CH), 1.2 (d, J=7 Hz, 12H, 2×(CH$_3$)$_2$CH).

MS m/z 353.

Example 23

3-(2,2-Dimethylchroman-6-ylmethylene)-5-fluoro-1,3-dihydroindol-2-one 2,2-Dimethyl-6-formylchromane (commercially available) was condensed with 5-fluoro-2-oxindole to give 0.3 g of 3-(2,2-Dimethylchroman-6-ylmethylene)-5-fluoro-1,3-dihydroindol-2-one as a yellow-orange solid.

Example 24

5-Chloro-3-[3,5-diisopropyl-4-(2-morpholin-4-ylethoxy)-benzylidene]-1,3-dihydroindol-2-one Triphenylphosphine (5.14 g, 19.58 mmol) was added to a solution of 3,5-diisopropyl-4-hydroxybenzaldehyde (4 g, 19.58 mmol) in tetrahydrofuran (40 ml) followed by addition of 2-hydroxyethylmorpholine (2.57 g, 19.58 mmol) and then the dropwise addition of diethylazodicarboxylate (3.41 g, 19.58 mmol). The mixture was stirred at room temperature for 12 hours. The reaction was concentrated under reduced pressure and partitioned between 2N hydrochloric acid (200 ml) and ethyl acetate (150 ml). The aqueous layer was extracted with ethyl acetate (2×150 ml), basified to pH 9 with solid sodium bicarbonate and extracted with ethyl acetate (3×150 ml). The organic layers were combined, dried over magnesium sulfate and concentrated to afford 900 mg (14%) of 3,5-diisopropyl-4-(2-morpholin-4-ylethoxy)-benzaldehyde as a yellowish oil.

$^1$HNMR (360 MHz, DMSO-d6) δ: 9.91 (s, 1H, CHO), 9.37 (s, 2H, 2×Ar—H), 3.85 (t, J=5 Hz, 2H, O—CH$_2$CH$_2$), 3.59 (m, J=5 and 4 Hz, 4H, 2× ringO—CH$_2$CH$_2$), 3.39 (sept, J=7 Hz, 2H, 2×CHCH$_3$), 2.72 (t, J=5 Hz, 2H, N—CH$_2$CH$_2$), 2.4 (m on DMSO, 4H, 2× ringN—CH$_2$CH$_2$), 1.2 (d, J=7 Hz, 12H, 4×CH$_3$).

A mixture of 3,5-diisopropyl-4-(2-morpholin-4-ylethoxy)-benzaldehyde (0.4 g, 1.26 mmol), 5-chloro-2-oxindole (0.21 g, 1.26 mmol) and pyrrolidine (0.5 ml, 6.3 mmol) in ethanol (2 ml) was held in sealed tube at 100° C. for 12 hours. The mixture was then poured into 1N hydrochloric acid (100 ml) and the solid which remained were filtered and washed with more water (50 ml). The solid was then dissolved in ethyl acetate (200 ml), the solution dried over magnesium sulfate, filtered and then concentrated. The solid which remained was chromatographed (silica, 4/4/1 dichloromethane/hexanes/methanol) to give 60 mg (10%) of 5-chloro-3-[3,5-diisopropyl-4-(2-morpholin-4-ylethoxy)-benzylidene]-1,3-dihydroindol-2-one as a brownish-orange solid.

$^1$HNMR (360 MHz, DMSO-d6) δ: 10.54 (s, 1H, NH), 9.43 (d, J=10 Hz, 1H, Ar—H), 7.58 (d, J=9 Hz, 1H, Ar—H), 7.46 (d, J=5 Hz, 2H, Ar—H), 7.3 (m, 1H, Ar—H), 7.19 (m, J=9 and 10 Hz, 1H, Ar—H), 6.99 (m, J=9 and 9 Hz, 1H, Ar—H), 6.83 (m, J=9 and 1 Hz, 1H, Ar—H) 3.61 (dd, J=9 and 22 HZ 1H, 1×CH$_2$CH), 3.43 (m, 1H, CHCH$_3$), 2.86 (dd, J=4 and 22 Hz, 1H, 1×CH$_2$CH), 1.35 (d, J=9 Hz, 3H, CH$_3$).

MS m/z 262.0 [M+1]$^+$.

Example 25

3-(3,5-Diisopropyl-4-methoxybenzylidene)-7-fluoro-1,3-dihydroindol-2-one 3,5-Diisopropyl-4-methoxybenzaldehyde was condensed with 7-fluoro-2-oxindole to give 0.25 g of 3-(3,5-diisopropyl-4-methoxybenzylidene)-7-fluoro-1,3-dihydroindol-2-one as a yellow-orange solid.

Example 26

3-(4-Methoxy-3-thiophen-3-ylbenzylidene)-5-(2-morpholin-4-yl-ethyl)-1,3-dihydroindol-2-one A solution of 5-chloroacetyl-2-oxindole (4.18 g) in trifluoroacetic acid (30 ml) was cooled in an ice bath and 4.65 g of triethylsilane added. The mixture was then stirred at room temperature for 3 hours. The mixture was poured into 150 ml of water and the precipitate which formed was collected by vacuum filtration, washed with 50 ml of water and dried to give 2.53 g (65% yield) of 5-(2-chloroethyl)-2-oxindole as a reddish-brown solid.

$^1$HNMR (360 MHz, DMSO-d6) δ: 10.26 (s, br, NH), 7.11 (s, 1H, H-4), 7.05 (d, J=8 Hz, 1H), 6.73 (d, J 8 Hz, 1H), 3.77 (t, J=7 Hz, 2H, CH$_2$), 3.42 (s, 2H, CH$_2$), 2.94 (t, J=7 Hz, 2H, CH$_2$).

A solution of 5-(2-chloroethyl)-2-oxindole (2.3 g), morpholine (1.2 ml) and diisopropylethylamine (1.2 ml) in dimethylsulfoxide (10 ml) was heated overnight at 100° C. The mixture was cooled, poured into water and extracted with ethyl acetate. The organic layer was washed with brine, dried and evaporated. The residue was chromatographed (silica gel, 5% methanol in chloroform) to give 0.9 g (31%) of 5-(2-morpholin-4-yl-ethyl)-2-oxindole as a white solid.

$^1$HNMR (360 MHz, DMSO-d6) δ: 10.21 (s, br, 1H, NH), 7.06 (s, br, 1H, H-4), 7.0 (d, J=8 Hz, 1H, H-6), 6.71 (d, J=8 Hz, 1H, H-7), 3.55–3.58 (m, 4H), 3.41 (s, 2H, H-3), 2.63–2.68 (m, 2H), 2.39–2.47 (m, 6H).

A mixture of 3(3-thiophene)-4-methoxybenzaldehyde (0.27 g, 1.22 mmol), 5-(2-morpholin-4-yl-ethyl)-2-oxindole (0.3 g, 1.22 mmol) and piperidine (0.6 ml, 6.1 mmol) in ethanol (4 ml) was held in a sealed tube at 100° C. for 12 hours. The reaction was cooled and poured into diethyl ether (150 ml) and hexanes (150 ml). The solid which remained was removed by filtration, washed with diethyl ether and then hexanes and dried to afford 0.27 g (50%) of 3-(4-methoxy-3-thiophen-3-ylbenzylidene)-5-(2-morpholin-4-yl-ethyl)-1,3-dihydroindol-2-one as an orange-yellow solid.

$^1$HNMR (360 MHz, DMSO-d6) δ: 10.41 (s, 1H, NH), 8.86 (d, J=2.15 Hz, 1H, Ar—H), 8.39 (dd, J=2 and 9 Hz, 1H, Ar—H), 7.8 (dd, 1H, J=1 and 3 Hz, Ar—H), 7.7 (s, 1H, Ar—CH=C), 7.6 (m, 1H, ArH), 7.5 (m, 2H, 2×ArH), 7.21 (d, J=9 Hz, 1H, Ar—H), 7.02 (dd, 1H, J=1 and 8 Hz, Ar—H), 6.73 (d, 1H, J=8 Hz, Ar—H), 3.93 (s, 3H, OCH$_3$), 3.58 (m, 4H, 2×OCH$_2$CH$_2$N), 2.7 (m, 2H, ArCH$_2$CH$_2$), 2.5 (m, 2H, ArCH$_2$CH$_2$N), 2.4 (m, 4H, 2×OCH$_2$CH$_2$N).

MS m/z 447.2 [M+1]$^+$.

Example 27

N-[3-(5-Isopropyl-4-methoxy-2-methylbenzylidene)-2-oxo-2,3-dihydro-1H-indol-6-yl]-acetamide A mixture of 5-isopropyl-4-methoxy-2-methylbenzaldehyde (0.25 g, 1.3 mmol), 6-acetamido-2-oxindole (0.25 g, 1.3 mmol) and pyrrolidine (0.54 ml, 6.5 mmol) in ethanol (4 ml) was held in a sealed tube at 100° C. for 12 hours. The reaction was cooled and then poured into water (100 ml). The solid which formed was removed by filtration, washed with water and then dissolved in ethyl acetate (200 ml). The ethyl acetate solution was dried over magnesium sulfate and concentrated. The resulting solid was triturated with dichloromethane/hexanes to afford 0.33 g (70%) of N-[3-(5-isopropyl-4-methoxy-2-methylbenzylidene)-2-oxo-2,3-dihydro-1H-indol-6-yl]-acetamide as a brownish yellow solid.

$^1$HNMR (360 MHz, DMSO-d6) δ: 10.46 (s, 1H, NH), 7.49 (s, 1H, Ar—H), 7.46 (s, 1H, Ar—H), 7.41 (s, 1H, Ar—H), 6.93 (m, 1H, Ar—CH=C), 6.83 (dd, 1H, J=2 and 8 Hz, Ar—H), 3.83 (s, 3H, OCH$_3$), 2.30 (s, 3H, Ar—CH$_3$), 2.02 (s, 3H, NHCOCH$_3$), 1.2 (m, 1H, CH(CH$_3$)$_2$), 1.1 (d, J=7 Hz, 6H, CH(CH$_3$)$_2$).

MS m/z 365.2 [M+1]$^+$.

Example 28

3-(3,5-Diisopropyl-4-methoxybenzylidene)-5-ethyl-1,3-dihydroindol-2-one

2-Oxindole (3 g) suspended in 1,2-dichloroethane was slowly treated with 3.2 ml of acetyl chloride. The resulting suspension was stirred at 50° C. for 5 hours, cooled, and poured into water. The resulting precipitate was collected by vacuum filtration, washed copiously with water and dried under vacuum to give 2.9 g (73% yield) of 5-acetyl-2-oxindole as a brown solid.

¹HNMR (360 MHz, DMSO-d6) δ: 10.75 (s, br, NH), 7.83 (d, J=8 Hz, 1H), 7.78 (s, 1H, H-4), 6.88 (d, J=8 Hz, 1H), 3.53 (s, 2H, CH$_2$), 2.49 (s, 3H, CH$_3$).

5-Acetyl-2-oxindole (2 g) and 15 ml of trifluoroacetic acid in an ice bath was slowly treated with 1.8 g of triethylsilane and then stirred at room temperature for 5 hours. One ml of triethylsilane was added and stirring continued overnight. The reaction mixture was poured into ice water and the resulting precipitate collected by vacuum filtration, washed copiously with water and dried under vacuum to give 1.3 g (71% yield) of 5-ethyl-2-oxindole as a yellow solid.

¹HNMR (360 MHz, DMSO-d6) δ: 10.25 (s, br, NH-1), 7.03 (s, 1H, H-4), 6.97 (d, J=8 Hz, 1H, H-6), 6.69 (d, J=8 Hz, 1H, H-7), 3.40 (s, 2H, CH$_2$-3), 2.51 (q, J=8 Hz, 2H, CH$_2$CH$_3$-5), and 1.12 (t, J=7 Hz, 3H, CH$_2$CH$_3$-5).

3,5-Diisopropyl-4-methoxybenzaldehyde was condensed with 5-ethyl-2-oxindole to give 0.3 g of 3-(3,5-diisopropyl-4-methoxybenzylidene)-5-ethyl-1,3-dihydroindol-2-one as a yellow-orange solid.

¹HNMR (360 MHz, DMSO-d6) δ: 10.42 (s, 1H, NH), 7.56 (s, 1H), 7.51 (s, 2H), 7.49 (s, br, 1H), 7.08 (dd, J=8 Hz, 1H), 6.79 (d, J=8 Hz, 1H), 3.74 (s, 3H, OCH3), 3.25–3.55 (m, 2H, 2×(CH$_3$)$_2$CH), 2.44 (q, J=8 Hz, 2H, CH$_3$CH$_2$), 1.22 (d, J=7 Hz, 12H, 2×(CH$_3$)$_2$CH), 1.08 (t, J=8 Hz, 3H, CH$_3$CH$_2$).

MS APCI m/z 364.3 [M+1]$^+$.

Example 28

N-[2'-Methoxy-5'-(2-oxo-1,2-dihydroindol-3-ylidenemethyl)-biphenyl-3-yl]-acetamide A mixture of 3-bromo-p-anisaldehyde (1 g, 4.65 mmol), pyrrolidine (1.9 ml, 23.2 mmol) and oxindole (0.62 g, 4.65 mmol) in dimethylformamide (7 ml) was held in a sealed tube at 100° C. for 12 hours. The mixture was cooled to room temperature and poured into 1N hydrochloric acid (100 ml). The precipitate which formed was filtered and washed with water. The precipitate was then dissolved in ethyl acetate (200 ml), the solution washed with brine, dried over magnesium sulfate and then concentrated. The solid obtained was chromatographed (silica, 30–40% ethyl acetate/hexanes) to give 0.63 g (42%) of 3-(3-bromo-4-methoxybenzylidene)-1,3-dihydroindol-2-one as a yellow solid.

¹HNMR (360 MHz, DMSO-d6) δ: 10.5 (m, 1H, NH), 7.7 (m, 1H, Ar—H), 7.6 (m, 1H, Ar—CH=C), 7.5 (m, 1H, Ar—H), 7.2 (m, 2H, 2×Ar—H), 6.9 (m, 1H, Ar—H), 6.8 (m, 1H, Ar—H), 3.9 (s, 3H, OCH$_3$). MS m/z 330.0 and 332. [M]$^+$ and [M+2]$^+$.

Tetrakis(triphenylphosphine)palladium(0) (0.02 g, 0.02 mmol) was added to a solution of 3-(3-Bromo-4-methoxybenzylidene)-1,3-dihydroindol-2-one (0.2 g, 0.61 mmol) in toluene (1 ml) and ethanol (2 ml), followed by addition of 2M aqueous sodium carbonate (1.2 ml, 2.4 mmol). To this mixture was added 3-acetamidophenylboronic acid (0.12 g, 0.67 mmol), and the mixture was heated to 100° C. in a sealed tube and held there for 12 hours. The reaction was then poured into water (50 ml) and extracted with ethyl acetate (2×100 ml). The combined organic layers were washed with saturated aqueous sodium bicarbonate (50 ml) and brine (50 ml). The organic layer was dried over magnesium sulfate and concentrated. Chromatography (silica, 30–40% ethyl acetate/hexanes) afforded a waxy solid that was triturated with diethyl ether/hexanes and then dried to afford 0.05 g (22%) of N-[2'-methoxy-5'-(2-oxo-1,2-dihydroindol-3-ylidenemethyl)-biphenyl-3-yl]-acetamide as a reddish orange solid.

¹HNMR (360 MHz, DMSO-d6) δ: 10.6 (m, 1H, NH), 9.88 (s, 1H, NHAc), 7.7 (m, 1H, Ar—H), 7.5 (m, 3H, 2×Ar—H and Ar—CH=C), 7.2 (m, 4H, Ar—H), 7.0 (m, 2H, Ar—H), 6.8 (m, 2H, Ar—H), 3.9 (two s, 3H, OCH$_3$), 2.02 (2, 3H, COCH$_3$).

MS m/z 385.2 [M+1]$^+$.

Example 30

5-Fluoro-3-(5-isopropyl-4-methoxy-2-methylbenzylidene)-1,3-dihydroindol-2-one

5-Isopropyl-4-methoxy-2-methylbenzaldehyde was condensed with 5-fluoro-2-oxindole to give 0.25 g of 5-fluoro-3-(5-isopropyl-4-methoxy-2-methylbenzylidene)-1,3-dihydroindol-2-one as a yellow-orange solid.

¹HNMR (360 MHz, DMSO-d6) δ: 10.54 (s, 1H, NH), 7.72 (s, 1H), 7.47 (s, 1H), 7.1 (dd, 1H), 7.04 (ddd, 1H), 6.98 (s, 1H), 6.82–6.86 (m, 1H), 3.86 (s, 3H, OCH$_3$), 3.25–3.28 (m, 1H, (CH$_3$)$_2$CH), 2.32 (s, 3H, CH$_3$), 1.14 (d, 6H, (CH$_3$)$_2$CH).

EI MS m/z 325 [M]$^+$.

Example 31

N-[3-(4-Methoxy-3-thiophen-2-ylbenzylidene)-2-oxo-2,3-dihydro-1H-indol-6-yl]-acetamide Tetrakis(triphenylphosphine)palladium(0) (0.24 g) was added to a solution of 4-methoxy-3-bromobenzaldehyde (1.5 g) in toluene (15 ml) and ethanol (15 ml), followed by addition of 2M aqueous sodium carbonate (14 ml). To this mixture was added thiophene-2-boronic acid (0.98 g), and the mixture was heated to reflux. After 3 hours, the reaction was partitioned between water (100 ml) and ethyl acetate (250 ml). The organic layer was washed with saturated aqueous sodium bicarbonate (75 ml) and brine (75 ml), dried over magnesium sulfate and concentrated. Chromatography (silica, 20% ethyl acetate/hexanes) afforded 1.3 g (87%) of 3-(2-thiophene)-4-methoxybenzaldehyde as a yellow oil.

¹HNMR (360 MHz, DMSO-d6) δ: 9.92 (s, 1H, CHO), 8.2 (d, 1H, J=3 Hz, 1×Ar—H), 7.8 (dd, 1H, J=10 and 10 Hz, SCHCHCH), 7.65 (m, 1H, Ar—H), 7.60 (dd, 1H, J=2 and 6 Hz, Ar—H), 7.32 (d, 1H, J=10 Hz, SCHCHCH), 7.13 (d, 1H, J=10 and 6 Hz, SCHCHCH), 3.99 (s, 3H, OCH$_3$).

A mixture of 3-(2-thiophene)-4-methoxybenzaldehyde (0.25 g, 1.15 mmol), 6-acetamido-2-oxindole (0.22 g, 1.15 mmol) and pyrrolidine (0.48 ml, 5.75 mmol) in ethanol (4 ml) was held in a sealed tube at 100° C. for 12 hours. The reaction was cooled and the precipitate which formed was removed by filtration, washed with ethanol and then hexanes and dried to afford 0.15 g (33%) of N-[3-(4-methoxy-3-thiophen-2-ylbenzylidene)-2-oxo-2,3-dihydro-1H-indol-6-yl]-acetamide as a yellow solid.

¹HNMR (360 MHz, DMSO-d6) δ: 10.49 (s, 1H, NH), 9.95 (s, 1H, NHAc), 8.99 (d, J=2 Hz, 1H, Ar—H), 8.28 (dd, J=2 and 9 Hz, 1H, Ar—H), 7.6 (m, 2H, 2×Ar—H), 7.5 (m, 2H, Ar—H and Ar—CH=C), 7.38 (d, 1H, J=1 Hz, Ar—H), 7.22 (d, 1H, J=9 Hz, Ar—H), 7.14 (dd, 1H, J=4 and 5 Hz, Ar—H), 7.05 (dd, 1H, J=2 and 9 Hz, Ar—H), 3.97 (s, 3H, OCH$_3$), 2.04 (s, 3H, NHCOCH$_3$).

MS m/z 391.3 [M]$^+$ and [M+2]$^+$.

Example 32

6-Amino-3-(3,5-diisopropyl-4-methoxybenzylidene)-1,3-dihydroindol-2-one 3,5-Diisopropyl-4-methoxybenzaldehyde was condensed with 6-amino-2-oxindole to give 0.3 g of 6-amino-3-(3,5- diisopropyl-4-methoxybenzylidene)-1,3-dihydroindol-2-one as a yellow-orange solid.

Example 33

N-[3-(2,2-Dimethylchroman-6-ylmethylene)-2-oxo-2,3-dihydro-1H-indol-6-yl]-acetamide A mixture of 6-acetamido-2-oxindole (285 mg), 2,2-dimethylchroman-6-carboxaldehyde (285 mg) and piperidine (0.2 ml) was stirred at 90° C. overnight. The reaction mixture was cooled and diluted with 20 ml of water. The sticky solid which formed was filtered and chromatographed (2% ethanol in ethyl acetate) to give 240 mg (44%) of N-[3-(2,2-dimethylchroman-6-ylmethylene)-2-oxo-2,3-dihydro-1H-indol-6-yl]-acetamide as an orange red solid.

$^1$HNMR (360 MHz, DMSO-d6) δ: 10.44 (s, 1H, NH), 10.0 (s, 1H, NH), 7.6, 7.46, 7.42, 7.37, 6.93, 6.82 (m, 7H, 6 Ar—H and 1 vinyl-H), 2.8 (t, J=6 Hz, 2H, $CH_2$), 2.03 (s, 3H, $CH_3$), 1.83 (t, J=6 Hz, 2H, $CH_2$), 1.32 (s, 6H, 2×$CH_3$).

MS m/z 363.1 [M+1]$^+$.

Example 34

5-Bromo-3-(2,2-dimethylchroman-6-ylmethylene)-1,3-dihydroindol-2-one

2-Oxindole (1.3 g) in 20 ml of acetonitrile was cooled to −10° C. and 2.0 g of N-bromosuccinimide was slowly added with stirring. The reaction was stirred for 1 hour at −10° C. and then 2 hours at 0° C. The precipitate which formed was collected, washed with water and dried to give 1.9 g (90% yield) of 5-bromo-2-oxindole.

$^1$HNMR (360 MHz, DMSO-d6) δ: 10.44 (s, br, 1H, NH-1), 7.32–7.36 (m, 2H), 6.76 (d, J=8.5 Hz, 1H, H-7), 3.5 (s, 2H, $CH_2$). MS m/z 212.1 and 214.1, [M]$^+$ and [M+2]$^+$.

2,2-Dimethyl-6-formylchromane (commercially available) was condensed with 5-bromo-2-oxindole to give 0.3 g of 5-bromo-3-(2,2-dimethylchroman-6-ylmethylene)-1,3-dihydroindol-2-one as a yellow-orange solid.

Isomer 1 (67%): $^1$HNMR (360 MHz, DMSO-d6) δ: 10.65 (s, br, 1H, NH), 7.73 (d, 1H), 7.6 (s, 1H, vinyl), 7.5 (s, br, 1H), 7.47 (dd, 1H), 7.37 (dd, 1H), 6.86 (d, 1H), 6.82 (d, 1H), 2.77–2.81 (m, 4H, 2×$CH_2$), 1.81–1.84 (m, 4H, 2×$CH_2$), 1.32 (s, 6H, 2×$CH_3$).

Isomer 2 (33%): $^1$HNMR (360 MHz, DMSO-d6) δ: 10.63 (s, br, 1H, NH), 8.32 (dd, 1H), 8.27 (s, br, 1H), 7.89 (d, 1H), 7.81 (s, 1H, vinyl), 7.3 (dd, 1H), 6.79 (d, 1H), 6.76 (d, 1H), 2.77–2.81 (m, 4H, 233 $CH_2$), 1.81–1.84 (m, 4H, 2×$CH_2$), 1.31 (s, 6H, 233 $CH_3$).

MS APCI m/z 384.1 and 385.9, [M]$^+$ and [M+2]$^+$.

Example 35

3-(4-Methoxy-3-thiophen-3-ylbenzylidene)-1,3-dihydroindol-2-one

Tetrakis(triphenylphosphine)palladium(0) (0.02 g, 0.02 mmol) was added to a solution of 3-(3-bromo-4-methoxybenzylidene)-1,3-dihydroindol-2-one (0.2 g, 0.61 mmol) in toluene (1 ml) and ethanol (1 ml), followed by addition of 2M aqueous sodium carbonate (1.2 ml, 2.4 mmol). To this mixture was added thiophene-3-boronic acid (0.09 g, 0.67 mmol) and the mixture was held at 100° C. in a sealed tube for 12 hours. The reaction was then poured into water (50 ml) and extracted with ethyl acetate (2×100 ml). The combined organic layers were washed with saturated aqueous sodium bicarbonate (50 ml) and brine (50 ml), dried over magnesium sulfate and concentrated. Chromatography (silica, methylene chloride then 30–40% ethyl acetate/hexanes) afforded 0.1 g (50%) of 3-(4-methoxy-3-thiophen-3-ylbenzylidene)-1,3-dihydroindol-2-one as a yellow solid.

$^1$HNMR (360 MHz, DMSO-d6) δ: 10.54 (s, 1H, NH), 7.8 (m, 2H, 2×Ar—H), 7.6 (m, 5H, 4×Ar—H and Ar—CH=C), 7.2 (m, 2H, Ar—H), 6.8 (m, 2H, Ar—H), 3.92 (s, 3H, $OCH_3$).

MS m/z 334.3 [M+1]$^+$.

Example 36

5-Bromo-3-(5-isopropyl-4-methoxy-2-methylbenzylidene)-1,3-dihydroindol-2-one

5-Isopropyl-4-methoxy-2-methylbenzaldehyde was condensed with 5-bromo-2-oxindole to give 0.3 g of 5-bromo-3-(5-isopropyl-4-methoxy-2-methylbenzylidene)-1,3-dihydroindol-2-one as a yellow-orange solid.

$^1$HNMR ($d_6$-DMSO) δ: 10.5 (s, 1H, CONH), 7.7, 7.6, 7.5, 7.4, 7.0, 6.8 (m, 6H, aromatic, =CH—), 3.9 (s, 3H, $OCH_3$), 3.3 (m, 1H, CH), 2.3 (s, 3H, $CH_3$), 1.2 (d, 6H, 2×$CH_3$).

Example 37

5-Fluoro-3-(6-methoxybiphenyl-3-ylmethylene)-1,3-dihydroindol-2-one

4-Methoxy-3-phenylbenzaldehyde was condensed with 5-fluoro-2-oxindole to give 0.3 g of 5-fluoro-3-(6-methoxybiphenyl-3-ylmethylene)-1,3-dihydroindol-2-one as a yellow-orange solid.

Example 38

3-(3-Isopropyl-4-methoxybenzylidene)-4-methyl-1,3-dihydroindol-2-one

Diethyl oxalate (30 ml) in 20 ml of dry ether was added with stirring to 19 g of potassium ethoxide suspended in 50 ml of dry ether. The mixture was cooled in an ice bath and 20 ml of 3-nitro-o-xylene in 20 ml of dry ether was slowly added. The thick dark red mixture which formed was refluxed for 0.5 hour, concentrated to a dark red solid, and treated with 10% sodium hydroxide until almost all of the solid dissolved. The dark red mixture was treated with 30% hydrogen peroxide until the red color changed to yellow. The mixture was then treated alternately with 10% sodium hydroxide and 30% hydrogen peroxide until the dark red color no longer formed on addition of sodium hydroxide. The remaining solid was filtered and the filtrate acidified with 6 N hydrochloric acid. The resulting precipitate was collected by vacuum filtration, washed with water, and dried under vacuum to give 9.8 g (45% yield) of 1-methyl-6-nitrophenylacetic acid as an off-white solid. The solid was hydrogenated in methanol over 10% palladium on carbon to give 9.04 g of 4-methyl-2-oxindole as a white solid.

$^1$HNMR (360 MHz, DMSO-d6) δ: 10.27 (s, br, 1H, NH), 7.06 (t, J=8 Hz, 1H, H-6), 6.74 (d, J=8 Hz, H-5), 6.63 (d, J=8 Hz, 1H, H-7), 3.36 (s, 2H, $CH_2$), 2.18 (s, 3H, $CH_3$).

3-Isopropyl-4-methoxybenzaldehyde was condensed with 4-methyl-2-oxindole to give 0.25 g of 3-(3-isopropyl-4-methoxybenzylidene)-4-methyl-1,3-dihydroindol-2-one as a yellow-orange solid.

$^1$HNMR ($d_6$-DMSO) δ: 10.4(s, 1H, NH), 8.2, 8.1, 7.6, 7.2, 7.1, 6.8, 6.7 (m, 7H, aromatic, =CH—), 3.9 (s, 3H, $OCH_3$), 3.2 (m, 1H, CH), 2.6 (m, 1H, CH), 1.2 (d, 6H, 2×$CH_3$).

Example 39

3-(4,5-Dimethoxy-2-thiophen-2-ylbenzylidene)-1,3-dihydroindol-2-one

A mixture of 6-bromoveratraldehyde (1 g, 4.08 mmol), oxindole (0.54 g, 4.08 mmol) and pyrrolidine (1.7 ml, 20.4 mmol) in dimethylformamide (6 ml) was held in a sealed tube at 100° C. for 12 hours. The reaction mixture was cooled and added to 1N hydrochloric acid (100 ml). The precipitate which formed was filtered and washed with water. The precipitate was then dissolved in ethyl acetate (200 ml), the solution washed with brine, dried over magnesium sulfate and concentrated. The solid obtained was chromatographed (silica, 30-4-% ethyl acetate/hexanes) to give 1.2 g (81%) of 3-(3-bromo-4,5-dimethoxybenzylidene)-1,3-dihydroindol-2-one as a yellow solid.

$^1$HNMR (360 MHz, DMSO-d6) δ: 10.5 (s, 1H, NH), 7.4 (s, 1H, Ar—CH=C), 7.3 (m, 2H, 2×Ar—H), 7.2 m, 1H, Ar—H), 6.8 (m, 2H, 2×Ar—H), 3.8 (s, 3H, OCH$_3$), 3.7 (s, 3H, OCH$_3$).

MS m/z 360.5 and 362.5, [M]$^+$ and [M+2]$^+$.

Tetrakis(triphenylphosphine)palladium(0) (0.03 g, 0.03 mmol) was added to a solution of 3-(3-bromo-4,5-dimethoxybenzylidene)-1,3-dihydroindol-2-one (0.32 g, 0.89 mmol) in toluene (2 ml) and ethanol (2 ml), followed by additional of 2M aqueous sodium carbonate (1.8 ml, 3.6 mmol). To this mixture was added thiophene-2-boronic acid (0.13 g, 0.98 mmol), and the mixture was held at 100° C. in a sealed tube for 12 hours. The reaction mixture was poured into water (50 ml) and extracted with ethyl acetate (2×100 ml). The combined organic layers were washed with saturated aqueous sodium bicarbonate (50 ml) and brine (50 ml), dried over magnesium sulfate and concentrated. Chromatography (silica, 30–40% ethyl acetate/hexanes) afforded an orange solid that was triturated with methylene chloride and dried to afford 0.19 g (59%) Of 3-(4,5-dimethoxy-2-thiophen-2-ylbenzylidene)-1,3-dihydroindol-2-one as an orange solid.

$^1$HNMR (360 MHz, DMSO-d6) δ: 10.5 (m, 1H, NH), 7.6 (m, 1H, Ar—H), 7.5 (m, 2H, Ar—H), 7.3 (m, 1H, Ar—CH=C), 7.2 (m, 4H, Ar—H), 6.8 (m, 2H, Ar—H), 6.8 (m, 2H, Ar—H), 3.9 (two s, 3H, OCH$_3$), 3.7 (two s, 3H, COCH$_3$).

MS m/z 364.0 [M+1]$^+$.

Example 40

N-{3-[4-(2-Morpholin-4-ylethoxy)-3-thiophen-2-ylbenzylidene]-2-oxo-2,3-dihydro-1H-indol-6-yl}-acetamide Triphenylphosphine (6.85 g) was added to a solution of 3-bromo-4-hydroxybenzaldehye (5 g) in tetrahydrofuran (40 ml), followed by addition of 2-hydroxyethylmorpholine (3.01 ml) and then the dropwise addition of diethylazodicarboxylate (4.11 ml). After 12 hours, the reaction was concentrated under reduced pressure, poured into 2N hydrochloric acid (200 ml) and extracted with ethyl acetate (2×150 ml). The aqueous layer was basified to pH 9 with solid sodium bicarbonate and extracted with ethyl acetate (2×150 ml). The organic layers were dried over magnesium sulfate and concentrated to afford 4.4 g (56%) of 4-morpholinoethoxy-3-bromobenzaldehyde as a reddish oil.

$^1$HNMR (360 MHz, DMSO-d6) δ: 9.84 (s, 1H, NH), 8.07 (d, H, J=2 Hz, Ar—H), 7.90 (dd, 1H, J=2 and 8 Hz, Ar—H), 7.32 (d, 1H, J=8 Hz, Ar—H), 4.29 (t, 2H, J=6 Hz, Ar—OCH$_2$), 3.56 (m, 4H, OCH$_2$CH$_2$N), 2.76 (t, 2H, J=6 Hz, ArOCH$_2$—CH$_2$N), 2.50 (m, 4H, NCH$_2$CH$_2$O).

Tetrakis(triphenylphosphine)palladium(0) (0.23) was added to a solution of 4-morpholinoethoxy-3-bromobenzaldehyde (2.13 g) in toluene (10 ml) and ethanol (10 ml), followed by addition of 2M aqueous sodium carbonate (13 ml). To this mixture was added thiophene-2-boronic acid (1.13 g), and the mixture was refluxed for 12 hours. The reaction mixture was then poured into water (100 ml) and extracted into ethyl acetate (3×100 ml). The product was extracted into 1N hydrochloric acid (2×100 ml), the aqueous layers basified to pH 9 with solid sodium bicarbonate and extracted with ethyl acetate (2×100 ml). The organic layers were washed with brine (75 ml), dried over magnesium sulfate and concentrated to afford 1.7 g (75%) of 3-(2-thiophene)-4-morpholinoethoxybenzaldehyde as a greenish/yellow oil.

$^1$HNMR (360 MHz, DMSO-d6) δ: 9.93 (s, 1H, CHO), 8.2 (d, 1H, J=2 Hz, Ar—H), 7.82 (dd, 1H, J=2 and 8 Hz, Ar—H), 7.76 (dd, 1H, J=1 and 4 Hz, Ar—H), 7.59 (dd, 1H, J=1 and 5 Hz, Ar—H), 7.35 (d, 1H, J=9 Hz, Ar—H), 7.14 (dd, 1H, J=4 and 5 Hz, Ar—H), 4.34 (t, J=6 Hz, 2H, O—CH$_2$CH$_2$), 3.56 (m, 4H, 2× ringO—CH$_2$CH$_2$), 2.82 (t, J=6 Hz, 2H, N—CH$_2$CH$_2$), 2.5 (m on DMSO, 4H, 2× ringN—CH$_2$CH$_2$).

MS m/z 318.2 [M+1]$^+$.

A mixture of 3(2-thiophene)-4-morpholinoethoxybenzaldehyde (1.74 g), 6-acetamido-2-oxindole(1 g) and piperidine (2.6 ml) in ethanol (11 ml) was held in sealed tube at 100° C. for 12 hours. The reaction was cooled and added to diethyl ether and the ether decanted. The oily residue was dissolved in methylene chloride (10 ml) and precipitated in ether (200 ml) and hexanes (100 ml). The precipitate was removed by filtration, washed with ether and then hexanes and dried to afford a brownish solid. Chromatography (silica, 5% methanol/dichloromethane) afforded N-{3-[4-(2-morpholin-4-ylethoxy)-3-thiophen-2-ylbenzylidene]-2-oxo-2,3-dihydro-1H-indol-6-yl}-acetamide as a dark yellow solid.

$^1$HNMR (360 MHz, DMSO-d6) δ: 10.49 (s, 1H, NH), 10.01 (s, 1H, NHAc), 8.05 (d, J=2 Hz, 1H, Ar—H), 7.72 (m, 1H, Ar—H), 7.65 (m, 1H, Ar—H), 7.48 (m, 2H, 2×Ar—H), 7.47 (s, 1H, Ar—CH=C), 7.45 (d, 1H, J=2 Hz, Ar—H), 7.29 (d, 1H, J=9 Hz, Ar—H), 7.13 (m, 1H, Ar—H), 6.90 (dd, 1H, J=2 and 9 Hz, Ar—H), 4.32 (m, 2H, ArOCH$_2$CH$_2$N), 3.58 (m, 4H, 2×OCH$_2$CH$_2$N), 2.84 (m, 2H, ArOCH$_2$CH$_2$N), 2.5 (m under DMSO, 4H, 2×OCH$_2$CH$_2$N), 2.03 (s, 3H, NHCOCH$_3$).

MS m/z 490.0 [M+1]$^+$.

Example 41

3-(2,2-Dimethylchroman-6-ylmethylene)-4-methyl-1,3-dihydroindol-2-one 2,2-Dimethyl-6-formylchromane (commercially available) was condensed with 4-methyl-2-oxindole to give 0.25 g of 3-(2,2-dimethylchroman-6-ylmethylene)-4-methyl-1,3-dihydroindol-2-one as a yellow-orange solid.

$^1$HNMR (360 MHz, DMSO-d6) δ: 10.45 (s, br, 1H, NH), 8.17 (dd, J=2, 8 HZ, 1H), 8.02 (d, J=2 Hz, 1H), 7.6 (s, 1H, vinyl), 7.05 (t, J=8 Hz, 1H), 6.75 (t, 2H), 6.67 (d, J=8 Hz, 1H), 2.77 (t, J=7 Hz, 2H, CH$_2$), 2.55 (s, 3H, CH$_3$), 1.8 (t, J=7 Hz, 2H, CH$_2$), 1.31 (s, 6H, 2×CH$_3$).

MS APCI m/z 320.2 [M+1]$^+$.

Example 42

3-(2,3-Dihydrobenzofuran-5-ylmethylene)-5-fluoro-1,3-dihydroindol-2-one 2,3-Dihydro-5-formylbenzofuran (commercially available) was condensed with 5-fluoro-2-oxindole to give 0.25 g of 3-(2,3-dihydrobenzofuran-5-ylmethylene)-5-fluoro-1,3-dihydroindol-2-one as a yellow-orange solid.

Example 43

3-(3-Cyclohexyl-4-methoxybenzylidene)-5-fluoro-1,3-dihydroindol-2-one

2-Cyclohexylphenol was methylated then formylated. The aldehyde was condensed with 5-fluoro-2-oxindole to give 0.3 g of 3-(3-cyclohexyl-4-methoxybenzylidene)-5-fluoro-1,3-dihydroindol-2-one as a yellow-orange solid.

Example 44

5-Fluoro-3-(3-isopropyl-4-methoxybenzylidene)-1,3-dihydroindol-2-one

3-Isopropyl-4-methoxybenzaldehyde was condensed with 5-fluoro-2-oxindole to give 0.25 g of 5-fluoro-3-(3-isopropyl-4-methoxybenzylidene)-1,3-dihydroindol-2-one as a yellow-orange solid.

Example 45

3-(5-Isopropyl-4-methoxy-2-methylbenzylidene)-1,3-dihydro-pyrrolo[2,3-b]pyridin-2-one Zinc dust (6.5 g) was added to a solution of 3,3-dibromo-7-azaoxindole (2.9 g) in acetic acid (20 ml) and acetonitrile (30 ml). The mixture was stirred for 2 hours at room temperature. The solids were removed by filtration and the solvent evaporated. The residue was treated with ethyl acetate. The ethyl acetate solution containing insoluble solid was passed through a short column of silica gel. The collected ethyl acetate solution was evaporated and the residue dried under vacuum to give 1.8 g (91% yield) of 7-aza-2-oxindole acetic acid salt.

$^1$HNMR (360 MHz, DMSO-d6) δ: 10.90 (s, br, 1H, NH), 8.01, 7.52, 6.91 (m, 3H), 3.52 (s, 2H, $CH_2$).

MS APCI 135 (M+1).

5-Isopropyl-4-methoxy-2-methylbenzaldehyde condensed with 7-aza-2-oxindole to give 0.25 g of 3-(5-isopropyl-4-methoxy-2-methylbenzylidene)-1,3-dihydro-pyrrolo[2,3-b]pyridin-2-one as a yellow-orange solid.

$^1$HNMR ($d_6$-DMSO) δ: 10.5(s, 1H, CONH), 8.3–6.8(m, 6H, aromatic, =CH—), 3.9(s, 3H, $OCH_3$), 3.3(m, 1H, CH), 2.3(s, 3H, $CH_3$), 1.2(d, 6H, 2×$CH_3$).

Example 46

3-(3'-Ethoxy-6-methoxybiphenyl-3-ylmethylene)-1,3-dihydroindol-2-one

Tetrakis(triphenylphosphine)palladium(0) (0.02 g, 0.02 mmol) was added to a solution of 3-(bromo-4-methoxybenzylidene)-1,3-dihydroindol-2-one (0.2 g, 0.61 mmol) in toluene (1 ml) and ethanol (1 ml), followed by addition of 2M aqueous sodium carbonate (1.2 ml, 2.4 mmol). To this mixture was added 3-ethoxyphenylboronic acid (0.11 g, 0.67 mmol), and the mixture was held at 100° C. in a sealed tube for 12 hours. The reaction mixture was added to water (40 ml) and extracted with ethyl acetate (75 ml). The combined organic layers were washed with saturated aqueous sodium bicarbonate (50 ml) and brine (50 ml). The organic layer was dried over magnesium sulfate and concentrated. The resulting solid was triturated with dichloromethane/hexanes to afford 0.9 g (39%) of 3-(3'-ethoxy-6-methoxybiphenyl-3-ylmethylene)-1,3-dihydroindol-2-one as a yellow solid.

$^1$HNMR (360 MHz, DMSO-d6) δ: 10.57 (s, 1H, NH), 7.65 (m, 5H, 4×Ar—H and Ar—CH=C), 7.3 (m, 3H, 4×Ar—H), 7.15 (m, 2H, Ar—H), 6.9 (m, 2H, Ar—H), 4.05 (q, 2H, $OCH_2CH_3$), 3.85 (s, 3H, $OCH_3$), 1.35 (t, 3H, $OCH_2CH_3$).

MS m/z 372.5 [M+1]$^+$.

Example 47

3-(3-Cyclopentyl-4-methoxybenzylidene)-1,3-dihydropyrrolo[2,3-b]pyridin-2-one

3-Cyclopentyl-4-methoxybenzaldehyde was condensed with 7-aza-2-oxindole to give 0.25 g of 3-(3-cyclopentyl-4-methoxybenzylidene)-1,3-dihydropyrrolo[2,3-b]pyridin-2-one as a yellow-orange solid.

$^1$HNMR ($d_6$-DMSO) δ: 1.1 (s, 1H, CONH), 8.3–6.8 (m, 7H, aromatic, =CH—), 3.9(s, 3H, $OCH_3$), 3.2(m, 1H, CH), 1.8 (m, 8H, 4×$CH_2$).

Example 48

3-(3-Cyclopentyl-4-methoxybenzylidene)-4-methyl-1,3-dihydroindol-2-one

3-Cyclopentyl-4-methoxybenzaldehyde was condensed with 4-methyl-2-oxindole to give 0.25 g of 3-(3-cyclopentyl-4-methoxybenzylidene)-4-methyl-1,3-dihydroindol-2- as a yellow-orange solid.

$^1$HNMR ($d_6$-DMSO) δ: 10.4 (s, 1H, CONH), 8.3, 8.1, 7.6, 7.0, 7.0, 6.8, 6.6 (m, 7H, aromatic, =CH—), 3.9 (s, 3H, $OCH_3$), 3.2 (m, 1H, CH), 1.8 (m, 8H, 4×$CH_2$).

Example 49

3-(4,5,2'-Trimethoxybiphenyl-2-ylmethylene)-1,3-dihydroindol-2-one

Tetrakis(triphenylphosphine)palladium(0) (0.02 g, 0.02 mmol) was added to a solution of 3-(3-bromo-4,5-dimethoxybenzylidene)-1,3-dihydroindol-2-one (0.20 g, 0.56 mmol) in toluene (1 ml) and ethanol (1 ml), followed by addition of 2M aqueous sodium carbonate (1.1 ml, 2.2 mmol). To this mixture was added 2-methoxyphenylboronic acid (0.09 g, 0.62 mmol), and the mixture was held at 100° C. in a sealed tube for 12 hours. The reaction mixture was added to water (50 ml) and extracted with ethyl acetate (2×100 ml). The combined organic layers were washed with saturated aqueous sodium bicarbonate (50 ml) and brine (50 ml). The organic layer was dried over magnesium sulfate and concentrated. Chromatography (silica, 30–40% ethyl acetate/hexanes) afforded 0.14 g (64%) of 3-(4,5,2'-trimethoxybiphenyl-2-ylmethylene)-1,3-dihydroindol-2-one as an orange solid.

$^1$HNMR (360 MHz, DMSO-d6) δ: 10.4 (m, 1H, NH), 7.5 (m, 1H, Ar—H), 7.3 (m, 2H, Ar—H and Ar—CH=C), 7.2 (m, 4H, Ar—H), 6.9 (m, 4H, Ar—H), 3.8 (two s, 3H, $COCH_3$), 3.7 (two s, 3H, $OCH_3$), 3.5 (two s, 3H, $COCH_3$).

MS m/z 388.2 [M+1]$^+$.

Example 50

N-{3-[4-(2-Morpholin-4-ylethoxy)-3-thiophen-3-ylbenzylidene]-2-oxo-2,3-dihydro-1H-indol-6-yl}-acetamide Tetrakis(triphenylphosphine)palladium(0) (0.21 g) was added to a solution of 4-morpholinoethoxy-3-bromobenzaldehyde (1.92 g) in toluene (10 ml) and ethanol (10 ml), followed by addition of 2M aqueous sodium carbonate (12 ml). To this mixture was added thiophene-3-boronic acid (1.02 g), and the mixture was heated to reflux. After 12 hours, the reaction mixture was added to water (100 ml) and extracted into ethyl acetate (3×100 ml). The product was then extracted into 1N hydrochloric acid (2×100 ml), the aqueous layers basified to pH 9 with solid sodium bicarbonate and extracted with ethyl acetate (2×100 ml). The organic layers were washed with brine (75 ml), dried over magnesium sulfate and concentrated to afford 1.7 g (83%) of 3-(3-thiophene)-4-morpholinoethoxy benzaldehyde a reddish oil.

$^1$HNMR (360 MHz, DMSO-d6) δ: 9.91 (s, 1H, CHO), 8.08 (m, 2H, Ar—H), 7.83 (dd, 1H, J=2 and 9 Hz, Ar—H), 7.76 (dd, 1H, J=1 and 4 Hz, Ar—H), 7.59 (dd, 1H, J=1 and 5 Hz, Ar—H), 7.35 (d, 1H, J=9 Hz, Ar—H), 7.64 (dd, 1H, J=1 and 5 Hz, Ar—H), 7.58 (dd, 1H, J=3 and 5 Hz, Ar—H), 7.31 (d, 1H, J=9 Hz, Ar—H), 4.27 (t, J=5 Hz, 2H, O—CH$_2$CH$_2$), 3.56 (m, 4H, 2× ringO—CH$_2$CH$_2$), 2.75 (t, J=6 Hz, 2H, N—CH$_2$CH$_2$), 2.48 (m on DMSO, 4H, 2× ringN—CH$_2$CH$_2$).

MS m/z 318.2 [M+1]$^+$.

A mixture of 3-(3-thiophene)-4-morpholinoethoxybenzaldehyde (1.74 g), 6-acetamido-2-oxindole (1 g) (prepared as described in example 1) and piperidine (2.6 ml) in ethanol (11 ml) was held in a sealed tube at 100° C. for 12 hours. The reaction was cooled and added to diethyl ether (200 ml). The solvent was decanted, and the oily solid which remained was dissolved in dichloromethane (15 ml) and precipitated in diethyl ether (200 ml) and hexanes (200 ml), filtered, washed with diethyl ether and then hexanes and dried to afford a mustard yellow solid. Chromatography (silica, 5% methanol/dichloromethane) afforded N-{3-[4-(2-morpholin-4-ylethoxy)-3-thiophen-3-ylbenzylidene]-2-oxo-2,3-dihydro-1H-indol-6-yl}-acetamide as a yellow foam.

$^1$HNMR (360 MHz, DMSO-d6) δ: 10.47 (s, 1H, NH), 10.00 (s, 1H, NHAc), 8.07 (m, 1H, Ar—H), 7.91 (d, J=2 Hz, 1H, Ar—H), 7.63 (m, 2H, 2×Ar—H), 7.58 (m, 2H, 2×Ar—H), 7.48 (s, 1H, Ar—CH=C), 7.45 (d, 1H, J=2 Hz, Ar—H), 7.26 (d, 1H, J=9 Hz, Ar—H), 6.90 (dd, 1H, J=2 and 9 Hz, Ar—H), 4.26 (m, 2H, ArOCH2CH2N), 3.58 (m, 4H, 2×OCH$_2$CH$_2$N), 2.76 (m, 2H, ArOCH2CH2N), 2.48 (m under DMSO, 4H, 2×OCH$_2$CH$_2$N), 2.03 (s, 3H, NHCOCH$_3$).

MS m/z 490.0 [M+1]$^+$.

Example 51

5-Chloro-3-(3-cyclohexyl-4-methoxybenzylidene)-1,3-dihydroindol-2-one

2-Cyclohexylphenol was methylated and then formylated. The aldehyde was condensed with 5-chloro-2-oxindole to give 0.3 g of 5-chloro-3-(3-cyclohexyl-4-methoxybenzylidene)-1,3-dihydroindol-2-one as a yellow-orange solid.

$^1$HNMR (d$_6$-DMSO) δ: 10.6(s, 1H, CONH), 7.7–6.8(m, 7H, aromatic, =CH—), 3.9(s, 3H, OCH$_3$), 3.0 (m, 1H, CH), 1.8, 1.4 (m, 10H, 5×CH$_2$).

Example 52

[3-(3,5-Diisopropyl-4-methoxybenzylidene)-2-oxo-2,3-dihydro-1H-indol-6-yl]-carbamic acid tert-butyl ester 3,5-Diisopropyl-4-methoxybenzaldehyde was condensed with 6-tert-butyloxycarbonylamino-2-oxindole to give 0.35 g of [3-(3,5-diisopropyl-4-methoxybenzylidene)-2-oxo-2,3-dihydro-1H-indol-6-yl]-carbamic acid tert-butyl ester as a yellow-orange solid.

Example 53

3-(3,5-Diisopropyl-4-methoxybenzylidene)-4-methyl-1,3-dihydroindol-2-one 3,5-Diisopropyl-4-methoxybenzaldehyde was condensed with 4-methyl-2-oxindole to give 0.3 g of 3-(3,5-diisopropyl-4-methoxybenzylidene)-4-methyl-1,3-dihydroindol-2-one as a yellow-orange solid.

$^1$HNMR (d$_6$-DMSO) δ: 10.41 (s, 1H, CONH), 8.0 (s, 2H), 7.66 (s, 1H), 7.07 (t, 1H), 6.76 (d, 1H), 6.67 (d, 1H), 3.7 (s, 3H, OCH$_3$), 3.21–3.3 (m, 1H), 1.21 (d, 12H, 4×CH$_3$).

Example 54

5-Bromo-3-(3,5-diisopropyl-4-methoxybenzylidene)-1,3-dihydroindol-2-one 3,5-Diisopropyl-4-methoxybenzaldehyde was condensed with 5-bromo-2-oxindole to give 0.3 g of 5-bromo-3-(3,5-diisopropyl-4-methoxybenzylidene)-1,3-dihydroindol-2-one as a yellow-orange solid.

Example 55

N-{3-[3-tert-Butyl-4-(2-morpholin-4-ylethoxy)-benzylidene]-2-oxo-2,3-dihydro-1H-indol-6-yl}-acetamide Triphenylphosphine (5.89 g, 22.44 mmol) was added to a solution of 3-tert-butyl-4-hydroxybenzaldehyde (4 g, 22.44 mmol) in tetrahydrofuran (40 ml), followed by addition of 2-hydroxyethylmorpholine (2.94 g, 22.44 mmol) and then the dropwise addition of diethylazodicarboxylate (3.91 g, 22.44 mmol). The mixture was allowed to stir at room temperature for 3 days. The reaction was concentrated under reduced pressure and partitioned between 2N hydrochloric acid (200 ml) and ethyl acetate (150 ml). The aqueous layer was extracted with ethyl acetate (2×150 ml), basified to pH 9 with solid sodium bicarbonate, saturated with solid sodium chloride and extracted with ethyl acetate (3×150 ml). The combined organic layers were dried over magnesium sulfate and concentrated to afford 2.8 g (44%) of 3-tert-butyl-4-(2-morpholin-4-ylethoxy)benzaldehyde as a yellowish oil.

$^1$HNMR (360 MHz, DMSO-d6) δ: 9.8 (s, 1H, CHO), 7.75 (m, 2H, 2×Ar—H), 7.16 (d, J=10 Hz, 1H, Ar—H), 4.19 (t, J=7 Hz, 2H, O—CH$_2$CH$_2$), 3.55 (m, 4H, 2× ringO—CH$_2$CH$_2$), 2.75 (t, J=7 Hz, 2H, N—CH$_2$CH$_2$), 2.4 (m on DMSO, 4H, 2× ringN—CH$_2$CH$_2$), 1.36 (s, 9H, C(CH$_3$)$_3$).

MS m/z 292.0 [M+1]$^+$.

A mixture of 3-tert-butyl-4-(2-morpholin-4-ylethoxy)-benzaldehyde (0.25 g), 6-acetamido-2-oxindole (0.16 g) and piperidine (0.43 ml) in ethanol (3 ml) was held in a sealed tube at 100° C. for 12 hours. The reaction was cooled, added to ethyl acetate (250 ml), washed with 1N hydrochloric acid (100 ml) and brine (100 ml), dried with magnesium sulfate and concentrated. Some product went into the acid wash, so this was basified with solid sodium bicarbonate to pH 9 and extracted with ethyl acetate (2×150 ml). The organic layers were dried over magnesium sulfate, combined with the oil from the first crop of product and concentrated. Chromatography (silica, 40% ethyl acetate followed by 5–10% methanol/methylene chloride) afforded 100 mg 27%) of N-{3-[3-tert-butyl-4-(2-morpholin-4-ylethoxy)

benzylidene]-2-oxo-2,3-dihydro-1H-indol-6-yl}-acetamide as a yellow solid.

$^1$HNMR (360 MHz, DMSO-d6) δ: 10.46 (s, 1H, NH), 9.99 (s, 1H, NHAc), 7.58 (m, 3H, Ar—H), 7.41 (m, 2H, Ar—H and Ar—CH=C), 7.12 (d, 1H, Ar—H), 6.92 (dd, 1H, J=2 and 8 Hz, Ar—H), 4.18 (m, 2H, Ar—OCH$_2$), 3.57 (m, 4H, OCH$_2$CH$_2$N), 2.77 (m, 2H, ArOCH$_2$—CH$_2$N), 2.49 (m, 4H, NCH$_2$CH$_2$O), 2.02 (s, 3H, NHCOCH$_3$), 1.38 (s, 9H, Ar-tBu).

MS m/z 464.0 [M+1]$^+$.

Example 56

3-(4-Methoxy-3,5-dimethylbenzylidene)-1,3-dihydropyrrolo[2,3-b]pyridin-2-one 2,6-Dimethylphenol was methylated and then formylated.

$^1$HNMR (d$_6$-DMSO) δ: 10.1 (s, 1H, CHO), 6.9 (s, 2H, aromatic), 3.9 (s, 3H, OCH$_3$), 2.6 (s, 6H, 2×CH$_3$).

The aldehyde was condensed with 7-aza-2-oxindole to give 0.2 g of 3-(4-methoxy-3,5-dimethylbenzylidene)-1,3-dihydropyrrolo[2,3-b]pyridin-2-one as a yellow-orange solid.

$^1$HNMR (d$_6$-DMSO) δ: 1.5(s, 1H, CONH), 8.2–6.8(m, 6H, aromatic, =CH—), 3.8(s, 3H, OCH$_3$), 2.5(s, 6H, 2×CH$_3$), 2.4(s, 3H, CH$_3$).

Example 57

5-Bromo-3-[3,5-diisopropyl-4-(2-morpholin-4-ylethoxy)benzylidene]-1,3-dihydroindol-2-one A mixture of 3,5-diisopropyl-4-(2-morpholin-4-ylethoxy)-benzaldehyde (0.4 g), 5-bromo-2-oxindole (0.27 g) and pyrrolidine (0.5 ml) in ethanol (2 ml) was held in a sealed tube at 100° C. for 12 hours. The mixture was then added to 1N hydrochloric acid (100 ml) and the solids removed by filtration and washed with more water (50 ml). The solids were then dissolved in ethyl acetate (200 ml), the solution washed with 1N hydrochloric acid (75 ml) and brine (75 ml), dried with magnesium sulfate and concentrated. The crude solid was chromatographed (silica, 4:4:1 dichloromethane: hexanes: methanol) to give 80 mg (13%) of 5-bromo-3-[3,5-diisopropyl-4-(2-morpholin-4-ylethoxy)-benzylidene]-1,3-dihydroindol-2-one as a reddish-brown solid.

$^1$HNMR (360 MHz, DMSO-d6) δ: 10.54 (s, 1H, NH), 9.43 (d, J=10 Hz, 1H, Ar—H), 7.58 (d, J=9 Hz, 1H, Ar—H), 7.46 (d, J=5 Hz, 2H, Ar—H), 7.3 (m, 1H, Ar—H), 7.19 (m, J=9 and 10 Hz, 1H, Ar—H), 6.99 (m, J=9 and 9 Hz, 1H, Ar—H), 6.83 (m, J=9 and 1 Hz, 1H, Ar—H), 3.61 (dd, J=9 and 22 Hz 1H, 1×CH$_2$CH), 3.43 (m, 1H, CHCH$_3$), 2.86 (dd, J=4 and 22 Hz, 1H, 1×CH$_2$CH), 1.35 (d, J=9 Hz, 3H, CH$_3$).

MS m/z 262.0 [M+1]$^+$.

Example 58

3-(3'-Ethoxy -4,5-dimethoxybiphenyl-2-ylmethylene)-1,3-dihydroindol-2-one

Tetrakis(triphenylphosphine)palladium(0) (0.02 g, 0.02 mmol) was added to a solution of 3-(3-bromo-4,5-dimethoxybenzylidene)-1,3-dihydroindol-2-one (0.2 g, 0.56 mmol) in toluene (1 ml) and ethanol (1 ml), followed by addition of 2M aqueous sodium carbonate (1 ml, 2 mmol). To this mixture was added 3-ethoxyphenylboronic acid (0.1 g, 0.62 mmol) and the mixture was held at 100° C. in a sealed tube for 12 hours. The reaction mixture was then added to water (40 ml) and extracted with ethyl acetate (2×75 ml) The combined organic layers were washed with saturated aqueous sodium bicarbonate (50 ml) and brine (50 ml), dried over magnesium sulfate and concentrated. The resulting solid was triturated with methylene chloride/hexanes to afford 0.14 g (64%) of 3-(3'-ethoxy-4,5-dimethoxybiphenyl-2-ylmethylene)-1,3-dihydroindol-2-one as a yellow/orange solid.

$^1$HNMR (360 MHz, DMSO-d6) δ: 10.5 (s, 1H, NH), 7.6 (d, J=9 Hz, 1H, Ar—H), 7.2 (m, 4H, 3×Ar—H and Ar—CH=C), 7.08 (s, 2H, Ar—H), 6.8 (m, 5H, 5×Ar—H), 4.0 (q, J=8 Hz, 2H, OCH$_2$CH$_3$), 3.89 (s, 3H, OCH$_3$), 3.77 (s, 3H, OCH$_3$), 1.29 (t, J=8 Hz, 3H, OCH$_2$CH$_3$).

MS m/z 402.5 [M+1]$^+$.

Example 59

5-chloro-3-(4-Methoxy-3-thiophen-2-ylbenzylidene)-1,3-dihydroindol-2-one

A mixture of 3-(2-thiophene)-4-methoxybenzaldehyde (0.21 g), 5-chloro-2-oxindole (0.16 g) and pyrrolidine (0.4 ml) in ethanol (1 ml) was placed in a sealed tube and heated to 100° C. A precipitate formed within 10 minutes so the reaction was diluted with another 10 ml of ethanol and heating resumed. After 4 hours, the reaction was cooled and the solid which formed was removed by filtration and washed with ethanol and then hexanes to afford 0.21 g (60%) of 5-chloro-3-(4-methoxy-3-thiophen-2-ylbenzylidene)-1,3-dihydroindol-2-one as a yellow-orange solid.

$^1$HNMR (360 MHz, DMSO-d6) δ: 10.7 (s, 1H, NH), 7.8–9.1 (m, 3H, Ar—H), 7.6 (m, 3H, 2×Ar—H and Ar—CH=C), 7.2 (m, 3H, Ar—H), 6.9 (m, 1H, Ar—H), 3.9 (m, 3H, OCH$_3$).

MS m/z 368.1 and 369.9 [M]$^+$ and [M+2]$^+$.

Example 60

5-Chloro-3-4-methoxy-3-pryidin-3-ylbenzylidene)-1,3-dihydroindol-2-one

Tetrakis(triphenylphosphine)palladium(0) (0.2 g) was added to a solution of 3-bromo-4-methoxybenzldehyde (1.25 g) in toluene (10 ml) and ethanol (10 ml), followed by addition of 2M aqueous sodium carbonate (11 ml). To this mixture was added pyridine-3-boronic acid propane diol (1 g), and the mixture was heated to reflux. After 2 hours, the reaction was added to water (75 ml) and extracted with ethyl acetate (2×75 ml). The combined organic layers were washed with saturated aqueous sodium bicarbonate (100 ml) and brine (100 ml), dried over magnesium sulfate and concentrated. Chromatography (silica, 20–50% ethyl acetate/hexanes) afforded 1.08 g (87%) of 3-(3-pyridyl)-4-methoxybenzaldehyde as a white solid.

$^1$HNMR (360 MHz, DMSO-d6) δ: 9.93 (s, 1H, CHO), 8.7 (d, 1H, J=3 Hz, Ar—H), 8.56 (dd, 1H, J=1 and 6 Hz, Ar—H), 7.9 (m, 3H, 3×Ar—H), 7.46 (dd, 1H, J=6 and 9 Hz, Ar—H), 7.35 (d, 1H, J=10 Hz, Ar—H), 3.89 (s, 3H, OCH$_3$).

A mixture of 3-(3-pyridyl)-4-methoxybenzaldehyde (0.25 g), 5-chloro-2-oxindole (0.2 g) and pyrrolidine (0.5 ml) in ethanol (2 ml) was placed in a sealed tube and heated to 100° C. A precipitate formed within 10 minutes so the reaction was diluted with another 10 ml of ethanol and heating resumed. After 4 hours, the reaction was cooled and the solid was removed by filtration and washed with ethanol and then hexanes to afford 0.27 g (61%) of 5-chloro-3-(3-(3-pyridyl)-

4-methoxybenzylidene)-1,3-dihydroindol-2-one as a yellow-orange solid.

$^1$HNMR (360 MHz, DMSO-d6) δ: 0.67 (s, 1H, NH), 8.6 (m, 3H, 2×Ar—H and Ar—CH═C), 7.8 (m, 4H, Ar—H), 7.4 (m, 1H, Ar—H), 7.35 (m, 2H, Ar—H), 6.85 (m, 1H, Ar—H), 3.88 (s, 3H, OCH$_3$).

MS m/z 363.0 and 365.1, [M]$^+$ and [M+2]$^+$.

Example 61

5-Chloro-3-(4,5-3'-Trimethoxybiphenyl-2-ylmethylene)-1,3-dihydroindol-2-one Tetrakis(triphenylphosphine)palladium(0) (0.36 g) was added to a solution of 4,5-dimethoxy-2-bromobenzaldehyde (2.5 g) in toluene (20 ml) and ethanol (20 ml), followed by addition of 2M aqueous sodium carbonate (20 ml). To this mixture was added 3-methoxyphenylboronic acid (1.7 g), and the mixture was heated to reflux. After 1 hour, the reaction was partitioned between water (150 ml) and ethyl acetate (300 ml). The organic layer was washed with saturated aqueous sodium bicarbonate (150 ml) and brine (150 ml), dried over magnesium sulfate and concentrated. Chromatography (silica, 20–30–40% ethyl acetate/hexanes) afforded 2.7 g (98%) of 2-(3-methoxyphenyl)-4,5-dimethoxybenzaldehyde as a yellow oil which solidified upon standing.

$^1$HNMR (360 MHz, DMSO-d6) δ: 9.71 (s, 1H, CHO), 7.38 (m, 2H, 2×Ar—H), 7.0 (m, 4H, 4×Ar—H), 3.9 (s, 3H, OCH$_3$), 3.84 (s, 3H, OCH$_3$), 3.8 (s, 3H, OCH$_3$).

MS m/z 273.5 [M+1]$^+$.

A mixture of 2-(3-methoxyphenyl)-4,5-dimethoxybenzaldehyde (0.25 g), 5-chloro-2-oxindole (0.15 g) and pyrrolidine (0.4 ml) in ethanol (1 ml) was placed in a sealed tube and heated to 100° C. A precipitate formed within 10 minutes so the reaction was diluted with another 10 ml of ethanol and heating resumed. After 2.5 hours, the reaction was cooled, the solid was removed by filtration and washed with ethanol and then hexanes to afford 0.36 g (92%) of 3-(4,5-3'-trimethoxybiphenyl-2-ylmethylene)-1,3-dihydroindol-2-one as a yellow solid.

$^1$HNMR (360 MHz, DMSO-d6) δ: 10.67 (s, 1H, NH), 7.6 (d, J=2.5 Hz, 1H, Ar—H), 7.3 (m, 4H, Ar—H), 7.12 (s, 1H, Ar—CH═C), 6.9 (m, 4H, Ar—H), 3.9 (s, 3H, OCH$_3$), 3.79 (s, 3H, OCH$_3$), 3.75 (s, 3H, OCH$_3$).

MS m/z 422.0 and 424.1 [M]$^+$ and [M+2]$^+$.

Example 62

3-(4,5-Dimethoxy-2-naphthalen-2-ylbenzylidene)-1,3-dihydroindol-2-one

Tetrakis(triphenylphosphine)palladium(0) (0.02 g) was added to a solution of 3-(3-bromo-4,5-dimethoxybenzylidene)-1,3-dihydroindol-2-one (0.20 g) in toluene (1 ml) and ethanol (1 ml) followed by addition of 2M aqueous sodium carbonate (1.1 ml). To this mixture was added naphthalene-2-boronic acid (0.11 g), and the mixture was held at 100° C. in a sealed tube for 12 hours. The precipitate which formed was filtered, washed with ethanol and then dissolved in 20% methanol/toluene, filtered and concentrated. The resulting solid was triturated with hexanes and dried to afford 0.07 g (29%) of 3-(4,5-dimethoxy-2-naphthalen-2-ylbenzylidene)-1,3-dihydroindol-2-one as an orange solid.

$^1$HNMR (360 MHz, DMSO-d6) δ: 10.5 (m, 1H, NH), 7.9 (m, 4H, Ar—H), 7.7 (m, 1H, Ar—H), 7.5 (m, 3H, Ar—H), 7.4 (s, 1H, Ar—CH═C), 7.2 (m, 3H, Ar—H), 6.9 (m, 2H, Ar—H), 3.9 (two s, 3H, COCH$_3$), 3.8 (two s, 3H, OCH$_3$).

MS m/z 408.0 [M+1]$^+$.

Example 63

N-[3-(3'-Acetylamino-6-methoxyphenyl-3-ylmethylene)-2-oxo-2,3-dihydro-1H-indol-6-yl]-acetamide 3-Bromo-4-methoxybenzaldehyde was condensed with 6-acetamido-2-oxindole to give N-[3-(3-bromo-4-methoxybenzylidene)-2-oxo-2,3-dihydro-1H-indol-6-yl]-acetamide.

Tetrakis(triphenylphosphine)palladium(0) (0.01 g) was added to a solution of N-[3-(3-bromo-4-methoxybenzylidene)-2-oxo-2,3-dihydro-1H-indol-6-yl]-acetamide (0.14 g) in toluene (1 ml) and ethanol (1 ml) followed by addition of 2M aqueous sodium carbonate (0.72 ml). To this mixture was 3-acetylamino-phenylboronic acid (0.07 g), and the mixture was held at 100° C. in a sealed tube for 12 hours. The reaction mixture was added to water (50 ml) and extracted with ethyl acetate (2×100 ml).

The combined organic layers were washed with saturated aqueous sodium bicarbonate (50 ml) and brine (50 ml), dried over magnesium sulfate and concentrated. Chromatography (silica, dichloromethane then 5–10% methanol/dichloromethane) afforded 0.07 g (43%) of N-[3-(3'-acetylamino-6-methoxybiphenyl-3-ylmethylene)-2-oxo-2,3-dihydro-1H-indol-6-yl]-acetamide as a yellow solid. About 26% isomer by $^1$HNMR.

$^1$HNMR (360 MHz, DMSO-d6) δ: 10.49 (s, 1H, NH), 10.42 (s, 1H, NHAc), 9.95 (s, 1H, NHAc), 7.76 (m, 2H, 2×Ar—H), 7.58 (m, 3H, 3×Ar—H), 7.4 (m, 2H, Ar—H and Ar—CH═C), 7.3 (m, 2H, Ar—H), 7.18 (m, 1H, Ar—H), 6.9 (dd, 2H, J=2 and 8.5 Hz, Ar—H), 3.84 (s, 3H, OCH$_3$), 2.05 (s, 3H, NHCOCH$_3$), 2.03 (s, 3H, NHCOCH$_3$). MS m/z 442.2 [M+1]$^+$.

Example 64

6-Methoxy-3-(4-methoxy-3-thiophen-3-ylbenzylidene)-1,3-dihydroindol-2-one

A mixture of 3(3-thiophene)-4-methoxybenzaldehyde (0.53 g, 2.45 mmol), 6-methoxy-2-oxindole (0.4 g, 2.45 mmol) and piperidine (1.2 ml, 12.25 mmol) in 5 ml of ethanol was held in a sealed tube at 100° C. for 12 hours. The reaction was cooled and added to diethyl ether (150 ml) and hexanes (150 ml). The precipitate which formed was removed by filtration, washed with diethyl ether and then hexanes and dried to afford 0.57 g (64%) of 6-methoxy-3-(4-methoxy-3-thiophen-3-ylbenzylidene)-1,3-dihydroindol-2-one as a mustard yellow solid.

$^1$HNMR (360 MHz, DMSO-d6) δ: 10.45 (s, 1H, NH), 8.78 (d, J=2 Hz, 1H, Ar—H), 8.30 (dd, J=2 and 9 Hz, 1H, Ar—H), 7.8 (dd, 1H, J=1.5 and 3 Hz, Ar—H), 7.5 (m, 3H, 2×Ar—H and Ar—CH═C), 7.18 (d, J=9 Hz, 1H, Ar—H), 6.55 (dd, 1H, J=2 and 8.5 Hz, Ar—H), 6.39 (d, 1H, J=2 Hz, Ar—H), 3.91 (s, 3H, OCH$_3$), 3.76 (s, 3H, OCH$_3$), 2.04 (s, 3H, NHCOCH$_3$).

MS m/z 364.1 [M+1]$^+$.

Example 65

3-(6-Methoxybiphenyl-3-ylmethylene)-1,3-dihydroindol-2-one

4-Methoxy-3-phenylbenzaldehyde was condensed with 2-oxindole to give 0.3 g of 3-(6-methoxybiphenyl-3-ylmethylene)-1,3-dihydroindol-2-one as a yellow-orange solid.

¹HNMR (d₆-DMSO) δ: 10.5(s, 1H, CONH), 8.5, 8.5, 7.8, 7.7, 7.5, 7.5, 7.4, 7.4, 7.3, 7.2, 7.2, 7.0, 6.8(m, 13H, aromatic, =CH—), 3.9(s, 3H, OCH₃).

Example 66

3-(2,3-Dihydrobenzofuran-5-ylmethylene)-1,3-dihydroindol-2-one 2,3-Dihydro-5-formylbenzofuran (commercially available) was condensed with 2-oxindole to give 0.25 g of 3-(2,3-dihydrobenzofuran-5-ylmethylene)-1,3-dihydroindol-2-one as a yellow-orange solid.

¹HNMR (d₆-DMSO) δ: 10.4 (s, 1H, CONH), 8.6, 8.2, 7.7, 7.6, 7.2, 7.0, 6.9, 6.8 (m, 8H, aromatic, =CH—), 4.6(t, 2H, OCH₂), 3.2 (t, 2H, OCH₂).

Example 67

5-Chloro-3-(6-methoxybiphenyl-3-ylmethylene)-1,3-dihydroindol-2-one

4-Methoxy-3-phenylbenzaldehyde was condensed with 5-chloro-2-oxindole to give 0.3 g of 5-chloro-3-(6-methoxybiphenyl-3-ylmethylene)-1,3-dihydroindol-2-one as a yellow-orange solid.

¹HNMR (d₆-DMSO) δ: 11.5 (s, 1H, CONH), 7.8–6.8 (m, 12H, aromatic, =CH—), 3.9 (s, 3H, OCH₃).

Example 68

3-(3-Cyclohexyl-4-methoxybenzylidene)-4-methyl-1,3-dihydroindol-2-one

3-Cyclohexyl4-methoxybenzaldehyde was condensed with 4-methyl-2-oxindole to give 0.3 g of 3-(3-cyclohexyl-4-methoxybenzylidene)-4-methyl-1,3-dihydroindol-2-one as a yellow-orange solid.

¹HNMR (d₆-DMSO) δ: 10.6 (s, 1H, CONH), 7.7–6.8 (m, 7H, aromatic, =CH—), 3.9 (s, 3H, OCH₃), 3.0 (m, 1H, CH), 2.5 (s, 3H, CH₃), 1.8–1.4 (m, 10H, 5×CH₂).

Example 69

3-(2,3-Dihydrobenzofuran-5-ylmethylene)-4-methyl-1,3-dihydroindol-2-one 2,3-Dihydro-5-formylbenzofuran (commercially available) was condensed with 4-methyl-2-oxindole to give 0.25 g of 3-(2,3-dihydrobenzofuran-5-ylmethylene)-4-methyl-1,3-dihydroindol-2-one as a yellow-orange solid.

¹HNMR (d₆-DMSO) δ: 10.5(s, 1H, CONH), 8.4–6.6 (m, 7H, aromatic, =CH—), 4.6 (t, 2H, OCH₂), 3.2 (t, 2H, OCH₂), 2.5 (s, 3H, CH₃).

Example 70

3-(3-Isopropyl-4-methoxybenzylidene)-1,3-dihydrolyrrolo[2,3-b]pyridin-2-one

3-Isopropyl-4-methoxybenzaldehyde was condensed with 7-aza-2-oxindole to give 0.25 g of 3-(3-isopropyl-4-methoxybenzylidene)-1,3-dihydropyrrolo[2,3-b]pyridin-2-one as a yellow-orange solid.

¹HNMR (d₆-DMSO) δ: 11.5(s, 1H, CONH), 8.0–6.8 (m, 7H, aromatic, =CH—), 3.7 (s, 3H, OCH₃), 3.2 (m, 1H, CH), 1.2 (d, 6H, 2×CH₃).

Example 71

3-(6-Methoxybiphenyl-3-ylmethylene)-1,3-dihydryrrolo[2,3-b]pyridin-2-one

4-Methoxy-3-phenylbenzaldehyde was condensed with 7-aza-2-oxindole to give 0.25 g of 3-(6-methoxybiphenyl-3-ylmethylene)-1,3-dihydropyrrolo[2,3-b]pyridin-2-one as a yellow-orange solid.

¹HNMR (d₆-DMSO) δ: 10.5 (s, 1H, CONH), 8.5–6.8 (m, 12H, aromatic, =CH—), 3.9 (s, 3H, OCH₃).

Example 72

3-(3-Cyclohexyl-4-methoxybenzylidene)-1,3-dihydropyrrolo[2,3-b]pyridin-2-one

3-Cyclohexyl-4-methoxybenzaldehyde was condensed with 7-aza-2-oxindole to give 0.25 g of 3-(3-Cyclohexyl-4-methoxybenzylidene)-1,3-dihydropyrrolo[2,3-b]pyridin-2-one as a yellow-orange solid.

Example 73

3-(2,3-Dihydrobenzofuran-5-ylmethylene)-1,3-dihydropyrrolo[2,3-b]pyridin-2-one 2,3-Dihydro-5-formylbenzofuran (commercially available) was condensed with 7-aza-2-oxindole to give 0.2 g of 3-(2,3-dihydrobenzofuran-5-ylmethylene)-1,3-dihydropyrrolo[2,3-b]pyridin-2-one as a yellow-orange solid.

¹HNMR (d₆-DMSO) δ: 10.4 (s, 1H, CONH), 8.3–6.8 (m, 7H, aromatic, =CH—), 4.6 (t, 2H, OCH₂), 3.2 (t, 2H, OCH₂).

Example 74

3-(3,5-Diisopropyl-4-methoxybenzylidene)-1,3-dihydropyrrolo[2,3-b]pyridin-2-one 3,5-Diisopropyl-4-methoxybenzaldehyde was methylated and then formylated. The aldehyde was condensed with 7-aza-2-oxindole to give 0.2 g of 3-(3,5-diisopropyl-4-methoxybenzylidene)-1,3-dihydropyrrolo[2,3-b]pyridin-2-one as a yellow-orange solid.

¹HNMR (d₆-DMSO) δ: 11.5 (s, 1H, CONH), 8.0–6.8 (m, 7H, aromatic, =CH—), 3.7 (s, 3H, OCH₃), 3.2 (m, 2H, 2×CH), 1.2 (m, 12H, 4×CH₃).

Example 75

5-Bromo-3-(3-isopropyl-4-methoxybenzylidene)-1,3-dihydroindol-2-one

3-Isopropyl-4-methoxybenzaldehyde was condensed with 5-bromo-2-oxindole to give 0.3 g of 5-bromo-3-(3-isopropyl-4-methoxybenzylidene)-1,3-dihydroindol-2-one as a yellow-orange solid.

¹HNMR (d₆-DMSO) δ: 10.6 (s, 1H, CONH), 8.5, 8.4, 7.9, 7.9, 7.3, 7.1, 6.8 (m, 7H, aromatic, =CH—), 3.9 (m, 3H, OCH₃), 3.3 (m, 1H, CH), 1.2 (d, 6H, 2×CH₃).

Example 76

5-Bromo-3-(3-cyclopentyl-4-methoxybenzylidene)-1,3-dihydroindol-2-one

3-Cyclopentyl-4-methoxybenzaldehyde was condensed with 5-bromo-2-oxindole to give 0.3 g of 5-bromo-3-(3-cyclopentyl-4-methoxybenzylidene)-1,3-dihydroindol-2-one as a yellow-orange solid.

¹HNMR (d₆-DMSO) δ: 10.6 (s, 1H, CONH), 8.6–6.7 (m, 7H, aromatic, =CH—), 3.9 (s, 3H, OCH₃), 3.2 (m, 1H, CH), 1.8 (m, 8H, 4×CH₂).

Example 77

5-Chloro-3-(3-cyclopentyl-4-methoxybenzylidene)-4-methyl-1,3-dihydroindol-2-one

A suspension of 3.0 g of 4-methyl-2-oxindole was stirred in 50 ml of acetonitrile at room temperature while 3.3 g of N-chlorosuccinimide was added in portions. Trifluoroacetic acid (1 ml) was then added. The suspension was stirred at room temperature for 3 days during which time solids were always present. The solids were collected by vacuum filtration, washed with a small amount of cold acetone and dried overnight in a vacuum oven at 40° C. to give 2.5 g (68%) of 5-chloro-4-methyl-2-oxindole.

3-Cyclopentyl-4-methoxybenzaldehyde was condensed with 4-methyl-5-chloro-2-oxindole to give 0.3 g of 5-Chloro-3-(3-cyclopentyl-4-methoxybenzylidene)-4-methyl-1,3-dihydroindol-2-one as a yellow-orange solid.

Example 78

5-Chloro-3-(6-methoxybiphenyl-3-ylmethylene)-4-methyl-1,3-dihydroindol-2-one

4-Methoxy-3-phenylbenzaldehyde was condensed with 4-methyl-5-chloro-2-oxindole to give 0.3 g of 5-chloro-3-(6-methoxybiphenyl-3-ylmethylene)-4-methyl-1,3-dihydroindol-2-one as a yellow-orange solid.

Example 79

5-chloro-3-(5-isopropyl-4-methoxy-2-methylbenzylidene)-4-methyl-1,3-dihydroindol-2-one 5-Isopropyl-4-methoxy-2-methylbenzaldehyde was condensed with 4-methyl-5-chloro-2-oxindole to give 0.3 g of 5-chloro-3-(5-isopropyl-4-methoxy-2-methylbenzylidene)-4-methyl-1,3-dihydroindol-2-one as a yellow-orange solid.

Example 80

5-Chloro-3-(4-methoxy-3,5-dimethylbenzylidene)-4-methyl-1,3-dihydroindol-2-one 2,6-Dimethylphenol was methylated and then formylated. The aldehyde was condensed with 4-methyl-5-chloro-2-oxindole to give 0.3 g of 5-chloro-3-(4-methoxy-3,5-dimethylbenzylidene)-4-methyl-1,3-dihydroindol-2-one as a yellow-orange solid.

Example 81

3-(3,5-Diisopropyl-4-methoxybenzylidene)-6-trifluoromethyl-1,3-dihydroindol-2-one 3,5-Diisopropyl-4-methoxybenzaldehyde was condensed with 6-trifluoromethyl-2-oxindole to give 0.35 g of 3-(3,5-diisopropyl-4-methoxybenzylidene)-6-trifluoromethyl-1,3-dihydroindol-2-one as a yellow-orange solid.

Example 82

6-Chloro-3-(3,5-diisopropyl-4-methoxybenzylidene)-1,3-dihydroindol-2-one 3,5-Diisopropyl-4-methoxybenzaldehyde was condensed with 6-chloro-2-oxindole to give 0.3 g of 6-chloro-3-(3,5-diisopropyl-4-methoxybenzylidene)-1,3-dihydroindol-2-one as a yellow-orange solid.

Example 83

3-[3-(3,5-Diisopropyl-4-methoxybenzylidene)-2-oxo-2,3-dihydro-1H-indol-5-yl]-propionic acid Potassium cyanide (2.0 g) was added to 15 ml of dimethylsulfoxide and heated to 90° C. 5-chloroethyl-2-oxindole (3.0 g) dissolved in 5 ml of dimethylsulfoxide was added slowly with stirring, and the reaction was heated to 150° C. and stirred for 2 hours. The mixture was cooled, poured into ice water and the precipitate which formed was collected by vacuum filtration, washed with water, and dried to give crude product. The crude material was chromatographed on silica gel (5% methanol in chloroform) to give 1.2 g (42%) of 5-cyanoethyl-2-oxindole.

$^1$HNMR (360 MHz, DMSO-d6) δ: 10.28 (s, br, NH), 7.12 (s, 1H, H-4), 7.07 (d, J=8 Hz, 1H), 6.74 (d, J=8 Hz, 1H), 3.43 (s, 2H, CH$_2$), 2.71–2.82 (m, 4H, 2×CH$_2$).

5-Cyanoethyl-2-oxindole (4.02 g) in 10 ml of water containing 25 ml of concentrated hydrochloric acid was refluxed for 4 hours. The mixture was cooled, water added and the resulting solid collected by vacuum filtration, washed with water and dried to give 1.9 g (44% yield) of 5-carboxyethyl-2-oxindole as a yellow solid.

$^1$HNMR (360 MHz, DMSO-d6) δ: 12.00 (s, br, 1H, 5-CH$_2$CH$_2$COOH), 10.21 (s, 1H, NH-1), 7.05 (s, 1H, H-4), 6.99 (d, J=9 Hz, 1H, H-6), 6.69 (d, J=9 Hz, 1H, H-7), 3.40 (s, 2H, CH$_2$-3), 2.74 (t, J=7 Hz, 2H, 5-CH$_2$CH$_2$COOH) and 2.46 (t, J=7 Hz, 2H, 5-CH$_2$CH$_2$COOH).

3,5-Diisopropyl-4-methoxybenzaldehyde was condensed with 5-(2-carboxyethyl)-2-oxindole to give 0.35 g of 3-[3-(3,5-diisopropyl-4-methoxybenzylidene)-2-oxo-2,3-dihydro-1H-indol-5-yl]-propionic acid as a yellow-orange solid.

Example 84

3-(3,5-Diisopropyl-4-methoxybenzylidene)-6-methoxy-1,3-dihydroindol-2-one 3,5-Diisopropyl-4-methoxybenzaldehyde was condensed with 6-methoxy-2-oxindole to give 0.3 g of 3-(3,5-diisopropyl-4-methoxybenzylidene)-6-methoxy-1,3-dihydroindol-2-one as a yellow-orange solid.

Example 85

5-Butyl-3-(3,5-diisopropyl-4-methoxybenzylidene)-1,3-dihydroindol-2-one

To 15 g of aluminum chloride suspended in 30 ml of 1,2-dichloroethane in an ice bath was added 7.5 g of 2-oxindole and then 12 g of butyryl chloride. The resulting suspension was stirred at 50° C. overnight. The mixture was poured into ice water and extracted 3 times with ethyl acetate. The combined ethyl acetate layers were washed with brine, dried over sodium sulfate, and concentrated to dryness to give a brown solid. The solid was chromatographed on silica gel (50% ethyl acetate in hexane) to give 4.3 g (38%) of 5-butanoyl-2-oxindole as a yellow solid.

$^1$HNMR (360 MHz, DMSO-d6) δ: 10.67 (s, br, NH), 7.84 (d, J=8.39 Hz, 1H), s, 1H, H-4), 6.88 (d, J=8.39 Hz, 1H), 3.53 (s, 2H, CH2), 2.88 (t, J=7.16 Hz, 2H, CH2), 1.58–1.64 (m, 2H), 0.9 (t, J=7.58 Hz, 3H, CH3).

Triethylsilane (2.3 g) was added to 2 g of 5-butanoyl-2-oxindole in 20 ml of trifluoroacetic acid at room temperature and the solution stirred for 3 hours. The reaction was poured into ice water to give a red oil which solidified after standing. The solid was collected by vacuum filtration, washed with water and hexane and dried to give 1.7 g (91% yield) of 5-butyl-2-oxindole as an off-white solid.

$^1$HNMR (360 MHz, DMSO-d6) δ: 10.19 (s, br, NH), 7.01 (s, 1H, H-4), 6.95 (d, J=8 Hz, 1H), 6.69 (d, J=8 Hz, 1H), 3.4 (s, 2H, CH$_2$), 2.49 (t, J=8 Hz, 2H, CH$_2$), 1.48–1.52 (m, 2H), 1.25–1.31 (m, 2H), 0.88 (t, J=7 Hz, 3H).

3,5-Diisopropyl-4-methoxybenzaldehyde was condensed with 5-butyl-2-oxindole to give 0.3 g of 5-butyl-3-(3,5-diisopropyl-4-methoxybenzylidene)-1,3-dihydroindol-2-one as a yellow-orange solid.

Example 86

3-(3,5-Diisopropyl-4-methoxybenzylidene)-2-oxo-2, 3-dihydro-1H-indole-4-carboxylic acid Trimethylsilyldiazomethane in hexane (2 M) was added dropwise to the solution of 2-chloro-3-carboxynitrobenzene (2.01 g) in methanol (20 ml) at room temperature until no further gas evolution occurred. The excess trimethylsilyl-diazomethane was quenched with acetic acid. The reaction mixture was dried by rotary pump and the residue was further dried in oven for overnight. The product (2-chloro-3-methoxycarbonyl-nitrobenzene) was pure enough for the following reaction.

Dimethyl malonate (6.0 ml) was added to an ice-cold suspension of sodium hydride (2.1 g) in dimethylsulfoxide (15 ml). The reaction mixture was heated to 100° C., stirred for 1 hour and then cooled to room temperature. 2-Chloro-3-methoxycarbonylnitrobenzene (2.15 g) was added in one portion and the mixture was stirred at 100° C. for 1.5 hour. The reaction mixture was then cooled to room temperature and poured into ice water, acidified to pH 5, and extracted with ethyl acetate. The organic layer was washed with brine, dried over anhydrous sodium sulfate and concentrated to give 3.0 g of the dimethyl 2-methoxycarbonyl-6-nitrophenylmalonate.

Dimethyl 2-methoxycarbonyl-6-nitrophenylmalonate (3.0 g) was refluxed in 50 ml of 6 N hydrochloric acid overnight. The mixture was concentrated to dryness and refluxed for 2 hours with 1.1 g of tin(II) chloride in 20 ml of ethanol. The mixture was filtered through Celite, concentrated and chromatographed on silica gel (ethyl acetate-:hexane:acetic acid) to give 0.65 g (37% yield) of 4-carboxy-2-oxindole as a white solid.

$^1$HNMR (360 MHz, DMSO-d6) δ: 12.96 (s, br, 1H, COOH), 10.74 (s, br, 1H, NH), 7.53 (d, J=8 Hz, 1H), 7.39 (t, J=8 Hz, 1H, H-6), 7.12 (d, J=8 Hz, 1H, H-7), 3.67 (s, 2H, H-3).

3,5-Diisopropyl-4-methoxybenzaldehyde was condensed with 4-carboxy-2-oxindole to give 0.3 g of 3-(3,5-diisopropyl-4-methoxybenzylidene)-2-oxo-2,3-dihydro-1H-indole-4-carboxylic acid as a yellow-orange solid.

Example 87

3-(3,5-Diisopropyl-4-methoxybenzylidene)-6-(3-methoxyphenyl)-1,3-dihydroindol-2-one 3,5-Diisopropyl-4-methoxybenzaldehyde was condensed with 6-(3-methoxyphenyl)-2-oxindole to give 0.4 g of 3-(3,5-diisopropyl-4-methoxybenzylidene)-6-(3-methoxyphenyl)-1,3-dihydroindol-2-one as a yellow-orange solid.

Example 88

7-Chloro-3-(3,5-diisopropyl-4-methoxybenzylidene)-5-methyl-1,3-dihydroindol-2-one 3,5-Diisopropyl-4-methoxybenzaldehyde was condensed with 5-methyl-7-chloro-2-oxindole to give 0.35 g of 7-chloro-3-(3,5-diisopropyl-4-methoxybenzylidene)-5-methyl-1,3-dihydroindol-2-one as a yellow-orange solid.

Example 89

[3-(3,5-Diisopropyl-4-methoxybenzylidene)-2-oxo-2,3-dihydro-1H-indol-5-yl]-carbamic acid tert-butyl ester 3,5-Diisopropyl-4-methoxybenzaldehyde was condensed with 5-tert-butyloxy-carbonylamino-2-oxindole to give 0.4 g of [3-(3,5-diisopropyl-4-methoxybenzylidene)-2-oxo-2,3-dihydro-1H-indol-5-yl]-carbamic acid tert-butyl ester as a yellow-orange solid.

Example 90

5-Chloro-3-(3-isopropyl-4-methoxybenzylidene)-1, 3-dihydroindol-2-one

3-Isopropyl-4-methoxybenzaldehyde was condensed with 5-chloro-2-oxindole to give 0.3 g of 5-chloro-3-(3-isopropyl-4-methoxybenzylidene)-1,3-dihydroindol-2-one as a yellow-orange solid.

$^1$HNMR (d$_6$-DMSO) δ: 10.6 (s, 1H, CONH), 8.5, 8.4, 7.9, 7.8, 7.2, 7.1, 6.8 (m, 7H, aromatic, =CH—), 3.9 (s, 3H, OCH$_3$), 3.3 (m, 1H, CH), 1.2(d, 6H, 2×CH$_3$).

Example 91

5-Chloro-3-(3-cyclopentyl-4-methoxybenzylidene)-1,3-dihydroindol-2-one

3-Cyclopentyl-4-methoxybenzaldehyde was condensed with 5-chloro-2-oxindole to give 0.3 g of 5-chloro-3-(3-cyclopentyl-4-methoxybenzylidene)-1,3-dihydroindol-2-one as a yellow-orange solid.

$^1$HNMR (d$_6$-DMSO) δ: 10.6 (s, 1H, CONH), 8.5, 8.3, 7.9, 7.8, 7.2, 7.1, 6.8 (m, 7H, aromatic, =CH—), 3.9 (s, 3H, OCH$_3$), 3.3 (m, 1H, CH), 1.8 (m, 8H, 4×CH$_2$).

Example 92

3-(6-Methoxybiphenyl-3-ylmethylene)-4-methyl-1, 3-dihydroindol-2-one

4-Methoxy-3-phenylbenzaldehyde was condensed with 4-methyl-2-oxindole to give 0.3 g of 3-(6-methoxybiphenyl-3-ylmethylene)-4-methyl-1,3-dihydroindol-2-one as a yellow-orange solid.

$^1$HNMR (d$_6$-DMSO) δ: 10.5 (s, 1H, CONH), 8.3–6.7 (m, 12H, aromatic, =CH—), 3.9 (s, 3H, OCH$_3$), 2.6 (s, 3H, CH$_3$).

Example 93

3-(5-Isopropyl-4-methoxy-2-methylbenzylidene)-4-methyl-1,3-dihydroindol-2-one

5-Isopropyl-4-methoxy-2-methylbenzaldehyde was condensed with 4-methyl-2-oxindole to give 0.3 g of 3-(5-isopropyl-4-methoxy-2-methylbenzylidene)-4-methyl-1,3-dihydroindol-2-one as a yellow-orange solid.

$^1$HNMR (d$_6$-DMSO) δ: 10.3 (s, 1H, CONH), 8.2, 7.8, 7.1, 6.8, 6.8, 6.7 (m, 6H, aromatic, =CH—), 3.8 (s, 3H, OCH$_3$), 3.2 (m, 1H, CH), 2.5 (s, 3H, CH$_3$), 2.4 (s, 3H, CH$_3$), 1.2 (d, 6H, 2×CH$_3$).

Example 94

5-Bromo-3-(2,3-dihydrobenzofuran-5-ylmethylene)-1,3-dihydroindol-2-one 2,3-Dihydro-5-formylbenzofuran (commercially available) was condensed with 5-bromo-2-oxindole to give 0.3 g of 5-bromo-3-(2,3-dihydrobenzofuran-5-ylmethylene)-1,3-dihydroindol-2-one as a yellow-orange solid.

$^1$HNMR (d$_6$-DMSO) δ: 10.64 (s, 1H, CONH), 7.71 (d, 1H), 7.62 (vinyl, 1H), 7.61 (m, 1H), 7.52 (m, 1H), 7.37 (dd, 1H) 6.93 (d, 1H), 6.984 (d, 1H), 4.64 (t, 2H, CH$_2$), 3.22 (t, 2H, CH$_2$).

Example 95

5-Chloro-3-(3-isopropyl-4-methoxybenzylidene)-4-methyl-1,3-dihydroindol-2-one

3-Isopropyl-4-methoxybenzaldehyde was condensed with 4-methyl-5-chloro-2-oxindole to give 0.3 g of 5-chloro-3-(3-isopropyl-4-methoxybenzylidene)-4-methyl-1,3-dihydroindol-2-one as a yellow-orange solid.

Example 96

5-Chloro-3-(3,5-diisopropyl-4-methoxybenzylidene)-4-methyl-1,3-dihydroindol-2-one 3,5-Diisopropyl-4-methoxybenzaldehyde was condensed with 4-methyl-5-chloro-2-oxindole to give 0.4 g of 5-chloro-3-(3,5-diisopropyl-4-methoxybenzylidene)-4-methyl-1,3-dihydroindol-2-one as a yellow-orange solid.

Example 97

5-Chloro-3-(2,2-dimethylchroman-6-ylmethylene)-4-methyl-1,3-dihydroindol-2-one 2,2-Dimethyl-6-formylchromane (commercially available) was condensed with 4-methyl-5-chloro-2-oxindole to give 0.3 g of 5-chloro-3-(2,2-dimethyl-chroman-6-ylmethylene)-4-methyl-1,3-dihydroindol-2-one as a yellow-orange solid.

Example 98

3-(3,5-Diisopropyl-4-methoxybenzylidene)-2-oxo-2,3-dihydro-1H-indole-5-carboxylic acid 2-Oxindole (6.7 g) was added to a suspension of aluminum chloride (23 g) in dichloroethane (30 ml) cooled in an ice bath. Chloroacetyl chloride (11.3 g) was slowly added and hydrogen chloride gas was evolved. After ten minutes of stirring, the reaction was warmed to 40–50° C. for 1.5 hours. The mixture was cooled to room temperature and poured into ice water. The precipitate was collected by vacuum filtration, washed with water and dried under vacuum to give 10.3 g (98%) of 5-chloroacetyl-2-oxindole as an off-white solid.

A suspension of 9.3 g of 5-chloroacetyl-2-oxindole was stirred in 90 ml pyridine at 80–90° C. for 3 hours then cooled to room temperature. The precipitate was collected by vacuum filtration and washed with 20 ml of ethanol. The solid was dissolved in 90 ml of 2.5 N sodium hydroxide and stirred at 70 to 80° C. for 3 hours. The mixture was cooled to room temperature and acidified to pH 2 with 0.5 N hydrochloric acid. The precipitate was collected by vacuum filtration and washed thoroughly with water to give crude 5-carboxy-2-oxindole as a dark brown solid. After standing overnight the filtrate yielded 2 g of 5-carboxy-2-oxindole as a yellow solid. The crude dark brown product was dissolved in hot methanol, the insoluble material removed by filtration and the filtrate concentrated to give 5.6 g of 5-carboxy-2-oxindole as a brown solid. The combined yield was 97%.

$^1$HNMR (360 MHz, DMSO-d6) δ: 2.56 (s, br, 1H, COOH-5), 10.70 (s, 1H, NH-1), 7.82 (dd, J=2, 8 Hz, 1H, H-6), 7.74 (s, br, 1H, H-4), 6.87 (d, J=8 Hz, 1H, H-7), and 3.53 (s, 2H, CH$_2$-3).

MS m/z 178 [M+1]$^+$.

3,5-Diisopropyl-4-methoxybenzaldehyde was condensed with 5-carboxy-2-oxindole to give 0.4 g of 3-(3,5-diisopropyl-4-methoxybenzylidene)-2-oxo-2,3-dihydro-1H-indole-5-carboxylic acid as a yellow-orange solid.

Example 99

3-(3,5-Diisopropyl-4-methoxybenzylidene)-5,6-dimethoxy-1,3-dihydroindol-2-one 3,5-Diisopropyl-4-methoxybenzaldehyde was condensed with 5,6-dimethoxy-2-oxindole to give 0.4 g of 3-(3,5-diisopropyl-4-methoxybenzylidene)-5,6-dimethoxy-1,3-dihydroindol-2-one as a yellow-orange solid.

Example 100

N-[3-(3,5-Diisopropyl-4-methoxybenzylidene)-2-oxo-2,3-dihydro-1H-indol-6-yl]-methanesulfonamide 3,5-Diisopropyl-4-methoxybenzaldehyde was condensed with 6-methylsulfonylamino-2-oxindole to give 0.4 g of N-[3-(3,5-diisopropyl-4-methoxybenzylidene)-2-oxo-2,3-dihydro-1H-indol-6-yl]-methanesulfonamide as a yellow-orange solid.

Example 101

N-[3-(3,5-Diisopropyl-4-methoxybenzylidene)-2-oxo-2,3-dihydro-1H-indol-6-yl]-benzamide 3,5-Diisopropyl-4-methoxybenzaldehyde was condensed with 6-benzamido-2-oxindole to give 0.4 g of N-[3-(3,5-diisopropyl-4-methoxybenzylidene)-2-oxo-2,3-dihydro-1H-indol-6-yl]-benzamide as a yellow-orange solid.

Example 102

3-(3,5-Diisopropyl-4-methoxybenzylidene)-6-(3-ethoxyphenyl)-1,3-dihydroindol-2-one Tetrakis(triphenylphosphine)palladium (0.8 g) was added to a mixture of 4.2 g of 3-ethoxyphenylboronic acid, 5.0 g of 5-bromo-2-fluoronitrobenzene and 22 ml of 2 M sodium carbonate solution in 50 ml of toluene and 50 ml of ethanol. The mixture was heated to reflux for 2 hours. The cooled mixture was concentrated, water was added and the mixture was extracted twice with ethyl acetate. The ethyl acetate layer was washed with water, brine, dried, and concentrated. The residue was chromatographed on silica gel (5% ethyl acetate in hexane) to give 5.3 g (90% yield) of crude 4-fluoro-3'-ethoxy-3-nitrobiphenyl as a yellow oil.

Dimethyl malonate (11.4 ml) was added dropwise to 4.0 g of sodium hydride suspended in 20 ml of dimethylsulfoxide. The mixture was heated to 100° C. for 10 minutes and cooled to room temperature. Crude 4-fluoro-3'-ethoxy-3-nitrobiphenyl (5.3 g) in 25 ml of dimethylsulfoxide was added and the mixture was stirred at 100° C. for 2 hours. The reaction mixture was cooled and quenched with 300 ml of saturated ammonium chloride solution and extracted three times with ethyl acetate. The extracts were combined, washed with water and brine, dried over anhydrous sodium sulfate and concentrated to give crude dimethyl 3'-ethoxy-3-nitrobiphenyl-4-malonate as a yellow oil.

Crude dimethyl 3'-ethoxy-3-nitrobiphenyl-4-malonate in 60 ml of 6 N hydrochloric acid was stirred at 100° C. for 4 days and and then cooled. The precipitate which formed was collected by filtration, washed with water and hexane, and dried to give 4.7 g (77% based on 5-bromo-2-fluoronitrobenzene) of crude 3'-ethoxy-3-nitrobiphenyl-4-acetic acid as a light tan solid.

Iron chips (2.4 g) were added in one portion to 4.6 g of 3'-ethoxy-3-nitrobiphenyl-4-acetic acid in glacial acetic acid (40 ml). The mixture was refluxed for 2 hours. The reaction mixture was cooled and concentrated to dryness. The residue was treated repeatedly with ethyl acetate and filtered to remove insolubles. The filtrate was washed twice with 1 N hydrochloric acid and brine, dried over anhydrous sodium sulfate and concentrated to give 3.5 g (91%) of 6-(3-ethoxyphenyl)-2-oxindole as a light brown solid.

$^1$HNMR (360 MHz, DMSO-d6) δ: 10.4 (s, br, 1H, NH), 7.33 (t, J=8 Hz, 1H, H-3'), 7.35 (d, J=8 Hz, 1H), 7.19 (dd, J=1, 8 Hz, 1H), 7.13 (d, J=8 Hz, 1H), 7.07–7.08 (m, 1H) 7.0 (s, br, 1H), 6.9 (dd, J=3, 8 Hz, 1H), 4.08 (q, J=7 Hz, 2H, O CH$_2$CH$_3$), 3.49 (s, 2H, CH$_2$), 1.34 (t, J=7 Hz, 3H, OCH$_2$CH$_3$).

MS m/z 254.2 [M+1]$^+$.

3,5-Diisopropyl-4-methoxybenzaldehyde was condensed with 6-(3-ethoxyphenyl)-2-oxindole to give 0.4 g of 3-(3,5-diisopropyl-4-methoxybenzylidene)-6-(3-ethoxyphenyl)-1,3-dihydroindol-2-one as a yellow-orange solid.

Example 103

3-(3,5-Diisopropyl-4-methoxybenzylidene)-6-phenyl-1,3-dihydroindol-2-one

Tetrakis(triphenylphosphine)palladium (0.8 g) was added to a mixture of 3.1 g of benzeneboronic acid, 5 g of 5-bromo-2-fluoronitrobenzene and 22 ml of 2M aqueous sodium carbonate in 50 ml of toluene and 50 ml of ethanol. The mixture was refluxed for 2 hours, concentrated, and the residue extracted twice with ethyl acetate. The ethyl acetate layer was washed with water and brine, dried, and concentrated to give a yellow oil. The oil was chromatographed on silica gel (5% ethyl acetate in hexane) to give 4.75 g (96%) of 4-fluoro-3-nitrobiphenyl as a yellow oil.

Dimethyl malonate (10 ml) in 25 ml of dimethylsulfoxide was added dropwise to 3.5 g of sodium hydride suspended in 25 ml of dimethylsulfoxide and the mixture stirred at 100° C. for 10 minutes. The mixture was cooled to room temperature and 4.7 g of 4-fluoro-3-nitrobiphenyl in 25 ml of dimethylsulfoxide was added. The mixture was stirred at 100° C. for 2 hours, cooled and quenched with 300 ml of saturated ammonium chloride solution. The mixture was extracted three times with ethyl acetate and the combined organic layers washed with water and brine and evaporated to give a yellow oil, crude dimethyl-3-nitrobiphenyl-4-malonate.

Crude dimethyl-3-nitrobiphenyl-4-malonate was refluxed in 30 ml of 6 N hydrochloric acid for 24 hours. The precipitate was collected by filtration, washed with water and dried to give 4.5 g (80% based on 4-fluoro-3-nitrobiphenyl) of 3-nitrobiphenyl-4-acetic acid as a cream colored solid.

Iron chips (2.6 g) were added all at once to 4.5 g of 3-nitrobiphenyl-4-acetic acid in 40 ml of acetic acid. The mixture was refluxed for 2 hours, concentrated to dryness and the residue taken up in ethyl acetate. The solids were removed by filtration and the filtrate washed twice with 1 N hydrochloric acid and brine and dried over anhydrous sodium sulfate. The filtrate was concentrated to give 3.4 g (93% yield) of 6-phenyl-2-oxindole as a light brown solid.

$^1$HNMR (360 MHz, DMSO-d6) δ: 10.4 (s, br, 1H, NH-1), 7.57–7.6 (m, 2H), 7.42–7.46 (m, 2H), 7.32–7.37 (m, 1H), 7.27 (d, J=8, 1H, H-4), 7.19 (dd, J=2 and 8 Hz, 1H, H-5), 7.01 (d, J=2 Hz, 1H, H-7), 3.49 (s, 2H, CH$_2$).

MS m/z 210 [M+1]$^+$.

3,5-Diisopropyl-4-methoxybenzaldehyde was condensed with 6-phenyl-2-oxindole to give 0.4 g of 3-(3,5-diisopropyl-4-methoxybenzylidene)-6-phenyl-1,3-dihydroindol-2-one as a yellow-orange solid.

Example 104

3-(3,5-Diisopropyl-4-methoxybenzylidene)-5-fluoro-1,3-dihydroindol-2-one 3,5-Diisopropyl-4-methoxybenzaldehyde was condensed with 5-fluoro-2-oxindole to give 0.3 g of 3-(3,5-diisopropyl-4-methoxybenzylidene)-5-fluoro-1,3-dihydroindol-2-one as a yellow-orange solid.

Example 105

5-Fluoro-3-(4-methoxy-3,5-dimethylbenzylidene)-1,3-dihydroindol-2-one 3,5-Dimethyl-4-methoxybenzaldehyde was condensed with 5-fluoro-2-oxindole to give 0.3 g of 5-fluoro-3-(4-methoxy-3,5-dimethylbenzylidene)-1,3-dihydroindol-2-one as a yellow-orange solid.

Example 106

3-(2,2-Dimethylchroman-6-ylmethylene)-1,3-dihydroindol-2-one 2,2-Dimethyl-6-formylchromane (commercially available) was condensed with 2-oxindole to give 0.3 g of 3-(2,2-dimethylchroman-6-ylmethylene)-1,3-dihydroindol-2-one as a yellow-orange solid.

Example 107

3-{2-[6-(4-Fluorophenyl)-2-oxo-1,2-dihydroindol-3-ylidenemethyl]-5-methyl-1H-pyrrol-3-yl}prolionic acid 6-(4-Fluorophenyl)-1,3-dihydroindol-2-one (70 mg, 0.31 mmol) was condensed with 3-(2-formyl-5-methyl-1H-pyrrol-3-yl)-propionic acid (56 mg) to give the title compound.

$^1$HNMR (360 MHz, DMSO-d$_6$) δ13.38 (s, br, 1H, COOH), 12.08 (s, br, 1H, NH), 10.87 (s, br, 1H, NH), 7.79 (d, J=7.9 Hz, 1H), 7.63–7.69 (m, 3H), 7.23–7.29 (m, 3H), 7.07 (d, J=1.4 Hz, 1H), 6.06 (d, J=2.2 Hz, 1H), 2.96 (t, J=7.2 Hz, 2H, CH$_2$), 2.52 (t, J=7.2 Hz, 2H, CH$_2$), 2.32 (s, 3H, CH$_3$).

MS-EI m/z 390 [M$^+$].

Example 108

4-(2-Carboxyethyl)-5-[6-(4-fluorophenyl)-2-oxo-1,2-dihydro-indol-3-ylidenemethyl]-2-methyl-1H-pyrrole-3-carboxylic acid ethyl ester 6-(4-Fluorophenyl)-1,3-dihydroindol-2-one (60 mg, 0.26 mmol) was condensed with 4-(2-carboxyethyl)-5-formyl-2-methyl-1H-pyrrole-3-carboxylic acid ethyl ester (65 mg), prepared by formylation of 4-(2-carboxyethyl)-3-ethoxycarbonyl-2-methylpyrrole (Bulter, A. R., and George, S. D. (1993) Tetrahedron 49: 7017–7026), to give the title compound.

$^1$HNMR (360 MHz, DMSO-$d_6$) δ13.85 (s, br, 1H, NH), 12.03 (s, br, 1H, COOH), 11.05 (s, br, 1H, NH), 7.83 (d, J=7.9 Hz, 1H), 7.76 (s, 1H, H-vinyl), 7.66–7.70 (m, 2H), 7.25–7.30 (m, 3H), 7.08 (d, J=1.4 Hz, 1H), 4.22 (q, J=7.0 Hz, 2H, OCH$_2$CH$_3$), 3.20 (t, J=7.6 Hz, 2H, CH$_2$), 2.54 (s, 3H, CH$_3$), 2.45 (m, 2H, CH$_2$), 4.22 (t, J=7.0 Hz, 2H, OCH$_2$CH$_3$).

MS-EI m/z 462 [M$^+$].

Example 109

3-{2-[6-(2-Methoxyphenyl)-2-oxo-1,2-dihydroindol-3-ylidenemethyl]-5-methyl-1H-pyrrol-3-yl}-propionic acid 6-(2-Methoxyphenyl)-1,3-dihydroindol-2-one (71 mg, 0.3 mmol) was condensed with 3-(2-formyl-5-methyl-1H-pyrrol-3-yl)-propionic acid (54 mg) to give the title compound.

$^1$HNMR (300 MHz, DMSO-$d_6$) δ13.33 (s, br, 1H, NH), 12.07 (s, br, 1H, COOH), 10.74 (s, br, 1H, NH), 7.68 (d, J=7.8 Hz, 1H), 7.56 (s, 1H, H-vinyl), 7.25–7.28 (m, 2H), 6.94–7.05 (m, 4H), 5.99 (br s, 1H), 3.70 (s, 3H, OCH$_3$), 2.89 (m, 2H, CH$_2$), 2.45 (m, 2H, CH$_2$), 2.26 (s, 3H, CH$_3$).

MS-EI m/z 402 [M$^+$].

Example 110

4-(2-Carboxyethyl)-5-[6-(2-methoxyphenyl)-2-oxo-1,2-dihydro-indol-3-ylidenemethyl]-2-methyl-1H-pyrrole-3-carboxylic acid ethyl ester $^1$HNMR (300 MHz, DMSO-$d_6$) δ13.88 (s, br, 1H, NH), 12.07 (s, br, 1H, COOH), 10.99 (s, br, 1H, NH), 7.77 (d, J=7.8 Hz, 1H), 7.74 (s, 1H, H-vinyl), 7.28–7.36 (m, 2H), 7.07–7.1 (m, 2H), 6.99–7.04 (m, 2H), 4.21 (q, J=7.0 Hz, 2H, OCH$_2$CH$_3$), 3.76 (s, 3H, OCH$_3$), 3.19 (m, 2H, CH$_2$), 2.54 (s, 3H, CH$_3$), 2.50 (m, 2H, CH$_2$), 1.04 (t, J=7.0 Hz, 3H, OCH$_2$CH$_3$).

MS-EI m/z 474 [M$^+$].

Example 111

3-[2-(5-Chloro-2-oxo-1,2-dihydroindol-3-ylidenemethyl)-5-methyl-1H-pyrrol-3-yl]propionic acid 5-Chloro-1,3-dihydroindol-2-one (61 mg, 0.36 mmol) was condensed with 3-(2-formyl-5-methyl-1H-pyrrol-3-yl)-propionic acid (66 mg) to give the title compound.

MS-EI m/z 300 and 302 [M−1 and M+1].

Example 112

4-(2-Carboxyethyl)-5-(5-chloro-2-oxo-1,2-dihydroindol-3-ylidenemethyl)-2-methyl-1H-pyrrole-3-carboxylic acid ethyl ester $^1$HNMR (300 MHz, DMSO-$d_6$) δ13.88 (s, br, 1H, NH), 12.04 (s, br, 1H, COOH), 11.08 (s, br, 1H, NH), 7.93 (d, J=2.0 Hz, 1H), 7.83 (s, 1H, H-vinyl), 7.15 (dd, J=2.0, 8.3 Hz, 1H), 6.87 (d, J=8.3 Hz, 1H), 4.20 (q, J=7.1 Hz, 2H, OCH$_2$CH$_3$), 3.21 (t, J=7.6 Hz, 2H, CH$_2$), 2.53 (s, 3H, CH$_3$), 2.45 (t, J=7.6 Hz, 2H, CH$_2$), 1.28 (t, J=7.1 Hz, 3H, OCH$_2$CH$_3$).

MS-EI m/z 402 and 404 [M−1 and M+1].

Example 117

4-(2-Carboxyethyl)-3-methyl-5-(2-oxo-1,2-dihydroindol-3-ylidenemethyl)-1H-pyrrole-2-carboxylic acid ethyl ester Oxindole (0.25 g, 1.88 mmol) was condensed with 4-(2-carboxyethyl)-5-formyl-3-methyl-1H-pyrrole-2-carboxylic acid ethyl ester (0.5 g, 1.97 mmol) to give 0.45 g (65%) of the title compound.

$^1$HNMR (300 MHz, DMSO-$d_6$) δ13.85 (s, br, 1H, NH), 12.12 (s, br, 1H, COOH), 10.99 (s, br, 1H, NH), 7.78 (d, J=7.6 Hz, 1H), 7.70 (s, 1H, H-vinyl), 7.17 (m 1H), 6.99 (m, 1H), 4.25 (q, J=7.1 Hz, 2H, OCH$_2$CH$_3$), 2.93 (t, J=7.4 Hz, 2H, CH$_2$), 2.38 (t, J=7.4 Hz, 2H, CH$_2$), 2.24 (s, 3H, CH$_3$), 1.29 (t, J=7.1 Hz, 3H, OCH$_2$CH$_3$).

MS-EI m/z 368 [M$^+$].

Example 118

2-Methyl-5-(5-methylsulfamoyl-2-oxo-1,2-dihydroindol-3-ylidenemethyl)-4-(3-morpholin-4-ylpropyl)-1H-pyrrole-3-carboxylic acid ethyl ester 2-Oxo-2,3-dihydro-1H-indole-5-sulfonic acid methylamide was stirred with 5-formyl-2-methyl-4-(3-morpholin-4-ylpropyl)-1H-pyrrole-3-carboxylic acid ethyl ester overnight at room temperature to give the title compound.

$^1$HNMR (300 MHz, DMSO-$d_6$) δ13.86 (s, br, 1H, NH), 11.39 (s, br, 1H, NH), 8.16 (d, J=1.6 Hz, 1H, H-4), 7.82 (s, 1H, H-vinyl), 7.57 (dd, J=1.6 & 6.9 Hz, 1H, H-6), 7.21 (m, 1H, CH$_3$NHSO$_2$), 7.07 (d, J=6.9 Hz, 1H, H-7), 4.21 (q, J=7.0 Hz, 2H, OCH$_2$CH$_3$), 3.52 (m, 4H, 2×CH$_2$), 3.03 (m, 2H, CH$_2$), 2.55 (s, 3H, CH$_3$), 2.40 (d, J=5.0 Hz, 3H, CH$_3$NHSO$_2$), 2.25 (m, 6H, 3×CH$_2$), 1.69 (m, 2H, CH$_2$), 1.29 (t, J=7.0 Hz, 3H, OCH$_2$CH$_3$).

MS-EI m/z 516 [M$^+$].

Example 119

2-Methyl-4-[3-(4-methylpiperazin-1-y1)-propyl]-5-(5-methylsulfamoyl-2-oxo-1,2-dihydroindol-3-ylidenemethyl)-1H-pyrrole-3-carboxylic acid ethyl ester $^1$HNMR (300 MHz, DMSO-$d_6$) δ13.88 (s, br, 1H, NH), 11.38 (s, br, 1H, NH), 8.16 (d, J=1.6 Hz, 1H, H-4), 7.79 (s, 1H, H-vinyl), 7.57 (dd, J=1.6 & 6.6 Hz, 1H, H-6), 7.21 (m, 1H, CH$_3$NHSO$_2$), 7.05 (d, J=6.6 Hz, 1H, H-7), 4.21 (q, J=7.0 Hz, 2H, OCH$_2$CH$_3$), 3.01 (m, 2H, CH$_2$), 2.55 (s, 3H, CH$_3$), 2.40 (d, J=5.4 Hz, 3H, CH$_3$NHSO$_2$), 2.57 (m, 10H, 5×CH$_2$), 2.09 (s, 3H, CH$_3$N), 1.67 (m, 2H, CH$_2$), 1.29 (t, J=7.0 Hz, 3H, OCH$_2$CH$_3$).

MS-EI m/z 529 [M$^+$].

Example 120

4-(3-Dimethylaminopropyl)-5-(5-methoxy-2-oxo-1,2-dihydroindol-3-ylidenemethyl)-2-methyl-1H-pyrrole-3-carboxylic acid ethyl ester $^1$HNMR (360 MHz, DMSO-$d_6$) δ13.95 (s, br, 1H, NH), 10.76 (s, br, 1H, NH), 7.70 (s, 1H, H-vinyl), 7.31 (d, J=2.2 Hz, 1H, H-4), 6.78 (d, J=8.3 Hz, 1H, H-7), 6.73 (dd, J=2.2 & 8.3 Hz, 1H, H-6), 4.21 (q, J=7.0 Hz, 2H, OCH$_2$CH$_3$), 3.76 (s, 3H, OCH,), 2.98 (m, 2H, CH$_2$), 2.53 (s, 3H, CH$_3$) 2.19 (m, 2H, CH$_2$), 2.11 (s, 6H, N(CH$_3$)$_2$), 1.64 (m, 2H, CH$_2$), 1.30 (t, J=7.0 Hz, 3H, OCH$_2$CH$_3$).

MS-EI m/z 411 [M$^+$].

Example 121

5-(5-Methoxy-2-oxo-1,2-dihydroindol-3-ylidenemethyl)-2-methyl-4-(3-morpholin-4-ylpropyl)-1H-pyrrole-3-carboxylic acid ethyl ester $^1$HNMR (300 MHz, DMSO-d$_6$) δ14.0 (s, br, 1H, NH), 10.77 (s, br, 1H, NH), 7.65 (s, 1H, H-vinyl), 7.40 (m, 1H), 6.76 (m, 2H), 4.2 (q, J=7.0 Hz, 2H, OCH$_2$CH$_3$), 3.76 (s, 3H, OCH$_3$), 3.54 (m, 4H, 2×CH$_2$), 2.99 (m, 2H, CH$_2$), 2.52 (s, 3H, CH$_3$), 2.25 (m, 6H, 3×CH$_2$), 1.67 (m, 2H, CH$_2$), 1.29 (t, J=7.0 Hz, 3H, OCH$_2$CH$_3$).

MS-EI m/z 453 [M$^+$].

Example 122

5-(5-Methoxy-2-oxo-1,2-dihydroindol-3-ylidenemethyl)-2-methyl-4-[3-(4-methylpiperazin-1-yl)-propyl]-1H-pyrrole-3-carboxylic acid ethyl ester $^1$HNMR (300 MHz, DMSO-d$_6$)δ13.99 (s, br, 1H, NH), 10.78 (s, br, 1H, NH), 7.63 (s, 1H, H-vinyl), 7.39 (d, J=1.8 Hz, 1H, H-4), 6.76 (m, 2H), 4.2 (q, J=7.1 Hz, 2H, OCH$_2$CH$_3$), 3.77 (s, 3H, OCH$_3$), 2.97 (m, 2H, CH$_2$), 2.52 (s, 3H, CH$_3$), 2.25 (m, 10H, 5×CH$_2$), 2.08 (s, 3H, NCH$_3$), 1.66 (m, 2H, CH$_2$), 1.29 (t, J=7.1 Hz, 3H, OCH$_2$CH$_3$).

MS-EI m/z 466 [M$^+$].

Example 123

2-Methyl-4-(3-morpholin-4-ylpropyl)-5-(2-oxo-5-sulfamoyl-1,2-dihydroindol-3-ylidenemethyl)-1H-pyrrole-3-carboxylic acid ethyl ester $^1$HNMR (300 MHz, DMSO-d$_6$) δ13.85 (s, br, 1H, NH), 11.33 (s, br, 1H, NH), 8.19 (d, J=1.8 Hz, 1H, H-4), 7.75 (s, 1H, H-vinyl), 7.63 (dd, J=1.8 & 8.3 Hz, 1H, H-6), 7.16 (s, 2H, H$_2$NSO$_2$), 7.02 (d, J=8.3 Hz, 1H, H-7), 4.21 (q, J=7.3 Hz, 2H, OCH$_2$CH$_3$), 3.53 (m, 4H, 2×CH$_2$), 3.01 (m, 2H, CH$_2$), 2.55 (s, 3H, CH$_3$), 2.28 (m, 6H, 3×CH$_2$), 1.68 (m, 2H, CH$_2$), 1.29 (t, J=7.3 Hz, 3H, OCH$_2$CH$_3$).

MS-EI m/z 502 [M$^+$].

Example 124

2-Methyl-4-[3-(4-methylpiperazin-1-yl)-propyl]-5-(2-oxo-5-sulfamoyl-1,2-dihydroindol-3-ylidenemethyl)-1H-pyrrole-3-carboxylic acid ethyl ester $^1$HNMR (300 MHz, DMSO-d$_6$) δ13.85 (s, br, 1H, NH), 11.31 (s, br, 1H, NH), 8.18 (d, J=1.5 Hz, 1H, H-4), 7.74 (s, 1H, H-vinyl), 7.63 (dd, J=1.5 & 8.1 Hz, 1H, H-6), 7.15 (s, 2H, H$_2$NSO$_2$), 7.01 (d, J=8.1 Hz, 1H, H-7), 4.21 (q, J=7.1 Hz, 2H, OCH$_2$CH$_3$) 3.0 (2H, CH$_2$), 2.54 (s, 3H, CH$_3$), 2.26 (m, 10H, 5×CH$_2$), 2.09 (s, 3H, NCH$_3$), 1.67 (m, 2H, CH$_2$) 1.29 (t, J=7.1 Hz, 3H, OCH$_2$CH$_3$).

MS-EI m/Z 515 [M$^+$].

Example 125

3-[4-Ethoxycarbonyl-5-methyl-3-(3-morpholin-4-ylpropyl)-1H-pyrrol-2-ylmethylene]-2-oxo-2,3-dihydro-1H-indole-5-carboxylic acid $^1$HNMR (300 MHz, DMSO-d$_6$) δ13.88 (s, br, 1H, NH), 11.03 (s, br, 1H, COOH), 8.17 (s, 1H, H-4), 7.76 (d, J=8.4 Hz, 1H, H-6), 7.59 (s, 1H, H-vinyl), 6.80 (d, J=8.4 Hz, 1H, H-7), 4.21 (q, J=7.2 Hz, 2H, OCH$_2$CH$_3$), 3.54 (m, 4H, 2×CH$_2$), 2.98 (m, 2H, CH$_2$), 2.49 (s, 3H, CH$_3$), 2.29 (m, 6H, 3×CH$_2$), 1.64 (m, 2H, CH$_2$), 1.29 (t, J=7.2 Hz, 3H, OCH$_2$CH$_3$).

MS-EI m/Z 467 [M$^+$].

Example 126

2-Methyl-5-(5-methylsulfamoyl-2-oxo-1,2-dihydroindol-3-ylidenemethyl)-4-(3-pyrrolidin-1-ylpropyl)-1H-pyrrole-3-carboxylic acid ethyl ester $^1$HNMR (360 MHz, DMSO-d$_6$) δ13.84 (s, 1H, NH), 11.28 (br s, 1H, NH), 8.06 (d, J=2.1 Hz, 1H), 7.83 (s, 1H, H-vinyl), 7.57 (dd, J=2.1 & 8.3 Hz, 1H), 7.20 (m, 1H, HNCH$_3$), 7.06 (d, J=8.3 Hz, 1H), 4.22 (q, J=7.0 Hz, 2H, OCH$_2$CH$_3$), 3.04 (m, 2H, CH$_2$), 2.55 (s, 3H, CH$_3$), 2.40 (d, J=4.8 Hz, 3H, HNCH$_3$), 2.3–2.36 (m, 6H, 3×CH$_2$), 1.66–1.71 (m, 6H, 3×CH$_2$), 1.30 (t, J=7.0 Hz, 3H, OCH$_2$CH$_3$).

MS-EI mz/Z 500 [M$^+$].

Example 127

5-(5-Methoxy-2-oxo-1,2-dihydroindol-3-ylidenemethyl)-2-methyl-4-(3-pyrrolidin-1-ylpropyl)-1H-pyrrole-3-carboxylic acid ethyl ester $^1$HNMR (300 MHz, DMSO-d$_6$) δ13.96 (s, 1H, NH), 10.75 (br s, 1H, NH), 7.65 (s, 1H, H-vinyl), 7.28 (d, J=2.2 Hz, 1H), 6.71–6.79 (m, 2H), 4.20 (q, J=7.1 Hz, 2H, OCH$_2$CH$_3$), 3.75 (s, 3H, OCH$_3$), 3.0 (m, 2H, CH$_2$), 2.52 (s, 3H, CH$_3$), 2.26–2.35 (m, 6H, 3×CH$_2$), 1.65–1.71 (m, 6H, 3×CH$_2$), 1.29 (t, J=7.1 Hz, 3H, OCH$_2$CH$_3$).

MS-EI m/z 437 [M$^+$].

Example 128

3-[4-Ethoxycarbonyl-5-methyl-3-(3-pyrrolidin-1-ylpropyl)-1H-pyrrol-2-ylmethylene]-2-oxo-2,3-dihydro-1H-indole-5-carboxylic acid $^1$HNMR (300 MHz, DMSO-d$_6$) δ13.80 (s, 1H, NH), 11.26 (br s, 1H, NH), 8.2 (s, 1H), 7.77 (m, 2H), 6.92 (d, J=8.1 Hz, 1H), 4.23 (q, J=6.9 Hz, 2H, OCH$_2$CH$_3$), 3.03 (m, 2H, CH$_2$), 2.54 (s, 3H, CH$_3$), 2.40 (m, 6H, 3×CH$_2$), 1.68 (m, 6H, 3×CH$_2$), 1.29 (t, J=6.9 Hz, 3H, OCH$_2$CH$_3$).

MS-EI m/z 451 [M$^+$].

Example 130

2-Methyl-5-(2-oxo-5-sulfamoyl-1,2-dihydroindol-3-ylidenemethyl)-4-(3-pyrrolidin-1-ylpropyl)-1H-pyrrole-3-carboxylic acid ethyl ester $^1$HNMR (300 MHz, DMSO-d$_6$) δ13.98 (s, 1H, NH), 11.30 (br s, 1H, NH), 8.10 (d, J=1.9 Hz, 1H), 7.79 (s, 1H, H-vinyl), 7.63 (dd, J=1.9 & 8.2 Hz, 1H), 7.16 (br s, 2H, H$_2$NSO$_2$), 7.02 (d, J=8.2 Hz, 1H), 4.21 (q, J=6.9 Hz, 2H, OCH$_2$CH$_3$), 3.03 (m, 2H, CH$_2$), 2.54 (s, 3H, CH$_3$), 2.33 (m, 6H, 3×CH$_2$), 1.68 (m, 6H, 3×CH$_2$), 1.29 (t, J=6.9 Hz, 3H, OCH$_2$CH$_3$).

MS-EI m/z 486 [M$^+$].

Example 131

5-[4-(2-Hydroxyethyl)-2-oxo-1,2-dihydroindol-3-ylidenemethyl]-2-methyl-4-(3-morpholin-4-ylpropyl)-1H pyrrole-3-carboxylic acid ethyl ester $^1$HNMR (360 MHz, DMSO-d$_6$) δ13.93 (s, 1H, NH), 10.95 (br s, 1H, NH), 7.65 (s, 1H, H-vinyl), 7.06 (t, J=7.6

Hz, 1H), 6.83 (d, J=7.6 Hz, 1H), 6.77 (d, J=7.6 Hz, 1H), 4.85 (br s, 1H, OH), 4.21 (q, J=7.0 Hz, 2H, OCH$_2$CH$_3$), 3.73 (m, 2H, CH$_2$), 3.53 (m, 4H, 2×CH$_2$), 3.09 (m, 2H, CH$_2$), 2.92 (m, 2H, CH$_2$), 2.53 (s, 3H, CH$_3$), 2.31 (m, 6H, 3×CH$_2$), 1.68 (m, 2H, CH$_2$), 1.29 (t, J=7.0 Hz, 3H, OCH$_2$CH$_3$).

MS-EI m/z 467 [M$^+$].

Example 132

5-[4-(2-Hydroxyethyl)-2-oxo-1,2-dihydroindol-3-ylidenemethyl]-2-methyl-4-(3-pyrrolidin-1-ylpropyl)-1H-pyrrole-3-carboxylic acid ethyl ester $^1$HNMR (360 MHz, DMSO-d$_6$) δ13.93 (s, 1H, NH), 10.94 (br s, 1H, NH), 7.68 (s, 1H, H-vinyl), 7.06 (t, J=7.3 Hz, 1H), 6.83 (d, J=7.3 Hz, 1H), 6.77 (d, J=7.3 Hz, 1H), 4.87 (br s, 1H, OH), 4.21 (q, J=7.2 Hz, 2H, OCH$_2$CH$_3$), 3.72 (m, 2H, CH$_2$), 3.09 (m, 2H, CH$_2$), 2.94 (m, 2H, CH$_2$), 2.53 (s, 3H, CH$_3$), 2.38 (m, 6H, 3×CH$_2$), 1.67 (m, 6H, 3×CH$_2$), 1.29 (t, J=7.2 Hz, 3H, OCH$_2$CH$_3$).

MS-EI m/z 451 [M$^+$].

Example 133

4-(3-Dimethylaminopropyl)-2-methyl-5-(2-oxo-5-sulfamoyl-1,2-dihydroindol-3-ylidenemethyl)-1H-pyrrole-3-carboxylic acid ethyl ester $^1$HNMR (300 MHz, DMSO-d$_6$) δ13.73 (s, 1H, NH), 11.25 (br s, 1H, NH), 8.09 (d, J=1.6 Hz, 1H), 7.90 (s, 1H, H-vinyl), 7.62 (dd, J=1.6 & 8.1 Hz, 1H), 7.20 (br s, 2H, H$_2$NSO$_2$), 7.02 (d, J=8.1 Hz, 1H), 4.21 (q, J=7.1 Hz, 2H, OCH$_2$CH$_3$), 3.01 (m, 2H, CH$_2$), 2.54 (s, 3H, CH$_3$), 2.16 (m, 2H, CH$_2$), 2.11 (s, 6H, N(CH$_3$)$_2$), 1.66 (m, 2H, CH$_2$), 1.29 (t, J=7.1 Hz, 3H, OCH$_2$CH$_3$).

MS-EI m/z 460 [M$^+$].

Example 134

3-[3-(3-Dimethylaminopropyl)-4-ethoxycarbonyl-5-methyl-1H-pyrrol-2-ylmethylene]-2-oxo-2,3-dihydro-1H-indole-5-carboxylic acid $^1$HNMR (300 MHz, DMSO-d$_6$) δ13.77 (s, 1H, NH), 11.25 (br s, 1H, NH), 8.24 (s, 1H), 7.85 (s, 1H, H-vinyl), 7.76 (d, 1H), 6.82 (d, 1H), 4.21 (q, J=6.9 Hz, 2H, OCH$_2$CH$_3$), 3.0 (m, 2H, CH$_2$), 2.54 (s, 3H, CH$_3$), 2.20 (m, 2H, CH$_2$), 2.14 (s, 6H, N(CH$_3$)$_2$), 1.64 (m, 2H, CH$_2$), 1.29 (t, J=6.9 Hz, 3H, OCH$_2$CH$_3$).

MS m/z 426.2 [M+H].

Example 135

4-(3-Dimethylaminoropyl)-5-[4-(2-hydroxyethyl)-2-oxo-1,2-dihydroindol-3-ylidenemethyl]-2-methyl-1H-pyrrole-3-carboxylic acid ethyl ester $^1$HNMR (300 MHz, DMSO-d$_6$) δ13.95 (s, 1H, NH), 10.97 (br s, 1H, NH), 7.69 (s, 1H, H-vinyl), 7.05 (t, J=7.7 Hz, 1H), 6.82 (d, J=7.7 Hz, 1H), 6.75 (d, J=7.7 Hz, 1H), 4.90 (br s, 1H, OH), 4.20 (q, J=7.2 Hz, 2H, OCH$_2$CH$_3$), 3.72 (m, 2H, CH$_2$), 3.09 (m, 2H, CH$_2$), 2.90 (m, 2H, CH$_2$), 2.52 (s, 3H, CH$_3$), 2.20 (m, 2H, CH$_2$), 2.07 (s, 6H, N(CH$_3$)$_2$), 1.63 (m, 2H, CH$_2$), 1.28 (t, J=7.2 Hz, 3H, OCH$_2$CH$_3$).

MS-EI m/z 425 [M$^+$].

Example 136

5-[4-(2-Hydroxyethyl)-2-oxo-1,2-dihydroindol-3-ylidenemethyl]-2-methyl-4-[3-(4-methylpiperazin-1-yl)-propyl]-1H-pyrrole-3-carboxylic acid ethyl ester $^1$HNMR (360 MHz, DMSO-d$_6$) δ14.0 (s, 1H, NH), 10.94 (br s, 1H, NH), 7.70 (s, 1H, H-vinyl), 7.06 (t, J=7.4 Hz, 1H), 6.83 (d, J=7.4 Hz, 1H), 6.76 (d, J=7.4 Hz, 1H), 4.77 (br s, 1H, OH), 4.22 (q, J=7.21 Hz, 2H, OCH$_2$CH$_3$), 3.72 (m, 2H, CH$_2$), 3.36 (m, 2H, CH$_2$), 3.13 (m, 4H, 2×CH$_2$), 2.56 (m, 2H, CH$_2$), 2.53 (s, 3H, CH$_3$), 2.09 (m, 8H, 4×CH$_2$), 1.28 (t, J=7.1 Hz, 3H, OCH$_2$CH$_3$).

Example 137

4-(3-Dimethylaminopropyl)-2-methyl-5-(5-methylsulfamoyl-2-oxo-1,2-dihydroindol-3-ylidenemethyl)-1H-pyrrole-3-carboxylic acid ethyl ester 2-Oxo-2,3-dihydro-1H-indole-5-sulfonic acid methylamide (113 mg, 0.5 mmol) was condensed with 4-(3-dimethylamino-propyl)-5-formyl-2-methyl-1H-pyrrole-3-carboxylic acid ethyl ester (133 mg) to give 96 mg (40%) of the title compound.

$^1$HNMR (360 MHz, DMSO-d$_6$) δ13.73 (s, br, 1H, NH), 11.32 (s, br, 1H, NH), 8.05 (d, J=1.8 Hz, 1H, H-4), 7.92 (s, 1H, H-vinyl), 7.57 (dd, J=1.8 & 8.1 Hz, 1H, H-6), 7.22 (m, 1H, CH$_3$NHSO$_2$), 7.05 (d, J=8.1 Hz, 1H, H-7), 4.21 (q, J=7.1 Hz, 2H, OCH$_2$CH,), 3.01 (m, 2H, CH$_2$), 2.54 (s, 3H, CH$_3$), 2.41 (d, J=4.0 Hz, 3H, CH$_3$NHSO$_2$), 2.14 (s, 8H, CH$_2$ & N(CH$_3$)$_2$), 1.66 (m, 2H, CH$_2$), 1.29 (t, J=7.1 Hz, 3H, OCH$_2$CH$_3$).

MS-EI m/z 474 [M$^+$].

Example 138

4-(3-Dimethylaminopropyl)-2-methyl-5-(5-methylsulfamoyl-2-oxo-1,2-dihydroindol-3-ylidenemethyl)-1H-pyrrole-3-carboxylic acid A mixture of 4-(3-dimethylaminopropyl)-5-formyl-2-methyl-1H-pyrrole-3-carboxylic acid ethyl ester (300 mg, 1.13 mmol) and sodium hydroxide in MeOH (4 mL)/water (2 mL) was stirred at 80° C. for 19 hr. The reaction was then diluted with EtOAc. The aqueous layer was separated, neutralized and concentrated. The residue was dissolved in MeOH, filtered and the filtrate was concentrated to give 251 mg (94%) of 4-(3-dimethylaminopropyl)-5-formyl-2-methyl-1H-pyrrole-3-carboxylic acid.

$^1$HNMR (300 MHz, DMSO-d$_6$) δ11.88 (br s, 1H, NH), 9.50 (s, 1H, CHO), 2.96 (m, 2H, CH$_2$), 2.39 (s, 3H, CH$_3$), 2.22 (m, 2H, CH$_2$), 2.14 (s, 6H, N(CH$_3$)$_2$), 1.68 (m, 2H, CH$_2$CH$_2$ CH$_2$).

MS-EI m/z 238 [M$^+$].

2-Oxo-2,3-dihydro-1H-indole-5-sulfonic acid methylamide (113 mg) was condensed with 4-(3-dimethylaminopropyl)-5-formyl-2-methyl-1,7-pyrrole-3-carboxylic acid (119 mg) to give 50 mg 4-(3-dimethylaminopropyl)-2-methyl-5-(5-methylsulfamoyl-2-oxo-1,2-dihydro-indol-3-ylidenemethyl)-1H-pyrrole-3-carboxylic acid.

$^1$HNMR (360 MHz, DMSO-d$_6$) δ13.52 (s, br, 1H, NH), 11.25 (s, br, 1H, COOH), 8.01 (d, J=1.7 Hz, 1H, H-4), 7.84 (s, 1H, H-vinyl), 7.52 (dd, J=1.7 & 8.3 Hz, 1H, H-6), 7.22 (m, 1H, CH$_3$NHSO$_2$), 7.05 (d, J=8.3 Hz, 1H, H-7), 3.08 (m, 2H, CH$_2$), 2.56 (s, 3H, CH$_3$), 2.40 (m, 3H, CH$_3$NHSO$_2$), 2.17 (m, 8H, CH$_2$ & N(CH$_3$)$_2$), 1.72 (m, 2H, CH$_2$).

MS-EI m/z 446 [M$^+$].

Example 139

4-(2-Carboxyethyl)-3-methyl-5-(4-methyl-2-oxo-1,2-dihydroindol-3-ylidenemethyl)-1H-pyrrole-2-carboxylic acid ethyl ester $^1$HNMR (300 MHz, DMSO-d$_6$) δ13.97 (s, br, 1H, NH), 12.15 br s, 1H, COOH ), 11.03 (s, 1H, NH), 7.69 (s, 1H, H-vinyl), 7.10 (t, J=7.5 Hz, 1H), 6.83 (d, J=7.5 Hz, 1H), 6.76 (d, J=7.5 Hz, 1H), 4.28 (q, J=7.0 Hz, 2H, OCH$_2$CH$_3$), 2.88 (t, 2H, CH$_2$), 2.62 (s, 3H, CH$_3$), 2.43 (t, 2H, CH$_2$) 2.26 (s, 3H, CH$_3$), 1.31 (t, J=7.0 Hz, 3H, OCH$_2$CH$_3$).

MS-EI m/z 382 [M$^+$].

Example 140

4-(2-Carboxyethyl)-5-(5-methoxy-2-oxo-1,2-dihydroindol-3-ylidenemethyl)-3-methyl-1H-pyrrole-2-carboxylic acid ethyl ester $^1$HNMR (300 MHz, DMSO-d$_6$) δ13.97 (s, br, 1H, NH), 12.14 (br s, 1H, COOH ), 10.81 (s, 1H, NH), 7.71 (s, 1H, H-vinyl), 7.46 (m, 1H), 6.78 (m, 2H), 4.28 (q, J=7.0 Hz, 2H, OCH$_2$CH$_3$), 3.76 (s, 3H, OCH$_3$), 2.97 (t, 2H, CH$_2$), 2.40 (t, 2H, CH$_2$), 2.26 (s, 3H, CH$_3$), 1.31 (t, J=7.0 Hz, 3H, OCH$_2$CH$_3$).

MS-EI mn/z 398 [M$^+$].

Example 141

4-(2-Carboxyethyl)-5-(6-methoxy-2-oxo-1,2-dihydroindol-3-ylidenemethyl)-3-methyl-1H-pyrrole-2-carboxylic acid ethyl ester $^1$HNMR (300 MHz, DMSO-d$_6$) δ13.70 (s, br, 1H, NH), 12.11 br s, 1H, COOH ), 10.95 (s, 1H, NH), 7.0 (d, J=8.4 Hz, 1H, H-4), 7.55 (s, 1H, H-vinyl), 6.59 (dd, J=2.7 & 8.4 Hz, 1H, H-5), 6.45 (d, J=2.7 Hz, 1H, H-7), 4.27 (q, J=7.0 Hz, 2H, OCH$_2$CH$_3$), 3.76 (s, 3H, OCH$_3$), 2.92 (t, 2H, CH$_2$), 2.39 (t, 2H, CH$_2$), 2.25 (s, 3H, CH$_3$), 1.31 (t, J=7.0 Hz, 3H, OCH$_2$CH$_3$).

MS-EI m/z 398 [M$^+$].

Example 142

5-(6-Bromo-2-oxo-1,2-dihydroindol-3-ylidenemethyl)-4-(2-carboxy-ethyl)-3-methyl-1H-pyrrole-2-carboxylic acid ethyl ester $^1$HNMR (300 MHz, DMSO-d$_6$) δ13.77 (s, br, 1H, NH), 12.13 br s, 1H, COOH ), 11.14 (s, 1H, NH), 7.77 (br s, 2H), 0.12 (m, 2H), 4.28 (m, 2H, OCH$_2$CH$_3$), 2.95 (m, 2H, CH$_2$), 2.40 (m, 2H, CH$_2$), 2.26 (s, 3H, CH$_3$), 1.29 (m, 3H, OCH$_2$CH$_3$).

MS-EI m/z 446 & 448 [M−1 & M+1].

Example 143

5-(5-Bromo-2-oxo-1,2-dihydroindol-3-ylidenemethyl)-4-(2-carboxy-ethyl)-3-methyl-1H-pyrrole-2-carboxylic acid ethyl ester $^1$HNMR (300 MHz, DMSO-d$_6$) δ13.86 (s, br, 1H, NH), 12.2 (br s, 1H, COOH), 11.12 (s, 1H, NH), 8.11 (d, J=2.0 Hz, 1H, H-4), 7.83 (s, 1H, H-vinyl), 7.33 (dd, J=2.0 & 8.3 Hz, 1H, H-6), 6.83 (d, J=8.3 Hz, 1H, H-7), 4.28 (q, J=7.0 Hz, 2H, OCH$_2$CH$_3$), 2.98 (t, 2H, CH$_2$), 2.39 (m, 2H, CH$_2$), 2.25 (s, 3H, CH$_3$), 1.31 (t, J=7.0 Hz, 3H, OCH$_2$CH$_3$).

MS-EI m/z 446 & 448 [M−1 & M+1].

Example 144

4-(2-Carboxyethyl)-3-methyl-5-(2-oxo-6-phenyl-1,2-dihydroindol-3-ylidenemethyl) 1H-pyrrole-2-carboxylic acid ethyl ester $^1$HNMR (300 MHz, DMSO-d$_6$) δ13.86 (s, br, 1H, NH), 12.2 (br s, 1H, COOH ), 11.11 (s, 1H, NH), 7.89 (d, J=7.7 Hz, 1H), 7.77 (s, 1H, H-vinyl), 7.65 (m, 2H), 7.46 (t, 2H) 7.32–7.39 (m, 2H), 7.12 (d, J=1.6 Hz, 1H), 4.29 (q, J=7.0 Hz, 2H, OCH$_2$CH$_3$), 2.97 (m, 2H, CH$_2$), 2.42 (m, 2H, CH$_2$) 2.27 (s, 3H, CH$_3$), 1.31 (t, J=7.0 Hz, 3H, OCH$_2$CH$_3$).

MS-EI m/z 444 [M$^+$].

Example 145

4-(2-Carboxyethyl)-3-methyl-5-(2-oxo-5-sulfamoyl-1,2-dihydro-indol-3-ylidenemethyl)-1H-pyrrole-2-carboxylic acid ethyl ester $^1$HNMR (300 MHz, DMSO-d$_6$) δ13.84 (s, br, 1H, NH), 11.0 (br s, 2H), 8.26 (d, J=1.6 Hz, 1H, H-4), 7.88 (s, 1H, H-vinyl), 7.67 (dd, J=1.6 & 8.4 Hz, 1H, H-6), 7.22 (br m, 2H, H$_2$NSO$_2$), 7.03 (d, J=8.4 Hz, 1H, H-7), 4.29 (q, J=7.1 Hz, 2H, OCH$_2$CH$_3$), 2.97 (t, 2H, CH$_2$), 2.37 (m, 2H, CH$_2$), 2.26 (s, 3H, CH$_3$), 1.31 (t, J=7.1 Hz, 3H, OCH$_2$CH$_3$).

MS-EI m/z 447 [M$^+$].

Example 146

4-(2-Carboxyethyl)-3-methyl-5-(5-methylsulfamoyl-2-oxo-1,2-dihydroindol-3-ylidenemethyl)-1H-pyrrole-2-carboxylic acid ethyl ester $^1$HNMR (300 MHz, DMSO-d$_6$) δ13.89 (s, br, 1H, NH), 12.2 (br s, 1H, COOH), 11.43 (s, 1H, NH), 8.25 (d, J=1.8 Hz, 1H, H-4), 7.94 (s, 1H, H-vinyl), 7.62 (dd, J=1.8 & 8.4 Hz, 1H, H-6), 7.27 (m, 1H, HNSO$_2$), 7.07 (d, J=8.4 Hz, 1H, H-7), 4.29 (q, J=7.1 Hz, 2H, OCH$_2$CH$_3$), 3.01 (t, 2H, CH$_2$), 2.45 (m, 2H, CH$_2$), 2.42 (d, J=5.3 Hz, 3H, NCH$_3$), 2.27 (s, 3H, CH$_3$), 1.32 (t, J=7.1 Hz, 3H, OCH$_2$CH$_3$).

MS-EI m/z 461 [M$^+$].

Example 147

4-(2-Carboxyethyl)-5-(5-dimethylsulfamoyl-2-oxo-1,2-dihydro-indol-3-ylidenemethyl)-3-methyl -1H-pyrrole-2-carboxylic acid ethyl ester $^1$HNMR (300 MHz, DMSO-d$_6$) δ13.88 (s, br, 1H, NH), 12.14 (br s, 1H, COOH), 11.47 (s, 1H, NH), 8.26 (d, J=1.8 Hz, 1H, H-4), 8.0 (s, 1H, H-vinyl), 7.58 (dd, J=1.8 & 7.9 Hz, 1H, H-6), 7.10 (d, J=7.9 Hz, 1H, H-7), 4.29 (q, J=7.2 Hz, 2H, OCH$_2$CH$_3$), 3.03 (t, 2H, CH$_2$), 2.61 (s, 6H, N(CH$_3$)$_2$), 2.42 (t, 2H, CH$_2$), 2.26 (s, 3H, CH$_3$), 1.32 (t, J=7.2 Hz, 3H, OCH$_2$CH$_3$).

MS-EI m/z 489 [M$^+$].

Example 148

4-(2-Carboxyethyl)-5-(5-isopropylsulfamoyl-2-oxo-1,2-dihydro-indol-3-ylidenemethyl)-3-methyl-1H-pyrrole-2-carboxylic acid ethyl ester $^1$HNMR (300 MHz, DMSO-d$_6$) δ13.84 (s, br, 1H, NH), 11.0 (br s, 2H, COOH & NH), 8.23 (d, J=1.5 Hz, 1H, H-4), 7.92 (s, 1H, H-vinyl), 7.64 (dd, J=1.5 & 8.4 Hz, 1H, H-6) 7.43 (br m, 1H, HNC(CH$_3$)$_2$), 7.05 (d, J=8.4 Hz, 1H, H-7), 4.29 (q, J=7.1 Hz, 2H, OCH$_2$CH$_3$), 2.96 (t, 2H, CH$_2$), 2.34 (t, 2H, CH$_2$), 2.25 (s, 3H, CH$_3$), 1.31 (t, J=7.1 Hz, 3H, OCH$_2$CH$_3$), 0.95 (d, J=6.6 Hz, 6H, HNC(CH$_3$)$_2$).

MS-EI m/z 489 [M$^+$].

Example 149

3-[3-(3-Dimethylaminopropyl)-1H-indol-2-ylmethylene]-2-oxo-2,3-dihydro-1H-indole-5-sulfonic acid methylamide 2-Oxo-2,3-dihydro-1H-indole-5-sulfonic acid methylamide (98 mg, 0.43 mmol) was condensed with 3-(3- dimethylaminopropyl)-1H-indole-2-carbaldehyde (100 mg) to give the title compound as an orange solid.

$^1$HNMR (300 MHz, DMSO-d$_6$) δ12.90 (s, 1H, NH), 11.40 (br s, 1H, NH), 8.17 (d, J=1.5 Hz, 1H), 8.15 (s, 1H, H-vinyl), 7.68 (d, J=8.4 Hz, 1H), 7.63 (dd, J=1.5 & 8.4 Hz, 1H), 7.54 (d, J=8.7 Hz, 1H), 7.30 (m, 2H), 7.08 (m, 2H), 3.15 (t, J=6.6 Hz, 2H, CH$_2$), 2.43 (d, J=4.2 Hz, 3H, NCH$_3$), 2.17 (t, J=6.6 Hz, 2H, CH$_2$), 2.14 (s, 6H, N(CH$_3$)$_2$), 1.78 (m, 2H, CH$_2$).

MS-EI m/z 438 [M$^+$].

Example 150

3-[3-(3-Dimethylaminopropyl)-1H-indol-2-ylmethylene]-4-(2-hydroxyethyl)-1,3-dihydroindol-2-one $^1$HNMR (300 MHz, DMSO-d$_6$) δ13.12 (s, 1H, NH), 11.01 (br s, 1H, NH), 7.95 (s, 1H, H-vinyl), 7.66 (d, J=7.9 Hz, 1H), 7.52 (d, J=7.9 Hz, 1H), 7.26 (t, J=7.54 Hz, 1H), 7.11 (t, J=7.9 Hz, 1H), 7.06 (t, J=7.4 Hz, 1H), 6.87 (d, J=7.4 Hz, 1H), 6.78 (d, J=7.4 Hz, 1H), 4.91 (br s, 1H, OH), 3.79 (m, 2H, CH$_2$), 3.16 (m, 2H, CH$_2$), 3.04 (m, 2H, CH$_2$), 2.21 (m, 2H, CH$_2$), 2.09 (s, 6H, N(CH$_3$)$_2$), 1.77 (m, 2H, CH$_2$).

MS m/z 389 [M$^+$].

Example 151

3-[3-(3-Dimethylaminopropyl)-1H-indol-2-ylmethylene]-5-methoxy-1,3-dihydroindol-2-one $^1$HNMR (300 MHz, DMSO-d$_6$) δ13.11 (s, 1H, NH), 10.84 (br s, 1H, NH), 7.92 (s, 1H, H-vinyl), 7.65 (d, J=8.1 Hz, 1H), 7.50 (d, J=8.1 Hz, 1H), 7.44 (s, 1H), 7.26 (t, J=7.5 Hz, 1H), 7.05 (t, J=7.5 Hz, 1H), 6.79 (s, 2H), 3.79 (s, 3H, OCH$_3$), 3.11 (m, 2H, CH$_2$), 2.20 (m, 2H, CH$_2$), 2.12 (s, 6H, N(CH$_3$)$_2$), 1.76 (m, 2H, CH$_2$).

MS m/z 375 [M$^+$].

Example 152

5-Methyl-3-(3-methyl-1H-indol-2-ylmethylene)-1,3-dihydro-indol-2-one

3-Methylindole-2-carbaldehyde was prepared as described in the literature: 1) David W. M. Benzies, Pilar Matinez Fresneda and R. Alan Jones, *Synthetic Communications*, 16 (14), 1799–1807 (1986) and 2) Chatterjee, A. and Biswas, K. M., *J. Org. Chem.*, 1973, 38, 4002.

A mixture of 5-methyl-2-oxindole (59 mg), 3-methylindole-2-carbaldehyde (56 mg) and piperidine (30 mg) in ethanol (1 mL) was held in a sealed tube at 90° C. overnight. The mixture was cooled to room temperature. The solid was collected by vacuum filtration, washed with cold ethanol and dried in a vacuum oven to give 72 mg (74%) of 5-methyl-3-(3-methyl-1H-indol-2-ylmethylene)-1,3-dihydroindol-2-one.

$^1$H NMR (360 MHz, DMSO-d6) 13.03 (s, br, 1H, NH), 10.88 (s, br, 1H, N), 7.84 (s, 1H, vinyl), 7.71 (s, br, 1H) 6.62 (d, J=8 Hz, 1H), 7.48 (d, J=8 Hz, 1H), 7.26 (t, J=7 Hz, 1H), 7.06 (t, J=7 Hz, 1H), 7.0 (d, J=8 Hz, 1H), 6.78 (d, J=8 Hz, 1H), 2.59 (s, 3H, CH$_3$), 2.32 (s, 3H, CH$_3$).

MS m/z 289 [M+1]$^+$.

Example 153

3-(3-Methyl-1H-indol-2-ylmethylene)-2-oxo-2,3-dihydro-1H-indole-5-sulfonic acid amide A mixture of 5-aminosulfonyl-2-oxindole (84 mg), 3-methylindole-2-carbaldehyde (56 mg) (prepared according to *Synthetic Communications*, 1986, 16, 1799) and piperidine (30 mg) in ethanol (1 mL) was held in a sealed tube at 90° C. overnight. The mixture was cooled to room temperature. The solid was collected by vacuum filtration, washed with cold ethanol and dried in a vacuum oven to give 88 mg (71% yield) of 3-(3-methyl-1H-indol-2-ylmethylene)-2-oxo-2,3-dihydro-1H-indole-5-sulfonic acid amide.

$^1$H NMR (360 MHz, DMSO-d6) 12.86 (s, br, 1H, NH), 11.3 (s, br, 1H, NH), 8.3 (d, J=2 Hz, 1H), 7.97 (s, 1H, vinyl) 7.63 (dd, J=2 and 8 Hz, 1H), 7.6 (d, J=8 Hz, 1H), 7.47 (d, J=8 Hz, 1H), 7.24 (t, J=7.5 Hz, 1H), 7.12 (s, br, 2H, NH$_2$), 7.02 (t, J=7.5 Hz, 1H), 6.98 (d, J=8 Hz, 1H), 2.57 (s, 3H, CH$_3$).

MS m/z 354.1 [M+1]$^+$.

Example 154

3-(3-Methyl-1H-indol-2-ylmethylene)-2-oxo-2,3-dihydro-1H-indole-5-sulfonic acid methylamide A suspension of 5-chlorosulfonyl-2-oxindole (3.38 g) in 2M methylamine in tetrahydrofuran (10 mL) was stirred at room temperature for 4 hours at which time a white solid had formed. The solid was collected by vacuum filtration, washed twice with 5 mL of water and dried under vacuum at 40° C. to give 3.0 g (88% yield) of 5-methylaminosulfonyl-2-oxindole.

$^1$H NMR (300 MHz, DMSO-d6) δ10.87 (s, br, 1H, NH-1), 7.86 (s, br, 1H, 5-SO$_2$NHCH$_3$),7.61 (d, J=8 Hz 1H, H-6), 7.32 (d, J=5 Hz, 1H, H-4), 6.97 (d, J=8 Hz, 1H, H-7), 2.53 (s, 2H, CH$_2$-3), and 2.36 (s, 3H, 5-SO$_2$NHCH$_3$).

MS m/z 226.

A mixture of 5-methylaminosulfonyl-2-oxindole (90 mg), 3-methylindole-2-carbaldehyde (56 mg) (prepared according to *Synthetic Communications*, 1986, 16, 1799) and piperidine (30 mg) in ethanol (1 mL) was held in a sealed tube at 90° C. overnight. The mixture was cooled to room temperature. The solid was collected by vacuum filtration, washed with cold ethanol and dried in a vacuum oven to give 90 mg (70% yield) of 3-(3-methyl-1H-indol-2-ylmethylene)-2-oxo-2,3-dihydro-1H-indole-5-sulfonic acid methylamide (mixture of isomers).

$^1$H NMR (360 MHz, DMSO-d6) 11.13 (s, br, 1H, NH), 10.94 (s, br, 1H, NH), 8.84 (d, J=16 Hz, 1H), 7.98 (s, 1H), 6.97–7.66 (m, 6H, Ar—H), 2.6 (s, 3H, CH$_3$), 2.4 (d, J=5 Hz, 3H, CH$_3$N.

Example 155

3-(3-Methyl-1H-indol-2-ylmethylene)-2-oxo-2,3-dihydro-1H-indole-5-sulfonic acid dimethylamide A mixture of 5-dimethylaminosulfonyl-2-oxindole (96 mg), 3-methylindole-2-carbaldehyde (56 mg) (prepared according to *Synthetic Communications*, 1986, 16, 1799) and piperidine (30 mg) in ethanol (1 mL) was held in a sealed tube at 90° C. overnight. The mixture was cooled to room temperature. The solid was collected by vacuum filtration, washed with cold ethanol and dried in a vacuum oven to give 76 mg (57% yield) of 3-(3-methyl-1H-indol-2-ylmethylene)-2-oxo-2,3-dihydro-1H-indole-5-sulfonic acid dimethylamide (mixture of isomers).

$^1$H NMR (360 MHz, DMSO-d6) 11.09 (s, br, 1H, NH), 10.95 (s, br, 1H, NH), 8.78 (d, J=16 Hz, 1H), 7.8 (s, 1H, vinyl), 7.45–7.54 (m, 2H), 7.32 (d, J=8 Hz, 1H), 7.1 (t, 1H), 6.98 (d, J=8 Hz, 1H), 6.93 (t, 1H), 2.56 (s, 6H, 2×CH$_3$), 2.39 (s, 3H, CH$_3$).

Example 156

3-(3-Methyl-1H-indol-2-ylmethylene)-2-oxo-2,3-dihydro-1H-indole-5-carboxylic acid (piperidine salt)

A mixture of 5-carboxy-2-oxindole (113 mg), 3-methylindole-2-carbaldehyde (56 mg) (prepared according to *Synthetic Communications*, 1986, 16, 1799) and piperidine (30 mg) in ethanol (1 mL) was held in a sealed tube at 90° C. overnight. The mixture was cooled to room temperature. The solid was collected by vacuum filtration, washed with cold ethanol and dried in a vacuum oven to give 75 mg (58% yield) of 3-(3-methyl-1H-indol-2-ylmethylene)-2-oxo-2,3-dihydro-1H-indole-5-carboxylic acid (piperidine salt).

$^1$H NMR (360 MHz, DMSO-d6) 13.0 (s, br, 1H, NH), 8.35 (d, J=1.5 Hz, 1H, H-4), 7.91 (s, 1H, vinyl), 7.82 (dd, J=1.5 and 8 Hz, 1H, H-6), 7.63 (d, J=8 Hz, 1H), 7.49 (d, J=8 Hz, 1H), 7.26 (t, J=7.5 Hz, 1H), 7.06 (t, J=7.5 Hz, 1H), 6.87 (d, J=8 Hz, 1H), 2.91 (t, 4H, piperidine), 2.6 (s, 3H, CH$_3$), 1.6 (m, 4H, piperidine), 1.54 (m, 2H, piperidine).

Example 157

5-Acetyl-3-(3-methyl-1H-indol-2-ylmethylene)-1,3-dihydroindol-2-one

2-Oxindole (3 g) was suspended in 1,2-dichloroethane and 3.2 mL of acetyl chloride slowly added. The resulting suspension was stirred at 50° C. for 5 hours, cooled, and poured into water. The resulting precipitate was collected by vacuum filtration, washed copiously with water and dried under vacuum to give 2.9 g (73% yield) of 5-acetyl-2-oxindole as a brown solid.

$^1$H NMR (360 MHz, DMSO-d6) δ10.75 (s, br, NH), 7.83 (d, J=8 Hz, 1H), 7.78 (s, 1H, H-4), 6.88 (d, J=8 Hz, 1H), 3.53 (s, 2H, CH$_2$), 2.49 (s, 3H, CH$_3$).

A mixture of 5-acetyl-2-oxindole (70 mg), 3-methylindole-2-carbaldehyde (56 mg) (prepared according to *Synthetic Communications*, 1986, 16, 1799) and piperidine (30 mg) in ethanol (1 mL) was held in a sealed tube at 90° C. overnight. The mixture was cooled to room temperature. The solid was collected by vacuum filtration, washed with cold ethanol and dried in a vacuum to give 83 mg (75% yield) of 5-acetyl-3-(3-methyl-1H-indol-2-ylmethylene)-1,3-dihydro-indol-2-one.

$^1$H NMR (360 MHz, DMSO-d6) 12.86 (s, br, 1H, NH), 11.29 (s, br, 1H, NH), 8.43 (d, J=1.5 Hz, 1H, H-4), 8.01 (s, 1H, vinyl), 7.78 (dd, J=1.5 and 8 Hz, 1H, H-6), 7.58 (d, J=8 Hz, 1H), 7.45 (d, J=8 Hz, 1H), 7.23 (t, 1H), 7.01 (t, 1H), 6.92 (d, J=8 Hz, 1H), 2.58 (s, 3H, CH$_3$), 2.54 (s, 3H, CH$_3$).

MS m/z 317.2 [M+1]$^+$.

Example 158

5-Acetyl-3-(1H-indol-2-ylmethylene)-1,3-dihydro-indol-2-one

Indole-2-carbaldehyde was prepared as described in the literature: Michel Barbier, Michel Devys, Christiane Tempête, Albert Kollmann and Jean-François Bousquet, *Synthetic Communications*, 23(22), 3109–3117 (1993).

A mixture of 5-acetyl-2-oxindole (88 mg), indole-2-carbaldehyde (87 mg) and piperidine (4 mg) in ethanol (2 mL) was held in a sealed tube at 90° C. for 3 hours. The mixture was cooled to room temperature. The solid which formed was collected by vacuum filtration, washed with cold ethanol and dried in a vacuum oven to give 133 mg (88% yield) of 5-acetyl-3-(1H-indol-2-ylmethylene)-1,3-dihydro-indol-2-one as an orange solid.

$^1$H NMR (360 MHz, DMSO-d6) 12.81 (s, br, 1H, NH), 11.38 (s, br, 1H, NH), 8.38 (d, J=1 Hz, H-4), 8.17 (s, 1H, vinyl), 7.88 (dd, J=1 and 8 Hz, 1H, H-6), 7.69 (d, J=8 Hz, 1H), 7.58 (d, J=8 Hz, 1H), 7.29 (t, 1H), 7.21 (s, 1H), 7.09 (t, 1H), 7.0 (d, J=8 Hz, 1H), 2.59 (s, 3H, CH$_3$).

MS m/z 303.1 [M+1]$^+$.

Example 159

3-(1H-Indol-2-ylmethylene)-2-oxo-2,3-dihydro-1H-indole-5-sulfonic acid amide

A mixture of 5-aminosulfonyl-2-oxindole (106 mg), indole-2-carbaldehyde (87 mg) (prepared according to *Synthetic Communications*, 1993, 23, 3109) and piperidine (4 mg) in ethanol (2 mL) was held in a sealed tube at 90° C. for 3 hours. The mixture was cooled to room temperature. The solid was collected by vacuum filtration, washed with cold ethanol and dried in a vacuum oven to give 140 mg (83% yield) of 3-(1H-indol-2-ylmethylene)-2-oxo-2,3-dihydro-1H-indole-5-sulfonic acid amide as an orange solid.

$^1$H NMR (360 MHz, DMSO-d6) 12.81 (s, br, 1H, NH), 11.38 (s, br, 1H, NH), 8.18 (d, J=1 Hz, H-4), 8.12 (s, 1H, vinyl), 7.7 (m, 2H), 7.6 (d, J=8 Hz, 1H), 7.26–7.29 (m, 2H), 7.2 (s, 2H, NH$_2$), 7.05–7.11 (m, 2H).

MS m/z 340 [M+1]$^+$.

Example 160

5-Amino-3-(1H-indol-2-ylmethylene)-1,3-dihydro-indol-2-one

A mixture of 5-tert-butoxycarbonylamino-2-oxindole (124 mg), indole-2-carbaldehyde (87 mg) (prepared according to *Synthetic Communications*, 1993, 23, 3109) and piperidine (4 mg) in ethanol (2 mL was held in a sealed tube at 90° C. for 3 hours. The mixture was cooled to room temperature. The solid was collected by vacuum filtration, washed with cold ethanol and dried in a vacuum overn to give 196 mg of 5-tert-butoxycarbonylamino-3-(1H-indol-2-ylmethylene)-1,3-dihydro-indol-2-one as a bright orange solid. The product was then dissolved in trifluoroacetic acid/dichloromethane (2 mL each) and stirred at room temperature for 1 hour. The reaction mixture was then concentrated. The residue was dissolved in water and basified with saturated sodium bicarbonate solution. The solid was collected by vacuum filtration, washed with water and dried in a vacuum oven to give 129 mg of 5-amino-3-(1H-indol-2-ylmethylene)-1,3-dihydroindol-2-one as a brown solid.

$^1$H NMR (360 MHz, DMSO-d6) 13.1 (s, br, 1H, NH), 10.57 (s, br, 1H, NH), 7.65 (s, 1H, vinyl), 7.64 (d, J=8 Hz, 1H), 7.54 (d, J=8 Hz, 1H), 7.24 (t, 1H), 7.1 (s, 1H), 7.06 (t, 1H), 6.93 (d, J=2 Hz, 1H), 6.61 (d, J=8 Hz, 1H), 6.5 (dd, J=2 and 8 Hz, 1H), 4.8 (s, br, 2H, NH$_2$).

MS m/z 276.1 [M+1]$^+$.

Example 161

3-(1H-Indol-2-ylmethylene)-2-oxo-2,3-dihydro-1H-indole-5-carboxylic acid

A mixture of 5-carboxy-2-oxindole (88.5 mg), indole-2-carbaldehyde (87 mg) (prepared according to *Synthetic Communications*, 1993, 23, 3109) and piperidine (1 drop) in ethanol (3 mL) was held in a sealed tube at 95° C. for 4 hours. The mixture was cooled to room temperature. The solid was filtered and acidified with 2N hydrochloric acid. The resulting solid was collected by vacuum filtration, washed with cold ethanol and dried in vacuum oven to give 60 mg (40% yield) of 3-(1H-indol-2-ylmethylene)-2-oxo-2,3-dihydro-1H-indole-5-carboxylic acid as a mustard-colored solid.

$^1$H NMR (360 MHz, DMSO-d6) 12.8 (s, br, 1H, NH), 12.69 (s, 1H, COOH), 11.35 (s, br, 1H, NH), 8.33 (s, 1H), 8.16 (s, 1H), 7.86 (dd, J=1 and 8 Hz, 1H), 7.68 (d, J=8 Hz, 1H), 7.59 (d, J=8 Hz, 1H), 7.28 (t, 1H), 7.21 (s, 1H) 7.08 (t, 1H), 6.99 (d, J=8 Hz, 1H).

MS m/z 304 [M]$^+$.

Example 162

6-Chloro-3-(1H-indol-2-ylmethlene)-1,3-dihydro-indol-2-one

A mixture of 6-chloro-2-oxindole (41 mg) (commercially available), indole-2-carbaldehyde (42 mg) (prepared according to *Synthetic Communications,* 1993, 23, 3109) and piperidine (1 drop) in ethanol (3 mL) was held in a sealed tube at 95° C. for 3 hours. The mixture was cooled to room temperature. The solid was collected by vacuum filtration, washed with cold ethanol and dried in vacuum oven to give 62 mg (87% yield) of 6-chloro-3-(1H-indol-2-ylmethylene)-1,3-dihydroindol-2-one as a shiny orange solid.

$^1$H NMR (360 MHz, DMSO-d6) 12.83 (s, br, 1H, NH), 11.17 (s, br, 1H, NH), 7.98 (s, 1H), 7.74 (d, J=8 Hz, 1H), 7.67 (d, J=8 Hz, 1H), 7.58 (d, J=8 Hz, 1H), 7.28 (m, 1H), 7.15 (s, br, 1H), 7.08 (m, 2H), 6.91 (d, J=2 Hz, 1H).

MS m/z 293 and 295.

Example 163

3-(1H-Indol-2-ylmethylene)-1,3-dihydro-indol-2-one

A mixture of 2-oxindole (133 mg), indole-2-carbaldehyde (174 mg) (prepared according to *Synthetic Communications,* 1993, 23, 3109) and piperidine (10 mg) in ethanol was held in a sealed tube at 95° C. for 4 hours. The mixture was cooled to room temperature. The solid was collected by vacuum filtration, washed with cold ethanol and dried in a vacuum oven to give 3-(1H-indol-2-ylmethylene)-1,3-dihydro-indol-2-one.

$^1$H NMR (360 MHz, DMSO-d6) δ12.97 (s, br, 1H, NH), 11.01 (s, br, H, NH) 7.92 (s, 1H, H-vinyl), 7.72 (d, J=7 Hz, 1H), 7.66 (d, J=7 Hz, 1H), 7.57 (dd, J=1, 8 Hz, 1H), 7.27 (dt, J=1, 7 Hz, 1H), 7.21 (dt, J=1, 8 Hz, 1H), 7.13 (s, 1H), 7.01–7.1 (m, 2H), 6.91 (d, J=8 Hz, 1H).

MS El 260.

Example 164

5-Chloro-3-(1H-indol-2-ylmethylene)-1,3-dihydro-indol-2-one

A mixture of 5-chloro-2-oxindole (167 mg), indole-2-carbaldehyde (174 mg) (prepared according to *Synthetic Communications,* 1993, 23, 3109) and piperidine (10 mg) in ethanol was held in a sealed tube at 95° C. for 4 hours. The mixture was cooled to room temperature. The solid was collected by vacuum filtration, washed with cold ethanol and dried in a vacuum oven to give 5-chloro-3-(1H-indol-2-ylmethylene)-1,3-dihydroindol-2-one.

$^1$H NMR (360 MHz, DMSO-d6) δ12.88 (s, br, 1H, NH), 11.12 (s, br, 1H, NH), 8.07 (s, 1H, H-vinyl), 7.86 (d, J=2 Hz, 1H), 7.68 (d, J=8 Hz, 1H), 7.59 (dd, J=1, 8 Hz, 1H), 7.28 (m, 1H), 7.24 (dd, J=2, 8 Hz, 1H), 7.14 (s, 1H), 7.09 (dt, J=1, 8 Hz, 1H), 6.90 (d, J=8 Hz, 1H).

MS El 294 and 296.

Example 165

5-Bromo-3-(1H-indol-2-ylmethylene)-1,3-dihydro-indol-2-one

A mixture of 5-bromo-2-oxindole (212 mg), indole-2-carbaldehyde (174 mg) (prepared according to *Synthetic Communications,* 1993, 23, 3109) and piperidine (10 mg) in ethanol was held in a sealed tube at 95° C. for 4 hours. The mixture was cooled to room temperature. The solid was collected by vacuum filtration, washed with cold ethanol and dried in a vacuum oven to give 5-bromo-3-(1H-indol-2-ylmethylene)-1,3-dihydroindol-2-one.

$^1$HNMR (360 MHz, DMSO-d6) δ12.87 (s, br, 1H, NH), 11.12 (s, br, 1H, NH), 8.07 (s, 1H, H-vinyl), 7.98 (d, J=2 Hz, 1H), 7.68 (d, J=8 Hz, 1H), 7.59 (d, J=8 Hz, 7H), 7.36 (dd, J=2, 8 Hz, 1H), 7.28 (dt, J=1, 8 Hz, 1H), 7.14 (s, 1H), 7.08 (dt, J=1, 8 Hz, 1H), 6.86 (d, J=8 Hz, 1H).

MS El 338 and 340.

Example 166

3-(1H-indol-2-ylmethylene)-4-methyl-1,3-dihydro-indol-2-one

A mixture of 4-methyl-2-oxindole (147 mg), indole-2-carbaldehyde (174 mg) (prepared according to *Synthetic Communications,* 1993, 23, 3109) and piperidine (10 mg) in ethanol was held in a sealed tube at 95° C. for 4 hours. The mixture was cooled to room temperature. The solid was collected by vacuum filtration, washed with cold ethanol and dried in a vacuum oven to give 3-(1H-indol-2-ylmethylene)-4-methyl-1,3-dihydroindol-2-one.

$^1$H NMR (360 MHz, DMSO-d6) δ13.12 (s, br, 1H, NH), 11.02 (s, br, 1H, NH), 7.79 (s, 1H, H-vinyl), 7.64 (d, J=8 Hz, 1H), 7.57 (d, J=8 Hz, 1H), 7.27 (d, J=7 Hz, 1H), 7.23 (s, 1H), 7.05–7.14 (m, 2H), 6.84 (d, J=8 Hz, 1H), 6.78 (d, J=8 Hz, 1H), 2.61 (s, 3H, CH$_3$).

MS El 274.

Example 167

3-(3-Methyl-1H-indol-2-ylmethylene)-1,3-dihydro-indol-2-one

A mixture of 2-oxindole (133 mg), 3-methylindole-2-carbaldehyde (190 mg) (prepared according to *Synthetic Communications,* 1986, 16, 1799) and piperidine (10 mg) in ethanol was held in a sealed tube at 95° C. for 4 hours. The mixture was cooled to room temperature. The solid was collected by vacuum filtration, washed with cold ethanol and dried in a vacuum oven to give 3-(3-methyl-1H-indol-2-ylmethylene)-1,3-dihydroindole-2-one.

$^1$H NMR (360 MHz, DMSO-d6) δ13.01 (s, br, 1H, NH), 10.99 (s, br, 1H, NH), 7.89 (s, 1H, H-vinyl), 7.88 (d, J=7 Hz, 1H), 7.63 (d, J=8 Hz, 1H), 7.49 (d, J=8 Hz, 1H), 7.27 (dt, J=1, 8 Hz, 1H), 7.2 (dt, J=1, 8 Hz, 1H), 7.01–7.08 (m, 2H), 6.9 (d, J=8 Hz, 1H), 2.59 (s, 3H, CH$_3$).

MS El 274.

Example 168

5-Chloro-3-(3-methyl-1H-indol-2-ylmethylene)-1,3-dihydro-indol-2-one

A mixture of 5-chloro-2-oxindole (167 mg), 3-methylindole-2-carbaldehyde (190 mg) (prepared according to *Synthetic Communications,* 1986, 16, 1799) and piperidine (10 mg) in ethanol was held in a sealed tube at 95° C. for 4 hours. The mixture was cooled to room temperature. The solid was collected by vacuum filtration, washed with cold ethanol and dried in a vacuum oven to give 5-chloro-3-(3-methyl-1H-indol-2-ylmethylene)-1,3-dihydroindol-2-one.

$^1$H NMR (360 MHz, DMSO-d6) δ12.96 (s, br, 1H, NH), 11.09 (s, br, 1H, NH), 8.09 (d, J=2 Hz, 1H), 8.02 (s, 1H, H-vinyl), 7.63 (d, J=8 Hz, 1H), 7.5 (d, J=8 Hz, 1H), 7.29 (dt, J=1, 7 Hz, 1H), 7.21 (dd, J=2, 8 Hz, 1H), 7.07 (dt, J=1, 7 Hz, 1H), 6.89 (d, J=8 Hz, 1H), 2.61 (s, 3H, CH$_3$).

MS El 308.

Example 169

5-Bromo-3-(3-methyl-1H-indol-2-ylmethylene)-1,3-dihydro-indol-2-one

A mixture of 5-bromo-2-oxindole (212 mg), 3-methyl-indole-2-carbaldehyde (190 mg) (prepared according to *Synthetic Communications,* 1986, 16, 1799) and piperidine (10 mg) in ethanol was held in a sealed tube at 95° C. for 4 hours. The mixture was cooled to room temperature. The solid was collected by vacuum filtration, washed with cold ethanol and dried in a vacuum oven to give 5-bromo-3-(3-methyl-1H-indol-2-ylmethylene)-1,3-dihydro-indol-2-one.

$^1$H NMR (360 MHz, DMSO-d6) δ12.96 (s, br, 1H, NH), 1.09 (s, br, 1H, NH), 8.21 (d, J=2 Hz, 1H), 8.02 (s, 1H, H-vinyl), 7.63 (d, J=8 Hz, 1H), 7.5 (d, J=8 Hz, 1H), 7.33 dd, J=2, 8 Hz, 1H), 7.29 (dt, J=1, 7 Hz, 1H), 7.07 (dt, J=1, 7 Hz, 1H), 6.84 (d, J=8 Hz, 1H), 2.62 (s, 3H, CH$_3$).

MS El 352 and 354.

Example 170

4-Methyl-3-(3-methyl-1H-indol-2-ylmethylene)-1,3-dihydroindol-2-one

A mixture of 4-methyl-2-oxindole (147 mg), 3-methyl-indole-2-carbaldehyde (190 mg) (prepared according to *Synthetic Communications,* 1986, 16, 1799) and piperidine (10 mg) in ethanol was held in a sealed tube at 95° C. for 4 hours. The mixture was cooled to room temperature. The solid was collected by vacuum filtration, washed with cold ethanol and dried in a vacuum oven to give 4-methyl-3-(3-methyl-1H-indol-2-ylmethylene)-1,3-dihydro-indol-2-one.

$^1$H NMR (360 MHz, DMSO-d6) δ13.07 (s, br, 1H, NH), 11.0 (s, br, 1H, NH), 7.78 (s, 1H, H-vinyl), 7.64 (d, J=8 Hz, 1H), 7.51 (d, J=8 Hz, 1H), 7.27 (dt, J=1, 8 Hz, 1H), 7.04–7.12 (m, 2H), 6.85 (d, J=8 Hz, 1H), 6.78 (d, J=8 Hz, 1H), 2.64 (s, 3H, CH$_3$), 2.52 (s, 3H, CH$_3$).

MS El 288.

Example 171

3-(1H-indol-2-ylmethylene)-5-[(1H-indol-2-ylmethylene)-amino]-1,3-dihydroindol-2-one A mixture of 5-amino-2-oxindole (74 mg), indole-2-carbaldehyde (87 mg) (prepared according to *Synthetic Communications,* 1983, 23, 3109) and piperidine (4 mg) in ethanol (2 mL) was held in a sealed tube at 95° C. for 3 hours. The mixture was cooled to room temperature The solid was collected by vacuum filtration, washed with cold ethanol and dried in a vacuum oven. The crude solid was then chromatographed on silica gel to give 50 mg (25% yield) of 3-(1H-indol-2-ylmethylene)-5-[(1H-indol-2-ylmethylene)-amino]-1,3-dihydro-indol-2-one.

Example 172

3-(1H-Indol-3-ylmethylene)-2-oxo-2,3-dihydro-1H-indole-5-sulfonic acid amide $^1$HNMR (300 MHz, DMSO-d6) δ12.03 (br, s, 1H, NH), 10.80 (br, s, 1H, NH), 9.37 (s, 1H), 8.09–8.24 (m, 3H), 7.51 (m, 1H), 7.41 (m, 1H), 7.13 (m, 2H), 7.03 (s, 2H, NH$_2$), 6.85 (d, J=7.8 Hz, 1H).

MS-EI m/z 339 [M]$^+$.

Example 173

3-(1H-Indol-2-ylmethylene)-2-oxo-2,3-dihydro-1H-indole-5-sulfonic acid methylamide $^1$HNMR (300 MHz, DMSO-d6) δ12.75 (br, s, 1H, NH), 11.40 (br, s, 1H, NH), 8.15 (s, 1H, H-vinyl), 8.10 (d, J=1.5 Hz, 1H), 7.54–7.65 (m, 3H), 7.20–7.27 (m, 3H), 7.02–7.06 (m, 2H), 2.38 (d, J=4.8 Hz, 3H, CH$_3$).

MS-EI m/z 353 [M]$^+$.

Example 174

3-(1H-Indol-3-ylmethylene)-2-oxo-2,3-dihydro-1H-indole-5-carboxylic acid $^1$HNMR (300 MHz, DMSO-d6) δ12.13 (br, s, 1H, NH), 10.88 (br, s, 1H, NH), 8.22–8.50 (m, 2H), 7.66–7.94 (m, 2H), 7.52 (m, 1H), 7.23 (m, 2H), 6.94 (m, 1H).

MS-EI m/z 304 [M]$^+$.

Example 175

3-(3-Methyl-1H-indol-2-ylmethylene)-2-oxo-2,3-dihydro-1H-indole-5-sulfonic acid amide $^1$HNMR (360 MHz, DMSO-d6) δ12.92 (br, s, 1H, NH), 11.35 (br, s, 1H, NH), 8.36 (d, J=2.2 Hz, 1H), 8.03 (s, 1H, H-vinyl), 7.67 (m, 2H), 7.53 (d, J=7.6 Hz, 1H), 7.30 (m, 1H), 7.16 (s, 2H, NH$_2$), 7.08 (m, 1H), 7.03 (d, J=8.6 Hz, 1H), 2.63 (s, 3H, CH$_3$).

MS-EI m/z 353 [M]$^+$.

Example 176

3-(1H-Indol-5-ylmethylene)-2-oxo-2,3-dihydro-1H-indole-5-sulfonic acid methylamide $^1$HNMR (300 MHz, DMSO-d6) δ11.38 (br, s, 1H, NH), 10.85 (br, s, 1H, NH), 8.11 (m, 1H), 8.01 (m, 1H), 7.90 (m, 1H) 7.78 (m, 1H), 7.37–7.53 (m, 3H), 7.10 (m, 1H), 6.95 (m, 1H), 6.4 (m, 1H), 2.28 (s, 3H, CH$_3$).

MS-EI m/z 353 [M]$^+$.

Example 177

3-(1H-Indol-5-ylmethylene)-2-oxo-2,3-dihydro-1H-indole-5-carboxylic acid $^1$HNMR (300 MHz, DMSO-d6) δ12.54 (br, s, 1H, NH), 10.86 (br, s, 1H, NH), 8.56, 7.76, 7.46, 6.91 (m, 9H).

Example 178

3-(1H-Indol-3-ylmethylene)-2-oxo-2,3-dihydro-1H-indole-5-sulfonic acid methylamide $^1$HNMR (300 MHz, DMSO-d6) δ12.03 (br, s, 1H, NH), 10.84 (br, s, 1H, NH), 9.39 (s, 1H), 8.25 (s, 1H, H-vinyl), 8.22 (d, J=1.5 Hz, 1H), 8.16 (m, 1H), 7.40–7.46 (m, 2H), 7.06–7.15 (m, 2H), 7.04 (m, 1H, CH₃NH), 6.88 (d, J=7.8 Hz, 1H), 2.32 (d, J=5.1 Hz, 3H, CH₃).
MS-EI m/z 355 [M]⁺.

Example 179

5-Amino-3-(1H-indol-5-ylmethylene)-1,3-dihydro-indol-2-one

MS-EI m/z 275 [M]⁺.

Example 180

5-Amino-3-(3-methyl-1H-indol-2-ylmethylene)-1,3-dihydroindol-2-one

¹HNMR (300 MHz, DMSO-d6) δ13.13 (br, s, 1H, NH), 10.57 (br, s, 1H, NH), 7.63 (s, 1H, H-vinyl), 7.61 (d, J=7.6 Hz, 1H), 7.47 (d, J=7.6 Hz, 1H), 7.25 (t, J=7.6 Hz, 1H), 7.03–7.06 (m, 2H), 6.61 (d, J=8.3 Hz, 1H), 6.49 (dd, J=1.4 & 8.3 Hz, 1H), 4.70 (br s, 2H, NH₂), 2.55 (s, 3H, CH₃).
MS-EI m/z 289 [M]⁺.

Example 182

3-(2-Methyl-1H-indol-3-ylmethylene)-2-oxo-2,3-dihydro-1H-indole-5-carboxylic acid ¹HNMR (300 MHz, DMSO-d6) δ12.0 (br, s, 1H, NH), 10.85 (br, s, 1H, NH), 7.90 (s, 1H, H-vinyl), 7.79 (dd, 1H), 7.41–7.44 (m, 2H), 7.02–7.18 (m, 3H), 6.91 (d, 1H), 2.45 (s, 3H, CH₃).
MS-EI m/z 318 [M]⁺.

Example 183

3-(1H-Indol-5-ylmethylene)-2-oxo-2,3-dihydro-1H-indole-5-sulfonic acid dimethylamide MS-EI m/z 367 [M]⁺.

Example 184

3-(2-Methyl-1H-indol-3-ylmethylene)-2-oxo-2,3-dihydro-1H-indole-5-sulfonic acid dimethylamide ¹HNMR (300 MHz, DMSO-d6) δ11.95 (br, s, 1H, NH), 10.86 (br, s, 1H, NH), 7.84 (s, 1H, H-vinyl), 7.41 (dd, J=1.8 & 8.4 Hz, 1H), 7.33 (d, J=8.4 Hz, 1H), 7.04 (m, 1H), 6.85–6.95 (m, 4H).
MS-EI m/z 381 [M]⁺.

Example 185

3-(1H-Indol-5-ylmethylene)-2-oxo-2,3-dihydro-1H-indole-5-sulfonic acid amide

MS-EI m/z 339 [M]⁺.

Example 186

3-(1H-Indol-2-ylmethylene)-2-oxo-2,3-dihydro-1H-indole-5-sulfonic acid dimethylamide ¹HNMR (360 MHz, DMSO-d6) δ12.80 (br, s, 1H, NH), 11.44 (br, s, 1H, NH), 8.30 (s, 1H, H-vinyl), 8.15 (d, J=2.2 Hz, 1H), 7.70 (d, J=7.2 Hz, 1H), 7.60 (m, 2H), 7.30 (m, 1H), 7.23 (s, 1H), 7.07–7.12 (m, 2H), 2.63 (s, 6H, 2×CH₃).
MS-EI m/z 367 [M]⁺.

Example 187

5-Amino-3-(2-methyl-1H-indol-3-ylmethylene)-1,3-dihydroindol-2-one

MS-EI m/z 289 [M]⁺.

Example 188

3-(1H-Indol-3-ylmethylene)-2-oxo-2,3-dihydro-1H-indole-5-sulfonic acid dimethylamide ¹HNMR (360 MHz, DMSO-d6) δ12.11 (br, s, 1H, NH), 10.94 (br, s, 1H, NH), 9.50 (s, 1H), 8.44 (s, 1H), 8.33 (m, 2H) 7.51–7.53 (m, 2H), 7.25 (m, 2H), 7.03 (d, J=7.9 Hz, 1H) 2.63 (s, 6H, 2×CH₃).
MS-EI m/z 367 [M]⁺.

Example 189

3-(2-Methyl-1H-indol-3-ylmethylene)-2-oxo-2,3-dihydro-1H-indole-5-sulfonic acid amide MS-EI m/z 353 [M]⁺.

Example 190

3-[2-(2-Oxo-1,2-dihydro-indol-3-ylidenemethyl)-4,5,6,7-tetrahydro-1H-indol-3-yl]-propionic acid 1-(Morpholin-4-yl)cyclohexene (300 g), 214 g of triethylamine and 1400 mL of dichloromethane were refluxed for 15 minutes and then cooled in a water bath to 15–20° C. Ethyl succinyl chloride (266 g) dissolved in 500 mL of dichloromethane was added over 30 minutes. The mixture was refluxed for 30 minutes and cooled to ambient temperature in a water bath. The solid was collected by vacuum filtration, washed with 100 mL of dichloromethane and discarded. The filtrate was returned to the flask and the solvent removed by distillation to give 454 g of crude 4-(2-morpholin-4-yl-cyclohex-1-enyl)-4-oxo-butyric acid ethyl ester as an oil.

Crude 4-(2-morpholin-4-ylcyclohex-1-enyl)-4-oxo-butyric acid ethyl ester (454 g), 398 g of diethyl aminomalonate hydrochloride, 162 g of sodium acetate and 350 mL of glacial acetic acid were heated to 108° C. over 30 minutes. The mixture was held at 100–108° C. for 2 hours and then cooled to about 50° C. in a water bath. Water (2500 mL) and 700 mL of ethyl acetate were added. The ethyl acetate layer was separated and washed three times with brine, twice with saturated sodium bicarbonate solutiona and once with brine. The solution was dried over anhydrous sodium sulfate, and the ethyl acetate was removed using a rotary evaporator to give 494 g (105% yield) of crude 3-(2-ethoxycarbonylethyl)-4,5,6,7-tetrahydro-1H-indole-2-carboxylic acid ethyl ester as an oil. The crude mixture was chromatographed on a silica gel column using a 1:10 mixture of ethyl acetate:hexane as the eluent to give 122.1 g of pure 3-(2-ethoxycarbonylethyl)-4,5,6,7-tetrahydro-1H-indole-2-carboxylic acid ethyl ester as a low melting solid.

¹H NMR (d₆-DMSO): δ11.0 (s, 1H, pyrrole NH), 4.2, 4.0 (t, each 4H, COCH₂), 2.8, 2.4 (t, each 4H, —CH₂CH₂CO—), 2.4 (m, 4H, —CH₂—, —CH₂—), 1.7 (m, 4H, —CH₂CH₂—).

Purified 3-(2-ethoxycarbonylethyl)-4,5,6,7-tetrahydro-1H-indole-2-carboxylic acid ethyl ester (122.1 g) and 328 mL of 5N sodium hydroxide were refluxed for 80 minutes. The heat was turned off and 165 mL of 10 N hydrochloric acid was carefully added to the vigorously stirred mixture using an addition funnel over the reflux condenser. Hydrochloric acid was added until the pH was 2–3. The mixture was then cooled in an ice bath at which time the oil in the mixture solidified. The solid was collected by vacuum filtration, washed 3 times with water and dried under vacuum at 50–60° C. to give 54.9 g (71% yield) of 3-(4,5,6,7-tetrahydro-1H-indol-3-yl)-propionic acid as a dark brown solid.

$^1$H NMR (d$_6$-DMSO): δ13.1 (s, 1H, pyrrole NH), 11.8 (br s, 1H, COOH), 9.8 (s, 1H, CH), 2.5, 2.3 (t, 4H, —CH$_2$CH$_2$CO—), 2.4 (m, 4H, —CH$_2$—, —CH$_2$—), 1.7 (m, 4H, —CH$_2$CH$_2$—).

A mixture of 24 g of dimethylformamide and 300 mL of dichloromethane was cooled to −9° C. Phosphorus oxychloride (50 g) was rapidly added via an addition funnel. 3-(4,5,6,7-tetrahydro-1H-indol-3-yl)-propionic acid (54.9 g) was added in portions with vigorous stirring. The mixture was warmed to room temperature and then refluxed for 10 minutes. It was then cooled to 5° C. and diluted with 300 mL of water. The pH was adjusted to 10 using 10N sodium hydroxide. The layers were separated. The aqueous layer was cooled to 10° C. and the pH adjusted to 2–3 with about 130 mL of 10 N hydrochloric acid. The oil which formed solidified and was collected by vacuum filtration, washed three times with water and dried under vacuum at 50° C. to give 52.8 g (93% yield) of 3-(2-formyl-4,5,6,7-tetrahydro-1H-indol-3-yl)-propionic acid as a dark brown solid.

$^1$H NMR (d$_6$-DMSO): δ13.1 (s, 1H, pyrrole NH), 11.7 (br s, 1H, COOH), 9.4 (s, 1H, CHO), 2.8, 2.5(t, 4H, —CH$_2$CH$_2$CO—), 2.4 (m, 4H, —CH$_2$—, —CH$_2$—), 1.7 (m, 4H, —CH$_2$CH$_2$—).

3-(2-Formyl-4,5,6,7-tetrahydro-1H-indol-3-yl)-propionic acid (5.4 g), 3.6 g of 2-oxindole and 2.7 g of piperidine (or 2.2 g of pyrrolidine) in 25 mL of ethanol were refluxed for 4 hours. Upon slow addition of acetic acid (8 mL), a precipitate formed. The mixture was refluxed for 5 minutes and cooled to ambient temperature. The precipitate was collected by vacuum filtration and washed with 20 mL of ethanol. The solids were slurry-washed refluxing in 30 mL of ethanol, cooled, collected by vacuum filtration, washed with 30 mL of ethanol and dried under vacuum to give 5.5 g (68% yield) of 3-[2-(2-oxo-1,2-dihydroindol-3-ylidenemethyl)-4,5,6,7-tetrahydro-1H-indol-3-yl]-propionic acid as an orange solid: mp 263–265° C.

$^1$H NMR (d$_6$-DMSO): δ13.1 (s, 1H, pyrrole NH), 12.0 (br s, 1H, COOH), 10.7 (s, 1H, CONH), 7.7, 7.1, 6.9, 6.8 (m, each 4H, aromatic), 7.6 (s, 1H, —CH=), 2.9, 2.7 (t, each 4H, —CH$_2$CH$_2$CH—), 2.4 (m, 4H, —CH$_2$—, —CH$_2$—), 1.7 (m, 4H, —CH,CH$_2$—.

Example 191

3-[2-(5-Chloro-2-oxo-1,2-dihydroindol-3-ylidenemethyl)-4,5,6,7-tetrahydro-1H-indol-3-yl]-propionic acid 3-(2-Formyl-4,5,6,7-tetrahydro-1H-indol-3-yl)-propionic acid (5.4 g), 3.7 g of 5-chloro-2-oxindole and 2.7 g of piperidine (or 2.2 g of pyrrolidine) in 25 mL of ethanol was refluxed for 4 hours. Slow addition of acetic acid (8 mL) resulted in a precipitate. The mixture was refluxed for 5 minutes and cooled to ambient temperature. The precipitate was collected by vacuum filtration and washed with 20 mL of ethanol. The solids were slurry-washed by refluxing in 30 mL of ethanol, cooled, collected by vacuum filtration, washed with 30 mL of ethanol and dried under high vacuum to give 6.5 g (80% yield) 3-[2-(5-chloro-2-oxo-1,2-dihydroindol-3-ylidenemethyl)-4,5,6,7-tetrahydro-1-H-indol-3-yl]-propionic acid as an orange solid: mp 370–384° C.

$^1$H NMR (d$_6$-DMSO): δ13.3 (s, 1H, pyrrole NH), 12.0 (br s, 1H, COOH), 10.7 (s, 1H, CONH), 7.8, 7.1, 6.8 (m, each 3H, aromatic), 7.7 (s, 1H, —CH=), 2.9, 2.7 (t, each 4H, CH$_2$CH$_2$CO), 2.5 (m, 4H, —CH$_2$—, —CH$_2$—), 1.7 (m, 4H, —CH$_2$CH$_2$—).

Example 192

3-[2-(5-Bromo-2-oxo-1,2-dihydroindol-3-ylidenemethyl)-4,5,6,7-tetrahydro-1H-indol-3-yl]-propionic acid A mixture of 3-(2-Formyl-4,5,6,7-tetrahydro-1H-indol-3-yl)-propionic acid (3.4 g), 2.7 g of 5-bromo-2-oxindole and 1.4 g of pyrrolidine in 25 mL of ethanol was refluxed for 4 hours. Upon slow addition of acetic acid (8 mL), a precipitate formed. The mixture was refluxed for 5 minutes and cooled to ambient temperature. The precipitate was collected by vacuum filtration and washed with 20 mL of ethanol. The solids were slurry-washed by refluxing in 30 mL of ethanol, cooled, collected by vacuum filtration, washed with 30 mL of ethanol and dried under vacuum to give 5.2 g (98% yield) of 3-[2-(5-bromo-2-oxo-1,2-dihydroindol-3-ylidenemethyl)-4,5,6,7-tetrahydro-1H-indol-3-yl]-propionic acid as a red-orange solid, mp 286–289° C.

$^1$H NMR (d$_6$-DMSO): δ13.3 (s, 1H, pyrrole NH), 12.0 (br s, 1H, COOH), 10.7 (s, 1H, CONH), 7.9, 7.1, 6.8 (m, each 3H, aromatic), 7.7 (s, 1H, —CH=), 2.9, 2.7 (t, each 4H, —CH$_2$CH$_2$CO—), 2.5 (m, 4H, —CH$_2$—, —CH$_2$—), 1.7 (m, 4H, —CH$_2$CH$_2$—).

Example 193

3-[2-(4-Methyl-2-oxo-1,2-dihydroindol-3-ylidenemethyl)-4,5,6,7-tetrahydro-1H-indol-3-yl]-propionic acid Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was refluxed for 0.5 hr, concentrated, and treated with 10% sodium hydroxide until almost all of the solid dissolved. Hydrogen peroxide (30%) was then added to the dark red mixture until the red color changed to yellow. The mixture was treated alternately with 10% sodium hydroxide and 30% hydrogen peroxide until the dark red color was no longer present. The solid was filtered off and the filtrate acidified with 6 N hydrochloric acid. The resulting precipitate was collected by vacuum filtration, washed with water, and dried under vacuum to give 9.8 g (45% yield) of 1-methyl-6-nitrophenylacetic acid as an off-white solid. The solid was hydrogenated in methanol over 10% palladium on carbon to give 9.04 g of 4-methyl-2-oxindole as a white solid.

$^1$H NMR (d$_6$-DMSO, 360 MHz) δ10.27 (s, br, 1H, NH-1), 7.06 (t, 7.71 Hz, 1H, H-6), 6.74 (d, 7.73 Hz, H-5), 6.63 (d, 7.73 Hz, 1H, H-7), 3.36 (s, 2H, CH$_2$), 2.18 (s, 3H, CH$_3$).

A mixture of 3-(2-formyl-4,5,6,7-tetrahydro-1H-indol-3-yl)-propionic acid (5.4 g), 3.2 g of 4-methyl-2-oxindole and 2.7 g of piperidine in 25 mL of ethanol was refluxed for 4 hours. Upon slow addition of acetic acid (8 mL), a precipitate formed. The mixture was refluxed for 5 minutes and cooled to ambient temperature. The precipitate was collected by vacuum filtration and washed with 20 mL of ethanol. The solids were slurry-washed in 30 mL of refluxing ethanol, cooled, collected by vacuum filtration, washed with 30 mL of ethanol and dried under vacuum to give 6.2 g (80% yield) of 3-[2-(4-methyl-2-oxo-1,2-dihydroindol-3-ylidenemethyl)-4,5,6,7-tetrahydro-1H-indol-3-yl]-propionic acid as an orange solid.

$^1$H NMR (d$_6$-DMSO) δ13.3 (s, 1H, pyrrole NH), 12.0 (br s, 1H, COOH), 10.7 (s, 1H, CONH), 7.7 (s, 1H, —CH=), 7.0, 6.8 (m, each 2H, aromatic), 2.8, 2.7 (t, each 4H, —CH$_2$CH$_2$CO—), 2.6 (s, 1H, CH$_3$), 2.5 (m, 4H, —CH$_2$—, —CH$_2$—), 1.7 (m, 4H, —CH$_2$CH$_2$—).

Example 194

3-[2-(5-Methyl-2-oxo-1,2-dihydroindol-3-ylidenemethyl)-4,5,6,7-tetrahydro-1H-indol-3-yl]-propionic acid A mixture of 3-(2-formyl-4,5,6,7-tetrahydro-1H-indol-3-yl)-propionic acid (5.4 g), 3.2 g of 5-methyl-2-oxindole and 2.7 g of piperidine in 25 mL of ethanol was refluxed for 4 hours. Upon addition of acetic acid (8 mL), a precipitate formed. The mixture was refluxed for 5 minutes and cooled to ambient temperature. The precipitate was collected by vacuum filtration and washed with 20 mL of ethanol. The solids were slurry-washed with 30 mL of refluxing ethanol, cooled, collected by vacuum filtration, washed with 30 mL of ethanol and vacuum dried to give 6.2 g (80% yield) of 3-[2-(5-methyl-2-oxo-1,2-dihydroindol-3-ylidenemethyl)-4,5,6,7-tetrahydro-1H-indol-3-yl]-propionic acid as an orange solid.

$^1$H NMR (d$_6$-DMSO): δ13.3 (s, 1H, pyrrole NH), 12.0 (br s, 1H, COOH), 10.7 (s, 1H, CONH), 7.7 (s, 1H, —CH═), 7.0, 6.8 (m, each 3H aromatic), 2.8, 2.7 (t, each 4H, —CH$_2$CH$_2$CO—), 2.6 (s, 1H, CH$_3$), 2.5 (m, 4H, —CH$_2$—, —CH$_2$—), 1.7 (m, 4H, —CH$_2$CH$_2$—).

MS: m/z 349.

Example 195

3-[2-(6-Chloro-2-oxo-1,2-dihydroindol-3-ylidenemethyl)-4,5,6,7-tetrahydro-1H-indol-3-yl]-propionic acid A mixture of 3-(2-formyl-4,5,6,7-tetrahydro-1H-indol-3-yl)-propionic acid (5.4 g), 3.7 g of 6-chloro-2-oxindole and 2.7 g of piperidine in 25 mL of ethanol was refluxed for 4 hours. Upon slow addition of acetic acid (8 mL), a precipitate formed. The mixture was refluxed for 5 minutes and cooled to ambient temperature. The precipitate was collected by vacuum filtration and washed with 20 mL of ethanol. The solids were slurry-washed in 30 mL of refluxing ethanol, cooled, collected by vacuum filtration, washed with 30 mL of ethanol and vacuum dried to give 6.5 g (80%) of 3-[2-(6-chloro-2-oxo-1,2-dihydroindol-3-ylidenemethyl)-4,5,6,7-tetrahydro-1H-indol-3-yl]-propionic acid as an orange solid.

$^1$H NMR (d$_6$-DMSO): δ13.3 (s, 1H, pyrrole NH), 12.0 (br s, 1H, COOH), 10.7 (s, 1H, CONH), 7.7, 7.0, 6.9 (m, each 3H, aromatic), 7.6 (s, 1H, —CH═), 2.9, 2.7 (t, each 4H, —CH$_2$CH$_2$CO—), 2.4 (m, 4H, —CH$_2$—, —CH$_2$—), 1.7(m, 4H, —CH$_2$CH$_2$—).

MS: m/z 371.

Example 196

3-[2-(6-Methoxy-2-oxo-1,2-dihydroindol-3-ylidenemethyl)-4,5,6,7-tetrahydro-1H-indol-3-yl]-propionic acid A mixture of 3-(2-formyl-4,5,6,7-tetrahydro-1H-indol-3-yl)-propionic acid (5.4 g), 3.6 g of 6-methoxy-2-oxindole and 2.7 g of piperidine in 25 mL of ethanol was refluxed for 4 hours. Upon slow addition of acetic acid (8 mL), a precipitate formed. The mixture was refluxed for 5 minutes and cooled to ambient temperature. The precipitate was collected by vacuum filtration and washed with 20 mL of ethanol. The solids were slurry-washed in 30 mL of refluxing ethanol, cooled, collected by vacuum filtration, washed with 30 mL of ethanol and vacuum dried to give 6.4 g (80% yield) of 3-[2-(6-methoxy-2-oxo-1,2-dihydroindol-3-ylidenemethyl)-4,5,6,7-tetrahydro-1H-indol-3-yl]-propionic acid as an orange solid, mp 263–266° C.

$^1$H NMR (d$_6$-DMSO): δ13.0 (s, 1H, pyrrole NH), 12.0(s, 1H, COOH), 10.7 (s, 1H, CONH), 7.6, 6.5, 6.4 (m, each 3H, aromatic), 7.4 (s, 1H, —CH═), 3.7 (s, 3H, CH$_3$), 2.9, 2.7 (t, each 4H, —CH$_2$CH$_2$CO—), 2.5 (m, 4H —CH$_2$—, —CH$_2$—), 1.7 (m, 4H, —CH$_2$CH$_2$—).

MS: m/z 365.

Example 197

N,N-Dimethyl-3-[2-(2-oxo-1,2-dihydroindol-3-ylidenemethyl)-4,5,6,7-tetrahydro-1H-indol-3-yl]-propionamide 3-[2-(2-Oxo-1,2-dihydroindol-3-ylidenemethyl)-4,5,6,7-tetrahydro-1H-indol-3-yl]-propionic acid (10 g) was dissolved in 100 mL of dimethylformamide. Carbonyldiimidazole (6.3 g) was added and the mixture stirred at ambient temperature for 1 hour. Dimethylamine (2.7 g) and 30 mL of dimethylformamide were added and the stirring continued overnight at room temperature. Fifty mL of water was added to the mixture and stirring was continued for 10 minutes. The precipitate was collected by vacuum filtration, washed with 20 mL of water and then 20 mL of ethanol. The solid was slurry-washed in 30 mL of refluxing ethanol for 5 minutes and cooled to room temperature. The solid was collected by vacuum filtration, washed with 20 mL of ethanol and vacuum dried to give 8.9 g (83% yield) of N,N-dimethyl-3-[2-(2-oxo-1,2-dihydroindol-3-ylidenemethyl)-4,5,6,7-tetrahydro-1H-indol-3-yl]-propionamide.

$^1$H NMR (d$_6$-DMSO): δ13.1 (s, 1H, pyrrole NH), 10.7 (s, 1H, CONH), 7.7, 7.1, 6.9, 6.8 (m, each 4H, aromatic), 7.6 (s, 1H, —CH═), 3.3 (s, 6H, CH$_3$), 2.9, 2.7 (t, each 4H, —CH$_2$CH$_2$CO—), 2.5 (m, 4H —CH$_2$—, —CH$_2$—), 1.7(m, 4H, —CH$_2$H$_2$—).

MS: m/z 364.

Example 198

3-[3-(3-Dimethylaminoproryl)-4,5,6,7-tetrahydro-1H-indol-2-ylmethylene]-1,3-dihydroindol-2-one 3-(4,5,6,7-tetrahydro-1H-indol-3-yl)-propionic acid (9.7 g) in 100 mL of tetrahydrofuran was stirred with 8.1 g of carbonyl diimidazole for 1 hour. Dimethylamine (2.5 g) was added and the mixture stirred for 2 hours. The solvent was evaporated and the residue taken up in ethyl acetate, washed with water, 0.1 N hydrochloric acid, water, and brine, dried over sodium sulfate and evaporated to give 7.7 g (70% yield) of 3-(4,5,6,7-tetrahydro-1H-indol-3-yl)-propionic acid dimethyl amide.

3-(4,5,6,7-Tetrahydro-1H-indol-3-yl)-propionic acid dimethyl amide (7.7 g) and 13 g of borane-tetrahydrofuran complex in 50 mL of tetrahydrofuran was refluxed for 3 hours. The reaction was quenched with acetone and then water and evaporated to dryness. The residue was chromatographed on silica gel to give 2 g (20% yield) of 3-(3-dimethylaminopropyl)-4,5,6,7-tetrahydro-1H-indole as a yellow oil.

Dimethylformamide (0.8 g) and 13 mL of dichloromethane was cooled to −9° C. Phosphorus oxychloride (1.7 g) was rapidly added via a dropping funnel. 3-(3-dimethylaminopropyl)-4,5,6,7-tetrahydro-1H-indole (2 g) was added in portions with vigorous stirring. The mixture was warmed to room temperature and then refluxed for 10 minutes. It was then cooled to 5° C., and diluted with 20 mL of water. The pH was adjusted to 10 with 10N sodium hydroxide. The layers were separated. The organic layer was washed with water and brine, dried over anhydrous sodium sulfate and evaporated to give 1.8 g (80%) of 3-(3-dimethylaminopropyl)-2-formyl-4,5,6,7-tetrahydro-1H-indole as a dark oil which solidified.

3-(3-Dimethylaminopropyl)-2-formyl-4,5,6,7-tetrahydro-1H-indole (1.8 g), 1 g of 2-oxindole and 0.1 g of piperidine in 10 mL of ethanol was refluxed for 4 hours and then cooled to room temperature. The precipitate which formed was collected by vacuum filtration and washed with 4 mL of ethanol. The solids were slurry-washed with 8 mL of refluxing ethanol, cooled, collected by vacuum filtration, washed with 3 mL of ethanol and vacuum dried to give 1.8 g (70% yield) of 3-[3-(3-dimethylaminopropyl)-4,5,6,7-tetrahydro-1H-indol-2-ylmethylene]-1,3-dihydroindol-2-one as an orange solid.

$^1$H NMR (d$_6$-DMSO): δ13.1 (s, 1H, pyrrole NH), 10.7 (s, 1H, CONH), 7.6, 7.1, 7.0, 6.8 (m, each 4H, aromatic), 7.6 (s, 1H, —CH═), 3.3 (s, 6H, CH$_3$), 2.7 (m, 4H, —CH$_2$—, —CH$_2$—), 2.5, 2.3, 1.4 (t, each 6H, —CH$_2$CH$_2$CH$_2$N—), 1.7 (m, 4H, —CH$_2$CH$_2$—).

MS: m/z 350.

Example 199

3-[2-(2-Oxo-1,2-dihydroindol-3-ylidenemethyl)-4,5,6,7-tetrahydro-1H-indol-3-yl]-propionamide 3-[2-(2-Oxo-1,2-dihydroindol-3-ylidenemethyl)-4,5,6,7-tetrahydro-1H-indol-3-yl]-propionic acid (10 g) was dissolved in 100 mL of dimethylformamide. Carbonyldiimidazole (6.3 g) was added and the mixture stirred at ambient temperature for 1 hour. Ammonia (1 g) in 30 mL of dimethylformamide was added and the stirring continued overnight. Fifty mL of water was added to the mixture and stirring was continued for 10 minutes. The precipitate that formed was collected by vacuum filtration, washed with 20 mL of water and then 20 mL of ethanol. The solid was slurry-washed with 30 mL of refluxing ethanol for 5 minutes and cooled to room temperature. The solid was collected by vacuum filtration, washed with 20 mL of ethanol and vacuum dried to give 11 g (83% yield) of 3-[2-(2-oxo-1,2-dihydroindol-3-ylidenemethyl)-4,5,6,7-tetrahydro-1H-indol-3-yl]-propionamide.

$^1$H NMR (d$_6$-DMSO): δ13.3 (s, 1H, pyrrole NH), 12.0 (br s, 1H, COOH), 10.7 (s, 1H, CONH), 7.6, 7.1, 6.9, 6.8 (m, each 4H, aromatic), 7.6 (s, 1H, —CH═), 7.2, 6.7 (s, each 2H, NH$_2$), 2.9, 2.7 (t, 4H, —CH$_2$CH$_2$CO—), 2.4 (m, 4H, —CH$_2$—, —CH$_2$—), 1.7 (m, 4H, —CH$_2$CH$_2$—).

MS: m/z 336.

Example 200

3-[3-(3-Morpholin-4-yl-3-oxopropyl)-4,5,6,7-tetrahydro-1H-indol-2-ylmethylene]-1,3-dihydroindol-2-one 3-[2-(2-oxo-1,2-dihydroindol-3-ylidenemethyl)-4,5,6,7-tetrahydro-1H-indol-3-yl]-propionic acid (10 g) was dissolved in 100 mL of dimethylformamide. Carbonyldiimidazole (6.3 g) was added and the mixture stirred at ambient temperature for 1 hour. Morpholine (5.2 g) in 30 mL of dimethylformamide was added and the stirring continued overnight. Fifty mL of water was added to the mixture and stirring was continued for 10 minutes. The precipitate was collected by vacuum filtration, washed with 20 mL of water and then 20 mL of ethanol. The solid that formed was slurry-washed with 30 mL of refluxing ethanol for 5 minutes and cooled to room temperature. The solid was collected by vacuum filtration, washed with 20 mL of ethanol and vacuum dried to give 9.6 g (80%) of 3-[3-(3-morpholin-4-yl-3-oxopropyl)-4,5,6,7-tetrahydro-1H-indol-2-ylmethylene]-1,3-dihydroindol-2-one as an orange solid.

$^1$H NMR (d$_6$-DMSO): δ13.3 (s, 1H, pyrrole NH), 12.0 (br s, 1H, COOH), 10.7 (s, 1H, CONH), 7.6, 7.1, 6.9, 6.8 (m, each 4H, aromatic), 7.6 (s, 1H, —CH═), 3.3 (multipets, 8H, morpholine CH$_2$), 2.9, 2.7 (t, each 4H, —CH$_2$CH$_2$CO—), 2.5 (m, 4H, CH$_2$, CH$_2$), 1.7 (m, 4H, —CH$_2$CH$_2$—).

MS: m/z 406.

Example 201

N-Methyl-3-[2-(2-oxo-1,2-dihydroindol-3-ylidenemethyl)-4,5,6,7-tetrahydro-1H-indol-3-yl]-propionamide 3-[2-(2-oxo-1,2-dihydroindol-3-ylidenemethyl)-4,5,6,7-tetrahydro-1H-indol-3-yl]-propionic acid (10 g) was dissolved in 100 mL of dimethylformamide. Carbonyldiimidazole (6.3 g) was added and the mixture stirred at ambient temperature for 1 hour. Methyl amine (1.8 g) in 30 mL of dimethylformamide was added and the stirring continued overnight. Fifty mL of water was added to the mixture and stirring was continued for 10 minutes. The precipitate was collected by vacuum filtration, washed with 20 mL of water and then 20 mL of ethanol. The solid was slurry-washed in 30 mL of refluxing ethanol for 5 minutes and cooled to room temperature. The solid was collected by vacuum filtration, washed with 20 mL of ethanol and vacuum dried to give 8.3 g (80% yield) of N-methyl-3-[2-(2-oxo-1,2-dihydroindol-3-ylidenemethyl)-4,5,6,7-tetrahydro-1H-indol-3-yl]-propionamide as an orange solid.

MS: m/z 350.

Example 202

N-(2-Morpholin-4-ylethyl)-3-[2-(2-oxo-1,2-dihydroindol-3-ylidenemethyl)-4,5,6,7-tetrahydro-1H-indol-3-yl]-propionamide 3-[2-(2-oxo-1,2-dihydroindol-3-ylidenemethyl)-4,5,6,7-tetrahydro-1H-indol-3-yl]-propionic acid (10 g) was dissolved in 100 mL of dimethylformamide. Carbonyldiimidazole (6.3 9) was added and the mixture stirred at ambient temperature for 1 hour. 4-(2-Aminoethyl)morpholine (7.7 g) and 30 mL of dimethylformamide were added and the stirring continued overnight. Fifty mL of water was added to the mixture and stirring was continued for 10 minutes. The precipitate was collected by vacuum filtration, washed with 20 mL of water and then 20 mL of ethanol. The solid was slurry-washed in 30 mL of refluxing ethanol for 5 minutes and cooled to room temperature. The solid was collected by vacuum filtration, washed with 20 mL of ethanol and vacuum dried to give 1 g (83%) of N-(2-morpholin-4-ylethyl)-3-[2-(2-oxo-1,2-dihydro-indol-3-ylidenemethyl)-4,5,6,7-tetrahydro-1H-indol-3-yl]-propionamide, mp 256–258° C.

$^1$H NMR (d$_6$-DMSO): δ13.1 (s, 1H, pyrrole NH), 10.7 (s, 1H, —CONH—), 7.7 (t, 1H, —CONHCH$_2$—), 7.6, 7.1, 6.9, 6.8 (m, each 4H, aromatic), 7.5 (s, 1H, —CH═), 3.5 (t, each 4H, —CH$_2$CH$_2$—), 3.1, 2.8 (m, each 2H, —CH$_2$NCH$_2$—), 2.7, 2.5 (t, each 4H, —CH$_2$CH$_2$CO—), 2.3, 2.2 (m, each 4H, —NHCH$_2$CH$_2$N—), 2.2 (m, 4H, —CH$_2$—, —CH$_2$—), 1.7 (m, 4H, —CH$_2$CH$_2$—).

Example 203

3-[2-(2-Oxo-1,2-dihydropyrrolo[2,3-b]pyridin-3-ylidenemethyl)-4,5,6,7-tetrahydro-1H-indol-3-yl]-propionic acid A mixture of 7-azaoxindole (99 mg), 110 mg of 3-(2-formyl-4,5,6,7-tetrahydro-1H-indol-3-yl)-propionic acid and 2 drops of piperidine in 2 mL of ethanol was refluxed for 5 h. The reaction mixture was cooled and concentrated. The residue was acidified with acetic acid to pH 6. The resulting precipitate was collected by vacuum filtration, washed with water and dried in a vacuum oven at 40° C. to give 25.4 mg (13% yield) of 3-[2–2-oxo-1,2-dihydropyrrolo[2,3-b]pyridin-3-ylidenemethyl)-4,5,6,7-tetrahydro-1H-indol-3-yl]-propionic acid.

MS: m/z 338.

Example 204

3-[2-[6-(3-Methoxyphenyl)-2-oxo-1,2-dihydro-indol-3-ylidenemethyl]-4,5,6,7-tetrahydro-1H-indol-3-yl]-propionic acid A mixture of 103 mg 6-(3-methoxyphenyl)-2-oxindole, 95 mg 3-(2-formyl-4,5,6,7-tetrahydro-1H-indol-3-yl)-propionic acid and piperidine (3 drops) in ethanol (2 mL) was heated in sealed tube to 90° C. and held there overnight. The reaction mixture was concentrated and acidified with 6 N hydrochloric acid. The precipitate that formed was collected by filtration and washed with water and hexane to give 156 mg of 3-{2-[6-(3-methoxyphenyl)-2-oxo-1,2-dihydroindol-3-ylidenemethyl]-4,5,6,7-tetrahydro-1H-indol-3-yl}-propionic acid as a brown solid (82%).

$^1$H NMR (d$_6$-DMSO, 360 MHz): δ13.26 (s, br, 1H, NH-1) 1.78 (s, br, 1H, NH-1), 7.72 (d, 8.1 Hz, 1H, H-4), 7.65 (s, 1H, H-vinyl), 7.35 (d, 7.9 Hz, 1H), 7.26 (dd, 1.3 Hz, 8.1 Hz, 1H, H-5), 7.18 (d, 7.9 Hz 1H), 7.13 (t, 2.0 Hz, 1H ), 7.09 (d, 1.3 Hz, 1H, H-7), 6.90 (dd,, 2.0 Hz, 1H), 3.82 (s, 3H, OCH$_3$), 2.91 (t, 7.4 Hz, 2H, CH$_2$CH$_2$COOH), 2.66 (t, 5.9 Hz, 2H, H-7'), 2.38–2.46 (m, 4H, CH$_2$CH$_2$COOH and H-4'), 1.69–1.76 (m, 4H, H-5',6'). MS: m/z 443.2.

Example 205

3-{2-[6-(4-Methoxymhenyl)-2-oxo-1,2-dihydro-indol-3-ylidenemethyl]-4,5,6,7-tetrahydro-1H-indol-3-yl}-prorionic acid A mixture of 103 mg 6-(4-methoxyphenyl)-2-oxindole, 95 mg 3-(2-formyl-4,5,6,7-tetrahydro-1H-indol-3-yl)-propionic acid and piperidine (3 drops) in ethanol (2 mL) was heated to 90° C. in a sealed tube and held there for 4 hrs. The reaction mixture was concentrated and acidified with 6 N hydrochloric acid. Ethyl acetate was added upon which a solid precipitated from the aqueous layer. The precipitate was collected by filtration, and washed with water and hexane to give 57 mg of 3-{2-[6-(4-Methoxyphenyl)-2-oxo-1,2-dihydroindol-3-ylidenemethyl]-4,5,6,7-tetrahydro-1H-indol-3-yl}-propionic acid as a brown solid (30%).

$^1$H NMR (d$_6$-DMSO, 360 MHz): δ13.24 (s, br, 1H, NH-1), 11.61 (s, br, 1H, COOH), 10.76 (s, br, 1H, NH-1), 7. (d, 8.1 Hz, 1H, H-4), 7.61 (s, 1H, H-vinyl), 7.56 (d, 8.8 Hz, 2H, H-3, 5), 7.21 (dd, 1.5 Hz, 8.1 Hz, 1H, H-5), 7.04 (d, J=1.5 Hz, 1H, H-7), 7.01 (d, 8.8 Hz, 2H, H-2",6"), 3.79 (s, 3H, OCH,), 2.91 (t, 7.4 Hz, 2H, CH$_2$CH$_2$COOH), 2.67 (t, 5.9 Hz, 2H, H-7'), 2.40–2.46 (m, 4H, CH$_2$CH$_2$COOH and H-4'), 1.72–1.78 (m, 4H, H-5',6').

MS: m/z 441.2.

Example 206

3-[2-(2-Oxo-6-phenyl-1,2-dihydroindol-3-ylidenemethyl)-4,5,6,7-tetrahydro-1H-indol-3-yl]-propionic acid A mixture of 90 mg 6-phenyl-2-oxindole, 95 mg 3-(2-formyl-4,5,6,7-tetrahydro-1H-indol-3-yl)-propionic acid and piperidine (3 drops) in ethanol (2 mL) was held in a sealed tube at 90° C. for 4 hrs. The reaction mixture was concentrated and acidified with 6 N hydrochloric acid. The precipitate was collected by filtration and washed with water and hexane to give 59 mg of 3-[2-(2-oxo-6-phenyl-1,2-dihydro-indol-3-ylidenemethyl)-4,5,6,7-tetrahydro-1H-indol-3-yl]-propionic acid as a brown solid (31% yield).

$^1$H NMR (d$_6$-DMSO, 360 MHz): δ13.27 (s, br, 1H, NH-1') 12.06 (s, v br, 1H, COOH), 10.80 (s, br, 1H, NH-1), 7.74 (d, 7.9 Hz, 1H, H-4), 7.64 (s, 1H, H-vinyl), 7.62 (d, 7.7 Hz, 2H), 7.44 (t, 7.7 Hz, 2H), 7.32 (dd, 7.7 Hz, 1H), 7.27 (dd, 1.1, 7.9 Hz 1H, H-5), 7.10 (d, 1.1 Hz, 1H, H-7), 2.92 (t, 7.3 Hz, 2H, CH$_2$CH$_2$COOH), 2.67 (t, 5.5 Hz, 2H, H-7'), 2.41–2.46 (m, 4H, CH$_2$CH$_2$COOH and H-4'), 1.73–1.76 (m, 4H, H-5',6').

MS: m/z 411.2.

Example 207

3-{2-[6-(2-Methoxyphenyl)-2-oxo-1,2-dihydro-indol-3-ylidenemethyl]-4,5,6,7-tetrahydro-1H-indol-3-yl}-proionic acid Tetrakis(triphenylphosphine)palladium (1 g) was added to a mixture of 5 g of 2-methoxyphenylboronic acid, 6.6 g of 5-bromo-2-fluoronitrobenzene and 30 mL of 2 M sodium carbonate solution in 50 mL of toluene and 50 mL of ethanol. The mixture was refluxed for 2 hours, concentrated, and the residue extracted twice with ethyl acetate. The ethyl acetate layer was washed with water and brine, dried, and concentrated to give a dark green oil which solidified on standing to give crude 4-fluoro-2'-methoxy-3-nitrobiphenyl.

Dimethyl malonate (14 mL) was added dropwise to 2.9 g of sodium hydride suspended in 50 mL of dimethylsulfoxide. The mixture was stirred at 100° C. for 15 minutes and cooled to room temperature. Crude 4-fluoro-2'-methoxy-3-nitrobiphenyl in 60 mL of dimethylsulfoxide was added and the mixture stirred at 100° C. for 2 hours. The reaction mixture was cooled, quenched with 300 mL of saturated ammonium chloride solution and extracted twice with ethyl acetate. The extracts were combined, washed with saturated ammonium chloride, water, and brine, dried over anhydrous sodium sulfate and concentrated to give crude dimethyl 2'-methoxy-3-nitrobiphenyl-4-malonate as a yellow oil.

Crude 2'-methoxy-3-nitrobiphenyl-4-malonate was stirred at 100° C. in 50 mL of 6 N hydrochloric acid for 24 hours and cooled. The precipitate that formed was collected by filtration, washed with water and hexane, and dried to give 9.8 of 2'-methoxy-2-nitrobiphenyl-4-acetic acid as a light tan solid.

Iron chips (5 g) were added in one portion to 9.8 g of 2'-methoxy-3-nitrobiphenyl-4-acetic acid in 50 mL of glacial acetic acid and the mixture was stirred at 100° C. for 3 hours. The reaction mixture was concentrated to dryness, sonicated in ethyl acetate and filtered to remove insolubles. The filtrate was washed twice with 1 N hydrochloric acid, then with water and brine, dried over anhydrous sodium sulfate and concentrated. The residue was chromatographed on silica gel using ethyl acetate:hexane 1:2 as the eluent to give 5.4 g (69% based on 5-bromo-2-fluoronitrobenzene) of 6-(2-methoxyphenyl)-2-oxindole as a rose colored solid.

A mixture of 103 mg of 6-(2-methoxyphenyl)-2-oxindole, 95 mg of 3-(2-formyl-4,5,6,7-tetrahydro-1H-indol-3-yl)-propionic acid and piperidine (3 drops) in ethanol (2 mL) was held in a sealed tube at 90° C. for 4 hrs. The reaction mixture was concentrated and acidified with 6 N hydrochloric acid. The precipitate was collected by filtration and washed with water and hexane to give 67 mg of 3-{2-[6-(2-methoxyphenyl)-2-oxo-1,2-dihydroindol-3-ylidenemethyl]-4,5,6,7-tetrahydro-1H-indol-3-yl}-propionic acid as a brown solid (35% yield).

$^1$H NMR (d$_6$-DMSO, 360 MHz): δ13.26 (s, br, 1H, H1, 20, vr H OH) 10.71 (s, br, 1H, NH-1), 7.67 (d, 7.7 Hz, 1H, H-4), 7.61 (s, 1H, H-vinyl), 7.27–7.34 (m, 2H,), 7.01–7.10 (m, 2H), 7.05 (dd, 1.2, 7.7 Hz, 1H, H-5), 6.99 (d, 1.2 Hz, 1H, H-7), 3.75 (s, 3H, OCH$_3$), 2.91 (t, 7.5 Hz, 2H, CH$_2$CH$_2$COOH), 2.68 (t, 7 Hz, 2H, H-7'), 2.40–2.46 (m, 4H, CH$_2$CH$_2$COOH and H-4'), 1.71–1.78 (m, 4H, H-5',6')

MS m/z 441.2.

Example 208

3-[2-(5-Isopropylaminosulfonyl-2-oxo-1,2-dihydroindol-3-ylidenemethyl)-4,5,6,7-tetrahydro-1H-indol-3-yl]-propionic acid To a 100 mL flask charged with 27 mL of chlorosulfonic acid was slowly added 13.3 g of 2-oxindole. The reaction temperature was maintained below 30° C. during the addition. After the addition, the reaction mixture was stirred at room temperature for 1.5 hr, heated to 68° C. and stirred an additional 1 hr, cooled, and poured into water. The precipitate was washed with water and dried in a vacuum oven to give 11.0 g of 5-chlorosulfonyl-2-oxindole (50% yield) which was used without further purification.

A suspension of 3 g of 5-chlorosulfonyl-2-oxindole, 1.15 g of isopropylamine and 1.2 mL of pyridine in 50 mL of dichloromethane was stirred at room temperature for 4 hours at which time a white solid was present. The solid was collected by vacuum filtration, slurry-washed with hot ethanol, cooled, collected by vacuum filtration and vacuum dried at 40° C. to give 1.5 g (45%) of 5-isopropylaminosulfonyl-2-oxindole.

$^1$H NMR (d$_6$-DMSO, 300 MHz) δ10.69 (s, br, 1H, NH), 7.63 (dd, 1.8 Hz, 1H, H-6), 7.59 (d, 1 Hz, 1H, H-4), 7.32 (d, 7 Hz, 1H, NH—SO$_2$—), 6.93 (d, 8 Hz, 1H, H-7), 3.57 (s, 2H, H-3), 3.14–3.23 (m, 1H, CH—(CH$_3$)$_2$), 0.94 (d, 7 Hz, 6H, CH$_3$).

A mixture of (2-Formyl-4,5,6,7-tetrahydro-1H-indol-3-yl)-propionic acid (5.4 g), 5.7 g of 5-isopropylaminosulfonyl-2-oxindole and 2.7 g of piperidine in 25 mL of ethanol was refluxed for 4 hours. Upon addition of acetic acid (8 mL), a precipitate formed. The mixture was refluxed for 5 minutes and cooled to ambient temperature. The precipitate was collected by vacuum filtration and washed with 20 mL of ethanol. The solids were slurry-washed in 30 mL of refluxing ethanol, cooled, collected by vacuum filtration, washed with 30 mL of ethanol and vacuum dried to give 8.1 g (80% yield) of 3-[2-(5-isopropylaminosulfonyl-2-oxo-1,2-dihydroindol-3-ylidenemethyl)-4,5,6,7-tetrahydro-1H-indol-3-yl]-propionic acid as an orange solid.

$^1$H NMR (d$_6$-DMSO): δ13.3 (s, 1H, pyrrole NH), 12.0 (br s, 1H, COOH), 10.7 (s, 1H, CONH), 8.1, 7.5, 7.3, 7.0 (m, each 4H, aromatic), 7.7 (s, 1H, —CH=), 2.3 (m, 1H, —CH—), 2.9, 2.7 (t, each 4H, —CH$_2$CH$_2$CO—), 2.4 (m, 4H, —CH$_2$—, —CH$_2$—), 1.7 (m, 4H, —CH$_2$CH$_2$—), 0.9 (d, 6H, CH$_3$).

MS m/z 458.

Example 209

3-[2-(6-Morpholin-4-yl-2-oxo-1,2-dihydroindol-3-ylidenemethyl)-4,5,6,7-tetrahydro-1H-indol-3-yl]-propionic acid A mixture of 4 g of 6-(morpholin-4-yl)-2-oxindole, 3.75 g of 3-(2-formyl-4,5,6,7-tetrahydro-1H-indol-3-yl) propionic acid, and 1.8 mL of piperidine in ethanol (60 mL) was refluxed for 6 hrs. The reaction mixture was concentrated and acidified with 6 N hydrochloric acid to pH 6. The precipitate was collected by filtration, washed once with water, twice with ethyl acetate and twice with methanol to give 2.6 g of 3-[2-(6-Morpholin-4-yl-2-oxo-1,2-dihydroindol-3-ylidenemethyl)-4,5,6,7-tetrahydro-1H-indol-3-yl]propionic acid as an orange solid (34% yield).

$^1$H NMR (d$_6$-DMSO, 360 MHz): δ13.04 (s, br, 1H, NH-1'), 12.05 (s, vbr, 1H, COOH), 10.60 (s, br, 1H, NH-1), 7.50 (d, 8.0 Hz, 1H, H-4), 7.39 (s, 1H, H-vinyl), 6.60 (d, 8.0 Hz, 1H, H-5), 6.43 (s, 1H, H-7), 3.73 (d, 4.7, 4H, H-2", 6"), 3.09 (s, 4H, H-3", 5"), 2.86 (t, 7.1 Hz, 2H, CH$_2$CH$_2$COOH), 2.64 (s, br, 2H, H-7'), 2.37–2.43 (m, 4H, CH$_2$CH$_2$COOH and H-4'), 1.71–1.75 (m, 4H, H-5',6').

MS m/z 422.3.

Example 210

3-[2-(5-Chloro-4-methyl-2-oxo-1,2-dihydro-indol-3-ylidenemethyl)-4,5,6,7-tetrahydro-1H-indol-3-yl]-propionic acid A suspension of 3.0 g of 4-methyl-2-oxindole was stirred in 50 mL of acetonitrile at room temperature while 3.3 g of N-chlorosuccinimide was added in portions. Trifluoroacetic acid (1 mL) was then added. A white precipitate formed. The suspension was stirred at room temperature for 3 days. The white solid was collected by vacuum filtration, washed with a small amount of cold acetone and dried overnight in a vacuum oven at 40° C. to give 2.5 g (68%) of 5-chloro-4-methyl-2-oxindole.

A mixture of (2-Formyl-4,5,6,7-tetrahydro-1H-indol-3-yl)-propionic acid (5.4 g), 4.0 g of 5-chloro-4-methyl-2-oxindole and 2.7 g of piperidine in 25 mL of ethanol was refluxed for 4 hours. Addition of acetic acid (8 mL) resulted in the formation of a precipitate. The mixture was refluxed for 5 minutes and cooled to ambient temperature. The precipitate was collected by vacuum filtration and washed with 20 mL of ethanol. The solids were slurry-washed with 30 mL of refluxing ethanol, cooled, collected by vacuum filtration, washed with 30 mL of ethanol and vacuum dried to give 6.8 g (80%) of 3-[2-(5-Chloro-4-methyl-2-oxo-1,2-dihydroindol-3-ylidenemethyl)-4,5,6,7-tetrahydro-1H-indol-3-yl]-propionic acid as an orange solid.

$^1$H NMR (d$_6$-DMSO) δ13.1 (s, 1H, pyrrole NH), 12.0 (br s, 1H, COOH), 10.7 (s, 1H, CONH), 7.6 (s, 1H, —CH=), 7.3, 6.7(m, each 2H, aromatic), 2.9, 2.7 (t, each 4H, —CH$_2$CH$_2$CO—), 2.7 (s, 3H, CH$_3$), 2.4(m, 4H, —CH$_2$—, —CH$_2$—), 1.7 (m, 4H, —CH$_2$CH—).

Example 211

3-[2-(5-Bromo-4-methyl-2-oxo-1,2-dihydroindol-3-ylidenemethyl)-4,5,6,7-tetrahydro-1H-indol-3-yl]-propionic acid

A mixture of (2-Formyl-4,5,6,7-tetrahydro-1H-indol-3-yl)-propionic acid (5.4 g), 5.0 g of 5-bromo-4-methyl-2-oxindole and 2.7 g of piperidine in 25 mL of ethanol was refluxed for 4 hours. Acetic acid (8 mL) was slowly added and a precipitate formed. The mixture was refluxed for 5 minutes and cooled to ambient temperature. The precipitate was collected by vacuum filtration and washed with 20 mL of ethanol. The solids were slurry-washed in 30 mL of refluxing ethanol, cooled, collected by vacuum filtration, washed with 30 mL of ethanol and vacuum dried to give 7.6 g (80%) of 3-[2-(5-bromo-4-methyl-2-oxo-1,2-dihydroindol-3-ylidenemethyl)-4,5,6,7-tetrahydro-1H-indol-3-yl]-propionic acid as an red-orange solid.

$^1$H NMR (d$_6$-DMSO): δ13.1 (s, 1H, pyrrole NH), 12.0 (br s, 1H, COOH), 10.7 (s, 1H, CONH), 7.8 (s, 1H, —CH═), 7.3, 6.7, (m, each 2H, aromatic), 2.9, 2.7 (t, each 4H, —CH$_2$CH$_2$CO—), 2.7 (s, 3H, CH$_3$), 2.4 (m, 4H —CH$_2$—, —CH$_2$—), 1.7 (m, 4H, —CH$_2$CH$_2$—).

MS: m/z 427,429.

Example 212

3-[2-(5-Bromo-2-oxo-1,2-dihydroindol-3-ylidenemethyl)-4,5,6,7-tetrahydro-1H-indol-3-yl]-N-(2-morpholin-4-ylethyl)-propionamide

3-[2-(5-Bromo-2-oxo-1,2-dihydroindol-3-ylidenemethyl)-4,5,6,7-tetrahydro-1H-indol-3-yl]-propionic acid (12.3 g) was dissolved in 150 mL of dimethylformamide. Carbonyldiimidazole (6.3 g) was added and the mixture stirred at ambient temperature for 1 hour. 4-(2-Aminoethyl)morpholine (7.7 g) and 30 mL of dimethylformamide were added and the stirring continued overnight at room temperature. Fifty mL of water was added to the mixture and stirring was continued for 10 minutes. The precipitate was collected by vacuum filtration, washed with 20 mL of water and then 20 mL of ethanol. The solid was slurry-washed in 30 mL of refluxing ethanol for 5 minutes and cooled to room temperature. The solid was collected by vacuum filtration, washed with 20 mL of ethanol and vacuum dried to give 12.5 g (80%) of 3-[2-(5-bromo-2-oxo-1,2-dihydroindol-3-ylidenemethyl)-4,5,6,7-tetrahydro-1H-indol-3-yl]-N-(2-morpholin-4-ylethyl)-propionamide.

Example 213

3-[2-(5-Chloro-2-oxo-1,2-dihydroindol-3-ylidenemethyl)-4,5,6,7-tetrahydro-1H-indol-3-yl]-N-(2-morpholin-4-ylethyl)-propionamide

3-[2-(5-Chloro-2-oxo-1,2-dihydroindol-3-ylidenemethyl)-4,5,6,7-tetrahydro-1H-indol-3-yl]-propionic acid (11 g) was dissolved in 150 mL of dimethylformamide. Carbonyldiimidazole (6.3 g) was added and the mixture stirred at ambient temperature for 1 hour. 4-(2-Aminoethyl)morpholine (7.7 g) and 30 mL of dimethylformamide were added and the stirring continued overnight at room temperature. Fifty mL of water was added to the mixture and stirring was continued for 10 minutes. The precipitate was collected by vacuum filtration, washed with 20 mL of water and then 20 mL of ethanol. The solid was slurry-washed in 30 mL of refluxing ethanol for 5 minutes and cooled to room temperature. The solid was collected by vacuum filtration, washed with 20 mL of ethanol and vacuum dried to give 11.5 g (80%) of 3-[2-(5-chloro-2-oxo-1,2-dihydroindol-3-ylidenemethyl)-4,5,6,7-tetrahydro-1H-indol-3-yl]-N-(2-morpholin-4-ylethyl)-propionamide.

Example 214

3-[2-(2-Oxo-1,2-dihydroindol-3-ylidenemethyl)-phenyl]-propionic acid

To a solution of 13.4 g of phthalic dicarboxaldehye in 100 mL of dichloromethane was added in portions over 5 minutes 35 g of ethyl (triphenylphosphoranylidene)acetate. The reaction mixture was stirred at room temperature overnight and concentrated. The residue was stirred in 500 mL of a 6:1 mixture of hexanes:ethyl acetate for 1 hr. The solids were removed by fitration and the filtrates concentrated. The product was chromatographed on a silica gel column to give 10 g of ethyl 3-(2-formylphenyl)propenate as a mixture of E and Z isomers.

The above mixture was dissolved in 100 mL of ethyl acetate containing 100 mg of 5% palladium on carbon and stirred under hydrogen (balloon pressure) for 10 hrs. The mixture was filtered through a bed of celite which was washed with ethyl acetate. The combined filtrates were concentrated to give 8 g of ethyl 3-(2-formylphenyl)propionate.

A mixture of 1 g of ethyl 3-(2-formylphenyl)propenate, 500 mg oxindole and 0.1 mL piperidine in 5 mL of ethanol was stirred at 90° C. overnight. The mixture was evaporated and purified on a silica gel column to give 450 mg of ethyl (E)-3-[(2-oxo-1,2-dihydroindol-3-ylidenemethyl)phenyl]-propionate (M+1=322).

To 300 mg of ethyl (E)-3-[(2-oxo-1,2-dihydroindol-3-ylidenemethyl)phenyl]-propionate in 3 mL of ethanol was added 2 mL of 2N sodium hydroxide. The mixture was stirred at 90° C. for 2 hrs, cooled and acidified with 6 N hydrochloric acid to pH 3. The solid was collected by filtration and washed with cold ethanol to give 30 mg of 3-[2-(2-oxo-1,2-dihydroindol-3-ylidenemethyl)-phenyl]-propionic acid as a yellow solid.

$^1$H NMR (d$_6$-DMSO): δ12.1 (s, 1H, COOH),10.6 (S, 1H, CONH), 7.7 (s, 1H, ═CH) 7.6, 7.4, 7.3, 7.2, 7.0, 6.8,6.7 (m, 8H, aromatic), 2.9, 2.5 (t, each 4H, CH$_2$CH$_2$).

MS: m/z 294.

Example 215

3-[4-Methyl-2-(2-oxo-1,2-dihydroindol-3-ylidenemethyl)-1H-pyrrol-3-yl]-prorionic acid

3,5-Dimethyl-4-(2-methoxycarbonylethyl)-1H-pyrrole-2-carboxylic acid ethyl ester (127 g) was dissolved in acetic acid (1900 mL), water (1900 mL) and tetrahydrofuran (1900 mL) and cooled to −30° C. Cerric ammonium nitrate (1097 g) was added in portions with stirring to give a reddish-orange suspension. The suspension was stirred at 0° C. for 2 hours, neutralized to pH 7 with sodium bicarbonate and extracted with ethyl acetate (2000 mL). The ethyl acetate layer was separated, washed with brine (200 mL) and dried over anhydrous sodium sulfate (20 g). The solvent was removed to give 80.2 g (60%) of 5-formyl-4-(2-methoxycarbonylethyl)-3-methyl-1H-pyrrole-2-carboxylic acid ethyl ester as an oil.

5-Formyl-4-(2-methoxycarbonylethyl)-3-methyl-1H-pyrrole-2-carboxylic acid ethyl ester (80.2 g), 2-oxindole (37.9 g) and ethanol (300 mL) were warmed to 70° C. in a 500 mL, 3-neck round bottom flask equipped with mechanical stirring and a reflux condenser. Piperidine (1.3 g) was added and the mixture was refluxed for 4 hours. The mixture was cooled to 10° C. and the orange precipitate collected by vacuum filtration and washed with 30 mL of ethanol. The solid was slurry-washed in 150 mL of refluxing ethanol, cooled, collected by vacuum filtration, washed with 30 mL of ethanol and vacuum dried to give 81.7 g (75%) of 4-(2-Methoxycarbonylethyl)-3-methyl-5-(2-oxo-1,2-dihydroindol-3-ylidenemethyl)-1H-pyrrole-2-carboxylic acid ethyl ester as an orange solid.

4-(2-Methoxycarbonylethyl)-3-methyl-5-(2-oxo-1,2-dihydro-indol-3-ylidenemethyl)-1H-pyrrole-2-carboxylic acid ethyl ester (81.7 g) ), 56.5 g of potassium hydroxide, 200 mL of ethanol and 200 mL of water were charged to a 1 L, 3 neck round bottom flask equipped with mechanical stirring and a thermometer. The mixture was stirred at 90° C. for 90 minutes, cooled to room temperature, and acidified with acetic acid until a precipitate formed. The precipitate was collected by vacuum filtration, washed with 50 mL of water and vacuum dried to give 69.1 g (85 %) of 4-(2-carboxyethyl)-3-methyl-5-(2-oxo-1,2-dihydroindol-3-ylidenemethyl)-1H-pyrrole-2-carboxylic acid as a red solid.

4-(2-carboxyethyl)-3-methyl-5-(2-oxo-1,2-dihydroindol-3-ylidenemethyl)-1H-pyrrole-2-carboxylic acid (10 g) suspended in 50 mL of ethylene glycol (b.p. 198° C.) was sealed in a 1 L pressure reactor, the reactor was pressurized to 120 psi with nitrogen and then heated to 150° C. for 3 hours. The reaction mixture was cooled to room temperature and then diluted with 50 mL of water. The resulting precipitate was collected by vacuum filtration and was washed twice with 100 mL of water to give a mixture of 3-[4-methyl-2-(2-oxo-1,2-dihydroindol-3-ylidenemethyl)-1H-pyrrol-3-yl]-propionic acid and 3-[4-methyl-2-(2-oxo-1,2-dihydroindol-3-ylidenemethyl)-1H-pyrrol-3-yl]-propionic acid 2-hydroxyethyl ester as a dark orange solid. The solid was used in the next step without drying.

$^1$H NMR ($d_6$-DMSO) δ13.3 (s, br, 1H, NH), 10.77 (s, 1 H. NH), 7.6 (s, 1 H, H-vinyl), 7.67, 7.08, 6.97, 6.85 (m, 4 H, Ar—H), 4.73 (t, J=6 Hz, 1 H, OH), 3.97–4.0 (m, 2H, $CH_2$), 3.5–3.55 (m, 2 H, $CH_2$), 2.98 (t, J=7.5 Hz, 2 H, $CH_2$), 2.51 (t, J=7.5 Hz, 2 H, $CH_2$), 2.04 (s, 3 H, $CH_3$).

MS m/z 341 (M+1).

3-[4-methyl-2-(2-oxo-1,2-dihydroindol-3-ylidenemethyl)-1H-pyrrol-3-yl]-propionic acid and 3-[4-methyl-2-(2-oxo-1,2-dihydroindol-3-ylidenemethyl)-1H-pyrrol-3-yl]-propionic acid 2-hydroxyethyl ester, 1.9 g of potassium hydroxide, 50 mL of water, and 50 mL of ethanol in a 500 mL 3 neck round bottom flask were stirred at 70° C. for 1 hour. The mixture was cooled to room temperature and acidified with 2 N hydrochloric acid until a precipitate formed. The precipitate was collected by vacuum filtration and washed with ethanol:water mixture (1:1, 100 mL). The solid was slurry-washed with ethyl acetate:ethanol mixture (1:1, 100 mL) at 70° C. for 30 minutes and then cooled to room temperature. The product was collected by vacuum filtration and vacuum dried at 40° C. overnight to give 7.8 g (90% overall yield) of 3-[4-methyl-2-(2-oxo-1,2-dihydroindol-3-ylidenemethyl)-1H-pyrrol-3-yl]-propionic acid as a dark orange solid. (R. B. Woodward et al., *Tetrahedron*, 1990, 46 (22), 7599–7659)

$^1$HNMR ($d_6$-DMSO) δ13.28 (s, br, 1 H, NH), 12.05 (s, 1 H, COOH), 10.78 (s, 1 H, NH), 7.68 (d, J=7 Hz, 1 H, Ar—H), 7.64 (s, 1 H, H-vinyl), 7.11 (t, J=7 Hz, 1 H, Ar—H), 7.11 (s, 1 H), 6.97 (t, J=7 Hz, 1 H, Ar—H), 6.86 (d, J=7 Hz, 1 H, Ar—H), 2.94 (t, J=7.5 Hz, 2 H, $CH_2$), 2.41 (t, J=7.5 Hz, 2 H, $CH_2$), 2.04 (s, 3H, $CH_3$).

Example 216

3-[2-(5-Chloro-2-oxo-1,2-dihydroindol-3-ylidenemethyl)-4-methyl-1H-pyrrol-3-yl]-propionic acid 5-Formyl-4-(2-ethoxycarbonylethyl)-3-methyl-1H-pyrrole-2-carboxylic acid ethyl ester (281 mg), 5-chloro-2-oxindole (168 mg), and piperidine (2 drops) in ethanol (2 mL) were refluxed for 2 hours. The reaction mixture was cooled and the precipitate that formed was filtered, washed with ethanol and hexanes, and dried to give 369 mg (86%) of 4-(2-ethoxycarbonylethyl)-3-methyl-5-(5-chloro-2-oxo-1,2-dihydro-indol-3-ylidenemethyl)-1H-pyrrole-2-carboxylic acid ethyl ester as a light yellow needle crystals.

A mixture of 4-(2-ethoxycarbonylethyl)-3-methyl-5-(5-chloro-2-oxo-1,2-dihydroindol-3-ylidenemethyl)-1H-pyrrole-2-carboxylic acid ethyl ester (346 mg) and potassium hydroxide (560 mg) in ethanol (5 mL) was heated to 95° C. and then cooled, upon which red crystals formed. The crystals were dissolved in water and acidified with 2 N hydrochloric acid to pH 2. The precipitate was filtered, washed with water, and dried in a vacuum oven overnight to give 299 mg (100%) of 4-(2-carboxyethyl)-3-methyl-5-(5-chloro-2-oxo-1,2-dihydroindol-3-ylidenemethyl)-1H-pyrrole-2-carboxylic acid as a brown solid.

4-(2-carboxyethyl)-3-methyl-5-(5-chloro-2-oxo-1,2-dihydroindol-3-ylidenemethyl)-1H-pyrrole-2-carboxylic acid suspended in ethylene glycol (5 mL) was heated in a sealed tube in a pre-heated oil bath at 200° C. for 2 hours. The reaction mixture was cooled to 90° C. and potassium hydroxide (2 pellets) were added. The mixture was then heated at 90° C. for 30 minutes, after which time it was cooled, poured into water, and acidified with 2 N hydrochloric acid to pH 2. The precipitate that formed was filtered, washed with water, and dried in a vacuum oven overnight to give 77 mg (29%) of 3-[2-(5-Chloro-2-oxo-1,2-dihydroindol-3-ylidenemethyl)-4-methyl-1H-pyrrol-3-yl]-propionic acid.

$^1$HNMR ($d_6$-DMSO) δ13.31 (s, br. 1 H, NH), 12.05 (s, 1 H, COOH), 10.89(s, br, 1 H, NH), 7.85 (d, J=2 Hz, 1 H, H-4), 7.75 (s, 1 H, H-vinyl), 7.16 (d, J=3 Hz, 1 H), 7.11 (dd, J=2.8 Hz, 1 H, H-6), 6.84 (d, J 8 Hz, 1 H, H-7), 2.97 (t, J=7.5 Hz, 2 H, $CH_2$), 2.41 (t, J=7.5 Hz, 2 H, $CH_2$), 2.04 (s, 3 H, $CH_3$).

MS m/z 331 (M+1).

Example 217

3-[2-(6-Methoxy-2-oxo-1,2-dihydroindol-3-ylidenemethyl)-4-methyl-1H-pyrrol-3-yl]-propionic acid 5-Formyl-4-(2-ethoxycarbonylethyl)-3-methyl-1H-pyrrole-2-carboxylic acid ethyl ester (591 mg), 6-methoxy-2-oxindole (333 mg) and piperidine (0.1 mL) in ethanol (4 mL) were stirred at 90° C. for 2 hours. Potassium hydroxide (537 mg) was added to the mixture and it was then stirred at 95° C. for and additional hour. The reaction mixture was cooled and concentrated, dissolved in water, and acidified with 2 N hydrochloric acid to pH 2. The precipitate was filtered, washed with water, and dried in a vacuum oven overnight to give 730 mg (99%) of 4-(2-carboxyethyl)-3-methyl-5-(6-methoxy-2-oxo-1,2-dihydroindol-3-ylidenemethyl)-1H-pyrrole-2-carboxylic acid.

4-(2-carboxyethyl)-3-methyl-5-(6-methoxy-2-oxo-1,2-dihydroindol-3-ylidenemethyl)-1H-pyrrole-2-carboxylic acid (501 mg) suspended in ethylene glycol (10 mL) was heated in a sealed tube in a pre-heated oil bath at 200° C. for 2 hours. The reaction mixture was cooled to 90° C. and potassium hydroxide (2 pellets) was added. The mixture was then stirred at 90° C. for 30 minutes, after which time it was cooled, poured into water, and acidified with 2 N hydrochloric acid to pH 2. The precipitate was filtered, washed with water, and dried in a vacuum oven overnight to give 221 mg (48%) of 3-[2-(6-methoxy-2-oxo-1,2-dihydro-indol-3-ylidenemethyl)-4-methyl-1H-pyrrol-3-yl]-propionic acid.

$^1$HNMR (d$_6$-DMSO) δ13.09 (s, 1 H, NH), 12.05 (s, 1 H, COOH), 10.74 (s, 1 H, NH), 7.58 (d, J=8 Hz, 1 H, H-4), 7.48 (s, 1 H, H-vinyl), 7.04 (d, J=2 Hz, 1 H), 6.56 (dd, J=2.8 Hz, 1 H, H-5), 6.43 (d, J=2 Hz, 1 H), 3.75 (s, 3 H, OCH$_3$), 2.91 (t, J=7.5 Hz, 2 H, CH$_2$), 2.4 (t, J=7.5 Hz, 2 H, CH$_2$), 2.03 (s, 3 H, CH$_3$).

MS m/z 325 (M−1).

Example 218

3-[2-(4-Methyl-2-oxo-1,2-dihydroindol-3-ylidenemethyl)-4-methyl-1H-iyrrol-3-yl]-propionic acid A mixture of 5-formyl-4-(2-ethoxycarbonylethyl)-3-methyl-1H-pyrrole-2-carboxylic acid ethyl ester (281 mg), 4-methyl-2-oxindole (147 mg) and piperidine (2 drops) in ethanol (2 mL) was stirred at 90° C. for 2 hours. Potassium hydroxide (213 mg) was added, the temperature was increased to 95° C. and held there for 1 hour. The reaction mixture was cooled and concentrated. The residue was dissolved into water and acidified with 2 N hydrochloric acid to pH 2. The precipitate was filtered, washed with water and dried in a vacuum oven overnight to give 337 mg (95%) of 4-(2-carboxyethyl)-3-methyl-5-(4-methyl-2-oxo-1,2-dihydroindol-3-ylidenemethyl)-1H-pyrrole-2-carboxylic acid.

4-(2-carboxyethyl)-3-methyl-5-(4-methyl-2-oxo-1,2-dihydroindol-3-ylidenemethyl)-1H-pyrrole-2-carboxylic acid (300 mg) suspended in ethylene glycol (5 mL) was heated in a sealed tube in a pre-heated oil bath at 200° C. for 2 hours. The reaction mixture was cooled to 90° C. and potassium hydroxide (1 pellet) was added. It was then stirred at 90° C. for 30 minutes. The reaction mixture was cooled, poured into water, and acidified with 2 N hydrochloric acid to pH 2. The precipitate was filtered, washed with water, and purified on a silica gel column to give 115 mg (44% yield) of 3-[2-(4-methyl-2-oxo-1,2-dihydroindol-3-ylidenemethyl)-4-methyl-1H-pyrrol-3-yl]-propionic acid.

$^1$HNMR (d$_6$-DMSO) δ13.37 (s, 1 H, NH), 12.04 (s, 1 H, COOH), 10.81 (s, 1 H, NH), 7.69 (s, 1 H, H-vinyl), 7.09 (d, J=2.5 Hz, 1 H), 7.01 (t, J=7.5 HZ, 1 H, Ar—H), 6.79 (d, J=7.5 Hz, 1 H, Ar—H), 6.74 (d, J=7.5 Hz, 1 H, Ar—H), 2.88 (t, J=7.2 Hz, 2 H, CH$_2$), 2.61 (s, 3 H, CH$_3$-4), 2.44 (t, J=7.2 Hz, 2 H, CH$_2$), 2.04 (s, 3 H, CH$_3$).

MS m/z 309 (M−1).

Example 219

3-[2-(6-Chloro-2-oxo-1,2-dihydroindol-3-ylidenemethyl)-4-methyl-1H-pyrrol-3-yl]-propionic acid 5-Formyl-4-(2-ethoxycarbonylethyl)-3-methyl-1H-pyrrole-2-carboxylic acid ethyl ester (281 mg), 6-chloro-2-oxindole (168 mg) and piperidine (2 drops) in ethanol (2 mL) were stirred at 90° C. for 2 hours. Potassium hydroxide (537 mg) was added to the mixture and it was then stirred at 95° C. for and additional hour. The reaction mixture was cooled and concentrated. The residue was dissolved into water and acidified with 2 N hydrochloric acid to pH 2. The precipitate was filtered, washed with water, and dried in a vacuum oven overnight to give 270 mg (72%) of 4-(2-carboxy-ethyl)-3-methyl-5-(6-chloro-2-oxo-1,2-dihydroindol-3-ylidenemethyl)-1H-pyrrole-2-carboxylic acid.

4-(2-carboxyethyl)-3-methyl-5-(6-chloro-2-oxo-1,2-dihydro-indol-3-ylidenemethyl)-1H-pyrrole-2-carboxylic acid (240 mg) suspended in ethylene glycol (5 mL) was held in a sealed tube in a pre-heated oil bath at 200° C. for 2 hours. The reaction mixture was cooled to 90° C. and potassium hydroxide (2 pellets) was added. It was then stirred at 90° C. for 30 minutes. The reaction mixture was cooled, poured into water, and acidified with 2 N hydrochloric acid to pH 2. The precipitate was filtered, washed with water, and purified on a silica gel column using ethyl acetate:hexanes:glacial acetic acid 50:50:10 as eluent to give 45 mg (21%) of 3-[2-(6-chloro-2-oxo-1,2-dihydroindol-3-ylidenemethyl)-4-methyl-1H-pyrrol-3-yl]-propionic acid.

$^1$HNMR (d$_6$-DMSO) δ13.2 (s, 1H, NH), 12.04 (s, 1 H, COOH), 10.92 (s, 1 H, NH), 7.72 (d, J=8 Hz, 1 H, H-4), 7.68 (s, 1 H, H-vinyl), 7.15 (d, J=2.4 HZ, 1 H), 7.01 (dd, J=2.8 Hz, 1 H, H-6), 6.86 (d, J=2 Hz, 1 H, H-7), 2.94 (t, J=7.5 Hz, 2 H, CH$_2$), 2.4 (t, J=7.5 Hz, 2 H, CH$_2$), 2.03 (s, 3 H, CH$_3$).

MS m/z 329 (M−1).

Example 220

3-[2-(5-Bromo-2-oxo-1,2-dihydroindol-3-ylidenemethyl)-4-methyl-1H-pyrrol-3-yl]-propionic acid A mixture of 5-formyl-4-(2-ethoxycarbonylethyl)-3-methyl-1H-pyrrole-2-carboxylic acid ethyl ester (281 mg) 5-bromo-2-oxindole (220 mg), and piperidine (2 drops) in ethanol (2 mL) was stirred at 90° C. for 2 hours. Potassium hydroxide (537 mg) was added and the temperature was increased to 95° C. for 1 hour. The reaction mixture was cooled and concentrated. The residue was dissolved into water and acidified with 2 N hydrochloric acid to pH 2. The precipitate that formed was filtered, washed with water and dried in a vacuum oven overnight to give 411 mg (98%) of 4-(2-carboxyethyl)-3-methyl-5-(5-bromo-2-oxo-1,2-dihydro-indol-3-ylidenemethyl)-1H-pyrrole-2-carboxylic acid.

4-(2-carboxyethyl)-3-methyl-5-(5-bromo-2-oxo-1,2-dihydro-indol-3-ylidenemethyl)-1H-pyrrole-2-carboxylic acid (380 mg) suspended in ethylene glycol (5 mL) was held in a sealed tube in a pre-heated oil bath at 200° C. for 2 hours. The reaction mixture was cooled to 90° C. and potassium hydroxide (1 pellet) was added. It was then stirred at 90° C. for 30 minutes. The reaction mixture was cooled, poured into water, and acidified with 2 N hydrochloric acid to pH 2. The precipitate was filtered, washed with water, and purified using silica gel column chromatography to give 168 mg (49% yield) of 3-[2-(5-bromo -2-oxo-1,2-dihydroindol-3-ylidenemethyl)-4-methyl-1H-pyrrol-3-yl]-propionic acid.

$^1$HNMR (d$_6$-DMSO) δ13.32 (s, 1 H, NH), 12.0 (s, 1 H, COOH), 10.9 (s, 1 H, NH), 7.97 (d, J=2 HZ, 1 H, h-4), 7.75 (s, 1 H, H-vinyl), 7.23 (dd, v=2.8 Hz, 1 H, H-6), 7.16 (d, v=2.6 Hz, 1 H), 6.8 (d, J=8 Hz, 1 H, H-7), 2.97 (t, J=7.7 Hz, 2 H, CH$_2$), 2.41 (t, J=7.7 Hz, 2 H, CH$_2$), 2.04 (s, 3 H, CH$_3$).

MS m/z 375/377.

Example 221

3-[2-(5-Methyl-2-oxo-1,2-dihydroindol-3-ylidenemethyl)-4-methyl-1H-pyrrol-3-yl]-propionic acid 5-Methylisatin (15.0 g) and 60 mL of hydrazine hydrate were heated to 140–160° C. for 4 hours. Thin layer chromatography (ethyl acetate:hexane 1:2, silica gel) showed no starting material remaining. The reaction mixture was cooled to room temperature, poured into 300 mL of ice water, and acidified to pH 2 with 6 N hydrochloric acid. After standing at room temperature for 2 days, the precipitate was collected by vacuum filtration, washed with water, and dried under vacuum to give 6.5 g (47%) of 5-methyl-2-oxindole.

$^1$HNMR (360 MHz, DMSO-$d_6$) δ10.20 (s, br, 1 H, NH-1), 6.99 (s, 1 H, H-4), 6.94 (d, J=8.11 Hz, 1 H, H-6), 6.68 (d, J=8.11 Hz, 1 H, H-7), 3.39 (s, 2 H, $CH_{2-3}$), and 2.22 (s, 3 H, $CH_3$-5).

5-Formyl-4-(2-ethoxycarbonylethyl)-3-methyl-1H-pyrrole-2-carboxylic acid ethyl ester (560 mg), 5-methyl-2-oxindole (300 mg), and piperidine (4 drops) in ethanol (4 mL) were stirred at 90° C. for 2 hours. Potassium hydroxide (537 mg) was added to the mixture and it was then stirred at 95° C. for an additional hour. The reaction mixture was cooled and concentrated. The residue was dissolved into water and acidified with 2 N hydrochloric acid to pH 2. The precipitate was filtered, washed with water, and dried in a vacuum oven overnight to give 496 mg of 4-(2-carboxyethyl)-3-methyl-s-(5-methyl-2-oxo-1,2-dihydroindol-3-ylidenemethyl)-1H-pyrrole-2-carboxylic acid.

4-(2-carboxyethyl)-3-methyl-5-(5-methyl-2-oxo-1,2-dihydroindol-3-ylidenemethyl)-1H-pyrrole-2-carboxylic acid (496 mg) suspended in ethylene glycol (2 mL) was held in a sealed tube in a pre-heated oil bath at 200° C. for 2 hours. The reaction mixture was cooled to 90° C. and potassium hydroxide (157 mg) was added. It was then stirred at 90° C. for 30 minutes. The reaction mixture was cooled, poured into water, and acidified with 2 N hydrochloric acid to pH 2. The precipitate was filtered, washed with water, and dried in a vacuum oven overnight to give 128 mg (29%) of 3-[2-(5-methyl-2-oxo-1,2-dihydroindol-3-ylidenemethyl)-4-methyl-1H-pyrrol-3-yl]-propionic acid.

$^1$HNMR ($d_6$-DMSO) δ13.31 (s, 1 H, NH), 12.07 (s, 1 H, COOH), 10.68 (s, 1 H, NH), 7.59 (s, 1 H), 7.51 (br s, 1 H, H-4), 7.09 (d, J=2.7 Hz, 1H), 6.91 (br d, J=8 HZ, 1 H, H-6), 6.73 (d, J=8 Hz, 1 H, H-7), 2.93 (t, J=7.5 Hz, 2 H, $CH_2$), 2.41 (t, J=7.5 Hz, 2 H, $CH_2$), 2.3 (s, $CH_3$-5), 2.04 (s, 3 H, $CH_3$). MS m/z 311 (M+1).

Example 222

3-[2-(5-Methoxy-2-oxo-1,2-dihydroindol-3-ylidenemethyl)-4-methyl-1H-pyrrol-3-yl]-prorionic acid A mixture of 5-formyl-4-(2-ethoxycarbonylethyl)-3-methyl-1H-pyrrole-2-carboxylic acid ethyl ester (562 mg), 5-methoxy-2-oxindole (326 mg), and piperidine (2 drops) in ethanol (2 mL) were stirred at 90° C. for 2 hours. Potassium hydroxide (537 mg) was added, the temperature was increased to 95° C. and held there for 1 hour. The reaction mixture was cooled and concentrated. The residue was dissolved into water and acidified with 2 N hydrochloric acid to pH 2. The precipitate was filtered, washed with water, and dried in a vacuum oven overnight to give 240 mg (65%) of 4-(2-carboxy-ethyl)-3-methyl-5-(5-methoxy-2-oxo-1,2-dihydroindol-3-ylidenemethyl)-1H-pyrrole-2-carboxylic acid.

4-(2-carboxyethyl)-3-methyl-5-(5-methoxy-2-oxo-1,2-dihydroindol-3-ylidenemethyl)-1H-pyrrole-2-carboxylic acid (240 mg) suspended in ethylene glycol (2 mL) was held in a sealed tube in a pre-heated oil bath at 200° C. for 2 hours. The reaction mixture was cooled to 90° C. and potassium hydroxide (1 pellet) was added. It was then stirred at 90° C. for 30 minutes. The reaction mixture was cooled, poured into water and acidified with 2 N hydrochloric acid to pH 2. The precipitate was filtered, washed with water, and dried in a vacuum oven overnight to give 30.5 mg (14%) of 3-[2-(5-methoxy-2-oxo-1,2-dihydroindol-3-ylidenemethyl)-4-methyl-1H-pyrrol-3-yl]-propionic acid.

$^1$HNMR ($d_6$-DMSO) δ13.38 (s, 1 H, NH), 12.07 (s, 1 H, COOH), 10.59 (s, 1 H, NH), 7.63 (s, 1 H, H-vinyl), 7.1 (d, J=2.1 Hz, 1 H), 6.75 (d, J=8 Hz, 1 H, H-7), 6.69 (dd, J=2.8 Hz, 1 H, H-6), 3.76 (s, 3 H, $OCH_3$), 2.96 (t, J=7.4 Hz, 2 H, $CH_2$), 2.41 (t, J=7.4 Hz, 2 H, $CH_2$), 2.04 (s, 3 H, $CH_3$).
MS m/z 327 (M+1).

Example 223

3-{2-[6-(3-Methoxyphenyl)-2-oxo-1,2-dihydro-indol-3-ylidenemethyl]-4-methyl-1H-pyrrol-3-yl}-propionic acid Tetrakis(triphenylphosphine)palladium (0.7 g) was added to a mixture of 5 g of 3-methoxyphenylboronic acid, 3.8 g of 5-bromo-2-fluoronitrobenzene, and 11 mL of 2 M sodium carbonate solution in 100 mL of toluene. The mixture was refluxed for 2 hours, diluted with water and extracted with ethyl acetate. The ethyl acetate was washed with saturated sodium bicarbonate and brine, dried, and concentrated to give an oily solid. The solid was purified on a silica gel column using a 1:6 mixture of ethyl acetate:hexane as eluent, to give 4.3 g (77%) of 4-fluoro-3'-methoxy-3-nitrobiphenyl.

Dimethyl malonate (9.7 mL) was added dropwise to 2.0 g of sodium hydride suspended in 50 mL of dimethylsulfoxide. The mixture was stirred at 100° C. for 35 minutes and cooled to room temperature. 4-Fluoro-2'-methoxy-3-nitrobiphenyl (4.2 g) in 50 mL of dimethylsulfoxide was added and the mixture was stirred at 100° C. for 1 hour. The reaction mixture was cooled, quenched with 300 mL of saturated ammonium chloride solution and extracted twice with ethyl acetate. The extracts were combined, washed with brine, dried over anhydrous sodium sulfate and concentrated to give crude dimethyl 3'-methoxy-3-nitrobiphenyl-4-malonate as a pale yellow solid.

Crude 3'-methoxy-3-nitro-biphenyl4-malonate was stirred at 110° C. in 45 mL of 6 N hydrochloric acid for 4 days and then cooled. The precipitate which formed was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g of 10% palladium on carbon for 3 hours at room temperature. The catalyst was removed by filtration, washed with methanol, and the filtrates combined and concentrated to give a brown solid. The solid was purified on a silica gel column, using a 33:66:1 mixture of ethyl acetate:hexane:acetic acid as eluent, to give 3.0 g (75% based on 4-fluoro-3'-methoxy-3-nitrobiphenyl) of 6-(3-methoxypheny)-2-oxindole as a pink solid.

$^1$HNMR (360 MHz, DMSO-$_6$) δ10.39 (s, br, 1 H, NH), 7.35 (t, J=7.85 Hz, 1 H), 7.26 (d, J=7.78 Hz, 1 H), 7.19 (dd,

J=1.22, 7.8 Hz, 1 H), 7.13–7.16 (m, 1 H), 7.09–7.1 (m, 1 H), 7.01 (d, J=1.48 Hz, 1 H), 6.90–6.93 (m, 1 H), 3.8 (s, 3 H, OCH$_3$), 3.49 (s, 2H, CH$_2$).

MS m/z (relative intensity, %) 240.0 ([M+1]$^+$, 100).

5-Formyl-4-(2-ethoxycarbonylethyl)-3-methyl-1H-pyrrole-2-carboxylic acid ethyl ester (281 mg), 6-(3-methoxy-phenyl)-2-oxindole (287 mg), and piperidine (2 drops) in ethanol (5 mL) were stirred at 90° C. overnight. The precipitate was filtered and washed with ethanol. The yellow orange solid and potassium hydroxide (4 pellets) were stirred in ethanol (3 mL) at 90° C. for 2.5 hours. The reaction mixture was cooled and concentrated. The residue was dissolved into water and acidified with 2 N hydrochloric acid to pH 2. The precipitate was filtered, washed with water, and dried in a vacuum oven overnight to give 413 mg of 4-(2-Carboxyethyl)-5-[6-(3-methoxyphenyl)-2-oxo-1,2-dihydroindol-3-ylidenemethyl]-3-methyl-1H-pyrrole-2-carboxylic acid.

4-(2-Carboxyethyl)-5-[6-(3-methoxyphenyl)-2-oxo-1,2-dihydroindol-3-ylidenemethyl]-3-methyl-1H-pyrrole-2-carboxylic acid (413 mg) suspended in ethylene glycol (5 mL) was held in ealed tube in a pre-heated oil bath at 200° C. for 2½ hours. The reaction mixture was cooled to 90° C. and potassium hydroxide (4 pellets) was added. It was then stirred at 100° C. for 2 more hours. The reaction mixture was cooled, poured into water and acidified with 2 N hydrochloric acid to pH 2. The precipitate was filtered, washed with water and dried in a vacuum oven overnight. The crude solid was purified on a silica gel column using 33:66:1 ethyl acetate:hexanes:glacial acetic acid as eluent to give 75 mg (20%) of 3-{2-[6-(3-methoxyphenyl)-2-oxo-1,2-dihydroindol-3-ylidenemethyl]-4-methyl-1H-pyrrol-3-yl}-propionic acid as an orange-red solid.

$^1$HNMR (d$_6$-DMSO) δ13.27 (s, 1 H, NH), 12.06 (s, 1 H, COOH), 10.86 (s, 1 H, NH), 7.76 (d, J 8 Hz, 1 H, H-4), 7.68 (s, 1 H, H-vinyl), 7.36 (t, J=8 Hz, 1 H), 7.29 (dd, J=1.5, 8 Hz, 1 H), 6.92, 7.09, 7.13, 7.2 (m, 5 H, Ar—H), 3.82 (s, 3 H, OCH$_3$), 2.96 (t, J=7.4 Hz, 2 H, CH$_2$), 2.42 (t, J=7.4 Hz, 2 H, CH$_2$), 1.97 (s, 3H, CH$_3$).

Example 224

3-{2-[6-(3-Ethoxyphenyl)-2-oxo-1,2-dihydroindol-3-ylidenemethyl]-4-methyl-1H-pyrrol-3-yl}-propionic acid A mixture of 5-formyl-4-(2-ethoxycarbonylethyl)-3-ethyl-1H-pyrrole-2-carboxylic acid ethyl ester (281 mg), 6-(3-ethoxyphenyl)-2-oxindole (304 mg), and piperidine (2 drops) in ethanol (5 mL) were held at 90° C. overnight. The precipitate that formed was filtered, washed with ethanol. The precipitate, an orange solid, was stirred with potassium hydroxide (4 pellets) in ethanol (3 mL) at 90° C. for 2.5 hours. The reaction mixture was cooled and concentrated. The residue was dissolved into water and acidified with 2N hydrochloric acid to pH 2. The precipitate was filtered, washed with water, and dried in a vacuum oven overnight to give 370 mg of 4-(2-Carboxyethyl)-5-[6-(3-ethoxyphenyl)-2-oxo-1,2-dihydroindol-3-ylidenemethyl]-3-methyl-1H-pyrrole-2-carboxylic acid.

4-(2-Carboxyethyl)-5-[6-(3-ethoxyphenyl)-2-oxo-1,2-dihydroindol-3-ylidenemethyl]-3-methyl-1H-pyrrole-2-carboxylic acid (350 mg) suspended in ethylene glycol (5 mL) was held in a sealed tube in a pre-heated oil bath at 200° C. for 2.5 hours. The reaction mixture was cooled to 100° C. and potassium hydroxide (4 pellets) was added. It was then stirred at 100° C. for 2 hours. The reaction mixture was cooled, poured into water, and acidified with 2 N hydrochloric acid to pH 2. The precipitate was filtered, washed with water, and dried in a vacuum oven overnight. The crude solid was purified on a silica gel column using 33:66:1 ethyl acetate:hexanes:glacial acetic acid to give 140 mg (44%) of 3-{2-[6-(3-ethoxyphenyl)-2-oxo-1,2-dihydroindol-3-ylidenemethyl]-4-methyl-1H-pyrrol-3-yl}-propionic acid as a brown solid.

$^1$HNMR (d$_6$-DMSO) δ13.28 (s, 1 H, NH), 12.04 (s, 1 H, COOH), 10.86 (s, 1 H, NH), 7.76 (d, J=8 Hz, 1 H, H-4), 7.68 (s, 1 H, H-vinyl), 7.34 (t, J=8 Hz, 1 H), 7.28 (dd, J=2, 8 Hz, 1 H, H-5), 7.08 (d, J=2 Hz, 1 H, H-7), 7.18, 7.13, 6.9 (m, 4 H, Ar—H), 4.1 (q, J 7 Hz, 2 H, OC$\underline{H}_2$CH$_3$), 2.96 (t, J=7.5 Hz, 2 H, CH$_2$), 2.43 (t, J=7.5 Hz, 2 H, CH$_2$), 2.05 (s, 3 H, CH$_3$), 1.35 (t, J=7 Hz, 3 H, OCH$_2$C$\underline{H}_3$).

5. Biological Evaluation

It will be appreciated that, in any given series of compounds, a spectrum of biological activity will be afforded. In its presently preferred embodiments, this invention relates to 3-methylidenyl-2-indolinones which demonstrate the ability to modulate RTK, CTK, and STK activity. The assays employed to select those compounds demonstrating of the desired activity are set forth below. Table 2 shows the results of testing of compounds of this invention using the described assays. The results shown are not to be construed as limiting the scope of this invention in any manner whatsoever.

TABLE 2

| Compound | HER-2 kinase IC$_{50}$ (μM) | BrdU HER-2 driven IC$_{50}$ (μM) | BrdU EGF driven IC$_{50}$ (μM) | SKOV3 growth (2% FBS) IC$_{50}$ (μM) | A431 growth (2% FBS) IC$_{50}$ (μM) | blo FLK1 IC$_{50}$ (μM) % If Inhibition at 100 (μM) | blo flkGST IC$_{50}$ (μM) | blo fgfR1 IC$_{50}$ (μM) | blo PDGF IC$_{50}$ (μM) | blo EGFr IC$_{50}$ (μM) | blo pyk2 IC$_{50}$ (μM) | cell EGF IC$_{50}$ (μM) | blo arc IC$_{50}$ (μM) | HUVEC-VEGF IC$_{50}$ (μM) | HUVEC aFGF IC$_{50}$ (μM) | PDGF-Induced BrdU Incorp. IC$_{50}$ (μM) | FGF-Induced BrdU Incorp. IC$_{50}$ (μM) |
|---|---|---|---|---|---|---|---|---|---|---|---|---|---|---|---|---|---|
| 1 | 13.8 | 8.7 | 6.6 | 5.5 | 5.4 | >50 | | | >100 | >100 | | 45.7 | | | | | |
| 2 | 13.7 | ND | 6.5 | 4.8 | 4.5 | >50 | | | >100 | >100 | | >100 | | | | | |
| 3 | 6.4 | 9.1 | 11 | 2.6 | 2.2 | | | | | | | | | | | | |
| 4 | 5.8 | 4.4 | 26.6 | 7 | 5.1 | | | | | | | | | | | | |
| 5 | 6.5 | 10.5 | 7.2 | 5.4 | 4.3 | | | | | | | | | | | | |
| 6 | 15.3 | 4.7 | 12 | 19.4 | 2.9 | | | | | | | 20.06 | | | | | |
| 7 | >100 | 16.5 | 24.5 | 2.5 | 1.2 | | | | | | | 21.47 | | | | | |
| 8 | 8.36 | 33.4 | >50 | 0.96 | 0.95 | | | | | | | 40.47 | | | | | |
| 9 | >100 | 4.5 | 11 | 14.5 | 17.3 | | | | | | | 40.37 | | | | | |
| 10 | 45.78 | 14.1 | 29 | 11.2 | 8.5 | | | | | | | 43.66 | | | | | |
| 11 | 57.3 | 9.3 | 23.3 | 15 | 12.5 | | 24.12 | | >100 | >100 | | 34.59 | | | | | |
| 12 | >100 | 31.9 | 30.6 | 10.1 | 7.9 | | | | | | | 56.07 | | | | | |
| 13 | >100 | 9 | 26.6 | 21.3 | 9 | | | | >100 | >100 | | 72.94 | | | | | |
| 14 | 22.7 | ND | ND | ND | ND | | | | | | | 71.92 | | | | | |
| 15 | 19 | 4.4 | 7.8 | 7 | 4.8 | | | | | | | 30.78 | | | | | |
| 16 | 9.9 | 4.2 | 6.4 | 5.9 | 4.1 | | | | 26.52 | >100 | | >100 | | | | | |
| 17 | 7.8 | 5.5 | 7.4 | 6.1 | 4.3 | | | | >100 | >100 | | 46.52 | | | | | |
| 18 | 8.4 | >50 | >50 | 1 | 0.6 | | | | 86.93 | >100 | | 44.46 | | | | | |
| 19 | 9.2 | 3.3 | 9.3 | 5.9 | 4.3 | | | | | >100 | | 67.98 | | | | | |
| 20 | 38.6 | 15.7 | 30 | 35.5 | 29.5 | | | | | >100 | | 34.8 | | | | | |
| 21 | 11.8 | 6.6 | 8 | 13 | 15.3 | | | | | >100 | | 78.08 | | | | | |
| 22 | 12.4 | ND | ND | ND | ND | | | | | >100 | | 18.45 | | | | | |
| 23 | 33.2 | 27.1 | 32.9 | 17.8 | 14.5 | | | | | >100 | | >100 | | | | | |
| 24 | 13.6 | 7.1 | 7.5 | 6.5 | 4.5 | | | | >100 | >100 | | 37.71 | | | | | |
| 26 | 15.3 | >50 | >50 | 5.4 | 3 | | | | | >100 | | 38.47 | | | | | |
| 27 | 15.8 | 23.4 | 26.8 | 5.1 | 6.4 | | | | | >100 | | 93.99 | | | | | |
| 28 | 16.92 | | | | | | | | >100 | >100 | | 30.58 | | | | | |
| 29 | 17.1 | 8.1 | 15.2 | 7.9 | 5.6 | | | | >100 | >100 | | >100 | | | | | |
| 30 | 28.02 | 8.1 | 30.3 | 16 | 9.9 | | | | >100 | >100 | | 63.44 | | | | | |
| 31 | 12.92 | 28.7 | 38.6 | 0.4 | 0.3 | | | | | >100 | | 29.57 | | | | | |
| 32 | 90.18 | ND | ND | ND | ND | | | | | >100 | | >100 | | | | | |
| 33 | 20.2 | ND | ND | 10.3 | 6.7 | | | | >100 | >100 | | 53.19 | | | | | |
| 34 | >100 | 3.5 | 11 | 7.6 | 4.4 | | | | 56.68 | >100 | | 38.19 | | | | | |
| 35 | 20.7 | 13.8 | 28.1 | 16.2 | 13.4 | | | | >100 | >100 | | >100 | | | | | |
| 36 | 21.4 | 21.4 | 31 | >25 | >25 | | | | >100 | >100 | | 66.81 | | | | | |
| 37 | 22.5 | ND | ND | ND | ND | | | | >100 | >100 | | >100 | | | | | |
| 38 | 32.3 | ND | ND | ND | ND | | | | >100 | >100 | | >100 | | | | | |
| 39 | 33.7 | 5.4 | 16.2 | 9.6 | 9.2 | | | | >100 | >100 | | >100 | | | | | |
| 40 | 36.6 | 22.6 | 28.6 | 22.5 | 14.2 | | | | >100 | >100 | | 78.95 | | | | | |
| 41 | 39.8 | ND | ND | ND | ND | | | | >100 | >100 | | >100 | | | | | |
| 42 | 47.5 | ND | ND | ND | ND | | | | 43.08 | >100 | | >100 | | | | | |
| 43 | 52.9 | ND | ND | ND | ND | | | | 10.99 | >100 | | >100 | | | | | |
| 44 | 53.6 | ND | ND | ND | ND | | | | >100 | >100 | | 76.93 | | | | | |
| 45 | 56.9 | >50 | >50 | 7.7 | 3.2 | | | | | 23.9 | | >100 | | | | | |
| 46 | 59.9 | 25.3 | 45.7 | ND | 5.5 | | | | >100 | >100 | | >100 | | | | | |
| 47 | 60.6 | >50 | >50 | 46.9 | 40.4 | | | | | 36.82 | | >100 | | | | | |

TABLE 2-continued

| Compound | HER-2 kinase IC$_{50}$ (µM) | BrdU HER-2 driven IC$_{50}$ (µM) | BrdU EGF driven IC$_{50}$ (µM) | SKOV3 growth (2% FBS) IC$_{50}$ (µM) | A431 growth (2% FBS) IC$_{50}$ (µM) | blo FLK1 IC$_{50}$ (µM) % Inhibition at 100 (µM) | blo flkGST IC$_{50}$ (µM) | blo fgfR1 IC$_{50}$ (µM) | blo PDGF IC$_{50}$ (µM) | blo EGFr IC$_{50}$ (µM) | blo pyk2 IC$_{50}$ (µM) | cell EGF IC$_{50}$ (µM) | blo src IC$_{50}$ (µM) | HUVEC-VEGF IC$_{50}$ (µM) | HUVEC aFGF IC$_{50}$ (µM) | PDGF-Induced BrdU Incorp. IC$_{50}$ (µM) | FGF-Induced BrdU Incorp. IC$_{50}$ (µM) |
|---|---|---|---|---|---|---|---|---|---|---|---|---|---|---|---|---|---|
| 48 | 65 | ND | ND | ND | ND | | | | | | | >100 | | | | | |
| 49 | 65.5 | 9.1 | 24.1 | 20.6 | 20.7 | | | | >100 | >100 | | >100 | | | | | |
| 50 | 67.6 | 31.1 | 37.9 | 14.5 | ND | | | | >100 | >100 | | >100 | | | | | |
| 51 | 71.8 | ND | ND | ND | ND | | | | | >100 | | >100 | | | | | |
| 52 | 72.8 | ND | ND | ND | ND | | | | | >100 | | >100 | | | | | |
| 53 | 80.7 | ND | ND | ND | ND | | | | | >100 | | 85.04 | | | | | |
| 54 | 85.6 | ND | ND | ND | ND | | | | | >100 | | 79.32 | | | | | |
| 55 | 89.3 | ND | ND | ND | ND | | | | >100 | >100 | | 78.36 | | | | | |
| 56 | 96.2 | ND | ND | >20 | ND | | | | | >100 | | >100 | | | | | |
| 57 | >100 | 9.6 | 12.3 | 4 | 5.8 | | | | >100 | 10.1 | | >100 | | | | | |
| 58 | >100 | 13.5 | 27.5 | 22 | 10.5 | | | | >100 | >100 | | >100 | | | | | |
| 59 | >100 | 14.4 | 44.5 | 17.2 | 6 | | | | >100 | >100 | | >100 | | | | | |
| 60 | >100 | 40 | >50 | 4.8 | 5.9 | | | | 24.49 | >100 | | >100 | | | | | |
| 61 | >100 | >50 | >50 | >25 | >25 | | | | >100 | >100 | | >100 | | | | | |
| 62 | >100 | 28.8 | >50 | 6.1 | 6 | | | | >100 | >100 | | >100 | | | | | |
| 63 | >100 | 20.4 | 30.5 | >25 | 11 | | | | >100 | >100 | | >100 | | | | | |
| 64 | >100 | | | | | | | | | >100 | | >100 | | | | | |
| 65 | >100 | | | | | | | | | >100 | | >100 | | | | | |
| 66 | >100 | | | | | | | | | >100 | | >100 | | | | | |
| 67 | >100 | | | | | | | | | >100 | | >100 | | | | | |
| 68 | >100 | | | | | | | | | >100 | | >100 | | | | | |
| 69 | >100 | | | | | | | | | >100 | | >100 | | | | | |
| 70 | >100 | | | | | | 2.15 | 6.16 | <0.78 | 22.6 | | >100 | | | | | |
| 71 | >100 | | | | | | 1.08 | 2.57 | 2.97 | 29.6 | | >100 | | | | | |
| 72 | >100 | | | | | | 2.68 | >20 | 2.79 | 11.8 | | >100 | | | | | |
| 73 | >100 | | | | | | 3.05 | 17.46 | 3.15 | 7.9 | | >100 | | | | | |
| 74 | >100 | | | | | | 0.43 | 0.47 | 0.01 | 13.2 | | >50 | | | | | |
| 107 | | | | | | | 2.36 | >20 | 0.02 | >100 | | >100 | | | | | |
| 108 | | | | | | | 3.31 | 4.26 | 0.05 | >100 | | >100 | | | | | |
| 109 | | | | | | | 0.1 | 0.29 | 0.02 | >100 | | >100 | | | | | |
| 110 | | | | | | | 13.54 | >20 | 0.02 | >100 | | >100 | | | | | |
| 111 | | | | | | | 9.29 | | >100 | >100 | | >100 | | | | | |
| 112 | | | | | | | 6.33 | | >100 | >100 | | >100 | | | | | |
| 114 | 61.73 | | | | | | 6.32 | | | | 4.24 | | | | | | |
| 116 | 6.07 | | | | | | 1 | | | | 2.02 | | | | | | |
| 117 | | | | | | | 0.51 | | 9.97 | | | | | | | | |
| 118 | | | | | | | 16.88 | | 26.66 | | 4.71 | | | | | | |
| 119 | | | | | | | 13.91 | | 2.13 | | 4.21 | | | | | | |
| 120 | | | | | | | | | 15.21 | | | | | | | | |
| 121 | | | | | | | | | 33.89 | | | | | | | | |
| 122 | | | | | | | | | 5.73 | | | | | | | | |
| 123 | | | | | | | | | | | | | | | | | |
| 124 | | | | | | | | | 63.28 | | | | | | | | |
| 125 | | | | | | | 14.8 | | 0.96 | | | | | | | | |
| 126 | | | | | | | | | | | | | | | | | |
| 127 | | | | | | | | | 17.11 | | | | | | | | |
| 128 | | | | | | | | | | | | | | | | | |

TABLE 2-continued

| Compound | HER-2 kinase IC$_{50}$ (μM) | BrdU HER-2 driven IC$_{50}$ (μM) | BrdU EGF driven IC$_{50}$ (μM) | SKOV3 growth (2% FBS) IC$_{50}$ (μM) | A431 growth (2% FBS) IC$_{50}$ (μM) | blo FLK1 IC$_{50}$ (μM) % If Inhibition at 100 (μM) | blo flkGST IC$_{50}$ (μM) | blo fgfR1 IC$_{50}$ (μM) | blo PDGF IC$_{50}$ (μM) | blo EGFr IC$_{50}$ (μM) | blo pyk2 IC$_{50}$ (μM) | cell EGF IC$_{50}$ (μM) | blo arc IC$_{50}$ (μM) | HUVEC-VEGF IC$_{50}$ (μM) | HUVEC aFGF IC$_{50}$ (μM) | PDGF-Induced BrdU Incorp. IC$_{50}$ (μM) | FGF-Induced BrdU Incorp. IC$_{50}$ (μM) |
|---|---|---|---|---|---|---|---|---|---|---|---|---|---|---|---|---|---|
| 129 | | | | | | | | | | | | | | | | | |
| 130 | | | | | | | 12.88 | | 31.69 | | | | | | | | |
| 131 | | | | | | | | | 2.32 | | | | | | | | |
| 132 | | | | | | | | | 23.18 | | 2.18 | | | | | | |
| 133 | | | | | | | 8.18 | | 0.65 | | 0.22 | | | | | | |
| 134 | | | | | | | | | 2.69 | | | | | | | | |
| 135 | | | | | | | | | 4.88 | | | | | | | | |
| 136 | | | | | | | | | | 0.19 | | | | | | | |
| 137 | | | | | | | 0.56 | | 0.5 | | | | | | | | |
| 138 | | | | | | | 7.54 | | 26.95 | | 2.77 | | | | | | |
| 139 | | | | | | | 17.65 | 12.57 | 6.17 | >100 | >10 | | | | | | |
| 140 | | | | | | | 7.56 | 12.83 | 26.24 | >100 | 2.18 | | | | | | |
| 141 | | | | | | | 6.65 | 8.38 | >100 | >100 | | | | | | | |
| 142 | | | | | | | 11.53 | 5.9 | >100 | >100 | | | | | | | |
| 143 | | | | | | | 21.14 | 16.56 | 85.11 | >100 | | | | | | | |
| 144 | | | | | | | 26.92 | 2.77 | >100 | >100 | | | | | | | |
| 145 | | | | | | | 9.03 | 15.57 | >100 | >100 | | | | | | | |
| 146 | | | | | | | 11.79 | >20 | >100 | >100 | | | | | | | |
| 147 | | | | | | | 15.6 | >20 | >100 | >100 | | | | | | | |
| 148 | | | | | | | 15.26 | >20 | >100 | >100 | | | | | | | |
| 149 | | | | | | | 23.94 | >20 | >100 | >100 | 5.02 | | | | | | |
| 150 | | | | | | | 2.66 | 0.77 | 5.26 | >100 | 0.01 | | | | | | |
| 151 | | | | | | | 0.2 | | 0.34 | >100 | | | | | | | |
| 152 | >100 | | | | | | 0.71 | | 0.65 | >100 | | | | | | | |
| 153 | >100 | | | | | | | | | | | | | | | | |
| 154 | >100 | | | | | | | | | | | | | | | | |
| 155 | >100 | | | | | | | | | | | | >100 | | | | |
| 156 | >100 | | | | | 4.2 | | | | | | | 0.15 | | | | |
| 157 | | | | | | | | | | | | | >100 | | | | |
| 158 | >100 | | | | | | 0.26 | 3.6 | 18.03 | 8.2 | 0.22 | | 9 | | | | |
| 159 | >100 | | | | | | 2.87 | >20 | 74.08 | 30.8 | 12.35 | | | | | | |
| 160 | >100 | | | | | 1.53 | 0.12 | >20 | 2.72 | >100 | 9.6 | | | | | | |
| 161 | | | | | | 2.1 | <0.008 | 5.27 | 25.06 | >100 | 0.68 | | | | | | |
| 162 | | | | | | | | >20 | 8.02 | >100 | 3.4 | | | | | | |
| 163 | | | | | | | | >20 | >100 | >100 | | >100 | | | | | |
| 164 | >100 | | | | | | | >20 | 48.71 | >100 | | >100 | | | | | |
| 165 | >100 | | | | | | | >20 | >100 | >100 | | >100 | | | | | |
| 166 | >100 | | | | | | | >20 | >100 | >100 | | >100 | | | | | |
| 167 | | | | | | | | >20 | >100 | >100 | | >100 | | | | | |
| 168 | | | | | | | | >20 | >100 | 17.8 | | >100 | | | | | |
| 169 | | | | | | 15.8 | | >20 | >100 | >100 | | >100 | | | | | |
| 170 | | | | | | 10.7 | | >20 | 68.56 | >100 | 14.75 | >100 | | | | | |
| 171 | | | | | | 20.35 | | 0.28 | 89.41 | 22.04 | 9.8 | >100 | | | | | |
| 172 | | | | | | | 10.47 | 0.29 | 69.14 | >100 | 2.57 | >100 | | | | | |
| 173 | | | | | | | 11.05 | 0.41 | 2.5 | >100 | 5.53 | >100 | | | | | |
| 174 | | | | | | | 1.85 | | 55.38 | | | >100 | | | | | |
| 175 | | | | | | | 1.51 | 0.73 | | | | | | | | | |

TABLE 2-continued

| Compound | HER-2 kinase IC$_{50}$ (μM) | BrdU HER-2 driven IC$_{50}$ (μM) | BrdU EGF driven IC$_{50}$ (μM) | SKOV3 growth (2% FBS) IC$_{50}$ (μM) | A431 growth (2% FBS) IC$_{50}$ (μM) | blo FLK1 IC$_{50}$ (μM) % If Inhibition at 100 (μM) | blo flkGST IC$_{50}$ (μM) | blo fgfR1 IC$_{50}$ (μM) | blo PDGF IC$_{50}$ (μM) | blo EGFr IC$_{50}$ (μM) | blo pyk2 IC$_{50}$ (μM) | cell EGF IC$_{50}$ (μM) | blo arc IC$_{50}$ (μM) | HUVEC-VEGF IC$_{50}$ (μM) | HUVEC aFGF IC$_{50}$ (μM) | PDGF-Induced BrdU Incorp. IC$_{50}$ (μM) | FGF-Induced BrdU Incorp. IC$_{50}$ (μM) |
|---|---|---|---|---|---|---|---|---|---|---|---|---|---|---|---|---|---|
| 176 | | | | | | | 2.08 | 0.75 | 79.22 | >100 | 66.08 | >100 | | | | | |
| 177 | | | | | | | 1.34 | 1.6 | >100 | 6.13 | >100 | >100 | | | | | |
| 178 | | | | | | | >20 | 3.23 | >100 | >100 | 57.09 | >100 | | | | | |
| 179 | | | | | | | 1.84 | 4.52 | >100 | >100 | >100 | >100 | | | | | |
| 180 | | | | | | | 1.11 | 5.42 | 1.11 | >100 | <0.78 | >100 | | | | | |
| 181 | | | | | | | 12.53 | 5.74 | >100 | >100 | >100 | >100 | | | | | |
| 182 | | | | | | | 18.68 | 5.94 | 5.4 | >100 | 37.09 | >100 | | | | | |
| 183 | | | | | | | 1.55 | 7.68 | >100 | >100 | >100 | >100 | | | | | |
| 184 | | | | | | | >20 | 8.6 | >100 | >100 | >100 | >100 | | | | | |
| 185 | | | | | | | 3.39 | 9.43 | >100 | >100 | >100 | >100 | | | | | |
| 186 | | | | | | | 6.12 | 10.38 | >100 | >100 | >100 | >100 | | | | | |
| 187 | | | | | | | >20 | 13.82 | >100 | >100 | 75.8 | >100 | | | | | |
| 188 | | | | | | | >20 | 17.47 | >100 | >100 | 66.41 | >100 | | | | | |
| 189 | | | | | | | >20 | >20 | >100 | >100 | >100 | >100 | | | | | |
| 190 | | | | | | 0.06 | 0.087 | 5.85 | 2.08 | >100 | <0.78 | >100 | 0.11 | 0.0019 | 0.0159 | 2.9 | 18.2 |
| 191 | | | | | | 0.02 | 0.04 | 0.04 | 0.05 | >100 | 68.5 | >100 | 11.96 | 0.00004 | 0.25 | 1.1 | 23.6 |
| 192 | | | | | | 0.03 | 0.03 | 1.81 | 0.004 | >100 | 4.87 | >100 | 10.49 | 0.0003 | 0.076 | 1.4 | 15.7 |
| 193 | | | | | | 0.02 | 3.60 | 0.02 | 44.55 | 90.72 | 17.32 | | 48.59 | 0.00094 | 0.0025 | 13.5 | 26.7 |
| 194 | | | | | | 0.001 | 6.67 | 0.04 | 81.35 | >100 | 4.09 | >100 | 20.58 | 0.001 | 0.0044 | 14.2 | 30.1 |
| 195 | | | | | | 0.03 | 4.35 | 0.02 | 2.04 | 36.48 | 10.70 | | 0.26 | | | 3.7 | 30.2 |
| 196 | | | | | | 0.89 | 0.41 | 0.05 | 33.68 | >100 | 2.37 | >100 | 11.25 | 0.02 | 1.6 | 3 | 42.1 |
| 197 | | | | | | 2.10 | 0.61 | | >100 | >100 | 11.98 | >100 | | <0.003 | 202 | 4.9 | >50 |
| 198 | | | | | | 7.44 | 5.84 | | 0.04 | >100 | 1.5 | >100 | 2.34 | 0.29 | 1.7 | 4.2 | >50 |
| 199 | | | | | | 0.13 | 0.17 | | 0.89 | >100 | 2.83 | >100 | | <0.03 | 0.1 | 3.5 | >50 |
| 200 | | | | | | 0.97 | 1.29 | | 11.80 | >100 | 5.62 | >100 | | 0.22 | 9.2 | 8.6 | >50 |
| 201 | | | | | | 0.16 | 0.57 | | 1.73 | >100 | 6.61 | >100 | | <0.03 | 0.16 | 3.9 | >50 |
| 202 | | | | | | 0.63 | 2.54 | | 9.58 | >100 | | >100 | | <0.03 | 2.1 | 5.2 | >50 |
| 203 | | | | | | 0.14 | | | 0.15 | 12.5 | | >12.5 | >50 | | | | |
| 204 | | | | | | 0.36 | 0.07 | 2.27 | 0.68 | 7.09 | | >100 | 4.44 | | | | |
| 205 | | | | | | 0.52 | 0.44 | 0.59 | 5.43 | 16.21 | | >100 | 1.34 | | | | |
| 206 | | | | | | 6.08 | 0.06 | 2.02 | 0.04 | >100 | | >100 | 0.74 | | | | |
| 207 | | | | | | 2.72 | 1.50 | 1.18 | 11.80 | >100 | | >100 | 7.52 | | | | |
| 208 | | | | | | <0.78 | 0.38 | 7.70 | 0.87 | >100 | | >100 | 1.84 | | | | |
| 209 | | | | | | | | | 23.45 | >100 | 0.13 | >100 | | | | | |
| 214 | | | | | | 50.64 | | 30.24 | 84.59 >100 | >100 | | >100 | | | | | |
| 215 | | >100 | | | | 0.02 | 0.08 | 0.07 | 0.50 | >100 | 6.9 | >100 | 5.59 | 0.07 | 1.1 | 20 | 25 |
| 216 | | >50 | | | | 2.91 | | | 0.22 | >100 | 23.86 | >100 | 4.75 | <0.07 | 1.4 | N/A* | N/A* |
| 217 | | >50 | | | | 1.47 | | | 0.21 | >100 | 2.89 | >100 | 3.68 | 0.62 | 4.8 | 8.7 | 8.7 |
| 218 | | 43.5 | | | | 0.20 | 0.48 | 0.10 | 2.11 | >100 | 32.27 | >100 | | <0.07 | 0.35 | 24.8 | >50 |
| 219 | | >50 | | | | 0.19 | | | 0.47 | 98.06 | 4.15 | >100 | 0.08 | 0.016 | 0.26 | 7.9 | >50 |
| 220 | | >50 | | | | 0.35 | 0.11 | | 0.62 | >100 | 1.89 | >100 | 6.48 | 0.04 | 0.49 | 8.5 | >50 |
| 222 | | >50 | | | | <0.78 | 0.08 | 0.09 | 3.75 | >100 | | >100 | 5.77 | | | >50 | 35 |
| 223 | | | | | | 28.25 | 0.57 | 1.22 | 0.781 | 13.29 | | >100 | 1.06 | | | | |
| 224 | | | | | | 1.0 | 0.67 | 4.24 | 2.38 | >100 | | | 1.16 | | | | |

A. Assay Procedures.

The following in vitro assays may be used to determine the level of activity and effect of the different compounds of the present invention on one or more of the PKS. Similar assays can be designed along the same lines for any PK using techniques well known in the art.

The cellular/catalytic assays described herein are performed in an ELISA format. The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound. The cellular/biologic assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as Bromodeoxyuridine (BrdU) or 3H-thymidine is added. The amount of labeled DNA is detected with either an anti-BrdU antibody or by measuring radioactivity and is compared to control cells not contacted with a test compound.

Cellular/Catalytic Assays

Enzyme linked immunosorbent assays (ELISA) may be used to detect and measure the presence of PK activity. The ELISA may be conducted according to known protocols which are described in, for example, Voller, et al., 1980, "Enzyme-Linked Immunosorbent Assay," In: Manual of Clinical Immunology, 2d ed., edited by Rose and Friedman, pp 359–371 Am. Soc. Of Microbiology, Washington, D.C.

The disclosed protocol may be adapted for determining activity with respect to a specific PK. That is, the preferred protocols for conducting the ELISA experiments for specific PKs is provided below. However, adaptation of these protocols for determining a compound's activity for other members of the RTK family, as well as for CTKs and STKs, is well within the scope of knowledge of those skilled in the art.

FLK-1 Assay

An ELISA assay is conducted to measure the kinase activity of the FLK-1 receptor and more specifically, the inhibition or activation of TK activity on the FLK-1 receptor. Specifically, the following assay can be conducted to measure kinase activity of the FLK-1 receptor in cells genetically engineered to express Flk-1.

Materials and Reagents.
a. Corning 96-well ELISA plates (Corning Catalog No. 25805-96),
b. Cappel goat anti-rabbit IgG (catalog no. 55641),
c. PBS (Gibco Catalog No. 450-1300EB),
d. TBSW Buffer (50 mM Tris (pH 7.2), 150 mM NaCl and 0.1% Tween-20),
e. Ethanolamine stock (10% ethanolamine (pH 7.0), stored at 4° C.),
f. HNTG buffer (20 mM HEPES buffer (pH 7.5), 150 mM NaCl, 0.2% Triton X-100, and 10% glycerol),
g. EDTA (0.5 M (pH 7.0) as a 100×stock),
h. Sodium orthovanadate (0.5 M as a 100×stock),
i. Sodium pyrophosphate (0.2 M as a 100×stock),
j. NUNC 96 well V bottom polypropylene plates (Applied Scientific Catalog No. AS-72092),
k. NIH3T3 C7#3 Cells (FLK-1 expressing cells),
l. DMEM with 1×high glucose L-Glutamine (catalog No. 11965-050),
m. FBS, Gibco (catalog no. 16000-028),
n. L-glutamine, Gibco (catalog no. 25030-016),
o. VEGF, PeproTech, Inc. (catalog no. 100-20) (kept as 1 $\mu$g/100 $\mu$l stock in Milli-Q dH$_2$O and stored at −20° C.,
p. Affinity purified anti-FLK-1 antiserum,
q. UB40 monoclonal antibody specific for phosphotyrosine (see, Fendley, et al., 1990, Cancer Research 50:1550–1558),
r. EIA grade Goat anti-mouse IgG-POD (BioRad catalog no. 172-1011),
s. 2,2-azino-bis(3-ethylbenz-thiazoline-6-sulfonic acid (ABTS) solution (100 mM citric acid (anhydrous), 250 mM Na$_2$HPO$_4$ (pH 4.0), 0.5 mg/ml ABTS (Sigma catalog no. A-1888)), solution should be stored in dark at 4° C. until ready for use,
t. H$_2$O$_2$ (30% solution) (Fisher catalog no. H325),
u. ABTS/H$_2$O$_2$ (15 ml ABTS solution, 2 $\mu$l H$_2$O$_2$) prepared 5 minutes before use and left at room temperature,
v. 0.2 M HCl stock in H$_2$O,
w. dimethylsulfoxide (100%) (Sigma Catalog No. D-8418), and
y. Trypsin-EDTA (Gibco BRL Catalog No. 25200-049).

Protocol.
1. Coat Corning 96-well ELISA plates with 1.0 $\mu$g per well Cappel Anti-rabbit IgG antibody in 0.1M Na$_2$CO$_3$ pH 9.6. Bring final volume to 150 $\mu$l per well. Coat plates overnight at 4° C. Plates can be kept up to two weeks when stored at 4° C.
2. Grow cells in Growth media (DMEM, supplemented with 2.0 mM L-Glutamine, 10% FBS) in suitable culture dishes until confluent at 37° C., 5% CO$_2$.
3. Harvest cells by trypsinization and seed in Corning 25850 polystyrene 96-well round bottom cell plates, 25,000 cells/well in 200 $\mu$l of growth media.
4. Grow cells at least one day at 37° C., 5% CO$_2$.
5. Wash cells with D-PBS 1×.
6. Add 200 $\mu$l/well of starvation media (DMEM, 2.0 mM 1-Glutamine, 0.1% FBS). Incubate overnight at 37° C., 5% CO$_2$.
7. Dilute Compounds 1:20 in polypropylene 96 well plates using starvation media. Dilute dimethylsulfoxide 1:20 for use in control wells.
8. Remove starvation media from 96 well cell culture plates and add 162 $\mu$l of fresh starvation media to each well.
9. Add 18 $\mu$l of 1:20 diluted compound dilution (from step 7) to each well plus the 1:20 dimethylsulfoxide dilution to the control wells (+/− VEGF), for a final dilution of 1:200 after cell stimulation. Final dimethylsulfoxide is 0.5%. Incubate the plate at 37° C., 5% CO$_2$ for two hours.

10. Remove unbound antibody from ELISA plates by inverting plate to remove liquid. Wash 3 times with TBSW+0.5% ethanolamine, pH 7.0. Pat the plate on a paper towel to remove excess liquid and bubbles.

11. Block plates with TBSW+0.5% ethanolamine, pH 7.0, 150 µl per well. Incubate plate thirty minutes while shaking on a microtiter plate shaker.

12. Wash plate 3 times as described in step 10.

13. Add 0.5 µg/well affinity purified anti-FLU-1 polyclonal rabbit antiserum. Bring final volume to 150 µl/well with TBSW+0.5% ethanolamine pH 7.0. Incubate plate for thirty minutes while shaking.

14. Add 180 µl starvation medium to the cells and stimulate cells with 20 µl/well 10.0 mM sodium orthovanadate and 500 ng/ml VEGF (resulting in a final concentration of 1.0 mM sodium orthovanadate and 50 ng/ml VEGF per well) for eight minutes at 37° C., 5% $CO_2$. Negative control wells receive only starvation medium.

15. After eight minutes, media should be removed from the cells and washed one time with 200 µl/well PBS.

16. Lyse cells in 150 µl/well HNTG while shaking at room temperature for five minutes. HNTG formulation includes sodium ortho vanadate, sodium pyrophosphate and EDTA.

17. Wash ELISA plate three times as described in step 10.

18. Transfer cell lysates from the cell plate to ELISA plate and incubate while shaking for two hours. To transfer cell lysate pipette up and down while scrapping the wells.

19. Wash plate three times as described in step 10.

20. Incubate ELISA plate with 0.02 µg/well UB40 in BSW+05% ethanolamine. Bring final volume to 150 µl/well. Incubate while shaking for 30 minutes.

21. Wash plate three times as described in step 10.

22. Incubate ELISA plate with 1:10,000 diluted EIA grade goat anti-mouse IgG conjugated horseradish peroxidase in TBSW plus 0.5% ethanolamine, pH 7.0. Bring final volume to 150 µl/well. Incubate while shaking for thirty minutes.

23. Wash plate as described in step 10.

24. Add 100 µl of $ABTS/H_2O_2$ solution to well. Incubate ten minutes while shaking.

25. Add 100 µl of 0.2 M HCl for 0.1 M HCl final concentration to stop the color development reaction. Shake 1 minute at room temperature. Remove bubbles with slow stream of air and read the ELISA plate in an ELISA plate reader at 410 nm.

EGF Receptor-HER2 Chimeric Receptor Assay in Whole Cells

HER2 kinase activity in whole EGFR-NIH3T3 cells are measured as described below:

Materials and Reagents a. EGF: stock concentration: 16.5 ILM, EGF 201, TOYOBO, Co., Ltd. Japan.

b. 05-101 (UBI) (a monoclonal antibody recognizing an EGFR extracellular domain).

c. Anti-phosphotyrosine antibody (anti-Ptyr) (polyclonal) (see, Fendley, et al., supra).

d. Detection antibody: Goat anti-rabbit lgG horseradish peroxidase conjugate, TAGO, Inc., Burlingame, Calif.

| | | |
|---|---|---|
| e. TBST buffer: | | |
| Tris-HCl pH 7.2 | | 50 mM |
| NaCl | | 150 mM |
| Triton X-100 | | 0.1 |
| f. HNTG 5X stock: | | |
| HEPES | | 0.1M |
| NaCl | | 0.75M |
| Glycerol | | 50% |
| Triton X-100 | | 1.0% |
| g. ABTS stock: | | |
| Citric Acid | | 100 mM |
| $Na_2HPO_4$ | | 250 mM |
| HCl, conc. | | 0.5 mM |
| ABTS* | | 0.5 mg/ml |

*(2,2'-azinobis(3-ethylbenzthiazolinesulfonic acid)). Keep solution in dark at 4° C. until use.

h. Stock reagents of:
EDTA 100 mM pH 7.0
$Na_3VO_4$ 0.5 M
$Na_4(P_2O_7)$ 0.2 M

Procedure

Pre-coat ELISA Plate

1. Coat ELISA plates (Corning, 96 well, Cat. #25805-96) with 05-101 antibody at 0.5 µg per well in PBS, 100 µl final volume/well, and store overnight at 4° C. Coated plates are good for up to 10 days when stored at 4° C.

2. On day of use, remove coating buffer and replace with 100 µl blocking buffer (5% Carnation Instant Non-Fat Dry Milk in PBS) Incubate the plate, shaking, at room temperature (about 23° C. to 25° C.) for 30 minutes. Just prior to use, remove blocking buffer and wash plate 4 times with TBST buffer.

Seeding Cells

1. An NIH3T3 cell line overexpressing a chimeric receptor containing the EGFR extracellular domain and intracellular HER2 kinase domain can be used for t.is assay.

2. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.

3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 µl per well, in a 96 well microtiter plate. Incubate seeded cells in 5% $CO_2$ at 37° C. for about 40 hours.

Assay Procedures

1. Check seeded cells for contamination using an inverted microscope. Dilute drug stock (10 mg/ml in DMSO) 1:10 in DMEM medium, then transfer 5 µl to a TBST well for a final drug dilution of 1:200 and a final DMSO concentration of 1%. Control wells receive DMSO alone. Incubate in 5% $CO_2$ at 37° C. for two hours.

2. Prepare EGF ligand: dilute stock EGF in DMEM so that upon transfer of 10 µl dilute EGF (1:12 dilution,, 100 nM final concentration is attained.

3. Prepare fresh HNTG* sufficient for 100 µl per well, and place on ice.

| HNTG* (10 ml): | |
| --- | --- |
| HNTG stock | 2.0 ml |
| milli-Q H$_2$O | 7.3 ml |
| EDTA, 100 mM, pH 7.0 | 0.5 ml |
| Na$_3$VO$_4$ (0.5M) | 0.1 ml |
| Na$_4$(P$_2$O$_7$) (0.2M) | 0.1 ml |

4. After 120 minutes incubation with drug, add prepared SGF ligand to cells, 10 μl per well, to a final concentration of 100 nM. Control wells receive DMEM alone. Incubate with shaking, at room temperature, for 5 minutes.
5. Remove drug, EGF, and DMEM. Wash cells twice with PBS. Transfer HNTG* to cells, 100 μl per well. Place on ice for 5 minutes. Meanwhile, remove blocking buffer from other ELISA plate and wash with TBST as described above.
6. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
7. Remove lysate and wash 4 times with TBST. Transfer freshly diluted anti-Ptyr antibody to ELISA plate at 100 μl per well. Incubate shaking at room temperature for 30 minutes in the presence of the anti-Ptyr antiserum (1:3000 dilution in TBST).
8. Remove the anti-Ptyr antibody and wash 4 times with TBST. Transfer the freshly diluted TAGO anti-rabbit IgG antibody to the ELISA plate at 100 μl per well. Incubate shaking at room temperature for 30 minutes (anti-rabbit IgG antibody: 1:3000 dilution in TBST).
9. Remove TAGO detection antibody and wash 4 times with TBST. Transfer freshly prepared ABTS/H$_2$O$_2$ solution to ELISA plate, 100 μl per well. Incubate shaking at room temperature for 20 minutes. (ABTS/H$_2$O$_2$ solution: 1.0 μl 30% H$_2$O$_2$ in 10 ml ABTS stock)
10. Stop reaction by adding 50 μl 5N H$_2$SO$_4$ (optional), and determine O.D. at 410 nm.
11. The maximal phosphotyrosine signal is determined by subtracting the value of the negative controls from the positive controls. The percent inhibition of phosphotyrosine content for extract-containing wells is then calculated, after subtraction of the negative controls.

PDGF-R Assay

All cell culture media, glutamine, and fetal bovine serum can be purchased from Gibco Life Technologies (Grand Island, N.Y.) unless otherwise specified. All cells are grown in a humid atmosphere of 90–95% air and 5–10% CO$_2$ at 37° C. All cell lines are routinely subcultured *twice a week and are negative for mycoplasma as determined by the Mycotect method (Gibco).

For ELISA assays, cells (U1242, obtained from Joseph Schlessinger, NYU) are grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium, cells are changed to serum-free medium and treated with test compound for 2 hr in a 5% CO$_2$, 37° C. incubator. Cells are then stimulated with ligand for 5–10 minute followed by lysis with HNTG (20 mM Hepes, 150 mM NaCl, 10% glycerol, 5 mM EDTA, 5 mM Na$_3$VO$_4$, 0.2% Triton X-100, and 2 mM NaPyr). Cell lysates (0.5 mg/well in PBS) are transferred to ELISA plates previously coated with receptor-specific antibody and which had been blocked with 5% milk in TBST (50 mM Tris-HCl pH 7.2, 150 mM NaCl and 0.1% Triton X-100) at room temperature for 30 min. Lysates are incubated with shaking for 1 hour at room temperature. The plates are washed with TBST four times and then incubated with polyclonal anti-phosphotyrosine antibody at room temperature for 30 minutes. Excess anti-phosphotyrosine antibody is removed by rinsing the plate with TBST four times. Goat anti-rabbit IgG antibody is added to the ELISA plate for 30 min at room temperature followed by rinsing with TBST four more times. ABTS (100 mM citric acid, 250 mM Na$_2$HPO$_4$ and 0.5 mg/mL 2,2'-azino-bis(3-ethylbenzthiazoline-6-sulfonic acid)) plus H$_2$O$_2$ (1.2 mL 30% H$_2$O$_2$ to 10 ml ABTS) is added to the ELISA plates to start color development. Absorbance at 410 nm with a reference wavelength of 630 nm is recorded about 15 to 30 min after ABTS addition.

IGF-1 Receptor Assay

The following protocol may be used to measure phosphotyrosine level on IGF-1 receptor, which indicates IGF-1 receptor tyrosine kinase activity.

Materials and Reagents a. The cell line used in this assay is 3T3/IGF-1R, a cell line genetically engineered to overexpresses IGF-1 receptor.
b. NIH3T3/IGF-1R is grown in an incubator with 5% CO$_2$ at 37° C. The growth media is DMEM+10% FBS (heat inactivated)+2 mM L-glutamine.
c. Affinity purified anti-IGF-1R antibody 17-69.

| d. D-PBS: | |
| --- | --- |
| KH$_2$PO$_4$ | 0.20 g/l |
| KH$_2$PO$_4$ | 2.16 g/l |
| KCl | 0.20 g/l |
| NaCl | 8.00 g/l (pH 7.2) | e. Blocking Buffer: TBST plus 5% Milk (Carnation Instant Non-Fat Dry Milk).
f. TBST buffer:

| Tris-HCl | 50 mM |
| --- | --- |
| NaCl | 150 mM (pH 7.2/HCl 10N) |
| Triton X-100 | 0.1% |

Stock solution of TBS (10×) is prepared, and Triton X-100 is added to the buffer during dilution.

g. HNTG buffer:

| HEPES | 20 mM |
| --- | --- |
| NaCl | 150 mM (pH 7.2/HCl 1N) |
| Glycerol | 10% |
| Triton X-100 | 0.2 |

Stock solution (5×) is prepared and kept at 4° C.

h. EDTA/HCl: 0.5 M pH 7.0 (NaOH) as 100×stock.
i. Na$_3$VO$_4$: 0.5 M as 100×stock and aliquots are kept at 80° C.
j. Na$_4$P$_2$O$_7$: 0.2 M as 100×stock.
k. Insulin-like growth factor-1 from Promega (Cat# G5111).

l. Rabbit polyclonal anti-phosphotyrosine antiserum.
m. Goat anti-rabbit IgG, POD conjugate (detection antibody), Tago (Cat. No. 4520, Lot No. 1802): Tago, Inc., Burlingame, Calif.
n. ABTS (2,2'-azinobis(3-ethylbenzthiazolinesulfonic acid)) solution:

| | |
|---|---|
| Citric acid | 100 mM |
| $Na_2HPO_4$ | 250 mM (pH 4.0/1N HCl) |
| ABTS | 0.5 mg/ml |

ABTS solution should be kept in dark and 4° C. The solution should be discarded when it turns green.
o. Hydrogen Peroxide: 30% solution is kept in the dark and at 4° C.

Procedure

All the following steps are conducted at room temperature unless specifically indicated otherwise. All ELISA plate washings are performed by rinsing the plate with tap water three times, followed by one TBST rinse. Pat plate dry with paper towels.

Cell Seeding
1. The cells, grown in tissue culture dish (Corning 25020-100) to 80–90% confluence, are harvested with Trypsin-EDTA (0.25%, 0.5 ml/D-100, GIBCO).
2. Resuspend the cells in fresh DMEM+10% FBS+2 mM L-Glutamine, and transfer to 96-well tissue culture plate (Corning, 25806-96) at 20,000 cells/well (100 µl/well). Incubate for 1 day then replace medium to serum-free medium (90/µl) and incubate in 5% $CO_2$ and 37° C. overnight.

ELISA Plate Coating and Blocking
1. Coat the ELISA plate (Corning 25805-96) with Anti-IGF-1R Antibody at 0.5 µg/well in 100 µl PBS at least 2 hours.
2. Remove the coating solution, and replace with 100 µl Blocking Buffer, and shake for 30 minutes. Remove the blocking buffer and wash the plate just before adding lysate.

Assay Procedures
1. The drugs are tested under serum-free condition.
2. Dilute drug stock (in 100% DMSO) 1:10 with DMEM in 96-well poly-propylene plate, and transfer 10 µl/well of this solution to the cells to achieve final drug dilution 1:100, and final DMSO concentration of 1.0%. Incubate the cells in 5% $CO_2$ at 37° C. for 2 hours.
3. Prepare fresh cell lysis buffer (HNTG*)

| | |
|---|---|
| HNTG | 2 ml |
| EDTA | 0.1 ml |
| $Na_3VO_4$ | 0.1 ml |
| $Na_4(P_2O_7)$ | 0.1 ml |
| $H_2O$ | 7.3 ml |

4. After drug incubation for two hours, transfer 10 µl/well of 200 nM IGF-1 Ligand in PBS to the cells (Final Conc. is 20 nM), and incubate at 5% $CO_2$ at 37° C. for 10 minutes.
5. Remove media and add 100 µl/well HNTG* and shake for 10 minutes. Look at cells under microscope to see if they are adequately lysed.
6. Use a 12-channel pipette to scrape the cells from the plate, and homogenize the lysate by repeated aspiration and dispensing. Transfer all the lysate to the antibody coated ELISA plate, and shake for 1 hour.
7. Remove the lysate, wash the plate, transfer anti-pTyr (1:3,000 with TBST) 100 µl/well, and shake for 30 minutes.
8. Remove anti-pTyr, wash the plate, transfer TAGO (1:3,000 with TBST) 100 µl/well, and shake for 30 minutes.
9. Remove detection antibody, wash the plate, and transfer fresh ARTS/$H_2O_2$ (1.2 µl $H_2O_2$ to 10 ml ABTS) 100 µl/well to the plate to start color development.

Measure OD at 410 nm with a reference wavelength of 630 nm in Dynatec MR5000.

EGFR Assay

EGF Receptor kinase activity in cells genetically engineered to express human EGF-R can be measured as described below:

Materials and Reagents.
a. EGF Ligand: stock concentration=16.5 µM, EGF 201, TOYOBO, Co., Ltd. Japan.
b. 05-101 (UBI) (a monoclonal antibody recognizing an EGFR extracellular domain).
c. Anti-phosphotyosine antibody (anti-Ptyr) (polyclonal).
d. Detection antibody: Goat anti-rabbit IgG horse radish peroxidase conjugate, TAGO, Inc., Burlingame, Calif.

| | |
|---|---|
| e. TBST buffer: | |
| Tris-HCl, pH 7 | 50 mM |
| NaCl | 150 mM |
| Triton X-100 | 0.1 |
| f. HNTG 5X stock: | |
| HEPES | 0.1M |
| NaCl | 0.75M |
| Glycerol | 50 |
| Triton X-100 | 1.0% |
| g. ABTS stock: | |
| Citric Acid | 100 mM |
| $Na_3VO_4$ | 250 mM |
| HCl, conc. | 4.0 pH |
| ABTS* | 0.5 mg/ml |

Keep solution in dark at 4° C. until used.
h. Stock reagents of:
EDTA 100 mM pH 7.0
$Na_3VO_4$ 0.5 M
$Na_4(P_2O_7)$ 0.2 M Procedure.

Pre-coat ELISA Plate
1. Coat ELISA plates (Corning, 96 well, Cat. #25805-96) with 05-101 antibody at 0.5 µg per well in PBS, 150 µl final volume/well, and store overnight at 4° C. Coated plates are good for up to 10 days when stored at 4° C.
2. on day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.

Seeding Cells
1. NIH 3T3/C7 cell line (Honegger, et al., Cell 51:199–209, 1987) can be use for this assay.
2. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm at room temperature for 5 minutes.

3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 µl per well, in a 96 well microtiter plate. Incubate seeded cells in 5% $CO_2$ at 37° C. for about 40 hours.

Assay Procedures.

1. Check seeded cells for contamination using an inverted microscope. Dilute test compounds stock (10 mg/ml in DMSO) 1:10 in DMEM medium, then transfer 5 µl to a test well for a test compounds drug dilution of 1:200 and a final DMSO concentration of 1%. Control wells receive DMSO alone. Incubate in 5% $CO_2$ at 37° C. for one hour.
2. Prepare EGF ligand: dilute stock EGF in DMEM so that upon transfer of 10 µl dilute EGF (1:12 dilution), 25 nM final concentration is attained.
3. Prepare fresh 10 ml HNTG* sufficient for 100 µl per well wherein HNTG* comprises: HNTG stock (2.0 ml), milli-Q $H_2O$ (7.3 ml), EDTA, 100 mM, pH 7.0 (0.5 ml), $Na_3VO_4$ 0.5 M (0.1 ml) and $Na_4(P_2O_7)$, 0.2 M (0.1 ml).
4. Place on ice.
5. After two hours incubation with drug, add prepared EGF ligand to cells, 10 µl per well, to yield a final concentration of 25 nM. Control wells receive DMEM alone. Incubate, shaking, at room temperature, for 5 minutes.
6. Remove test compound, EGF, and DMEM. Wash cells twice with PBS. Transfer HNTG* to cells, 100 µl per well. Place on ice for 5 minutes. Meanwhile, remove blocking buffer from other ELISA plate and wash with TBST as described above.
7. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
8. Remove lysate and wash 4 times with TBST. Transfer freshly diluted anti-Ptyr antibody to ELISA plate at 100 µl per well. Incubate shaking at room temperature for 30 minutes in the presence of the anti-Ptyr antiserum (1:3000 dilution in TBST).
9. Remove the anti-Ptyr antibody and wash 4 times with TBST. Transfer the freshly diluted TAGO 30 anti-rabbit IgG antibody to the ELISA plate at 100 µl per well. Incubate shaking at room temperature for 30 minutes (anti-rabbit IgG antibody: 1:3000 dilution in TBST).
10. Remove detection antibody and wash 4 times with TBST. Transfer freshly prepared $ABTS/H_2O_2$ solution to ELISA plate, 100 µl per well. Incubate at room temperature for 20 minutes. $ABTS/H_2O_2$ solution: 1.2 µl 30% $H_2O_2$ in 10 ml ABTS stock.
11. Stop reaction by adding 50 µl 5N $H_2SO_4$ (optional), and determine O.D. at 410 nm.
12. The maximal phosphotyrosine signal is determined by subtracting the value of the negative controls from the positive controls. The percent inhibition of phosphotyrosine content for extract-containing wells is then calculated, after subtraction of the negative controls.

Met Autophosphorylation Assay

This assay determines Met tyrosine kinase activity by analyzing Met protein tyrosine kinase levels on the Met receptor.

Reagents a. HNTG (5×stock solution): Dissolve 23.83 g HEPES and 43.83 g NaCl in about 350 ml $dH_2O$. Adjust pH to 7.2 with HCl or NaOH, add 500 ml glycerol and 10 ml Triton X-100, mix, add $dH_2O$ to 1 L total volume. To make 1 L of 1×working solution add 200 ml 5×stock solution to 800 ml $dH_2O$, check and adjust pH as necessary, store at 4° C.
b. PBS (Dulbecco's Phosphate-Buffered Saline), Gibco Cat. # 450-1300EB (1×solution).
c. Blocking Buffer: in 500 ml $dH_2O$ place 100 g BSA, 12.1 g Tris-pH7.5, 58.44 g NaCl and 10 ml Tween-20, dilute to 1 L total volume.
d. Kinase Buffer: To 500 ml $dH_2O$ add 12.1 g TRIS (pH 7.2), 58.4 g NaCl, 40.7 g $MgCl_2$ and 1.9 g EGTA, bring to 1 L total volume with $dH_2O$.
e. PMSF (Phenylmethylsulfonyl fluoride), Sigma Cat. # P-7626, to 435.5 mg, add 100% ethanol to 25 ml total volume, vortex.
f. ATP (Bacterial Source), Sigma Cat. # A-7699, store powder at −20° C., to make up solution for use, dissolve 3.31 mg in 1 ml $dH_2O$.
g. RC-20H HRPO Conjugated Anti-Phosphotyrosine, Transduction Laboratories Cat. # E120H.
h. Pierce 1-Step™ Turbo TMB-ELISA (3,3',5,5'-tetramethylbenzidine, Pierce Cat. # 34022.
i. $H_2SO_4$, add 1 ml conc. (18 N) to 35 ml $dH_2O$.
j. TRIS HCL, Fischer Cat. # BP152-5, to 121.14 g of material, add 600 ml MilliQ $H_2O$, adjust pH to 7.5 (or 7.2) with HCl, bring volume to 1 L with MilliQ $H_2O$.
k. NaCl, Fischer Cat. # S271-10, make up 5M solution.
l. Tween-20, Fischer Cat. # S337-500.
m. $Na_3VO_4$, Fischer Cat. # S454-50, to 1.8 g material add 80 ml MilliQ $H_2O$, adjust pH to 10.0 with HCl or NaOH, boil in microwave, cool, check pH, repeat procedure until pH stable at 10.0, add MilliQ $H_2O$ to 100 ml total volume, make 1 ml aliquots and store at −80° C.
n. $MgCl_2$, Fischer Cat. # M33-500, make up 1M solution.
o. HEPES, Fischer Cat. # BP310-500, to 200 ml MilliQ $H_2O$, add 59.6 g material, adjust pH to 7.5, bring volume to 250 ml total, sterile filter.
p. Albumin, Bovine (BSA), Sigma Cat. # A-4503, to 30 grams material add sterile distilled water to make total volume of 300 ml, store at 4° C.
q. TBST Buffer: to approx. 900 ml $dH_2O$ in a 1 L graduated cylinder add 6.057 g TRIS and 8.766 g NaCl, when dissolved, adjust pH to 7.2 with HCl, add 1.0 ml Triton X-100 and bring to 1 L total volume with $dH_2O$.
r. Goat Affinity purified antibody Rabbit IgG (whole molecule), Cappel Cat. # 55641.
s. Anti h-Met (C-28) rabbit polyclonal IgG antibody, Santa Cruz Chemical Cat. # SC-161.
t. Transiently Transfected EGFR/Met chimeric cells (EMR) (Komada, et al., Oncogene, 8:2381–2390 (1993).
u. Sodium Carbonate Buffer, ($Na_2CO_4$, Fischer Cat. # S495): to 10.6 g material add 800 ml MilliQ $H_2O$, when dissolved adjust pH to 9.6 with NaOH, bring up to 1 L total volume with MilliQ $H_2O$, filter, store at 4° C.

Procedure

All of the following steps are conducted at room temperature unless it is specifically indicated otherwise. All ELISA plate washing is by rinsing 4× with TBST.

EMR Lysis

This procedure can be performed the night before or immediately prior to the start of receptor capture.

1. Quick thaw lysates in a 37° C. waterbath with a swirling motion until the last crystals disappear.
2. Lyse cell pellet with 1×HNTG containing 1 mM PMSF. Use 3 ml of HNTG per 15 cm dish of cells. Add ½ the calculated HNTG volume, vortex the tube for 1 min., add the remaining amount of HNTG, vortex for another min.
3. Balance tubes, centrifuge at 10,000×g for 10 min at 4° C.
4. Pool supernatants, remove an aliquot for protein determination.
5. Quick freeze pooled sample in dry ice/ethanol bath. This step is performed regardless of whether lysae will be stored overnight or used immediately following protein determination.
6. Perform protein determination using standard bicinchoninic acid (BCA) method (BCA Assay Reagent Kit from Pierce Chemical Cat. # 23225).

ELISA Procedure

1. Coat Corning 96 well ELISA plates with 5 µg per well Goat anti-Rabbit antibody in Carbonate Buffer for a total well volume of 50 µl. Store overnight at 4° C.
2. Remove unbound Goat anti-rabbit antibody by inverting plate to remove liquid.
3. Add 150 µl of Blocking Buffer to each well. Incubate for 30 min. with shaking.
4. Wash 4× with TBST. Pat plate on a paper towel to remove excess liquid and bubbles.
5. Add 1 µg per well of Rabbit anti-Met antibody diluted in TBST for a total well volume of 100 µl.
6. Dilute lysate in HNTG (90 µg lysate/100 µl)
7. Add 100 µl of diluted lysate to each well. Shake for 60 min.
8. Wash 4× with TBST. Pat on paper towel to remove excess liquid and bubbles.
9. Add 50 µl of 1×lysate buffer per well.
10. Dilute compounds/extracts 1:10 in 1×Kinase Buffer in a polypropylene 96 well plate.
11. Transfer 5.5 µl of diluted compound to ELISA plate wells. Incubate at room temperature with shaking for 20 min.
12. Add 5.5 µl of 60 µM ATP solution per well. Negative controls do not receive any ATP. Incubate for 90 min., with shaking.
13. Wash 4× with TBST. Pat plate on paper towel to remove excess liquid and bubbles.
14. Add 100 µl per well of RC20 (1:3000 dilution in Blocking Buffer). Incubate 30 min. with shaking.
15. Wash 4× with TBST. Pat plate on paper towel to remove excess liquid and bubbles.
16. Add 100 µl per well of Turbo-TMB. Incubate with shaking for 30–60 min.
17. Add 100 µl per well of 1M $H_2SO_4$ to stop reaction.
18. Read assay on Dynatech MR7000 ELISA reader. Test Filter=450 nm, reference filter=410 nm.

Biochemical src assay

This assay is used to determine src protein kinase activity measuring phosphorylation of a biotinylated peptide as the readout.

Materials and Reagents:

a. Yeast transformed with src (Sugen, Inc., Redwood City, Calif.).
b. Cell lysates: Yeast cells expressing src are pelleted, washed once with water, re-pelleted and stored at −80° C. until use.
c. N-terminus biotinylated EEEYEEYEEEYEEEYEEEY is prepared by standard procedures well known to those skilled in the art.
d. DMSO: Sigma, St. Louis, Mo.
e. 96 Well ELISA Plate: Corning 96 Well Easy Wash, Modified flat Bottom Plate, Corning Cat. #25805-96.
f. NUNC 96-well V-bottom polypropylene plates for dilution of compounds: Applied Scientific Cat. # A-72092.
g. Vecastain ELITE ABC reagent: Vector, Burlingame, Calif.
h. Anti-src (327) mab: *Schizosaccharomyces Pombe* is used to express recombinant Src (Superti-Furga, et al., *EMBO J.*, 12:2625–2634, Superti-Furga, et al., *Nature Biochem.*, 14:600–605). *S. Pombe* strain SP200 (h-s leu1.32 ura4 ade210) is grown as described and transformations are pRSP expression plasmids are done by the lithium acetate method (Superti-Furga, supra). Cells are grown in the presence of 1 µM thiamine to repress expression from the nmt1 promoter or in the absence of thiamine to induce expression.
i. Monoclonal anti-phosphotyrosine, UBI 05-321 (UB40 may be used instead).
j. Turbo TMB-ELISA peroxidase substrate: Pierce Chemical.

Buffer Solutions a. PBS (Dulbeccol's Phosphate-Buffered Saline): GIBCO PBS, GIBCO Cat. # 450-1300EB.
b. Blocking Buffer: 5% Non-fat milk (Carnation) in PBS.
c. Carbonate Buffer: $Na_2CO_3$ from Fischer, Cat. # S495, make up 100 mM stock solution.
d. Kinase Buffer: 1.0 ml (from 1M stock solution) $MgCl_2$, 0.2 ml (from a 1M stock solution) $MnCl_2$, 0.2 ml (from a 1M stock solution) DTT, 5.0 ml (from a 1M stock solution) HEPES, 0.1 ml TX-100, bring to 10 ml total volume with MilliQ $H_2O$.
e. Lysis Buffer: 5.0 HEPES (from 1M stock solution.), 2.74 ml NaCl (from 5M stock solution), 10 ml glycerol, 1.0 ml TX-100, 0.4 ml EDTA (from a 100 mM stock solution), 1.0 ml PMSF (from a 100 mM stock solution), 0.1 ml $Na_3VO_4$ (from a 0.1 M stock solution), bring to 100 ml total volume with MilliQ $H_2O$.
f. ATP: Sigma Cat. # A-7699, make up 10 mM stock solution (5.51 mg/ml).
g TRIS-HCl: Fischer Cat. # BP 152-5, to 600 ml MilliQ $H_2O$ add 121.14 g material, adjust pH to 7.5 with HCl, bring to 1 L total volume with MilliQ $H_2O$.
h. NaCl: Fischer Cat. # S271-10, Make up 5M stock solution with MilliQ $H_2O$.
i. $Na_3VO_4$: Fischer Cat. # S454-50, to 80 ml MilliQ $H_2O$, add 1.8 g material, adjust pH to 10.0 with HCl or NaOH, boil in a microwave, cool, check pH, repeat pH adjustment until pH remains stable after heating/cooling cycle, bring to 100 ml total volume with MilliQ $H_2O$, make 1 ml aliquots and store at −80° C.
j. $MgCl_2$: Fischer Cat. # M33-500, make up 1M stock solution with MilliQ $H_2O$.

k. HEPES: Fischer Cat. # BP 310-500, to 200 ml MilliQ H$_2$O, add 59.6 g material, adjust pH to 7.5, brine to 250 ml total volume with MilliQ H$_2$O, sterile filter (1M stock solution).

l. TBST Buffer: TBST Buffer: To 900 ml dH$_2$O add 6.057 g TRIS and 8.766 g NaCl, adjust pH to 7.2 with HCl, add 1.0 ml Triton-X100, bring to 1 L total volume with dH$_2$O.

m. MnCl$_2$: Fischer Cat. # M87-100, make up 1M stock solution with MilliQ H$_2$O.

n. DTT: Fischer Cat. # BP172-5.

o. TBS (TRIS Buffered Saline) : to 900 ml MilliQ H$_2$O add 6.057 g TRIS and 8.777 g NaCl, bring to 1 L total volume with MilliQ H$_2$O.

p. Kinase Reaction Mixture: Amount per assay plate (100 wells): 1.0 ml Kinase Buffer, 200 µg GST-ζ, bring to final volume of 8.0 ml with MilliQ H$_2$O.

q. Biotin labeled EEEYEEYEEEYEEEYEEEY: Make peptide stock solution (1 mM, 2.98 mg/ml) in water fresh just before use.

r. Vectastain ELITE ABC reagent: To prepare 14 ml of working reagent, add 1 drop of reagent A to 15 ml TBST and invert tube several times to mix. Then add 1 drop of reagent B. Put tube on orbital shaker at room temperature and mix for 30 minutes.

Procedures:

Preparation of src coated ELISA plate.

1. Coat ELISA plate with 0.5 µg/well anti-src mab in 100 µl of pH 9.6 sodium carbonate buffer, hold at 4° C. overnight.
2. Wash wells once with PBS.
3. Block plate with 0.15 ml 5% milk in PBS for 30 min. at room temperature.
4. Wash plate 5× with PBS.
5. Add 10 µg/well of src transformed yeast lysates diluted in Lysis Buffer (0.1 ml total volume per well). (Amount of lysate may vary between batches.) Shake plate for 20 minutes at room temperature.

Preparation of phosphotyrosine antibody-coated ELISA plate.

1. 4G10 plate: coat 0.5 µg/well 4G10 in 100 µl PBS overnight at 4° C. and block with 150 µl of 5% milk in PBS for 30 minutes at room temperature.

Kinase assay procedure.

1. Remove unbound proteins from plates and wash plates 5× with PBS.
2. Add 0.08 ml Kinase Reaction Mixture per well (containing 10 µl of 10×Kinase Buffer and 10 µM (final concentration) biotin-EEEYEEYEEEYEEEYEEEY per well diluted in water.
3. Add 10 µl of compound diluted in water containing 10% DMSO and pre-incubate for 15 minutes at room temperature.
4. Start kinase reaction by adding 10 µl/well of 0.05 mM ATP in water (5 µM ATP final).
5. Shake ELISA plate for 15 min. at room temperature.
6. Stop kinase reaction by adding 10 µl of 0.5 M EDTA per well.
7. Transfer 90 µl supernatant to a blocked 4G10 coated ELISA plate.
8. Incubate for 30 min. while shaking at room temperature.
9. Wash plate 5× with TBST.
10. Incubate with Vectastain ELITE ABC reagent (100 µl/well) for 30 min. at room temperature.
11. Wash the wells 5× with TBST.
12. Develop with Turbo TMB.

Biochemical lck Assay

This assay is used to determine lck protein kinase activities measuring phosphorylation of GST-ζ as the readout.

Materials and Reagents:

a. Yeast transformed with lck. *Schizosaccharomyces Pombe* is used to express recombinant Lck (Superti-Furga, et al., *EMBO J*, 12:2625–2634, Superti-Furga, et al., *Nature Biotech.*, 14:600–605). *S. Pombe* strain SP200 (h-s leul.32 ura4 ade210) is grown as described and transformations with pRSP expression plasmids are done by the lithium acetate method (Superti-Furga, supra). Cells are grown in the presence of 1 µM thiamine to induce expression.

b. Cell lysates: Yeast cells expressing lck are pelleted, washed once in water, re-pelleted and stored frozen at −80° C. until use.

c. GST-ζ: DNA encoding for GST-ζ fusion protein for expression in bacteria obtained from Arthur Weiss of the Howard Hughes Medical Institute at the University of California, San Francisco. Transformed bacteria are grown overnight while shaking at 25° C. GST-ζ is purified by glutathione affinity chromatography, Pharmacia, Alameda, Calif.

d. DMS0: Sigma, St. Louis, Mo.

e. 96-Well ELISA plate: Corning 96 Well Easy Wash, Modified Flat Bottom Plate, Corning Cat. #25805-96.

f. NUNC 96-well V-bottom polypropylene plates for dilution of compounds: Applied Scientific Cat. # AS-72092.

g. Purified Rabbit anti-GST antiserum: Amrad Corporation (Australia) Cat. #90001605.

h. Goat anti-Rabbit-IgG-HRP: Amersham Ca:. # V010301.

i. Sheep ant-mouse IgG (H+L): Jackson Labs Cat. # 5215-005-003.

j. Anti-Lck (3A5) mab: Santa Cruz Biotechnology Cat # sc-433.

k. Monoclonal anti-phosphotyrosine UBI 05-321 (UB40 may be used instead).

Buffer solutions:

a. PBS (Dulbecco's Phosphate-Buffered Saline) 1× solution: GIBCO PBS, GIBCO Cat. # 450-1300EB.

b. Blocking Buffer: 100 g. BSA, 12.1 g. TRIS (pH7.5), 58.44 g NaCl, 10 ml Tween-20, bring up to 1 L total volume with MilliQ H$_2$O.

c. Carbonate Buffer: Na$_2$CO$_4$ from Fischer, Cat. # S495, make up 100 mM solution with MilliQ H$_2$O.

d. Kinase Buffer: 1.0 ml (from 1M stock solution) MgCl$_2$, 0.2 ml (from a 1M stock solution) MnCl$_2$, 0.2 ml (from a 1M stock solution) DTT, 5.0 ml (from a 1M stock solution) HEPES, 0.1 ml TX-100, bring to 10 ml total volume with MilliQ H$_2$O.

e. Lysis Buffer: 5.0 HEPES (from 1M stock solution.), 2.74 ml NaCl (from 5M stock solution), 10 ml glycerol, 1.0 ml TX-100, 0.4 ml EDTA (from a 100 mM stock solution), 1.0 ml PMSF (from a 100 mM stock solution), 0.1 ml Na$_3$VO$_4$ (from a 0.1 M stock solution), bring to 100 ml total volume with MilliQ H$_2$O.

f. ATP: Sigma Cat. # A-7699, make up 10 mM stock solution (5.51 mg/ml).

g TRIS-HCl: Fischer Cat. # BP 152-5, to 600 ml MilliQ H₂O add 121.14 g material, adjust pH to 7.5 with HCl, bring to 1 L total volume with MilliQ H₂O.

h. NaCl: Fischer Cat. # S271-10, Make up 5M stock solution with MilliQ H₂O.

i Na₃VO₄: Fischer Cat. # S454-50, to 80 ml MilliQ H₂O, add 1.8 g material, adjust pH to 10.0 with HCl or NaOH, boil in a microwave, cool, check pH, repeat pH adjustment until pH remains stable after heating/cooling cycle, bring to 100 ml total volume with MilliQ H₂O, make 1 ml aliquots and store at −80° C.

j. MgCl₂: Fischer Cat. # M33-500, make up 1M stock solution with MilliQ H₂O.

k. HEPES: Fischer Cat. # BP 310-500, to 200 ml MilliQ H₂O, add 59.6 g material, adjust pH to 7.5, bring to 250 ml total volume with MilliQ H₂O, sterile filter (1M stock solution).

l. Albumin, Bovine (BSA), Sigma Cat. # A4503, to 150 ml MilliQ H₂O add 30 g material, bring 300 ml total volume with MilliQ H₂O, filter through 0.22 μm filter, store at 4° C.

m. TBST Buffer: To 900 ml dH₂O add 6.057 g TRIS and 8.766 g NaCl, adjust pH to 7.2 with HCl, add 1.0 ml Triton-X100, bring to 1 L total volume with dH₂O.

n. MnCl2: Fischer Cat. # M87-100, make up 1M stock solution with MilliQ H₂O.

o. DTT: Fischer Cat. # BP172-5.

p. TBS (TRIS Buffered Saline): to 900 ml MilliQ H₂O add 6.057 g TRIS and 8.777 g NaCl, bring to 1 L total volume with MilliQ H₂O.

q Kinase Reaction.Mixture: Amount per assay plate (100 wells): 1.0 ml Kinase Buffer, 200 μg GST-ζ, bring to final volume of 8.0 ml with MilliQ H₂O.

Procedures:
Preparation of Lck coated ELISA plate.

1. Coat 2.0 μg/well Sheep anti-mouse IgG in 100 μl of pH 9.6 sodium carbonate buffer at 4° C. overnight.
2. Wash well once with PBS.
3. Block plate with 0.15 ml of blocking Buffer for 30 min. at room temp.
4. Wash plate 5× with PBS.
5. Add 0.5 μg/well of anti-lck (mab 3A5) in 0.1 ml PBS at room temperature for 1–2 hours.
6. Wash plate 5× with PBS.
7. Add 20 μg/well of lck transformed yeast lysates diluted in Lysis Buffer (0.1 ml total volume per well) Shake plate at 4° C. overnight to prevent loss of activity.

Preparation of phosphotyrosine antibody-coated ELISA plate.

1. UB40 plate: 1.0 μg/well UB40 in 100 μl of PBS overnight at 4° C. and block with 150 μl of Blocking Buffer for at least 1 hour.

Kinase assay procedure.

1. Remove unbound proteins from plates and wash plates 5× with PBS.
2. Add 0.08 ml Kinase Reaction Mixture per well (containing 10 μl of 10×Kinase Buffer and 2 μg GST-ζ per well diluted with water).
3. Add 10 μl of compound diluted in water containing 10% DMSO and pre-incubate for 15 minutes at room temperature.
4. Start kinase reaction by adding 10 μl/well of 0.1 mM ATP in water (10 M ATP final).
5. Shake ELISA plate for 60 min. at room temperature.
6. Stop kinase reaction by adding 10 μl of 0.5 M EDTA per well.
7. Transfer 90 μl supernatant to a blocked 4G10 coated ELISA plate from section B, above.
8. Incubate while shaking for 30 min. at room temperature.
9. Wash plate 5× with TBST.
10. Incubate with Rabbit anti-GST antibody at 1:5000 dilution in 100 μl TBST for 30 min. at room temperature.
11. Wash the wells 5× with TBST.
12. Incubate with Goat anti-Rabbit-IgG-HRP at 1:20,000 dilution in 100 μl of TBST for 30 min. at room temperature.
13. Wash the wells 5× with TBST.
14. Develop with Turbo TMB.

Assay measuring phosphorylating function of RAF.

The following assay reports the amount of RAF-catalyzed phosphorylation of its target protein MEK as well as MEK's target MAPK. The RAF gene sequence is described in Bonner et al., 1985, *Molec. Cell. Biol.*, 5:1400–1407, and is readily accessible in multiple gene sequence data banks. Construction of the nucleic acid vector and cell lines utilized for this portion of the invention are fully described in Morrison et al., 1988, *Proc. Natl. Acad. Sci. USA*, 85:8855–8859.

Materials and Reagents

1. Sf9 (Spodoptera frugiperda) cells, GIBCO-BRL, Gaithersburg, Md.
2. RIPA buffer: 20 mM Tris/HCl pH 7.4, 137 mM NaCl, 10% glycerol, 1 mM PMSF, 5 mg/L Aprotenin, 0.5 % Triton X-100,
3. Thioredoxin-MEK fusion protein (T-MEK): T-MEK expression and purification by affinity chromatography are performed according to the manufacturer's procedures. Catalog# K 350-01 and R 350-40, Invitrogen Corp., San Diego, Calif.
4. His-MAPK (ERK 2), His-tagged MAPK is expressed in XL1 Blue cells transformed with pUC18 vector encoding His-MAPK. His-MAPK is purified by Ni-affinity chromatography. Cat# 27-4949-01, Pharmacia, Alameda, Calif., as described herein.
5. Sheep anti mouse IgG: Jackson laboratories, West Grove, Pa. Catalog, # 515-006-008, Lot# 28563
6. RAF-1 protein kinase specific antibody: URP2653 from UBI.
7. Coating buffer: PBS, phosphate buffered saline, GIBCO-BRL, Gaithersburg, Md.
8. Wash buffer: TBST (50 mM Tris/HCL pH 7.2, 150 mM NaCl, 0.1 % Triton X-100).
9. Block buffer: TBST, 0.1% ethanolamine pH 7.4
10. DMSO, Sigma, St. Louis, Mo.
11. Kinase buffer (KB): 20 mM HEPES/HCl pH 7.2, 150 mM NaCl, 0.1% Triton X-100, 1 mM PMSF, 5 mg/L Aprotenin, 75 mM sodium orthovanadate, 0.5 MM DTT and 10 mM MgCl₂.
12. ATP mix: 100 mM MgCl₂, 300 mM ATP, 10 mCi γ³³P ATP (Dupont-NEN)/mL.
13 Stop solution: 1% phosphoric acid, Fisher, Pittsburgh, Pa.
14. Wallac Cellulose Phosphate Filter mats, Wallac, Turku, Finnland.

15. Filter wash solution: 1% phosphoric acid, Fisher, Pittsburgh, Pa.
16. Tomtec plate harvester, Wallac, Turku, Finnland.
17. Wallac beta plate reader # 1205, Wallac, Turku, Finnland.
18. NUNC 96-well V bottom polypropylene plates for compounds Applied Scientific Catalog # AS-72092.

Procedure

All of the following steps are conducted at room temperature unless specifically indicated otherwise.

1. ELISA plate coating: ELISA wells are coated with 100 ml of Sheep anti mouse affinity purified antiserum (1 mg/lao mL coating buffer) over night at 40° C. ELISA plates can be used for two weeks when stored at 40° C.
2. Invert the plate and remove liquid. Add 100 mL of blocking solution and incubate for 30 min.
3. Remove blocking solution and wash four times with wash buffer. Pat the plate on a paper towel to remove excess liquid.
4. Add 1 mg of antibody specific for RAF-1 to each well and incubate for 1 hour. Wash as described in step 3.
5. Thaw lysates from RAS/RAF infected Sf9 cells and dilute with TBST to 10 mg/100 mL. Add 10 mg of diluted lysate to the wells and incubate for 1 hour. Shake the plate during incubation. Negative controls receive no lysate. Lysates from RAS/RAF infected Sf9 insect cells are prepared after cells are infected with recombinant baculoviruses at a MOI of 5 for each virus, and harvested 48 hours later. The cells are washed once with PBS and lysed in RIPA buffer. Insoluble material is removed by centrifugation (5 min at 10,000× g). Aliquots of lysates are frozen in dry ice/ethanol and stored at −80° C. until use.
6. Remove non-bound material and wash as outlined above (step 3).
7. Add 2 mg of T-MEK and 2 mg of His-MAEPK per well and adjust the volume to 40 ml with kinase buffer. Methods for purifying T-MEK and MAPK from cell extracts are provided herein by example.
8. Pre-dilute compounds (stock solution 10 mg/ml DMSO) or extracts 20 fold in TEST plus 1% DMSO. Add 5 ml of the pre-diluted compounds/extracts to the wells described in step 6. Incubate for 20 min. Controls receive no drug.
9. Start the kinase reaction by addition of 5 ml ATP mix, Shake the plates on an ELISA plate shaker during incubation.
10. Stop the kinase reaction after 60 min by addition of 30 mL stop solution to each well.
11. Place the phosphocellulose mat and the ELISA plate in the Tomtec plate harvester. Harvest and wash the filter with the filter wash solution according to the manufacturer's recommendation. Dry the filter mats. Seal the filter mats and place them in the holder. Insert the holder into radioactive detection apparatus and quantify the radioactive phosphorous on the filter mats.

Alternatively, 40 mL aliquots from individual wells of the assay plate can be transferred to the corresponding positions on the phosphocellulose filter mat. After air drying the filters, put the filters in a tray. Gently rock the tray, changing the wash solution at 15 min intervals for 1 hour. Air-dry the filter mats. Seal the filter mats and place them in a holder suitable for measuring the radioactive phosphorous in the samples. Insert the holder into a detection device and quantify the radioactive phosphorous on the filter mats.

CDK2/Cyclin A—Inhibition Assay

This assay analyzes the protein kinase activity of CDK2 in exogenous substrate.

Reagents:

A. Buffer A: (80 mM Tris (pH 7.2), 40 MM $MgCl_2$), 4.84 g. Tris (F.W. =121.1 g/mol), 4.07 9. $MgCl_2$ (F.W.= 203.31 g/mol) dissolved in 500 ml $H_2O$. Adjust pH to 7.2 with HCl.
B. Histone H1 solution (0.45 mg/ml Histone H1 and 20 mM HEPES pH 7.2: 5 mg Histone H1 (Boehinger Mannheim) in 11.111 ml 20 mM HEPES pH 7.2 (477 mg HEPES (F.W.=238.3 g/mol) dissolved in 100 ml $ddH_2O$, stored in 1 ml aliquots at −80° C.
C. ATP solution (60 µM ATP, 300 µg/ml BSA, 3 mM DTT): 120 µl 10 mM ATP, 600 µl 10 mg/ml BSA to 20 ml, stored in 1 ml aliquots at −80° C.
D. CDK2 solution: cdk2/cyclin A in 10 mM HEPES pH 7.2, 25 mM NaCl, 0.5 mM DTT, 10% glycerol, stored in 9 µl aliquots at −80° C.

Protocol

1. Prepare solutions of inhibitors at three times the desired final assay concentration in $ddH_2O$/15% DMSO by volume.
2. Dispense 20 µl of inhibitors to wells of polypropylene 96-well plates (or 20 µl 15% DMSO for positive and negative controls).
3. Thaw Histone H1 solution (1 ml/plate), ATP solution (1 ml/plate plus 1 aliquot for negative control), and CDK2 solution (9 µl/plate). Keep CDK2 on ice until use. Aliquot CDK2 solution appropriately to avoid repeated freeze-thaw cycles.
4. Dilute 9 µl CDK2 solution into 2.1 ml Buffer A (per plate). Mix. Dispense 20 µl into each well.
5. Mix 1 ml Histone Hi solution with 1 ml ATP solution (per plate) into a 10 ml screw cap tube. Add $\gamma^{33}P$ ATP to a concentration of 0.15 µCi/20 µl (0.15 µCi/well in assay). Mix carefully to avoid BSA frothing. Add 20 µl to appropriate wells. Mix plates on plate shaker. For negative control, mix ATP solution with an equal amount of 20 mM HEPES pH 7.2 and add $\gamma^{33}P$ ATP to a concentration of 0.15 µCi/20 µl solution. Add 20 µl to appropriate wells.
6. Let reactions proceed for 60 minutes.
7. Add 35 µl 10% TCA to each well. Mix plates on plate shaker.
8. Spot 40 µl of each sample onto P30 filter mat squares. Allow mats to dry (approx. 10–20 minutes).
9 Wash filter mats 4×10 minutes with 250 ml 1% phosphoric acid (10 ml phosphoric acid per liter $ddH_2O$).
10. Count filter mats with beta plate reader.

Cellular/Biologic Assays

PDGF-Induced BrdU Incorporation Assay

Materials and Reagents:

(1) PDGF: human PDGF B/B, 1276-956, Boehringer Mannheim, Germany.
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.

(6) PBS Washing Solution: 1×PBS, pH 7.4 (Sugen, Inc., Redwood City, Calif.).
(7) Albumin, Bovine (BSA): fraction V powder, A-8551, Sigma Chemical Co., USA.
(8) 3T3 cell line genetically engineered to express human PDGF-R.

Protocol (1) Cells are seeded at 8000 cells/well in DMEM, 10% CS, 2 mM Gln in a 96 well plate. Cells are incubated overnight at 37° C. in 5% $CO_2$.
(2) After 24 hours, the cells are washed with PBS, and then are serum starved in serum free medium (0%CS DMEM with 0.1% BSA) for 24 hours.
(3) On day 3, ligand (PDGF, 3.8 nM, prepared in DMEM with 0.1% BSA) and test compounds are added to the cells simultaneously. The negative control wells receive serum free DMEM with 0.1% BSA only, the positive control cells receive the ligand (PDGF) but no test compound. Test compounds are prepared in serum free DMEM with ligand in a 96 well plate, and serially diluted for 7 test concentrations.
(4) After 20 hours of ligand activation, diluted BrdU labeling reagent (1:100 in DMEM, 0.1% BSA) is added and the cells are incubated with BrdU (final concentration=10 $\mu$M) for 1.5 hours.
(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.
(6) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 $\mu$l/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

EGF-Induced BrdU Incorporation Assay Materials and Reagents (1) EGF: mouse EGF, 201, Toyobo, Co., Ltd. Japan.
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.

(6) PBS Washing Solution: 1×PBS, pH 7.4 (Sugen, Inc., Redwood City, Calif.).
(7) Albumin, Bovine (BSA): fraction V powder, A-8551, Sigma Chemical Co., USA.
(8) 3T3 cell line genetically engineered to express human EGF-R.

Protocol (1) Cells are seeded at 8000 cells/well in 10% CS, 2 mM Gln in DMEM, in a 96 well plate. Cells are incubated overnight at 37° C. in 5% $CO_2$.
(2) After 24 hours, the cells are washed with PBS, and then are serum starved in serum free medium (0% CS DMEM with 0.1% BSA) for 24 hours.
(3) On day 3, ligand (EGF, 2 nM, prepared in DMEM with 0.1% BSA) and test compounds are added to the cells simultaneously. The negative control wells receive serum free DMEM with 0.1% BSA only, the positive control cells receive the ligand (EGF) but no test compound. Test compounds are prepared in serum free DMEM with ligand in a 96 well plate, and serially diluted for 7 test concentrations.
(4) After 20 hours of ligand activation, diluted BrdU labeling reagent (1:100 in DMEM, 0.1% BSA) is added and the cells are incubated with BrdU (final concentration =10 $\mu$M) for 1.5 hours.
(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.
(6) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 $\mu$l/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

EGF-Induced Her2-Driven BrdU Incoxoration Materials and Reagents (1) EGF: mouse EGF, 201, Toyobo, Co., Ltd. Japan
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.

(6) PBS Washing Solution: 1×PBS, pH 7.4, made in house.
(7) Albumin, Bovine (BSA): fraction V powder, A-8551, Sigma Chemical Co., USA.
(8) 3T3 cell line engineered to express a chimeric receptor having the extra-cellular domain of EGF-R and the intra-cellular domain of Her2.

Protocol (1) Cells are seeded at 8000 cells/well in DMEM, 10% S, 2 mM Gln in a 96-well plate. Cells are incubated overnight at 37° C. in 5% $CO_2$.
(2) After 24 hours, the cells are washed with PBS, and then are serum starved in serum free medium (0% CS DMEM with 0.1% BSA) for 24 hours.
(3) On day 3, ligand (EGF=2 nM, prepared in DMEM with 0.1% BSA) and test compounds are added to the cells simultaneously. The negative control wells receive serum free DMEM with 0.1% BSA only, the positive control cells receive the ligand (EGF) but no test compound. Test compounds are prepared in serum free DMEM with ligand in a 96 well plate, and serially diluted for 7 test concentrations.
(4) After 20 hours of ligand activation, diluted BrdU labeling reagent (1:100 in DMEM, 0.1% BSA) is added and the cells are incubated with BrdU (final concentration=10 μM) for 1.5 hours.
(5) After incubation with labeling reagent, the medium is removed by decanting and tapping the inverted plate on a paper towel. FixDenat solution is added (50 μl/well) and the plates are incubated at room temperature for 45 minutes on a plate shaker.
(6) The FixDenat solution is thoroughly removed by decanting and tapping the inverted plate on a paper towel. Milk is added (5% dehydrated milk in PIBS, 200 μl/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 μl/well) and the plate is incubated for 90 minutes at room temperature on a plate shaker.
(8) The antibody conjugate is thoroughly removed by *decanting and rinsing the wells 5 times with PBS, and the plate is dried by inverting and tapping on a paper towel.
(9) TMB substrate solution is added (100 μl/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

IGF1-Induced BrdU Incorporation Assay Materials and Reagents (1) IGF1 Ligand: human, recombinant, G511, Promega Corp, USA.
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1×PBS, pH 7.4 (Sugen, Inc., Redwood City, Calif.).
(7) Albumin, Bovine (BSA): fraction V powder, A-8551, Sigma Chemical Co., USA.
(8) 3T3 cell line genetically engineered to express human IGF-1 receptor.

Protocol (1) Cells are seeded at 8000 cells/well in DMEM, 10% CS, 2 mM Gln in a 96- well plate. Cells are incubated overnight at 37° C. in 5% $CO_2$.
(2) After 24 hours, the cells are washed with PBS, and then are serum starved in serum free medium (0%CS DMEM with 0.1% BSA) for 24 hours.
(3) On day 3, ligand (IGF1=3.3 nM, prepared in DMEM with 0.1% BSA) and test compounds are added to the cells simultaneously. The negative control wells receive serum free DMEM with 0.1% BSA only, the positive control cells receive the ligand (IGF1) but no test compound. Test compounds are prepared in serum free DMEM with ligand in a 96 well plate, and serially diluted for 7 test concentrations.
(4) After 16 hours of ligand activation, diluted BrdU labeling reagent (1:100 in DMEM, 0.1% BSA) is added and the cells are incubated with BrdU (final concentration=10 μM) for 1.5 hours.
(5) After incubation with labeling reagent, the medium is removed by decanting and tapping the inverted plate on a paper towel. FixDenat solution is added (50 μl/well) and the plates are incubated at room temperature for 45 minutes on a plate shaker.
(6) The FixDenat solution is thoroughly removed by decanting and tapping the inverted plate on a paper towel. Milk is added (5% dehydrated milk in PBS, 200 μl/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 μl/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 μl/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

FGF-Induced BrdU incorporation Assay

This assay measures FGF-induced DNA synthesis in 3Tc7/EGFr cells that express endogenous FGF receptors.

Materials and Reagents:
1. FGF: human FGF2/bFGF (Gibco BRL, No. 13256-029).
2. BrdU Labeling reagent, (10 mM PBS (pH 7.4), Boehringer Mannheim Cat No. 1 647 229).
3. Fixdenat fixation solution (Boehringer Mannheim Cat No. 1 647 229).
4. Anti-BrdU-POD (mouse monoclonal antibody conjugated with peroxidase, Boehringer Mannheim Cat. No. 1 647 229).
5. TMB (tetramethylbenzidine, Boehringer Mannheim Cat. No. 1 647 229).
6. PBS washing solution, pH 7.4 (Sugen, Inc.).
7. Albumin, bovine (BSA), fraction V powder (Sigma Chemical Co., Cat. No. A-8551)

Procedure
1. 3T3 engineered cell line: 3T3c7/EGFr.
2. Cells are seeded at 8,000 cells/well in DMEM, 10% CS and 2 mM Gln in a 96-well plate. Incubate 24 hours at 37° C. in 5% $CO_2$.
3. After 24 hours, wash cells with PBS then serum starve in serum free medium (0% DMEM, 0.1% BSA) for 24 hours.
4. Add ligand (FGF2 (1.5 nM in DMEM with 0.1% BSA) and test compound simultaneously. Negative control wells receive serum free DMEM with 0.1% BSA only, positive control wells receive FGF2 ligand but no test compound. Test compounds are prepared in serum-free DMEM with ligand in a 96-well plate and serially diluted to make seven (7) test concentrations.
5. After 20 hours, add diluted BrdU labeling reagent (1:100 BrdU:DMEM, 0.1% BSA, final concentration is 10 μM) to the cells and incubate for 1.5 hours.
6. Decant medium. Remove traces of material with paper towel. Add FixDenat (50 μl/well) and incubate at room temperature for 45 minutes on a plate shaker.
7. Remove Fixdenat solution. Add blocking solution (5% dehydrated milk in PBS (200 μl/well)) and incubate for 30 minutes at room temperature on a plate shaker.
8. Decant blocking solution, wash wells once with PBS. Add anti-BrdU-POD solution (1:100 dilution in PBS, 0.1% BSA), incubate for 90 minutes at room temperature on a plate shaker.
9. Decant antibody conjugate, rinse wells 5 times with PBS. Dry plate by inverting on paper towel and tapping.
10. Add TMB solution (100 μl/well), incubate 20 minutes at room temperature on a plate shaker until color development is sufficient for photometric detection.
11. Measure absorbance at 410 nM on a Dynatech ELISA plate reader using "Dual wavelength" mode with a filter at 490 nM.

Biochemical EGFR Assay

This assay measures the in vitro kinase activity of EGFR using ELISA.

Materials and Reagents
1. Corning 96-well Elisa plates (Corning Catalog No. 25805-96).
2. SUMO1 monoclonal anti-EGFR antibody (Biochemistry Lab, SUGEN, Inc.).
3. PBS (Dulbecco's Phosphate-Buffered Saline, Gibco Catalog No. 450–1300EB).

4. TBST Buffer

| Reagent | M.W. | Working Concentration | Amount per L |
|---|---|---|---|
| Tris | 121.14 | 50 mM | 6.057 g |
| NaCl | 58.44 | 150 mM | 8.766 g |
| Triton X-100 | NA | 0.1% | 1.0 ml |

5. Blocking Buffer:

| Reagent | M.W. | Working Concentration | Amount per 100 ml |
|---|---|---|---|
| Carnation Instant Non-Fat Milk | | 5% | 5.0 g |
| PBS | NA | NA | 100 ml |

6. A431 cell lysate (Screening Lab, SUGEN, Inc.)

7. TBS Buffer:

| Reagent | M.W. | Working Concentration | Amount per L |
|---|---|---|---|
| Tris | 121.14 | 50 mM | 6.057 g |
| NaCl | 58.44 | 150 mM | 8.766 g |

8. TBS + 10% DMSO

| Reagent | M.W. | Working Concentration | Amount per L |
|---|---|---|---|
| Tris | 121.14 | 50 mM | 1.514 g |
| NaCl | 58.44 | 150 mM | 2.192 g |
| DMSO | NA | 10% | 25 ml |

9. Adenosine-5'-triphosphate (ATP, from Equine muscle, Sigma Cat. No. A-5394).

Prepare a 1.0 mM solution in $dH_2O$. This reagent should be made up immediately prior to use and kept on ice.

10. $MnCl_2$.

Prepare a 1.0 M stock solution in dH2O.

11. ATP/$MnCl_2$ phosphorylation mix

| Reagent | Stock solution | Amount per 10 ml | Working Concentration |
|---|---|---|---|
| ATP | 1.0 mM | 300 μl | 30 μM |
| $MnCl_2$ | 1.0 M | 500 μl | 50 mM |
| $dH_2O$ | | | 9.2 ml |

This reagent should be prepared immediately before use and kept on ice.

12. NUNC 96-well V bottom polypropylene plates (Applied Scientific Cat. No. AS-72092).
13. Ethylenediaminetetraacetic acid (EDTA)

Prepare 200 mM working solution in $dH_2O$. Adjust to pH 8.0 with 10 N NaOH.

14. Rabbit polyclonal anti-phosphotyrosine serum (Biochemistry Lab, SUGEN, Inc.)
15. Goat anti-rabbit IgG peroxidase conjugate (Biosource Cat. No. ALI0404)
16. ABTS (2,2'-azino-bis(3-ethylbenzthiazoline-6-sulfonic acid), Sigma Cat. No. A-1888).

| Reagent | M.W. | Working Concentration | Amount per L |
|---------|------|----------------------|--------------|
| Citric Acid | 192.12 | 100 mM | 19.21 g |
| Na2HPO4 | 141.96 | 250 mM | 35.49 g |
| ABTS | NA | 0.5 mg/ml | 500 mg |

Mix first two ingredients in about 900 ml dH$_2$O, adjust pH to 4.0 with phosphoric acid. Add ABTS, cover, let sit about 0.5 hr., filter. The solution should be kept in the dark at 4° C. until ready to use.

17. Hydrogen peroxide 30% solution (Fisher Cat. No. H325)
18. ABTS/H$_2$O$_2$

Mix 15 ml ABTS solution and 2.0 µl H$_2$O$_2$. Prepare 5 minutes before use.

19. 0.2 M HCl

Procedure

1. Coat Corning 96 well ELISA plates with 0.5 µg SUMO1 in 100 µl PBS per well, store overnight at 4° C.
2. Remove unbound SUMO1 from wells by inverting plate to remove liquid. Wash 1× with dH$_2$O. Pat the plate on a paper towel to remove excess liquid.
3. Add 150 µl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in PBS (7 µg lysate/100 µl PBS).
6. Add 100 µl of diluted lysate to each well. Shake at room temperature for 60 min.
7. Wash plates as described in 4, above.
8. Add 120 µl TBS to ELISA plate containing captured EGFR.
9. Dilute test compound 1:10 in TBS in 96-well polypropylene plates (ie. 10 µl compound+90 µl TBS)
10. Add 13.5 µl diluted test compound to ELISA plate. To control wells (wells which do not receive any test compound), add 13.5 µl TBS+10% DMSO.
11. Incubate for 30 minutes while shaking at room temperature.
12. Add 15 µl phosphorylation mix directly to all wells except negative control well which does not receive ATP/MnCl$_2$ (final well volume should be approximately 150 µl with 3 µM ATP/5 mM MnCl$_2$ final concentration in each well.) Incubate 5 minutes while shaking.
13. After 5 minutes, stop reaction by adding 16.5 µl of 200 mM EDTA (pH 8.0) to each well, shaking continuously. After the EDTA has been added, shake for 1 min.
14. Wash 4× with deionized water, twice with TBST.
15. Add 100 µl anti-phosphotyrosine (1:3000 dilution in TBST) per well. Incubate 30–45 min. at room temperature, with shaking.
16. Wash as described in 4, above.
17. Add 100 µl Biosource Goat anti-rabbit IgG peroxidase conjugate (1:2000 dilution in TBST) to each well. Incubate 30 min. at room temperature, with shaking.
18. Wash as described in 4, above.
19. Add 100 µl of ABTS/H$_2$O$_2$ solution to each well.
20. Incubate 5 to 10 minutes with shaking. Remove any bubbles.
21. If necessary stop reaction with the addition of 100 µl 0.2 M HCl per well.
22. Read assay on Dynatech MR7000 ELISA reader. Test Filter: 410 nM Reference Filter: 630 Nm.

Biochemical PDGFR Assay

This assay measures the in vitro kinase activity of PDGFR using ELISA.

Materials and Reagents

Unless otherwise noted, the preparation of working solution of the following reagents is the same as that for the Biochemical EGFR assay, above.

1. Corning 96-well Elisa plates (Corning Catalog No. 25805-96).
2. 28D4C10 monoclonal anti-PDGFR antibody (Biochemistry Lab, SUGEN, Inc.).
3. PBS (Dulbecco's Phosphate-Buffered Saline, Gibco Catalog No. 450-1300EB)
4. TBST Buffer.
5. Blocking Buffer.
6. PDGFR-β expressing NIH 3T3 cell lysate (Screening Lab, SUGEN, Inc.).
7. TBS Buffer.
8. TBS+10% DMSO.
9. Adenosine-5'-triphosphate (ATP, from Equine muscle, Sigma Cat. No. A-5394).
10. MnCl$_2$.
11. Kinase buffer phosphorylation mix.

| Reagent | Stock solution | Amount per 10 ml | Working Concentration |
|---------|---------------|------------------|----------------------|
| Tris | 1M | 250 µl | 25 mM |
| NaCl | 5M | 200 µl | 100 mM |
| MnCl$_2$ | 1M | 100 µl | 10 mM |
| TX-100 | 100 mM | 50 µl | 0.5 mM |

12. NUNC 96-well V bottom polypropylene plates (Applied Scientific Cat. No. AS-72092).
13. Ethylenediaminetetraacetic acid (EDTA).
14. Rabbit polyclonal anti-phosphotyrosine serum (Biochemistry Lab, SUGEN, Inc.).
15. Goat anti-rabbit IgG peroxidase conjugate (Biosource Cat. No. ALI0404).
16. 2,2'-azino-bis(3-ethylbenzthiazoline-6-sulfonic acid) (ABTS, Sigma Cat. No. A-1888).
17. Hydrogen peroxide 30% solution (Fisher Cat. No. H325).
18. ABTS/H$_2$O$_2$.
19. 0.2 M HCl.

Procedure

1. Coat Corning 96 well ELISA plates with 0.5 µg 28D4C10 in 100 µl PBS per well, store overnight at 4° C.
2. Remove unbound 28D4C10 from wells by inverting plate to remove liquid. Wash 1× with dH$_2$O. Pat the plate on a paper towel to remove excess liquid.
3. Add 150 µl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 µg lysate/100 µl HNTG)
6. Add 100 µl of diluted lysate to each well. Shake at room temperature for 60 min.

7. Wash plates as described in 4, above.
8. Add 80 μl working kinase buffer mix to ELISA plate containing captured PDGFR.
9. Dilute test compound 1:10 in TBS in 96-well polypropylene plates (i.e., 10 μl compound+90 μl TBS).
10. Add 10 μl diluted test compound to ELISA plate. To control wells (wells which do not receive any test compound), add 10 μl TBS+10% DMSO.
11. Incubate for 30 minutes while shaking at room temperature.
12. Add 10 μl ATP directly to all wells except negative control well (final well volume should be approximately 100 μl with 20 μM ATP in each well.) Incubate 30 minutes while shaking.
13. After 30 minutes, stop reaction by adding 10 μl of 200 mM EDTA (pH 8.0) to each well.
14. Wash 4× with deionized water, twice with TBST.
15. Add 100 μl anti-phosphotyrosine (1:3000 dilution in TBST) per well. Incubate 30–45 min. at room temperature, with shaking.
16. Wash as described in 4, above.
17. Add 100 μl Biosource Goat anti-rabbit IgG peroxidase conjugate (1:2000 dilution in TBST) to each well. Incubate 30 min. at room temperature, with shaking.
18. Wash as described in 4, above.
19. Add 100 μl of ABTS/$H_2O_2$ solution to each well.
20. Incubate 10 to 30 minutes with shaking. Remove any bubbles.
21. If necessary stop reaction with the addition of 100 μl 0.2 M HCl per well.
22. Read assay on Dynatech MR7000 ELISA reader: test filter: 410 nM, reference filter: 630 nM.

Biochemical FGFR Assay

This assay measures in vitro kinase activity of the Myc-GyrB-FGFR fusion protein using ELISA.

Materials and Reagents

| 1. HNTG Reagent | M.W. | 5x Stock Concentration | Amount per L | 1x Working Concentration |
|---|---|---|---|---|
| HEPES | 238.3 | 100 mM | 23.83 g | 20 mM |
| NaCl | 58.44 | 750 mM | 43.83 g | 150 mM |
| Glycerol | NA | 50% | 500 ml | 10% |
| Triton X-100 | NA | 5% | 10 ml | 1.0% |

To make a liter of 5× stock solution, dissolve HEPES and NaCl in about 350 ml $dH_2O$, adjust pH to 7.2 with HCl or NaOH (depending on the HEPES that is used), add glycerol, Triton X-100 and then $dH_2O$ to volume.

2. PBS (Dulbecco's Phosphate-Buffered Saline, Gibco Catalog # 450-1300EB).
3. Blocking Buffer.
4. Kinase Buffer.

| Reagent | M.W. | 10x Stock Concentration | 1x Working Concentration |
|---|---|---|---|
| HEPES (pH 7.2) | 238.3 | 500 mM | 50 mM |
| $MnCl_2$ | | 20 mM | 2 mM |
| $MgCl_2$ | 203.32 | 200 mM | 10 mM |
| Triton-X-100 | | 1% | 0.1% |
| DTT | 380.35 | 5 mM | 0.5 mM |

5. Phenylmethylsulfonyl fluoride (PMSF, Sigma, Cat. No. P-7626):
   Working solution: 100 mM in ethanol.
6. ATP (Bacterial source, Sigma Cat. No. A-7699) Use 3.31 mg per ml MilliQ $H_2O$ for a stock concentration of 6 mM.
7. Biotin conjugated anti-phosphotyrosine mab (clone 4G10, Upstate Biotechnology Inc. Cat. No. 16-103, Ser. No. 14495).
8. Vectastain Elite ABC reagent (Avidin peroxidase conjugate, Vector Laboratories Cat. No. PK-6 100).
9. ABTS Solution.
10. Hydrogen peroxide 30% solution (Fisher Catalog # H325).
11. ABTS/$H_2O_2$.
12. 0.2 M HCl.
13. TRIS HCl (Fischer Cat. No. BP 152-5).
    Prepare 1.0 mM solution in MilliQ $H_2O$, adjust pH to 7.2 with HCl.
14. NaCl (Fisher Cat. No. S271-10).
    Prepare 5 M solution in MilliQ $H_2O$.
15. $MgCl_2$ (Fisher Cat. No. M33-500).
    Prepare 1 M solution in MilliQ $H_2O$.
16. HEPES (Fisher Cat. No. BP310-500).
    Prepare 1 M solution in MilliQ $H_2O$, adjust pH to 7.5, sterile filter.
17. TBST Buffer.
18. Sodium Carbonate Buffer (Fisher Cat. No. S495)
    Prepare 0.1 M solution in MilliQ $H_2O$, adjust pH to 9.6 with NaOH, filter.
19. Dithiothreitol (DTT, Fisher Cat. No. BP172-25).
    Prepare 0.5 mM working solution in MilliQ $H_2O$ just prior to use. Store at −20° C. until used, discard any leftover.
20. $MnCl_2$.
21. Triton X-100.
22. Goat α-Rabbit IgG (Cappel).
23. Affinity purified Rabbit α GST GyrB (Biochemistry Lab. SUGEN, Inc.).

Procedure

All of the following steps are conducted at room temperature unless otherwise indicated.

1. Coat Corning 96-well ELISA plates with 2 μg Goat α-Rabbit antibody per well in Carbonate Buffer such that total well volume is 100 μl. Store overnight at 4° C.
2. Remove unbound Goat α-Rabbit antibody by inverting plate to remove liquid. Pat plate on a paper towel to remove excess liquid and bubbles
3. Add 150 μl Blocking Buffer (5% Low Fat Milk in PBS) to each well. Incubate while shaking on a micro-titer plate shaker for 30 min.
4. Wash 4× with TBST. Pat plate on a paper towel to remove excess liquid and bubbles.
5. Add 0.5 μg Rabbit a-GyrB antibody per well. Dilute antibody in DPBS to a final volume of 100 μl per well. Incubate with shaking on a micro-titer plate shaker at room temperature for 1 hour.
6. Wash 4× with TBST as described in step 4.
7. Add 2 μg COS/FGFR cell lysate (Myc-GyrB-FGFR source) in HNTG to each well to give a final volume of 100 μl per well. Incubate with shaking on a micro-titer plate shaker for 1 hour.

8. Wash 4× with TBST as described in step 4.
9. Add 80 µl of 1×kinase buffer per well.
10. Dilute test compound 1:10 in 1×kinase buffer+1% DMSO in a polypropylene 96 well plate.
11. Transfer 10 µl of diluted test compound solution and control wells from polypropylene plate wells to the corresponding ELISA plate wells, incubate with shaking on a micro-titer plate shaker for 20 minutes.
12. Add 10 µl of 70 µM ATP diluted in kinase buffer to positive control and test wells (Final ATP concentration is 7 µM/well). Add 10 µl 1× kinase buffer to negative control wells. Incubate with shaking on a micro-titer plate shaker for 15 min.
13. Stop kinase reaction by adding 5 µl 0.5 M EDTA to all wells.
14. Wash 4× with TBST as described in step 4.
15. Add 100 µl biotin conjugated α-phosphotyrosine mab (b4G10) diluted in TBST to each well. Incubate with shaking on a micro-titer plate shaker for 30 minutes.
16. Prepare Vectastain ABC reagent. Add 1 drop reagent A to 15 ml TBST. Mix by inverting tube several times. Add 1 drop reagent B and mix again.
17. Wash 4× with TBST as described in step 4.
18. Add 100 µl ABC HRP reagent to each well. Incubate with shaking on a micro-titer plate shaker for 30 minutes.
19. Wash 4× with TBST as described in step 4.
20. Add 100 µl of ABTS/$H_2O_2$ solution to each well.
22. Incubate 5 to 15 minutes with shaking. Remove any bubbles.
23. If necessary stop reaction by adding 100 µl of 0.2M HCl/well.
24. Read assay on Dynatech MR7000 ELISA Plate Reader, test filter: 410 nM, reference filter: 630 nM.

Biochemical FLK-1 Assay

This assay evaluates flk-1 autophosphorylation activity in vitro using ELISA.

Materials And Reagents
1. 15 cm tissue culture dishes
2. Flk-1/NIH cells: NIH fibroblast line over-expressing human flk-1 clone 3 (SUGEN, Inc., obtained from MPI, Martinsried, Germany).
3. Growth medium: DMEM plus heat inactivated 10% FBS and 2 mM Glutamine (Gibco-BRL).
4. Starvation medium: DMEM plus 0.5% heat-inactivated FBS, 2 mM Glutamine (Gibco-BRL).
5. Corning 96-well ELISA plates (Corning Cat. No. 25805-96).
6. L4 or E38 monoclonal antibody specific for flk-1, Purified by Protein-A agarose affinity chromatography (SUGEN, Inc.).
7. PBS (Dulbecco's Phosphate-Buffered Saline) Gibco Cat. No. 450-1300EB).
8. HNTG (see BIOCHEMICAL FGFR for preparation).
9. Pierce BCA protein determination kit.
10. Blocking buffer
11. TBST (pH 7.0)
12. Kinase Buffer
13. Kinase Stop Solution: 200 mM EDTA.
14. Biotinylated 4G10, specific for phosphotyrosine (UBI, Cat. No. No. 16-103).
15. AB kit (Vector Laboratories Cat. No. PK 4000).
16. DMSO
17. NUNC 96-well V bottom polypropylene plates (Applied Scientific Cat. No. AS-72092).
18. Turbo-TMB (Pierce).
19. Turbo-TMB stop solution: 1 M $H_2SO_4$.
20. ATP (Sigma Cat. No. A-7699).
21. 20% DMSO in TBS (pH 7.0).

Procedure

Cell Growth and Lysate Preparation.
1. Seed cell into growth medium and grow for 2–3 days to 90–100% confluency at 37° C. and 5% $CO_2$. Do not exceed passage #20.
2. Remove the medium and wash the cells twice with PBS. Lyse with HNTG lysis buffer. Collect all lysates and vortex mix them for 20–30 seconds.
3. Remove insoluble material by centrifugation (5–10 min at about 10,000×g).
4. Determine the protein concentration using BCA kit.
5. Partition lysate into 1 mg aliquots, store at −80° C.

Assay Procedure
1. Coat Corning 96-well ELISA plates with 2 µg/well purified L4 (or E 38) in 100 µl of PBS. Store overnight at 4° C.
2. Remove unbound proteins from wells by inverting the plate to remove the liquid. Wash one time with $dH_2O$, pat plate on paper towel to remove excess liquid.
3. Block plates with 150 µl blocking buffer per well. Incubate for 45–60 minutes with shaking at 4° C.
4. Remove the blocking buffer and wash the ELISA plate three times with $dH_2O$ and one time with TBST. Pat plate on paper towel to remove excess liquid.
5. Dilute lysate in PBS to give final concentration of 50 µg/100 µl. Add 100 µl of diluted lysate to each well. Incubate with shaking at 40° C. overnight.
6. Remove unbound proteins from wells by inverting the plate. Wash as in step 4.
7. Add 80 µl of kinase buffer to wells (90 µl to negative control wells).
8. Dilute test compounds (normally 10-fold) into wells of a polypropylene plate containing 20% DMSO in TBS.
9. Add 10 µl of the diluted compounds to the ELISA wells containing immobilized flk-1 and shake. Control wells receive no compounds.
10. From stock 1 mM ATP, prepare 0.3 mM ATP solution in $dH_2O$ (alternatively, kinase buffer may be used).
11. Add 10 µl of 0.3 mM ATP to all wells except the negative controls. Incubate for 60 min. at room temperature with shaking.
12. After 1 hr stop the kinase reaction by adding 11 µl 200 mM EDTA. Shake for 1–2 min.
13. Wash the ELISA plate 4 times with $dH_2O$ and twice with TBST.
14. Add 100 µl of 1:5000 biotinylated 4G10:TBST to all wells. Incubate 45 min with shaking at room temperature.
15. While the above is incubating, add 50 µl of solutions A & B from the ABC kit to 10 ml of TBST. These solutions must be combined approximately 30 min prior to use.
16. Wash plates as in step 4.
17. Add 100 µl of the preformed A & B complex to all wells. Incubate 30 min with shaking at room temperature.

18. Wash plates as in step 4.
19. Add 100 µl turbo-TMB. Shake at room temperature for 10–15 min.
20. When the color in the positive control wells reaches an absorbance of about 0.35–0.4, stop the reaction with 100 µl of turbo-TMB stop solution.
21. Read plates on Dynatech MR7000 ELISA reader, test filter: 450 nM, reference filter: 410 nM.

HUV-EC-C Assay

The following protocol may also be used to measure a compound's activity against PDGF-R, FGF-R, VEGF, aFGF or Flk-1/KDR, all of which are naturally expressed by NUV-EC cells.

DAY 0

1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 cm$^2$ of tissue culture flask. Trypsinize with 0.05% trypsin-EDTA in non-enzymatic cell dissociation solution (Sigma Chemical ompany, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 cm$^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).
2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 cm$^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of 0.8–1.0×10$^5$ cells/ml.
3. Add cells to 96-well flat-bottom plates at 100 µl/well or 0.8–1.0×10$^4$ cells/well, incubate ~24 h at 37° C., 5% $CO_2$.

DAY 1

1. Make up two-fold test compound titrations in separate 96-well plates, generally 50 µM on down to 0 µM. Use the same assay medium as mentioned in day 0, step 2 above. Titrations are made by adding 90 µl/well of test compound at 200 µM (4× the final well concentration) to the top well of a particular plate column. Since the stock test compound is usually 20 mM in DMSO, the 200 µM drug concentration contains 2% DMSO. A diluent made up to 2% DMSO in assay medium (F12K+0.5% fetal bovine serum) is used as diluent for the test compound titrations in order to dilute the test compound but keep the DMSO concentration constant. Add this diluent to the remaining wells in the column at 60 µl/well. Take 60 µl from the 120 µl of 200 µM test compound dilution in the top well of the column and mix with the 60 µl in the second well of the column. Take 60 µl from this well and mix with the 60 µl in the third well of the column, and so on until two-fold titrations are completed. When the next-to-the-last well is mixed, take 60 µl of the 120 µl in this well and discard it. Leave the last well with 60 µl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.
2. Transfer 50 µl/well of the test compound dilutions to the 96-well assay plates containing the 0.8–1.0×10$^4$ cells/100 µl/well of the HUV-EC-C cells from day 0 and incubate ~2 h at 37° C., 5% $CO_2$.
3. In triplicate, add 50 µl/well of 80 µg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 µl test compound dilution, 50 µl growth factor or media, and 100 µl cells, which calculates to 200 µl/well total. Thus the 4× concentrations of test compound and growth factors become 1× once everything has been added to the wells.

DAY 2

1. Add $^3$H-thymidine (Amersham, catalogue no. TRK-686) at 1 µCi/well (10 µl/well of 100 µCi/ml solution made up in RPMI media+10% heat-inactivated fetal bovine serum) and incubate ≠24 h at 37° C., 5% $CO_2$. RPMI is obtained from Gibco BRL, catalogue no. 11875–051.

DAY 3

1. Freeze plates overnight at −20° C.

DAY 4

Thaw plates and harvest with a 96-well plate harvester (Tomtec Harvester 96®) onto filter mats (Wallac, catalogue no. 1205-401), read counts on a Wallac Betaplate™ liquid scintillation counter.

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Poylsen, 1969, *Acta Pathol. Microbial. Scand.* 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the ellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells and NIH 3T3 fibroblasts genetically engineered to overexpress EGFR, PDGFR, IGF-LR or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% trypsin-EDTA and pelleted at 450× g for 10 min. Pellets are resuspended in sterile PBS or media (without FES) to a particular concentration and the cells are implanted into the hindflank of the mice (8–10 mice per group, $2–10×10^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 µL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 µl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

Measurement of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index, i.e., $IC_{50}/LD_{50}$, $IC_{50}$, the dose required to achieve 50% inhibition, can be measured using standard techniques such as those described herein. $LD_{50}$, the dosage which results in 50% toxicity, can also be measured by standard techniques as well (Mossman, 1983, *J. Immunol.*

*Methods*, 65:55–63), by measuring the amount of LDH released (Korzeniewski and Callewaert, 1983, *J. Immunol. Methods*, 64:313, Decker and Lohmann-Matthes, 1988, *J. Immunol. Methods*, 115:61), or by measuring the lethal dose in animal models. Compounds with a large therapeutic index are preferred. The therapeutic index should be greater than 2, preferably at least 10, more preferably at least 50.

B. Examples

Biological Activity

Examples of the in vitro potency of compounds of this invention are shown in Table 2. The examples shown are not to be construed as limiting the scope of this invention in any manner whatsoever.

Conclusion

It will be appreciated that the compounds, methods and pharmaceutical compositions of the present invention are effective in modulating PK activity and therefore are expected to be effective as therapeutic agents against TK, CTK-, and STK-related disorders.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.
What is claimed:
1. A compound having the chemical structure:

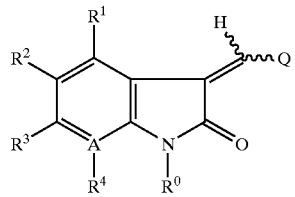

wherein:
A is carbon;
Q is

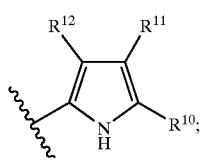

$R^0$ is selected from the group consisting of hydrogen, alkyl, —C(O)$R^{19}$ and —C(O)O$R^{19}$;
$R^1$ is hydrogen, alkyl, alkoxy, halo, aryl, —(CH$_2$)$_n$OC(O)$R^{19}$, C(O)NR$^{19}$, —C(O)O$R^{19}$ and —(CH$_2$)$_n$R$^{20}$, wherein;
  $R^{19}$ is selected from the group consisting of hydrogen, alkyl, alkenyl, alkynyl, cycloalkyl and aryl;
  n is 1, 2, 3, or 4;
  $R^{20}$ is selected from the group consisting of hydroxy, halo, —C(O)OR$^{19}$, —OC(O)NR$^{21}$R$^{22}$; —OC(S)NR$^{21}$R$^{22}$, —OC(O)NHSO$_2$R$^{21}$R$^{22}$ and —NR$^{21}$R$^{22}$;
$R^2$ is selected from the group consisting of hydrogen, alkyl, cycloalkyl, aryl, trihalomethyl, alkoxy, halo, —(CH$_2$)$_n$R$^{20}$, —SO$_2$NR$^{21}$R$^{22}$, —C(O)OR$^{19}$, —C(O)R$^{19}$, —NHC(O)OR$^{19}$, —NR$^{21}$R$^{22}$ and —N=CR$^{23}$ wherein
  $R^{21}$ and $R^{22}$ are independently selected from the group consisting of hydrogen, alkyl, alkenyl, alkynyl, cycloalkyl and aryl;
  $R^{23}$ is selected from the group consisting of alkyl, alkenyl, alkynyl, cycloalkyl and aryl;
$R^3$ is selected from the group consisting of hydrogen, alkyl, trihalomethyl, alkoxy, aryl, aryloxy, hydroxy, halo, —SO$_2$NR$^{21}$R$^{22}$, —NHSO$_2$R$^{19}$, —C(O)OR$^{19}$, —NR$^{21}$R$^{22}$ and —NHC(O)R$^{24}$, wherein
  $R^{24}$ is selected from the group consisting of alkyl, alkenyl, alkynyl and aryl;
$R^4$ is selected from the group consisting of hydrogen, alkyl, alkoxy and halo;
$R^{10}$ is selected from the group consisting of alkyl and —C(O)OR$^{19}$;
$R^{11}$ is selected from the group consisting of hydrogen, alkyl and —C(O)OR$^{19}$;
$R^{12}$ is —(CH$_2$)$_n$R$^{20}$; and,
physiologically acceptable salts thereof.
2. The compound of claim 1, wherein:
$R^1$ is selected from the group consisting of hydrogen, lower alkyl and —(CH$_2$)$_n$—R$^{20}$;
  n is 2 or 3;
  $R^{20}$ is selected from the group consisting of hydroxy and —C(O)OH;
$R^2$ is selected from the group consisting of hydrogen, halo, lower alkyl, lower alkoxy, —SO$_2$NR$^{21}$R$^{22}$ and —C(O)OH;
$R^3$ is selected from the group consisting of hydrogen, halo, lower alkyl, lower alkoxy and aryl optionally substituted with one or more lower alkyl groups; and,
$R^4$ is hydrogen.
3. The compound of claim 1, wherein:
$R^{11}$ is selected from the group consisting of hydrogen, lower alkyl and —C(O)—OR$^{19}$;
$R^{12}$ is —(CH$_2$)$_n$—R$^{20}$;
$R^{19}$ is selected from the group consisting of hydrogen and lower alkyl;
n is 2 or 3; and
$R^{20}$ is selected from the group consisting of hydroxy, —C(O)OH and —NR$^{21}$R$^{22}$.
4. The compound or salt of claim 1, wherein:
$R^{10}$ is selected from the group consisting of lower alkyl and —C(O)O(lower alkyl);
$R^{11}$ is selected from the group consisting of hydrogen, lower alkyl and —C(O)—OR$^{19}$;
$R^{12}$ is —(CH$_2$)$_n$—R$^{20}$;
$R^{19}$ is selected from the group consisting of hydrogen and lower alkyl;
n is 2 or 3; and
$R^{20}$ is selected from the group consisting of —C(O)OH and —N(lower alkyl)$_2$.
5. A pharmaceutical composition, comprising
a compound or salt of claim 1; and,
a pharmaceutically acceptable carrier or excipient.
6. A method of inhibiting the catalytic activity of a protein kinase comprising contacting said protein kinase with a compound or salt of claim 1.
7. The method of claim 6 wherein said protein kinase is selected from the group consisting of a receptor tyrosine kinase, a non-receptor tyrosine kinase and a serine-threonine kinase.
8. A method for treating a protein kinase related disorder in an organism comprising administering a therapeutically effective amount of a compound or salt of claim 1 to said organism.
9. The method of claim 8 wherein said protein kinase related disorder is selected from the group consisting of a receptor tyrosine kinase related disorder, a non-receptor tyrosine kinase related disorder and a serine-threonine kinase related disorder.
10. The method of claim 8 wherein said protein kinase related disorder is selected from the group consisting of an EGFR related disorder, a PDGFR related disorder, an IGFR related disorder and a flk related disorder.
11. The method of claim 8 wherein said protein kinase related disorder is a cancer selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.
12. The method of claim 8 wherein said protein kinase related disorder is selected from the group consisting of diabetes, an autoimmune disorder, a hyperproliferation disorder, restenosis, fibrosis, psoriasis, von Heppel-Lindau disease, osteoarthritis, rheumatoid arthritis, angiogenesis, an inflammatory disorder, an immunological disorder and a cardiovascular disorder.

13. The method of claim 8 wherein said organism is a human.

14. A compound having the structure:

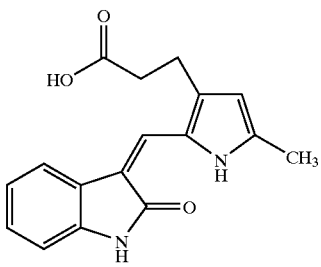

and named as 3-[5-methyl-2-(2-oxo-1,2-dihydroindol-3-ylidenemethyl)-1H-pyrrol-3-yl]-propionic acid or a physiologically acceptable salt thereof.

15. A pharmaceutical composition comprising a therapeutically effective amount of 3-[5-methyl-2-(2-oxo-1,2-dihydroindol-3-ylidenemethyl)-1H-pyrrol-3-yl]-propionic acid or a physiologically acceptable salt thereof and a pharmaceutically acceptable excipient.

16. A method of treating diabetic retinopathy in a patient in need of such treatment which method comprises administering to said patient a therapeutically effective amount of a pharmaceutical composition comprising 3-[5-methyl-2-(2-oxo-1,2-dihydroindol-3-ylidenemethyl)-1H-pyrrol-3-yl]-propionic acid or a physiologically acceptable salt thereof and a pharmaceutically acceptable excipient.

17. A method of activating the catalytic activity of a protein kinase comprising contacting said protein kinase with a compound or salt of claim 1.

* * * * *